US012540335B2

United States Patent

(12) United States Patent
Jiang et al.

(10) Patent No.: US 12,540,335 B2
(45) Date of Patent: Feb. 3, 2026

(54) COMPOSITIONS AND METHODS FOR THE TREATMENT OF METABOLIC LIVER DISORDERS

(71) Applicant: Poseida Therapeutics, Inc., San Diego, CA (US)

(72) Inventors: Jingjing Jiang, San Diego, CA (US); Julian Down, San Diego, CA (US); Xianghong Li, San Diego, CA (US); Eric M. Ostertag, San Diego, CA (US)

(73) Assignee: Poseida Therapeutics, Inc., San Diego, CA (US)

( * ) Notice: Subject to any disclaimer, the term of this patent is extended or adjusted under 35 U.S.C. 154(b) by 725 days.

(21) Appl. No.: 17/909,101

(22) PCT Filed: Mar. 4, 2021

(86) PCT No.: PCT/US2021/020929
§ 371 (c)(1),
(2) Date: Sep. 2, 2022

(87) PCT Pub. No.: WO2021/178707
PCT Pub. Date: Sep. 10, 2021

(65) Prior Publication Data
US 2023/0104091 A1 Apr. 6, 2023

Related U.S. Application Data

(60) Provisional application No. 63/121,488, filed on Dec. 4, 2020, provisional application No. 62/985,047, filed on Mar. 4, 2020.

(51) Int. Cl.
*A61K 48/00* (2006.01)
*A61P 1/16* (2006.01)
(Continued)

(52) U.S. Cl.
CPC .......... *C12N 15/86* (2013.01); *A61K 48/0058* (2013.01); *A61P 1/16* (2018.01);
(Continued)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,239,754 A | 12/1980 | Sache et al. |

(Continued)

FOREIGN PATENT DOCUMENTS

| | | |
|---|---|---|
| WO | WO-2010099296 A1 | 9/2010 |
| WO | 2011/126808 A2 | 10/2011 |

(Continued)

OTHER PUBLICATIONS

Kim JH, Kim YM, Lee BH, Cho JH, Kim GH, Choi JH, Yoo HW. Short-term efficacy of N-carbamylglutamate in a patient with N-acetylglutamate synthase deficiency. J Hum Genet. Jul. 2015;60(7):395-7. doi: 10.1038/jhg.2015.30. Epub Mar. 19, 2015. PMID: 25787344. (Year: 2015).*

(Continued)

*Primary Examiner* — Evelyn Y Pyla
*Assistant Examiner* — Jagamya Vijayaraghavan
(74) *Attorney, Agent, or Firm* — HALEY GUILIANO LLP; Brian M. Gummow; Maha M. Saber

(57) ABSTRACT

The present disclosure is directed to compositions and methods for the treatment of Metabolic Liver Disorders. The compositions and methods can comprise an adeno-associated virus (AAV) piggyBac polynucleotide comprising a transgene. The transgene may comprise ornithine transcarbamylase (OTC) or methylmalonyl-CoA mutase (MUT1).

18 Claims, 29 Drawing Sheets

Specification includes a Sequence Listing.

(51) Int. Cl.
*C12N 9/10* (2006.01)
*C12N 9/12* (2006.01)
*C12N 15/86* (2006.01)

(52) U.S. Cl.
CPC ......... *C12N 9/1018* (2013.01); *C12N 9/1241* (2013.01); *C12Y 201/03003* (2013.01)

(56) References Cited

U.S. PATENT DOCUMENTS

| | | | |
|---|---|---|---|
| 4,554,101 | A | 11/1985 | Hopp |
| 4,925,673 | A | 5/1990 | Steiner et al. |
| 5,168,062 | A | 12/1992 | Stinski |
| 5,266,491 | A | 11/1993 | Nagata et al. |
| 5,385,839 | A | 1/1995 | Stinski |
| 5,514,670 | A | 5/1996 | Friedman et al. |
| 5,770,222 | A | 6/1998 | Unger et al. |
| 5,814,599 | A | 9/1998 | Mitragotri et al. |
| 5,849,695 | A | 12/1998 | Cohen et al. |
| 5,871,753 | A | 2/1999 | Crabtree et al. |
| 5,879,681 | A | 3/1999 | Leone-Bay et al. |
| 6,218,182 | B1 | 4/2001 | Naughton et al. |
| 6,218,185 | B1 | 4/2001 | Shirk et al. |
| 6,962,810 | B2 | 11/2005 | Fraser et al. |
| 8,399,643 | B2 | 3/2013 | Ostertag et al. |
| 10,041,077 | B2 | 8/2018 | Minshull et al. |
| 10,307,469 | B2 | 6/2019 | Venditti et al. |
| 2018/0353623 | A1 | 12/2018 | Venditti et al. |

FOREIGN PATENT DOCUMENTS

| | | | |
|---|---|---|---|
| WO | WO-2012050919 | A2 | 4/2012 |
| WO | WO-2012074758 | A1 | 6/2012 |
| WO | 2014/003553 | A1 | 1/2014 |
| WO | WO-2015138348 | A1 | 9/2015 |
| WO | WO-2015139093 | A1 | 9/2015 |
| WO | 2017/021359 | A1 | 2/2017 |
| WO | WO-2017070428 | A1 | 4/2017 |
| WO | WO-2019049816 | A1 | 3/2019 |
| WO | WO-2019173636 | A1 | 9/2019 |
| WO | WO-2020051374 | A1 | 3/2020 |

OTHER PUBLICATIONS

Diez-Fernandez C, Häberle J. Targeting CPS1 in the treatment of Carbamoyl phosphate synthetase 1 (CPS1) deficiency, a urea cycle disorder. Expert Opin Ther Targets. Apr. 2017;21(4):391-399. doi: 10.1080/14728222.2017.1294685. Epub Feb. 20, 2017. PMID: 28281899. (Year: 2017).*

Qu, Wei1; Wei, Lin1; Zhu, Zhi-Jun1; Sun, Li-Ying1; Liu, Ying1; Zeng1, Zhi-Gui1. Considerations for Use of Domino Cross-auxiliary Liver Transplantation in Metabolic Liver Diseases: A Review of Case Studies. Transplantation 103(9):p. 1916-1920, Sep. 2019. | DOI: 10.1097/TP.0000000000002602 (Year: 2019).*

Scorza M, Elce A, Zarrilli F, Liguori R, Amato F, Castaldo G. Genetic diseases that predispose to early liver cirrhosis. Int J Hepatol. 2014;2014:713754. doi: 10.1155/2014/713754. Epub Jul. 14, 2014. PMID: 25132997; PMCID: PMC4123515. (Year: 2014).*

An et al. "Long-term efficacy and safety of mRNA therapy in two murine models of methylmalonic acidemia", EBioMedicine, (2019); 45:519-528.

An et al. "Systemic messenger RNA therapy as a treatment for methylmalonic acidemia", Cell Reports, (2017); 21(12):3548-3558.

Brassier et al. "Long-term outcomes in Ornithine Transcarbamylase deficiency: a series of 90 patients", Orphanet Journal of Rare Diseases, (2015); 10(1):1-4.

Bunting et al. Gene therapy with BMN 270 results in therapeutic levels of FVIII in mice and primates and normalization of bleeding in hemophilic mice. Molecular Therapy. Feb. 7, 2018;26(2):496-509.

Chandler et al. "Gene therapy for methylmalonic acidemia: past, present, and future", Human Gene Therapy, (2019); 30(10):1236-1244.

Chandler et al. "Long-term rescue of a lethal murine model of methylmalonic acidemia using adeno associated viral gene therapy", Molecular Therapy, (2010); 18(1):11-16.

Chandler et al. "Vector design influences hepatic genotoxicity after adeno-associated virus gene therapy", The Journal of Clinical Investigation, (2015); 125(2):870-880.

Clinical Trials NCT02991144 "Safety and Dose-Finding Study of DTX301 (scAAV8OTC) in Adults With Late-Onset Ornithine Transcarbamylase (OTC) Deficiency (CAPtivate)" First posted Dec. 13, 2016, Last Update Jan. 26, 2023, 23 pages.

Cooney, A.L. et al. "Hybrid Nonviral/Viral Vector Systems for Improved piggyBac DNA Transposon In Vivo Delivery", Mol Ther, (2015); 23(4):667-674.

Cunningham et al. "AAV-mediated gene delivery to the mouse liver", Viral Vectors for Gene Therapy: Methods and Protocols, (2019); 137:213-219.

Cunningham, S.C. et al. "Modeling Correction of Severe Urea Cycle Defects in the Growing Murine Liver Using a Hybrid Recombinant Adeno-Associated Virus/piggyBac Transposase Gene Delivery System", Hepatology, (2015); 62:417-428.

De Sabbata et al. "Long-term correction of ornithine transcarbamylase deficiency in Spf-Ash mice with a translationally optimized AAV vector", Molecular Therapy—Methods & Clinical Development, (2021); 20:169-180.

Ferla et al. "Non-clinical safety and efficacy of an AAV2/8 vector administered intravenously for treatment of mucopolysaccharidosis type VI", Molecular Therapy—Methods & Clinical Development. (2017); 6:143-158.

GenBank Accession No. AAA87375.2 "unknown protein [Trichoplusia ni]", Oct. 15, 2002, 2 pages.

GenBank Accession No. BAD11135.1 "putative transposase yabusame-1 [Bombyx mori]", Sep. 15, 2007, 2 pages.

Ginn et al. "Efficient in vivo editing of OTC-deficient patient-derived primary human hepatocytes", JHEP Reports, (2020); 2(1):100065, 12 pages.

Han et al. "Low-dose liver-targeted gene therapy for Pompe disease enhances therapeutic efficacy of ERT via immune tolerance induction", Molecular Therapy—Methods & Clinical Development, (2017); 4:126-136.

Kumari et al. "Mutation analyses in selected exons of the MUT gene in Indian patients with methylmalonic acidemia", Indian Journal of Clinical Biochemistry, (2017); 32:266-274.

Kyte et al. "A Simple Method for Displaying the Hydropathic Character of a Protein", J. Mol. Biol. 157(1), 1982, pp. 105-132.

Leebeek et al. "AMT-060 gene therapy in adults with severe or moderate-severe Hemophilia B confirm stable FIX expression and durable reductions in bleeding and factor IX consumption for up to 5 years", Blood, (2020); 136:26, 3 pages.

Lehninger, A.L., Biochemistry. The Molecular Basis of Cell Structure and Function. Second Edition. New York, NY: Worth Publishers, Inc., 1975; pp. 71-77.

Manoli et al. "FGF21 underlies a hormetic response to metabolic stress in methylmalonic acidemia", JCI Insight, (2018); 3(23):e124351, 17 pages.

Miesbach et al. "Gene therapy with adeno-associated virus vector 5-human factor IX in adults with hemophilia B", Blood, The Journal of the American Society of Hematology, (2018); 131(9):1022-1031.

Nathwani, A. et al., "Safe and efficient transduction of the liver after peripheral vein infusion of self-complementary AAV vector results in stable therapeutic expression of human FIX in nonhuman primates," Blood, Feb. 2007, 109(4):1414-1421.

Nathwani et al. "Long-Term Safety and Efficacy of Factor IX Gene Therapy in Hemophilia B" The New England Journal of Medicine, 371(21):1994-2004 (Nov. 20, 2014).

Nathwani et al. "Our journey to successful gene therapy for hemophilia B", Human Gene Therapy, (2014); 25(11):923-926.

Pasi et al. "Multiyear follow-up of AAV5-hFVIII-SQ gene therapy for hemophilia A", New England Journal of Medicine, (2020); 382(1):29-40.

(56) References Cited

OTHER PUBLICATIONS

Paulk et al. "Bioengineered AAV capsids with combined high human liver transduction in vivo and unique humoral seroreactivity", Molecular Therapy, (2018); 26(1):289-303.
Pekrun et al. "Using a barcoded AAV capsid library to select for clinically relevant gene therapy vectors", JCI Insight, (2019); 4(22):e131610, 19 pages.
Schmidt et al. "Mitochondrial protein import: from proteomics to functional mechanisms", Nature Reviews Molecular Cell Biology, (2010); 11(9):655-667.
Sprague, J. et al. (Feb. 1983) "Expression of a Recombinant DNA Gene Coding for the Vesicular Stomatitis Virus Nucleocapsid Protein" J Virol, 45(2):773-781.
Spronck et al. "Enhanced factor IX activity following administration of AAV5-R338L "Padua" factor IX versus AAV5 WT human factor IX in NHPs", Molecular Therapy—Methods & Clinical Development, (2019); 15:221-231.
Tatusova and Madden, "Blast 2 Sequences, a new tool for comparing protein and nucleotide sequences". FEMS Microbiol Lett., May 15, 1999; 174(2): 247-250.
Wang et al. "Hepatic gene transfer in neonatal mice by adeno-associated virus serotype 8 vector", Human Gene Therapy, (2012); 23(5):533-539.
Wang et al. "Preclinical evaluation of a clinical candidate AAV8 vector for ornithine transcarbamylase (OTC) deficiency reveals functional enzyme from each persisting vector genome", Molecular Genetics and Metabolism, (2012); 105(2):203-211.
Ye et al. "Differences in the human and mouse amino-terminal leader peptides of ornithine transcarbamylase affect mitochondrial import and efficacy of adenoviral vectors", Human Gene Therapy, (2001); 12(9):1035-1046.
Ye, X., et al., "Prolonged metabolic correction in adult ornithine transcarbamylase-deficient mice with adenoviral vectors." Biological Chem. Feb. 1996; 271(7): 3639-3646.
Yu et al. "Liver transplantation for urea cycle disorders: analysis of the united network for organ sharing database", Transplantation Proceedings. (2015); 47(8):2413-2418.
Zhang, W. et al. "Hybrid Adeno-Associated Viral Vectors Utilizing Transposase-Mediated Somatic Integration for Stable Transgene Expression in Human Cells", PLoS One, (2013); 8(10):e76771, 17 pages.
"Ornithine carbamoyltransferase, mitochondrial precursor [*Homo sapiens*]", Database: DDBJ/EMBL/GenBank [online], Accession No. NP_000522.3, Jan. 2, 2020, 6 Pages.

* cited by examiner

SEQUENCE LISTING

```
<160> NUMBER OF SEQ ID NOS: 146

<210> SEQ ID NO 1
<211> LENGTH: 178
<212> TYPE: DNA
<213> ORGANISM: Artificial Sequence
<220> FEATURE:
<223> OTHER INFORMATION: Synthetic Construct

<400> SEQUENCE: 1

ctgcgcgctc gctcgctcac tgaggccgcc cgggcaaagc ccgggcgtcg ggcgaccttt      60

ggtcgcccgg cctcagtgag cgagcgagcg cgcagagagg gagtggccaa ctccatcact     120

aggggttcct tgtagttaat gattaacccg ccatgctact tatctacgta gccatgct       178


<210> SEQ ID NO 2
<211> LENGTH: 178
<212> TYPE: DNA
<213> ORGANISM: Artificial Sequence
<220> FEATURE:
<223> OTHER INFORMATION: Synthetic Nucleic Acid

<400> SEQUENCE: 2

agcatggcta cgtagataag tagcatggcg ggttaatcat taactacaag gaacccctag      60

tgatggagtt ggccactccc tctctgcgcg ctcgctcgct cactgaggcc gggcgaccaa     120

aggtcgcccg acgcccgggc tttgcccggg cggcctcagt gagcgagcga gcgcgcag       178
```

```
<210> SEQ ID NO 3
<211> LENGTH: 130
<212> TYPE: DNA
<213> ORGANISM: Artificial Sequence
<220> FEATURE:
<223> OTHER INFORMATION: Synthetic Construct

<400> SEQUENCE: 3

cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct                                                           130


<210> SEQ ID NO 4
<211> LENGTH: 141
<212> TYPE: DNA
<213> ORGANISM: Artificial Sequence
<220> FEATURE:
<223> OTHER INFORMATION: Synthetic Nucleic Acid

<400> SEQUENCE: 4

aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag ctgcctgcag g                                              141


<210> SEQ ID NO 5
<211> LENGTH: 303
<212> TYPE: DNA
<213> ORGANISM: Artificial Sequence
<220> FEATURE:
<223> OTHER INFORMATION: Synthetic Nucleic Acid

<400> SEQUENCE: 5

tataacaaga aaatatatat ataataagtt atcacgtaag tagaacatga aataacaata     60

taattatcgt atgagttaaa tcttaaaagt cacgtaaaag ataatcatgc gtcattttga    120

ctcacgcggt cgttatagtt caaaatcagt gacacttacc gcattgacaa gcacgcctca    180

cgggagctcc aagcggcgac tgagatgtcc taaatgcaca gcgacggatt cgcgctattt    240

agaaagagag agcaatattt caagaatgca tgcgtcaatt ttacgcagac tatctttcta    300

ggg                                                                  303


<210> SEQ ID NO 6
<211> LENGTH: 238
<212> TYPE: DNA
<213> ORGANISM: Artificial Sequence
<220> FEATURE:
<223> OTHER INFORMATION: Synthetic Nucleic Acid

<400> SEQUENCE: 6

ccctagaaag ataatcatat tgtgacgtac gttaaagata atcatgcgta aaattgacgc     60

atgtgtttta tcggtctgta tatcgaggtt tatttattaa tttgaataga tattaagttt    120

tattatattt acacttacat actaataata aattcaacaa acaatttatt tatgtttatt    180

tatttattaa aaaaaaacaa aaactcaaaa tttcttctat aaagtaacaa aactttta      238


<210> SEQ ID NO 7
<211> LENGTH: 232
<212> TYPE: DNA
<213> ORGANISM: Artificial Sequence
<220> FEATURE:
```

<223> OTHER INFORMATION: Synthetic Nucleic Acid

<400> SEQUENCE: 7
gagggacagc cccccccaa agcccccagg gatgtaatta cgtccctccc ccgctagggg 60
gcagcagcga gccgcccggg gctccgctcc ggtccggcgc tccccccgca tccccgagcc 120
ggcagcgtgc ggggacagcc cgggcacggg gaaggtggca cgggatcgct ttcctctgaa 180
cgcttctcgc tgctctttga gcctgcagac acctgggggg atacggggaa aa 232

<210> SEQ ID NO 8
<211> LENGTH: 232
<212> TYPE: DNA
<213> ORGANISM: Artificial Sequence
<220> FEATURE:
<223> OTHER INFORMATION: Synthetic Nucleic Acid

<400> SEQUENCE: 8
ttttccccgt atccccccag gtgtctgcag gctcaaagag cagcgagaag cgttcagagg 60
aaagcgatcc cgtgccacct tccccgtgcc cgggctgtcc ccgcacgctg ccggctcggg 120
gatgcggggg gagcgccgga ccggagcgga gccccgggcg gctcgctgct gccccctagc 180
gggggaggga cgtaattaca tccctggggg ctttgggggg gggctgtccc tc 232

<210> SEQ ID NO 9
<211> LENGTH: 252
<212> TYPE: DNA
<213> ORGANISM: Artificial Sequence
<220> FEATURE:
<223> OTHER INFORMATION: Synthetic Nucleic Acid

<400> SEQUENCE: 9
tgtttgctgc ttgcaatgtt tgcccatttt agggtggaca caggacgctg tggtttctga 60
gccagggggc gactcagatc ccagccagtg gacttagccc ctgtttgctc ctccgataac 120
tggggtgacc ttggttaata ttcaccagca gcctcccccg ttgcccctct ggatccactg 180
cttaaatacg gacgaggaca gggccctgtc tcctcagctt caggcaccac cactgacctg 240
ggacagtgaa tc 252

<210> SEQ ID NO 10
<211> LENGTH: 449
<212> TYPE: DNA
<213> ORGANISM: Artificial Sequence
<220> FEATURE:
<223> OTHER INFORMATION: Synthetic Nucleic Acid

<400> SEQUENCE: 10
cccctaaaat gggcaaacat tgcaagcagc aaacagcaaa cacacagccc tccctgcctg 60
ctgaccttgg agctggggca gaggtcagag acctctctgg gcccatgcca cctccaacat 120
ccactcgacc ccttggaatt tcggtggaga ggagcagagg ttgtcctggc gtggtttagg 180
tagtgtgaga ggggaatgac tcctttcggt aagtgcagtg gaagctgtac actgcccagg 240
caaagcgtcc gggcagcgta ggcgggcgac tcagatccca gccagtggac ttagcccctg 300
tttgctcctc cgataactgg ggtgaccttg gttaatattc accagcagcc tcccccgttg 360
cccctctgga tccactgctt aaatacggac gaggacaggg ccctgtctcc tcagcttcag 420
gcaccaccac tgacctggga cagtgaatc 449

<210> SEQ ID NO 11
<211> LENGTH: 1214

<212> TYPE: DNA
<213> ORGANISM: Artificial Sequence
<220> FEATURE:
<223> OTHER INFORMATION: Synthetic Nucleic Acid

<400> SEQUENCE: 11
gctcagaggc acacaggagt ttctgggctc accctgcccc cttccaaccc ctcagttccc 60
atcctccagc agctgtttgt gtgctgcctc tgaagtccac actgaacaaa cttcagccta 120
ctcatgtccc taaaatgggc aaacattgca agcagcaaac agcaaacaca cagccctccc 180
tgcctgctga ccttggagct ggggcagagg tcagagacct ctctgggccc atgccacctc 240
caacatccac tcgacccctt ggaatttcgg tggagaggag cagaggttgt cctggcgtgg 300
tttaggtagt gtgagagggt ccggcgatta actgcaggct cagaggcaca caggagtttc 360
tgggctcacc ctgccccctt ccaacccctc agttcccatc ctccagcagc tgtttgtgtg 420
ctgcctctga agtccacact gaacaaactt cagcctactc atgtccctaa aatgggcaaa 480
cattgcaagc agcaaacagc aaacacacag ccctccctgc ctgctgacct tggagctggg 540
gcagaggtca gagacctctc tgggcccatg ccacctccaa catccactcg accccttgga 600
atttcggtgg agaggagcag aggttgtcct ggcgtggttt aggtagtgtg agagggtccg 660
gcgaattaat gctaccagtg gaacagccac taaggattct gcagtgagag cagagggcca 720
gctaagtggt actctcccag agactgtctg actcacgcca ccccctccac cttggacaca 780
ggacgctgtg gtttctgagc caggtacaat gactcctttc ggtaagtgca gtggaagctg 840
tacactgccc aggcaaagcg tccgggcagc gtaggcgggc gactcagatc ccagccagtg 900
gacttagccc ctgtttgctc ctccgataac tggggtgacc ttggttaata ttcaccagca 960
gcctcccccg ttgcccctct ggatccactg cttaaatacg gacgaggaca gggccctgtc 1020
tcctcagctt caggcaccac cactgacctg ggacagtgaa ttgcggtaag tatcaaggtt 1080
acaagacagg tttaaggaga ccaatagaaa ctgggcttgt cgagacagag aagactcttg 1140
cgtttctgat aggcacctat tggtcttact gacatccact ttgcctttct ctccacagac 1200
ctgggacagt gaat 1214

<210> SEQ ID NO 12
<211> LENGTH: 1214
<212> TYPE: DNA
<213> ORGANISM: Artificial Sequence
<220> FEATURE:
<223> OTHER INFORMATION: Synthetic Nucleic Acid

<400> SEQUENCE: 12
gctcagaggc acacaggagt ttctgggctc accctgcccc cttccaaccc ctcagttccc 60
atcctccagc agctgtttgt gtgctgcctc tgaagtccac actgaacaaa cttcagccta 120
ctcatgtccc taaaatgggc aaacattgca agcagcaaac agcaaacaca cagccctccc 180
tgcctgctga ccttggagct ggggcagagg tcagagacct ctctgggccc atgccacctc 240
caacatccac tcgacccctt ggaatttcgg tggagaggag cagaggttgt cctggcgtgg 300
tttaggtagt gtgagagggt ccggcgatta actgcaggct cagaggcaca caggagtttc 360
tgggctcacc ctgccccctt ccaacccctc agttcccatc ctccagcagc tgtttgtgtg 420
ctgcctctga agtccacact gaacaaactt cagcctactc atgtccctaa aatgggcaaa 480
cattgcaagc agcaaacagc aaacacacag ccctccctgc ctgctgacct tggagctggg 540
gcagaggtca gagacctctc tgggcccatg ccacctccaa catccactcg accccttgga 600
atttcggtgg agaggagcag aggttgtcct ggcgtggttt aggtagtgtg agagggtccg 660
gcgaattaat gctaccagtg gaacagccac taaggattct gcagtgagag cagagggcca 720
gctaagtggt actctcccag agactgtctg actcacgcca ccccctccac cttggacaca 780
ggacgctgtg gtttctgagc caggtacaat gactcctttc ggtaagtgca gtggaagctg 840
tacactgccc aggcaaagcg tccgggcagc gtaggcgggc gactcagatc ccagccagtg 900
gacttagccc ctgtttgctc ctccgataac tggggtgacc ttggttaata ttcaccagca 960
gcctcccccg ttgcccctct ggatccactg cttaaatacg gacgaggaca gggccctgtc 1020
tcctcagctt caggcaccac cactgacctg ggacagtgaa ttgcggtaag tatcaaggtt 1080
acaagacagg tttaaggaga ccaatagaaa ctgggcttgt cgagacagag aagactcttg 1140
cgtttctgat aggcacctat tggtcttact gacatccact ttgcctttct ctccacagac 1200
ctgggacagt gaat 1214

<210> SEQ ID NO 13
<211> LENGTH: 861
<212> TYPE: DNA
<213> ORGANISM: Artificial Sequence
<220> FEATURE:
<223> OTHER INFORMATION: Synthetic Nucleic Acid

<400> SEQUENCE: 13
aggttaattt ttaaaaagca gtcaaaagtc caagtggccc ttggcagcat ttactctctc 60
tgtttgctct ggttaataat ctcaggagca caaacattcc agatccaggt taatttttaa 120
aaagcagtca aaagtccaag tggcccttgg cagcatttac tctctctgtt tgctctggtt 180
aataatctca ggagcacaaa cattccagat ccggcgcgcc agggctggaa gctacctttg 240
acatcatttc ctctgcgaat gcatgtataa tttctacaga acctattaga aaggatcacc 300
cagcctctgc ttttgtacaa ctttccctta aaaaactgcc aattccactg ctgtttggcc 360
caatagtgag aactttttcc tgctgcctct tggtgctttt gcctatggcc cctattctgc 420
ctgctgaaga cactcttgcc agcatggact taaacccctc cagctctgac aatcctcttt 480
ctcttttgtt ttacatgaag ggtctggcag ccaaagcaat cactcaaagt tcaaacctta 540 tcatttttttg ctttgttcct cttggccttg gttttgtaca tcagctttga aaataccatc 600
ccagggttaa tgctggggtt aatttataac taagagtgct ctagttttgc aatacaggac 660
atgctataaa aatggaaaga tgttgctttc tgagagactg cagaagttgg tcgtgaggca 720
ctgggcaggt aagtatcaag gttacaagac aggtttaagg agaccaatag aaactgggct 780
tgtcgagaca gagaagactc ttgcgtttct gataggcacc tattggtctt actgacatcc 840
actttgcctt tctctccaca g 861

<210> SEQ ID NO 14
<211> LENGTH: 146
<212> TYPE: DNA
<213> ORGANISM: Artificial Sequence
<220> FEATURE:
<223> OTHER INFORMATION: Synthetic Nucleic Acid

<400> SEQUENCE: 14
gttaatcatt aagtcgttaa tttttgtggc ccttgcgatg tttgctctgg ttaataatct 60
caggacaaac agaggttaat aattttccag atctctctga gcaatagtat aaaaggccag 120
cagcagcctg accacatctc atcctc 146

<210> SEQ ID NO 15
<211> LENGTH: 716
<212> TYPE: DNA
<213> ORGANISM: Artificial Sequence
<220> FEATURE:
<223> OTHER INFORMATION: Synthetic Nucleic Acid

<400> SEQUENCE: 15
gctgtttgtg tgctgcctct gaagtccaca ctgaacaaac ttcagcctac tcatgtccct 60
aaaatgggca aacattgcaa gcagcaaaca gcaaacacac agccctccct gcctgctgac 120
cttggagctg gggcagaggt cagagacctc tctgagatct gctgtttgtg tgctgcctct 180
gaagtccaca ctgaacaaac ttcagcctac tcatgtccct aaaatgggca aacattgcaa 240
gcagcaaaca gcaaacacac agccctccct gcctgctgac cttggagctg gggcagaggt 300
cagagacctc tctggtaccc ggggatcttg ctaccagtgg aacagccact aaggattctg 360
cagtgagagc agagggccag ctaagtggta ctctcccaga gactgtctga ctcacgccac 420
cccctccacc ttggacacag gacgctgtgg tttctgagcc aggtacaatg actcctttcg 480
gtaagtgcag tggaagctgt acactgccca ggcaaagcgt ccgggcagcg taggcgggcg 540
actcagatcc cagccagtgg acttagcccc tgtttgctcc tccgataact ggggtgacct 600
tggttaatat tcaccagcag cctcccccgt tgcccctctg gatccactgc ttaaatacgg 660
acgaggacag ggccctgtct cctcagcttc aggcaccacc actgacctgg gacagt 716

<210> SEQ ID NO 16
<211> LENGTH: 1224
<212> TYPE: DNA
<213> ORGANISM: Artificial Sequence
<220> FEATURE:
<223> OTHER INFORMATION: Synthetic Nucleic Acid

<400> SEQUENCE: 16
tcgtcgacgg gctcagaggc acacaggagt ttctgggctc accctgcccc cttccaaccc 60
ctcagttccc atcctccagc agctgtttgt gtgctgcctc tgaagtccac actgaacaaa 120
cttcagccta ctcatgtccc taaaatgggc aaacattgca agcagcaaac agcaaacaca 180
cagccctccc tgcctgctga ccttggagct ggggcagagg tcagagacct ctctgggccc 240
atgccacctc caacatccac tcgacccctt ggaatttcgg tggagaggag cagaggttgt 300
cctggcgtgg tttaggtagt gtgagagggt ccggcgatta actgcaggct cagaggcaca 360
caggagtttc tgggctcacc ctgccccctt ccaacccctc agttcccatc ctccagcagc 420
tgtttgtgtg ctgcctctga agtccacact gaacaaactt cagcctactc atgtccctaa 480
aatgggcaaa cattgcaagc agcaaacagc aaacacacag ccctccctgc ctgctgacct 540
tggagctggg gcagaggtca gagacctctc tgggcccatg ccacctccaa catccactcg 600
accccttgga atttcggtgg agaggagcag aggttgtcct ggcgtggttt aggtagtgtg 660
agagggtccg gcgaattaat gctaccagtg gaacagccac taaggattct gcagtgagag 720
cagagggcca gctaagtggt actctcccag agactgtctg actcacgcca ccccctccac 780
cttggacaca ggacgctgtg gtttctgagc caggtacaat gactcctttc ggtaagtgca 840
gtggaagctg tacactgccc aggcaaagcg tccgggcagc gtaggcgggc gactcagatc 900
ccagccagtg gacttagccc ctgtttgctc ctccgataac tggggtgacc ttggttaata 960
ttcaccagca gcctcccccg ttgcccctct ggatccactg cttaaatacg gacgaggaca 1020
gggccctgtc tcctcagctt caggcaccac cactgacctg ggacagtgaa ttgcggtaag 1080

```
tatcaaggtt acaagacagg tttaaggaga ccaatagaaa ctgggcttgt cgagacagag   1140

aagactcttg cgtttctgat aggcacctat tggtcttact gacatccact ttgcctttct   1200

ctccacagac ctgggacagt gaat                                          1224


<210> SEQ ID NO 17
<211> LENGTH: 750
<212> TYPE: PRT
<213> ORGANISM: Artificial Sequence
<220> FEATURE:
<223> OTHER INFORMATION: Synthetic Nucleic Acid

<400> SEQUENCE: 17

Met Leu Arg Ala Lys Asn Gln Leu Phe Leu Leu Ser Pro His Tyr Leu
1               5                   10                  15

Arg Gln Val Lys Glu Ser Ser Gly Ser Arg Leu Ile Gln Gln Arg Leu
            20                  25                  30

Leu His Gln Gln Gln Pro Leu His Pro Glu Trp Ala Ala Leu Ala Lys
        35                  40                  45

Lys Gln Leu Lys Gly Lys Asn Pro Glu Asp Leu Ile Trp His Thr Pro
    50                  55                  60

Glu Gly Ile Ser Ile Lys Pro Leu Tyr Ser Lys Arg Asp Thr Met Asp
65                  70                  75                  80

Leu Pro Glu Glu Leu Pro Gly Val Lys Pro Phe Thr Arg Gly Pro Tyr
                85                  90                  95

Pro Thr Met Tyr Thr Phe Arg Pro Trp Thr Ile Arg Gln Tyr Ala Gly
            100                 105                 110

Phe Ser Thr Val Glu Glu Ser Asn Lys Phe Tyr Lys Asp Asn Ile Lys
        115                 120                 125

Ala Gly Gln Gln Gly Leu Ser Val Ala Phe Asp Leu Ala Thr His Arg
    130                 135                 140

Gly Tyr Asp Ser Asp Asn Pro Arg Val Arg Gly Asp Val Gly Met Ala
145                 150                 155                 160

Gly Val Ala Ile Asp Thr Val Glu Asp Thr Lys Ile Leu Phe Asp Gly
                165                 170                 175

Ile Pro Leu Glu Lys Met Ser Val Ser Met Thr Met Asn Gly Ala Val
            180                 185                 190

Ile Pro Val Leu Ala Asn Phe Ile Val Thr Gly Glu Glu Gln Gly Val
        195                 200                 205

Pro Lys Glu Lys Leu Thr Gly Thr Ile Gln Asn Asp Ile Leu Lys Glu
    210                 215                 220

Phe Met Val Arg Asn Thr Tyr Ile Phe Pro Pro Glu Pro Ser Met Lys
225                 230                 235                 240

Ile Ile Ala Asp Ile Phe Glu Tyr Thr Ala Lys His Met Pro Lys Phe
                245                 250                 255

Asn Ser Ile Ser Ile Ser Gly Tyr His Met Gln Glu Ala Gly Ala Asp
            260                 265                 270

Ala Ile Leu Glu Leu Ala Tyr Thr Leu Ala Asp Gly Leu Glu Tyr Ser
        275                 280                 285

Arg Thr Gly Leu Gln Ala Gly Leu Thr Ile Asp Glu Phe Ala Pro Arg
    290                 295                 300

Leu Ser Phe Phe Trp Gly Ile Gly Met Asn Phe Tyr Met Glu Ile Ala
305                 310                 315                 320

Lys Met Arg Ala Gly Arg Arg Leu Trp Ala His Leu Ile Glu Lys Met
                325                 330                 335
```

-continued

```
Phe Gln Pro Lys Asn Ser Lys Ser Leu Leu Leu Arg Ala His Cys Gln
            340                 345                 350

Thr Ser Gly Trp Ser Leu Thr Glu Gln Asp Pro Tyr Asn Asn Ile Val
        355                 360                 365

Arg Thr Ala Ile Glu Ala Met Ala Ala Val Phe Gly Gly Thr Gln Ser
    370                 375                 380

Leu His Thr Asn Ser Phe Asp Glu Ala Leu Gly Leu Pro Thr Val Lys
385                 390                 395                 400

Ser Ala Arg Ile Ala Arg Asn Thr Gln Ile Ile Ile Gln Glu Glu Ser
                405                 410                 415

Gly Ile Pro Lys Val Ala Asp Pro Trp Gly Gly Ser Tyr Met Met Glu
            420                 425                 430

Cys Leu Thr Asn Asp Val Tyr Asp Ala Ala Leu Lys Leu Ile Asn Glu
        435                 440                 445

Ile Glu Glu Met Gly Gly Met Ala Lys Ala Val Ala Glu Gly Ile Pro
    450                 455                 460

Lys Leu Arg Ile Glu Glu Cys Ala Ala Arg Arg Gln Ala Arg Ile Asp
465                 470                 475                 480

Ser Gly Ser Glu Val Ile Val Gly Val Asn Lys Tyr Gln Leu Glu Lys
                485                 490                 495

Glu Asp Ala Val Glu Val Leu Ala Ile Asp Asn Thr Ser Val Arg Asn
            500                 505                 510

Arg Gln Ile Glu Lys Leu Lys Lys Ile Lys Ser Ser Arg Asp Gln Ala
        515                 520                 525

Leu Ala Glu Arg Cys Leu Ala Ala Leu Thr Glu Cys Ala Ala Ser Gly
    530                 535                 540

Asp Gly Asn Ile Leu Ala Leu Ala Val Asp Ala Ser Arg Ala Arg Cys
545                 550                 555                 560

Thr Val Gly Glu Ile Thr Asp Ala Leu Lys Lys Val Phe Gly Glu His
                565                 570                 575

Lys Ala Asn Asp Arg Met Val Ser Gly Ala Tyr Arg Gln Glu Phe Gly
            580                 585                 590

Glu Ser Lys Glu Ile Thr Ser Ala Ile Lys Arg Val His Lys Phe Met
        595                 600                 605

Glu Arg Glu Gly Arg Arg Pro Arg Leu Leu Val Ala Lys Met Gly Gln
    610                 615                 620

Asp Gly His Asp Arg Gly Ala Lys Val Ile Ala Thr Gly Phe Ala Asp
625                 630                 635                 640

Leu Gly Phe Asp Val Asp Ile Gly Pro Leu Phe Gln Thr Pro Arg Glu
                645                 650                 655

Val Ala Gln Gln Ala Val Asp Ala Asp Val His Ala Val Gly Ile Ser
            660                 665                 670

Thr Leu Ala Ala Gly His Lys Thr Leu Val Pro Glu Leu Ile Lys Glu
        675                 680                 685

Leu Asn Ser Leu Gly Arg Pro Asp Ile Leu Val Met Cys Gly Gly Val
    690                 695                 700

Ile Pro Pro Gln Asp Tyr Glu Phe Leu Phe Glu Val Gly Val Ser Asn
705                 710                 715                 720

Val Phe Gly Pro Gly Thr Arg Ile Pro Lys Ala Ala Val Gln Val Leu
                725                 730                 735

Asp Asp Ile Glu Lys Cys Leu Glu Lys Lys Gln Gln Ser Val
            740                 745                 750
```

```
<210> SEQ ID NO 18
<211> LENGTH: 749
<212> TYPE: PRT
<213> ORGANISM: Artificial Sequence
<220> FEATURE:
<223> OTHER INFORMATION: Synthetic Nucleic Acid

<400> SEQUENCE: 18

Leu Arg Ala Lys Asn Gln Leu Phe Leu Leu Ser Pro His Tyr Leu Arg
1               5                   10                  15

Gln Val Lys Glu Ser Ser Gly Ser Arg Leu Ile Gln Gln Arg Leu Leu
            20                  25                  30

His Gln Gln Gln Pro Leu His Pro Glu Trp Ala Ala Leu Ala Lys Lys
        35                  40                  45

Gln Leu Lys Gly Lys Asn Pro Glu Asp Leu Ile Trp His Thr Pro Glu
    50                  55                  60

Gly Ile Ser Ile Lys Pro Leu Tyr Ser Lys Arg Asp Thr Met Asp Leu
65                  70                  75                  80

Pro Glu Glu Leu Pro Gly Val Lys Pro Phe Thr Arg Gly Pro Tyr Pro
                85                  90                  95

Thr Met Tyr Thr Phe Arg Pro Trp Thr Ile Arg Gln Tyr Ala Gly Phe
            100                 105                 110

Ser Thr Val Glu Glu Ser Asn Lys Phe Tyr Lys Asp Asn Ile Lys Ala
        115                 120                 125

Gly Gln Gln Gly Leu Ser Val Ala Phe Asp Leu Ala Thr His Arg Gly
    130                 135                 140

Tyr Asp Ser Asp Asn Pro Arg Val Arg Gly Asp Val Gly Met Ala Gly
145                 150                 155                 160

Val Ala Ile Asp Thr Val Glu Asp Thr Lys Ile Leu Phe Asp Gly Ile
                165                 170                 175

Pro Leu Glu Lys Met Ser Val Ser Met Thr Met Asn Gly Ala Val Ile
            180                 185                 190

Pro Val Leu Ala Asn Phe Ile Val Thr Gly Glu Glu Gln Gly Val Pro
        195                 200                 205

Lys Glu Lys Leu Thr Gly Thr Ile Gln Asn Asp Ile Leu Lys Glu Phe
    210                 215                 220

Met Val Arg Asn Thr Tyr Ile Phe Pro Pro Glu Pro Ser Met Lys Ile
225                 230                 235                 240

Ile Ala Asp Ile Phe Glu Tyr Thr Ala Lys His Met Pro Lys Phe Asn
                245                 250                 255

Ser Ile Ser Ile Ser Gly Tyr His Met Gln Glu Ala Gly Ala Asp Ala
            260                 265                 270

Ile Leu Glu Leu Ala Tyr Thr Leu Ala Asp Gly Leu Glu Tyr Ser Arg
        275                 280                 285

Thr Gly Leu Gln Ala Gly Leu Thr Ile Asp Glu Phe Ala Pro Arg Leu
    290                 295                 300

Ser Phe Phe Trp Gly Ile Gly Met Asn Phe Tyr Met Glu Ile Ala Lys
305                 310                 315                 320

Met Arg Ala Gly Arg Arg Leu Trp Ala His Leu Ile Glu Lys Met Phe
                325                 330                 335

Gln Pro Lys Asn Ser Lys Ser Leu Leu Leu Arg Ala His Cys Gln Thr
            340                 345                 350

Ser Gly Trp Ser Leu Thr Glu Gln Asp Pro Tyr Asn Asn Ile Val Arg
        355                 360                 365

Thr Ala Ile Glu Ala Met Ala Ala Val Phe Gly Gly Thr Gln Ser Leu
```

```
    370                 375                 380

His Thr Asn Ser Phe Asp Glu Ala Leu Gly Leu Pro Thr Val Lys Ser
385                 390                 395                 400

Ala Arg Ile Ala Arg Asn Thr Gln Ile Ile Ile Gln Glu Glu Ser Gly
                405                 410                 415

Ile Pro Lys Val Ala Asp Pro Trp Gly Gly Ser Tyr Met Met Glu Cys
            420                 425                 430

Leu Thr Asn Asp Val Tyr Asp Ala Ala Leu Lys Leu Ile Asn Glu Ile
        435                 440                 445

Glu Glu Met Gly Gly Met Ala Lys Ala Val Ala Glu Gly Ile Pro Lys
    450                 455                 460

Leu Arg Ile Glu Glu Cys Ala Ala Arg Arg Gln Ala Arg Ile Asp Ser
465                 470                 475                 480

Gly Ser Glu Val Ile Val Gly Val Asn Lys Tyr Gln Leu Glu Lys Glu
                485                 490                 495

Asp Ala Val Glu Val Leu Ala Ile Asp Asn Thr Ser Val Arg Asn Arg
            500                 505                 510

Gln Ile Glu Lys Leu Lys Lys Ile Lys Ser Ser Arg Asp Gln Ala Leu
        515                 520                 525

Ala Glu Arg Cys Leu Ala Ala Leu Thr Glu Cys Ala Ala Ser Gly Asp
    530                 535                 540

Gly Asn Ile Leu Ala Leu Ala Val Asp Ala Ser Arg Ala Arg Cys Thr
545                 550                 555                 560

Val Gly Glu Ile Thr Asp Ala Leu Lys Lys Val Phe Gly Glu His Lys
                565                 570                 575

Ala Asn Asp Arg Met Val Ser Gly Ala Tyr Arg Gln Glu Phe Gly Glu
            580                 585                 590

Ser Lys Glu Ile Thr Ser Ala Ile Lys Arg Val His Lys Phe Met Glu
        595                 600                 605

Arg Glu Gly Arg Arg Pro Arg Leu Leu Val Ala Lys Met Gly Gln Asp
    610                 615                 620

Gly His Asp Arg Gly Ala Lys Val Ile Ala Thr Gly Phe Ala Asp Leu
625                 630                 635                 640

Gly Phe Asp Val Asp Ile Gly Pro Leu Phe Gln Thr Pro Arg Glu Val
                645                 650                 655

Ala Gln Gln Ala Val Asp Ala Asp Val His Ala Val Gly Ile Ser Thr
            660                 665                 670

Leu Ala Ala Gly His Lys Thr Leu Val Pro Glu Leu Ile Lys Glu Leu
        675                 680                 685

Asn Ser Leu Gly Arg Pro Asp Ile Leu Val Met Cys Gly Gly Val Ile
    690                 695                 700

Pro Pro Gln Asp Tyr Glu Phe Leu Phe Glu Val Gly Val Ser Asn Val
705                 710                 715                 720

Phe Gly Pro Gly Thr Arg Ile Pro Lys Ala Ala Val Gln Val Leu Asp
                725                 730                 735

Asp Ile Glu Lys Cys Leu Glu Lys Lys Gln Gln Ser Val
            740                 745
```

<210> SEQ ID NO 19
<211> LENGTH: 2250
<212> TYPE: DNA
<213> ORGANISM: Artificial Sequence
<220> FEATURE:
<223> OTHER INFORMATION: Synthetic Nucleic Acid

<400> SEQUENCE: 19

```
atgctgcggg ccaagaatca actgttcctg ctgtcccctc actacctgcg gcaagtgaaa     60
gagagcagcg gcagcagact gatccagcag agactgctgc atcagcagca gccactgcac    120
cctgaatggg ccgctctggc taagaagcag ctcaagggca agaaccccga ggacctgatc    180
tggcacacac cagagggcat cagcatcaag cccctgtact ccaagcggga cacaatggat    240
ctgcccgagg aactgcctgg cgtgaagcct tttacaagag gcccctatcc taccatgtat    300
accttcagac cctggaccat ccggcagtac gccggctttt ctaccgtgga agagagcaac    360
aagttctaca aggacaacat caaggccggc cagcagggac tgagcgtggc atttgatctg    420
gctacccaca ggggctacga cagcgacaac cctagagtgc ggggagatgt tggaatggcc    480
ggcgtggcaa tcgacacagt ggaagatacc aagatcctgt tcgacggcat ccctctggaa    540
aagatgagcg tgtccatgac catgaacggc gctgtgatcc ccgtgctggc taactttatt    600
gtgaccggcg aggaacaggg cgtgcccaaa gaaaagctga ccggcaccat ccagaacgac    660
atcctgaaag agttcatggt tcgaaacacc tacatcttcc cacctgagcc gagcatgaag    720
atcattgccg acatcttcga gtacaccgcc aagcacatgc ccaagttcaa cagcatctcc    780
atcagcggct accacatgca agaggctggc gccgatgcca tcctggaact ggcttataca    840
ctggccgacg gcctggaata ctccagaaca ggactgcaag ccggcctgac catcgatgag    900
tttgccccta gactgagctt cttctggggc atcggcatga acttctacat ggaaatcgcc    960
aagatgagag ccggcagacg gctgtgggct cacctgatcg agaagatgtt ccagcctaag   1020
aacagcaaga gcctgctcct gagagcccac tgtcagacaa gtggctggtc cctgactgag   1080
caggacccct acaacaacat cgtgcgcaca gccatcgaag ctatggccgc cgtgtttggc   1140
ggaacacaga gcctgcacac caacagcttt gacgaggctc tgggcctgcc taccgtgaag   1200
tctgccagaa tcgcccggaa cacccagatc atcatccaag aggaaagcgg catccccaag   1260
gtggcagatc cttggggcgg cagctacatg atggaatgcc tgaccaacga cgtgtacgac   1320
gccgctctga agctgatcaa cgagatcgaa gagatgggcg gcatggctaa ggctgtggcc   1380
gagggaatcc ccaagctgag aatcgaggaa tgcgccgcca gacggcaggc cagaattgat   1440
agcggaagcg aagtgatcgt gggcgtgaac aagtaccagc tcgaaaaaga ggacgccgtc   1500
gaggtcctgg ctatcgacaa taccagcgtg cggaaccggc agattgagaa gctgaagaag   1560
atcaagagca gccgcgatca ggccctggcc gaaagatgtc ttgctgccct gacagagtgt   1620
gccgccagcg gcgacggaaa tattctggct ctggccgtgg atgccagccg ggctagatgt   1680
accgtgggcg agattacaga cgccctgaag aaggtgttcg gcgagcacaa ggccaacgac   1740
agaatggtgt ctggcgccta cagacaagag tttggcgaga gcaaagagat caccagcgcc   1800
atcaagcggg tccacaagtt catggaaaga gaaggcaggc ggcccagact gctggtggct   1860
aagatgggac aagacggcca tgacagaggc gccaaagtga tcgccacagg ctttgccgat   1920
ctgggcttcg acgtggacat cggccctctg tttcagaccc ctagagaggt ggcacagcag   1980
gccgttgatg ccgatgttca cgctgtgggc atctctacac tggctgccgg acacaagaca   2040
ctggtgcccg aactgatcaa agagctgaac agcctgggca gacccgacat ccttgtgatg   2100
tgtggcggag tgatcccacc gcaggactac gagttcctgt ttgaagtggg cgtgtccaac   2160
gtgttcggcc ctggcacaag aatccctaaa gccgccgtgc aggttctgga cgacatcgag   2220
aagtgcctgg aaaaaaagca gcagagcgtg                                    2250
```

<210> SEQ ID NO 20
<211> LENGTH: 2247
<212> TYPE: DNA
<213> ORGANISM: Artificial Sequence
<220> FEATURE:
<223> OTHER INFORMATION: Synthetic Nucleic Acid

<400> SEQUENCE: 20
ctgcgggcca agaatcaact gttcctgctg tcccctcact acctgcggca agtgaaagag 60
agcagcggca gcagactgat ccagcagaga ctgctgcatc agcagcagcc actgcaccct 120
gaatgggccg ctctggctaa gaagcagctc aagggcaaga accccgagga cctgatctgg 180
cacacaccag agggcatcag catcaagccc ctgtactcca agcgggacac aatggatctg 240
cccgaggaac tgcctggcgt gaagcctttt acaagaggcc cctatcctac catgtatacc 300
ttcagaccct ggaccatccg gcagtacgcc ggcttttcta ccgtggaaga gagcaacaag 360
ttctacaagg acaacatcaa ggccggccag cagggactga gcgtggcatt tgatctggct 420
acccacaggg gctacgacag cgacaaccct agagtgcggg gagatgttgg aatggccggc 480
gtggcaatcg acacagtgga agataccaag atcctgttcg acggcatccc tctggaaaag 540
atgagcgtgt ccatgaccat gaacggcgct gtgatccccg tgctggctaa ctttattgtg 600
accggcgagg aacagggcgt gcccaaagaa aagctgaccg gcaccatcca gaacgacatc 660
ctgaaagagt tcatggttcg aaacacctac atcttcccac ctgagccgag catgaagatc 720
attgccgaca tcttcgagta caccgccaag cacatgccca agttcaacag catctccatc 780
agcggctacc acatgcaaga ggctggcgcc gatgccatcc tggaactggc ttatacactg 840
gccgacggcc tggaatactc cagaacagga ctgcaagccg gcctgaccat cgatgagttt 900
gcccctagac tgagcttctt ctggggcatc ggcatgaact tctacatgga aatcgccaag 960
atgagagccg gcagacggct gtgggctcac ctgatcgaga agatgttcca gcctaagaac 1020
agcaagagcc tgctcctgag agcccactgt cagacaagtg gctggtccct gactgagcag 1080
gacccctaca acaacatcgt gcgcacagcc atcgaagcta tggccgccgt gtttggcgga 1140
acacagagcc tgcacaccaa cagctttgac gaggctctgg gcctgcctac cgtgaagtct 1200
gccagaatcg cccggaacac ccagatcatc atccaagagg aaagcggcat ccccaaggtg 1260
gcagatcctt ggggcggcag ctacatgatg gaatgcctga ccaacgacgt gtacgacgcc 1320
gctctgaagc tgatcaacga gatcgaagag atgggcggca tggctaaggc tgtggccgag 1380
ggaatcccca agctgagaat cgaggaatgc gccgccagac ggcaggccag aattgatagc 1440
ggaagcgaag tgatcgtggg cgtgaacaag taccagctcg aaaaagagga cgccgtcgag 1500
gtcctggcta tcgacaatac cagcgtgcgg aaccggcaga ttgagaagct gaagaagatc 1560
aagagcagcc gcgatcaggc cctggccgaa agatgtcttg ctgccctgac agagtgtgcc 1620
gccagcggcg acggaaatat tctggctctg gccgtggatg ccagccgggc tagatgtacc 1680
gtgggcgaga ttacagacgc cctgaagaag gtgttcggcg agcacaaggc caacgacaga 1740
atggtgtctg gcgcctacag acaagagttt ggcgagagca aagagatcac cagcgccatc 1800
aagcgggtcc acaagttcat ggaaagagaa ggcaggcggc ccagactgct ggtggctaag 1860
atgggacaag acggccatga cagaggcgcc aaagtgatcg ccacaggctt tgccgatctg 1920
ggcttcgacg tggacatcgg ccctctgttt cagaccccta gagaggtggc acagcaggcc 1980
gttgatgccg atgttcacgc tgtgggcatc tctacactgg ctgccggaca caagacactg 2040
gtgcccgaac tgatcaaaga gctgaacagc ctgggcagac ccgacatcct tgtgatgtgt 2100
ggcggagtga tcccaccgca ggactacgag ttcctgtttg aagtgggcgt gtccaacgtg 2160
ttcggccctg gcacaagaat ccctaaagcc gccgtgcagg ttctggacga catcgagaag 2220
tgcctggaaa aaaagcagca gagcgtg 2247

<210> SEQ ID NO 21
<211> LENGTH: 354
<212> TYPE: PRT
<213> ORGANISM: Artificial Sequence
<220> FEATURE:
<223> OTHER INFORMATION: Synthetic Nucleic Acid

<400> SEQUENCE: 21

Met Leu Phe Asn Leu Arg Ile Leu Leu Asn Asn Ala Ala Phe Arg Asn
1 5 10 15

Gly His Asn Phe Met Val Arg Asn Phe Arg Cys Gly Gln Pro Leu Gln
20 25 30

Asn Lys Val Gln Leu Lys Gly Arg Asp Leu Leu Thr Leu Lys Asn Phe
35 40 45

Thr Gly Glu Glu Ile Lys Tyr Met Leu Trp Leu Ser Ala Asp Leu Lys
50 55 60

Phe Arg Ile Lys Gln Lys Gly Glu Tyr Leu Pro Leu Leu Gln Gly Lys
65 70 75 80

Ser Leu Gly Met Ile Phe Glu Lys Arg Ser Thr Arg Thr Arg Leu Ser
85 90 95

Thr Glu Thr Gly Phe Ala Leu Leu Gly Gly His Pro Cys Phe Leu Thr
100 105 110

Thr Gln Asp Ile His Leu Gly Val Asn Glu Ser Leu Thr Asp Thr Ala
115 120 125

Arg Val Leu Ser Ser Met Ala Asp Ala Val Leu Ala Arg Val Tyr Lys
130 135 140

Gln Ser Asp Leu Asp Thr Leu Ala Lys Glu Ala Ser Ile Pro Ile Ile
145 150 155 160

Asn Gly Leu Ser Asp Leu Tyr His Pro Ile Gln Ile Leu Ala Asp Tyr
165 170 175

Leu Thr Leu Gln Glu His Tyr Ser Ser Leu Lys Gly Leu Thr Leu Ser
180 185 190

Trp Ile Gly Asp Gly Asn Asn Ile Leu His Ser Ile Met Met Ser Ala
195 200 205

Ala Lys Phe Gly Met His Leu Gln Ala Ala Thr Pro Lys Gly Tyr Glu
210 215 220

Pro Asp Ala Ser Val Thr Lys Leu Ala Glu Gln Tyr Ala Lys Glu Asn
225 230 235 240

Gly Thr Lys Leu Leu Leu Thr Asn Asp Pro Leu Glu Ala Ala His Gly
245 250 255

Gly Asn Val Leu Ile Thr Asp Thr Trp Ile Ser Met Gly Gln Glu Glu
260 265 270

Glu Lys Lys Lys Arg Leu Gln Ala Phe Gln Gly Tyr Gln Val Thr Met
275 280 285

Lys Thr Ala Lys Val Ala Ala Ser Asp Trp Thr Phe Leu His Cys Leu
290 295 300

Pro Arg Lys Pro Glu Glu Val Asp Asp Glu Val Phe Tyr Ser Pro Arg
305 310 315 320

Ser Leu Val Phe Pro Glu Ala Glu Asn Arg Lys Trp Thr Ile Met Ala
325 330 335

Val Met Val Ser Leu Leu Thr Asp Tyr Ser Pro Gln Leu Gln Lys Pro
340 345 350

Lys Phe

<210> SEQ ID NO 22
<211> LENGTH: 1062
<212> TYPE: DNA
<213> ORGANISM: Artificial Sequence
<220> FEATURE:
<223> OTHER INFORMATION: Synthetic Nucleic Acid

<400> SEQUENCE: 22
atgctgttca acctgcgcat cctgctgaac aacgccgcct tcagaaacgg ccacaacttc 60
atggttcgaa acttcagatg cggccagcct ctccagaaca aggtgcagct gaaaggcagg 120
gacctgctga ccctgaagaa cttcaccggc gaagagatca agtacatgct gtggctgtcc 180
gccgacctga agttcagaat caagcagaag ggcgagtacc tgcctctgct ccagggaaag 240
tctctgggca tgatcttcga gaagcggagc accagaacca gactgagcac cgagacaggc 300
tttgccctgc tcggaggaca cccctgcttt ctgacaaccc aggacatcca cctgggcgtg 360
aacgagagcc tgaccgatac agccagagtg ctgtcctcta tggccgatgc cgtgctggct 420
agagtgtata agcagagcga cctggacacc ctggctaaag aggccagcat tcccatcatc 480
aacggcctgt ccgacctgta tcaccccatc cagatcctgg ccgactacct gacactgcaa 540
gagcactaca gcagcctgaa gggactgacc ctgtcttgga tcggcgacgg caacaacatc 600
ctgcacagca ttatgatgag cgccgccaag ttcggaatgc acctccaggc cgctacaccc 660
aagggctatg aacctgatgc cagcgtgaca aagctggccg agcagtacgc caaagagaac 720
ggcacaaagc tgctgctgac caacgatccc ctggaagctg ctcacggcgg caatgtgctg 780
atcaccgata cctggatcag catgggccaa gaggaagaga agaagaagcg gctgcaagcc 840
ttccagggct accaagtgac catgaagaca gccaaggtgg ccgccagcga ttggaccttt 900
ctgcactgcc tgcctcggaa gcctgaagag gtggacgacg aggtgttcta cagccctaga 960
agcctggtgt tccccgaggc cgagaacaga aagtggacca tcatggctgt gatggtgtct 1020
ctgctgaccg actactcccc tcagctccag aagcctaagt tc 1062

<210> SEQ ID NO 23
<211> LENGTH: 1062
<212> TYPE: DNA
<213> ORGANISM: Artificial Sequence
<220> FEATURE:
<223> OTHER INFORMATION: Synthetic Nucleic Acid

<400> SEQUENCE: 23
atgctgttca acctgcgaat cctgctgaac aatgccgctt ttcggaacgg gcacaatttc 60
atggtgagga actttcgctg cggacagccc ctccagaaca aggtccagct gaagggcagg 120
gacctgctga ccctgaaaaa tttcacaggg gaggaaatca agtacatgct gtggctgtca 180
gccgatctga agttccggat caagcagaag ggcgaatatc tgcctctgct ccagggcaaa 240
agcctgggga tgatcttcga aaagcgcagt actcggacca gactgtcaac agagactgga 300
ttcgcactgc tgggaggaca cccatgtttt ctgaccacac aggacattca tctgggagtg 360
aacgagtccc tgaccgacac agcacgcgtc ctgagctcca tggctgatgc agtgctggct 420
cgagtctaca aacagtctga cctggatacc ctggccaagg aagcttctat cccaatcatt 480
aatggcctga gtgacctgta tcaccccatc cagattctgg ccgattacct gaccctccag 540

```
gagcattatt ctagtctgaa agggctgaca ctgagctgga ttggggacgg aaacaatatc    600

ctgcactcca ttatgatgag cgccgccaag tttggaatgc acctccaggc tgcaacccca    660

aaaggctacg aacccgatgc ctccgtgaca aagctggcag aacagtatgc caaagagaac    720

ggcactaagc tgctgctcac caatgaccct ctggaggccg ctcacggagg caacgtgctg    780

atcactgata cctggattag tatgggacag gaggaagaga agaagaagcg gctccaggcc    840

ttccagggct accaggtgac aatgaaaact gctaaggtcg cagccagcga ctggaccttt    900

ctgcattgcc tgcccagaaa gcctgaagag gtggacgatg aggtcttcta ctcacccaga    960

agcctggtgt ttcctgaagc tgagaatagg aagtggacaa tcatggcagt gatggtcagc   1020

ctgctgactg attattcccc tcagctccag aaaccaaagt tc                      1062
```

```
<210> SEQ ID NO 24
<211> LENGTH: 395
<212> TYPE: PRT
<213> ORGANISM: Artificial Sequence
<220> FEATURE:
<223> OTHER INFORMATION: Synthetic Nucleic Acid

<400> SEQUENCE: 24

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu Gly Gly Gly Gly
            100                 105                 110

Ser Gly Phe Gly Asp Val Gly Ala Leu Glu Ser Leu Arg Gly Asn Ala
        115                 120                 125

Asp Leu Ala Tyr Ile Leu Ser Met Glu Pro Cys Gly His Cys Leu Ile
    130                 135                 140

Ile Asn Asn Val Asn Phe Cys Arg Glu Ser Gly Leu Arg Thr Arg Thr
145                 150                 155                 160

Gly Ser Asn Ile Asp Cys Glu Lys Leu Arg Arg Arg Phe Ser Ser Leu
                165                 170                 175

His Phe Met Val Glu Val Lys Gly Asp Leu Thr Ala Lys Lys Met Val
            180                 185                 190

Leu Ala Leu Leu Glu Leu Ala Gln Gln Asp His Gly Ala Leu Asp Cys
        195                 200                 205

Cys Val Val Val Ile Leu Ser His Gly Cys Gln Ala Ser His Leu Gln
    210                 215                 220

Phe Pro Gly Ala Val Tyr Gly Thr Asp Gly Cys Pro Val Ser Val Glu
225                 230                 235                 240

Lys Ile Val Asn Ile Phe Asn Gly Thr Ser Cys Pro Ser Leu Gly Gly
                245                 250                 255

Lys Pro Lys Leu Phe Phe Ile Gln Ala Cys Gly Gly Glu Gln Lys Asp
            260                 265                 270
```

```
His Gly Phe Glu Val Ala Ser Thr Ser Pro Glu Asp Glu Ser Pro Gly
        275                 280                 285

Ser Asn Pro Glu Pro Asp Ala Thr Pro Phe Gln Glu Gly Leu Arg Thr
    290                 295                 300

Phe Asp Gln Leu Asp Ala Ile Ser Ser Leu Pro Thr Pro Ser Asp Ile
305                 310                 315                 320

Phe Val Ser Tyr Ser Thr Phe Pro Gly Phe Val Ser Trp Arg Asp Pro
                325                 330                 335

Lys Ser Gly Ser Trp Tyr Val Glu Thr Leu Asp Asp Ile Phe Glu Gln
            340                 345                 350

Trp Ala His Ser Glu Asp Leu Gln Ser Leu Leu Leu Arg Val Ala Asn
        355                 360                 365

Ala Val Ser Val Lys Gly Ile Tyr Lys Gln Met Pro Gly Cys Phe Asn
    370                 375                 380

Phe Leu Arg Lys Lys Leu Phe Phe Lys Thr Ser
385                 390                 395
```

<210> SEQ ID NO 25
<211> LENGTH: 1185
<212> TYPE: DNA
<213> ORGANISM: Artificial Sequence
<220> FEATURE:
<223> OTHER INFORMATION: Synthetic Nucleic Acid

<400> SEQUENCE: 25

```
atgggggtcc aggtggaaac aatctctccg gggggatgggc ggacattccc taaaaggggc     60

cagacctgcg tggtgcatta caccggcatg ctggaagatg gcaagaaggt ggacagcagc    120

cgggacagaa acaagccctt caagttcatg ctgggcaagc aagaagtgat cagaggctgg    180

gaagagggcg tcgcccagat gtctgttgga cagagagcca agctgacaat cagccccgat    240

tacgcctatg gcgccacagg acaccctggc atcattcctc cacatgccac actggtgttc    300

gacgtggaac tgctgaagct ggaaggcggc ggaggatctg gctttggaga tgtgggagcc    360

ctggaaagcc tgagaggcaa tgccgatctg gcctacatcc tgagcatgga accttgcggc    420

cactgcctga ttatcaacaa cgtgaacttc tgtagagaga gcggcctgcg gaccagaacc    480

ggcagcaata tcgattgcga gaagctgcgg cggagattca gcagcctgca cttcatggtg    540

gaagtgaagg gcgacctgac cgccaagaaa atggtgctgg ctctgctgga actggcccag    600

caagatcatg gcgccctgga ttgctgtgtg gtcgtgatcc tgtctcacgg ctgtcaggcc    660

agccaccttc aattccctgg cgccgtgtat ggcacagatg gctgtcctgt gtccgtggaa    720

aagatcgtga acatcttcaa cggcaccagc tgtcctagcc tcggcggaaa gcccaagctg    780

ttcttcatcc aagcctgtgg cggcgagcag aaggatcacg gatttgaggt ggccagcaca    840

agccccgagg atgagtctcc tggaagcaac cctgagcctg acgccacacc tttccaagag    900

ggcctgagaa ccttcgacca gctggacgct atcagctccc tgcctacacc tagcgacatc    960

ttcgtgtcct acagcacatt ccccggcttt gtgtcttggc gggaccctaa gtctggctct   1020

tggtacgtgg aaaccctgga cgacatcttt gagcagtggg ctcacagcga ggacctccag   1080

tctctgctgc tgagagtggc caatgccgtg tccgtgaagg gcatctacaa gcagatgcct   1140

ggctgcttca acttcctgcg gaagaagctg tttttcaaga ccagc                   1185
```

<210> SEQ ID NO 26
<211> LENGTH: 139
<212> TYPE: DNA
<213> ORGANISM: Artificial Sequence
<220> FEATURE:
<223> OTHER INFORMATION: Synthetic Nucleic Acid

<400> SEQUENCE: 26
attccgataa cttgtttatt gcagcttata atggttacaa ataaagcaat agcatcacaa 60
atttcacaaa taaagcattt ttttcactgc attctagttg tggtttgtcc aaactcatca 120
atgtatctta tcatgtctg 139

<210> SEQ ID NO 27
<211> LENGTH: 192
<212> TYPE: DNA
<213> ORGANISM: Artificial Sequence
<220> FEATURE:
<223> OTHER INFORMATION: Synthetic Nucleic Acid

<400> SEQUENCE: 27
cagacatgat aagatacatt gatgagtttg gacaaaccac aactagaatg cagtgaaaaa 60
aatgctttat ttgtgaaatt tgtgatgcta ttgctttatt tgtaaccatt ataagctgca 120
ataaacaagt taacaacaac aattgcattc attttatgtt tcaggttcag ggggaggtgt 180
gggaggtttt tt 192

<210> SEQ ID NO 28
<211> LENGTH: 18
<212> TYPE: PRT
<213> ORGANISM: Artificial Sequence
<220> FEATURE:
<223> OTHER INFORMATION: Synthetic Nucleic Acid

<400> SEQUENCE: 28

Glu Gly Arg Gly Ser Leu Leu Thr Cys Gly Asp Val Glu Glu Asn Pro
1 5 10 15

Gly Pro

<210> SEQ ID NO 29
<211> LENGTH: 21
<212> TYPE: PRT
<213> ORGANISM: Artificial Sequence
<220> FEATURE:
<223> OTHER INFORMATION: Synthetic Nucleic Acid

<400> SEQUENCE: 29

Gly Ser Gly Glu Gly Arg Gly Ser Leu Leu Thr Cys Gly Asp Val Glu
1 5 10 15

Glu Asn Pro Gly Pro
20

<210> SEQ ID NO 30
<211> LENGTH: 63
<212> TYPE: DNA
<213> ORGANISM: Artificial Sequence
<220> FEATURE:
<223> OTHER INFORMATION: Synthetic Nucleic Acid

<400> SEQUENCE: 30
ggatctggag agggaagggg aagcctgctg acctgtggag acgtggagga aaacccagga 60
cca 63

<210> SEQ ID NO 31
<211> LENGTH: 63
<212> TYPE: DNA
<213> ORGANISM: Artificial Sequence
<220> FEATURE:
<223> OTHER INFORMATION: Synthetic Nucleic Acid

<400> SEQUENCE: 31
ggatccggcg aaggcagagg ctcactgctt acttgtggcg acgtggagga gaaccccgga 60
cct 63

<210> SEQ ID NO 32
<211> LENGTH: 63
<212> TYPE: DNA
<213> ORGANISM: Artificial Sequence
<220> FEATURE:
<223> OTHER INFORMATION: Synthetic Nucleic Acid

<400> SEQUENCE: 32
ggctccggag aaggacgggg aagcctgctt acatgcggag atgtggagga gaatcctggt 60
ccc 63

<210> SEQ ID NO 33
<211> LENGTH: 20
<212> TYPE: PRT
<213> ORGANISM: Artificial Sequence
<220> FEATURE:
<223> OTHER INFORMATION: Synthetic Nucleic Acid

<400> SEQUENCE: 33

Gln Cys Thr Asn Tyr Ala Leu Leu Lys Leu Ala Gly Asp Val Glu Ser
1 5 10 15

Asn Pro Gly Pro
20

<210> SEQ ID NO 34
<211> LENGTH: 23
<212> TYPE: PRT
<213> ORGANISM: Artificial Sequence
<220> FEATURE:
<223> OTHER INFORMATION: Synthetic Nucleic Acid

<400> SEQUENCE: 34

Gly Ser Gly Gln Cys Thr Asn Tyr Ala Leu Leu Lys Leu Ala Gly Asp
1 5 10 15

Val Glu Ser Asn Pro Gly Pro
20

<210> SEQ ID NO 35
<211> LENGTH: 22
<212> TYPE: PRT
<213> ORGANISM: Artificial Sequence
<220> FEATURE:
<223> OTHER INFORMATION: Synthetic Nucleic Acid

<400> SEQUENCE: 35

Val Lys Gln Thr Leu Asn Phe Asp Leu Leu Lys Leu Ala Gly Asp Val
1 5 10 15

Glu Ser Asn Pro Gly Pro
20

<210> SEQ ID NO 36
<211> LENGTH: 25
<212> TYPE: PRT
<213> ORGANISM: Artificial Sequence
<220> FEATURE:
<223> OTHER INFORMATION: Synthetic Nucleic Acid

<400> SEQUENCE: 36

Gly Ser Gly Val Lys Gln Thr Leu Asn Phe Asp Leu Leu Lys Leu Ala
1 5 10 15

Gly Asp Val Glu Ser Asn Pro Gly Pro
20 25

<210> SEQ ID NO 37
<211> LENGTH: 19
<212> TYPE: PRT
<213> ORGANISM: Artificial Sequence
<220> FEATURE:
<223> OTHER INFORMATION: Synthetic Nucleic Acid

<400> SEQUENCE: 37

Ala Thr Asn Phe Ser Leu Leu Lys Gln Ala Gly Asp Val Glu Glu Asn
1 5 10 15

Pro Gly Pro

<210> SEQ ID NO 38
<211> LENGTH: 22
<212> TYPE: PRT
<213> ORGANISM: Artificial Sequence
<220> FEATURE:
<223> OTHER INFORMATION: Synthetic Nucleic Acid

<400> SEQUENCE: 38

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 39
<211> LENGTH: 594
<212> TYPE: PRT
<213> ORGANISM: Artificial Sequence
<220> FEATURE:
<223> OTHER INFORMATION: Synthetic Nucleic Acid

<400> SEQUENCE: 39

Met Gly Ser Ser Leu Asp Asp Glu His Ile Leu Ser Ala Leu Leu Gln
1 5 10 15

Ser Asp Asp Glu Leu Val Gly Glu Asp Ser Asp Ser Glu Ile Ser Asp
20 25 30

His Val Ser Glu Asp Asp Val Gln Ser Asp Thr Glu Glu Ala Phe Ile
35 40 45

Asp Glu Val His Glu Val Gln Pro Thr Ser Ser Gly Ser Glu Ile Leu
50 55 60

Asp Glu Gln Asn Val Ile Glu Gln Pro Gly Ser Ser Leu Ala Ser Asn
65 70 75 80

Arg Ile Leu Thr Leu Pro Gln Arg Thr Ile Arg Gly Lys Asn Lys His
85 90 95

Cys Trp Ser Thr Ser Lys Ser Thr Arg Arg Ser Arg Val Ser Ala Leu
100 105 110

Asn Ile Val Arg Ser Gln Arg Gly Pro Thr Arg Met Cys Arg Asn Ile
115 120 125

Tyr Asp Pro Leu Leu Cys Phe Lys Leu Phe Phe Thr Asp Glu Ile Ile
130 135 140

Ser Glu Ile Val Lys Trp Thr Asn Ala Glu Ile Ser Leu Lys Arg Arg
145 150 155 160

```
Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Tyr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
    530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
```

580 585 590

Cys Phe

<210> SEQ ID NO 40
<211> LENGTH: 594
<212> TYPE: PRT
<213> ORGANISM: Artificial Sequence
<220> FEATURE:
<223> OTHER INFORMATION: Synthetic Nucleic Acid

<400> SEQUENCE: 40

Met Gly Ser Ser Leu Asp Asp Glu His Ile Leu Ser Ala Leu Leu Gln
1 5 10 15

Ser Asp Asp Glu Leu Val Gly Glu Asp Ser Asp Ser Glu Val Ser Asp
20 25 30

His Val Ser Glu Asp Asp Val Gln Ser Asp Thr Glu Glu Ala Phe Ile
35 40 45

Asp Glu Val His Glu Val Gln Pro Thr Ser Ser Gly Ser Glu Ile Leu
50 55 60

Asp Glu Gln Asn Val Ile Glu Gln Pro Gly Ser Ser Leu Ala Ser Asn
65 70 75 80

Arg Ile Leu Thr Leu Pro Gln Arg Thr Ile Arg Gly Lys Asn Lys His
85 90 95

Cys Trp Ser Thr Ser Lys Ser Thr Arg Arg Ser Arg Val Ser Ala Leu
100 105 110

Asn Ile Val Arg Ser Gln Arg Gly Pro Thr Arg Met Cys Arg Asn Ile
115 120 125

Tyr Asp Pro Leu Leu Cys Phe Lys Leu Phe Phe Thr Asp Glu Ile Ile
130 135 140

Ser Glu Ile Val Lys Trp Thr Asn Ala Glu Ile Ser Leu Lys Arg Arg
145 150 155 160

Glu Ser Met Thr Ser Ala Thr Phe Arg Asp Thr Asn Glu Asp Glu Ile
165 170 175

Tyr Ala Phe Phe Gly Ile Leu Val Met Thr Ala Val Arg Lys Asp Asn
180 185 190

His Met Ser Thr Asp Asp Leu Phe Asp Arg Ser Leu Ser Met Val Tyr
195 200 205

Val Ser Val Met Ser Arg Asp Arg Phe Asp Phe Leu Ile Arg Cys Leu
210 215 220

Arg Met Asp Asp Lys Ser Ile Arg Pro Thr Leu Arg Glu Asn Asp Val
225 230 235 240

Phe Thr Pro Val Arg Lys Ile Trp Asp Leu Phe Ile His Gln Cys Ile
245 250 255

Gln Asn Tyr Thr Pro Gly Ala His Leu Thr Ile Asp Glu Gln Leu Leu
260 265 270

Gly Phe Arg Gly Arg Cys Pro Phe Arg Val Tyr Ile Pro Asn Lys Pro
275 280 285

Ser Lys Tyr Gly Ile Lys Ile Leu Met Met Cys Asp Ser Gly Thr Lys
290 295 300

Tyr Met Ile Asn Gly Met Pro Tyr Leu Gly Arg Gly Thr Gln Thr Asn
305 310 315 320

Gly Val Pro Leu Gly Glu Tyr Tyr Val Lys Glu Leu Ser Lys Pro Val
325 330 335

His Gly Ser Cys Arg Asn Ile Thr Cys Asp Asn Trp Phe Thr Ser Ile
340 345 350

Pro Leu Ala Lys Asn Leu Leu Gln Glu Pro Tyr Lys Leu Thr Ile Val
355 360 365

Gly Thr Val Arg Ser Asn Lys Arg Glu Ile Pro Glu Val Leu Lys Asn
370 375 380

Ser Arg Ser Arg Pro Val Gly Thr Ser Met Phe Cys Phe Asp Gly Pro
385 390 395 400

Leu Thr Leu Val Ser Tyr Lys Pro Lys Pro Ala Lys Met Val Tyr Leu
405 410 415

Leu Ser Ser Cys Asp Glu Asp Ala Ser Ile Asn Glu Ser Thr Gly Lys
420 425 430

Pro Gln Met Val Met Tyr Tyr Asn Gln Thr Lys Gly Gly Val Asp Thr
435 440 445

Leu Asp Gln Met Cys Ser Val Met Thr Cys Ser Arg Lys Thr Asn Arg
450 455 460

Trp Pro Met Ala Leu Leu Tyr Gly Met Ile Asn Ile Ala Cys Ile Asn
465 470 475 480

Ser Phe Ile Ile Tyr Ser His Asn Val Ser Ser Lys Gly Glu Lys Val
485 490 495

Gln Ser Arg Lys Lys Phe Met Arg Asn Leu Tyr Met Ser Leu Thr Ser
500 505 510

Ser Phe Met Arg Lys Arg Leu Glu Ala Pro Thr Leu Lys Arg Tyr Leu
515 520 525

Arg Asp Asn Ile Ser Asn Ile Leu Pro Lys Glu Val Pro Gly Thr Ser
530 535 540

Asp Asp Ser Thr Glu Glu Pro Val Met Lys Lys Arg Thr Tyr Cys Thr
545 550 555 560

Tyr Cys Pro Ser Lys Ile Arg Arg Lys Ala Asn Ala Ser Cys Lys Lys
565 570 575

Cys Lys Lys Val Ile Cys Arg Glu His Asn Ile Asp Met Cys Gln Ser
580 585 590

Cys Phe

<210> SEQ ID NO 41
<211> LENGTH: 593
<212> TYPE: PRT
<213> ORGANISM: Artificial Sequence
<220> FEATURE:
<223> OTHER INFORMATION: Synthetic Nucleic Acid

<400> SEQUENCE: 41

Gly Ser Ser Leu Asp Asp Glu His Ile Leu Ser Ala Leu Leu Gln Ser
1 5 10 15

Asp Asp Glu Leu Val Gly Glu Asp Ser Asp Ser Glu Ile Ser Asp His
20 25 30

Val Ser Glu Asp Asp Val Gln Ser Asp Thr Glu Glu Ala Phe Ile Asp
35 40 45

Glu Val His Glu Val Gln Pro Thr Ser Ser Gly Ser Glu Ile Leu Asp
50 55 60

Glu Gln Asn Val Ile Glu Gln Pro Gly Ser Ser Leu Ala Ser Asn Arg
65 70 75 80

Ile Leu Thr Leu Pro Gln Arg Thr Ile Arg Gly Lys Asn Lys His Cys
85 90 95

Trp Ser Thr Ser Lys Ser Thr Arg Arg Ser Arg Val Ser Ala Leu Asn
100 105 110

```
Ile Val Arg Ser Gln Arg Gly Pro Thr Arg Met Cys Arg Asn Ile Tyr
        115                 120                 125

Asp Pro Leu Leu Cys Phe Lys Leu Phe Phe Thr Asp Glu Ile Ile Ser
    130                 135                 140

Glu Ile Val Lys Trp Thr Asn Ala Glu Ile Ser Leu Lys Arg Arg Glu
145                 150                 155                 160

Ser Met Thr Gly Ala Thr Phe Arg Asp Thr Asn Glu Asp Glu Ile Tyr
                165                 170                 175

Ala Phe Phe Gly Ile Leu Val Met Thr Ala Val Arg Lys Asp Asn His
            180                 185                 190

Met Ser Thr Asp Asp Leu Phe Asp Arg Ser Leu Ser Met Val Tyr Val
        195                 200                 205

Ser Val Met Ser Arg Asp Arg Phe Asp Phe Leu Ile Arg Cys Leu Arg
    210                 215                 220

Met Asp Asp Lys Ser Ile Arg Pro Thr Leu Arg Glu Asn Asp Val Phe
225                 230                 235                 240

Thr Pro Val Arg Lys Ile Trp Asp Leu Phe Ile His Gln Cys Ile Gln
                245                 250                 255

Asn Tyr Thr Pro Gly Ala His Leu Thr Ile Asp Glu Gln Leu Leu Gly
            260                 265                 270

Phe Arg Gly Arg Cys Pro Phe Arg Met Tyr Ile Pro Asn Lys Pro Ser
        275                 280                 285

Lys Tyr Gly Ile Lys Ile Leu Met Met Cys Asp Ser Gly Tyr Lys Tyr
    290                 295                 300

Met Ile Asn Gly Met Pro Tyr Leu Gly Arg Gly Thr Gln Thr Asn Gly
305                 310                 315                 320

Val Pro Leu Gly Glu Tyr Tyr Val Lys Glu Leu Ser Lys Pro Val His
                325                 330                 335

Gly Ser Cys Arg Asn Ile Thr Cys Asp Asn Trp Phe Thr Ser Ile Pro
            340                 345                 350

Leu Ala Lys Asn Leu Leu Gln Glu Pro Tyr Lys Leu Thr Ile Val Gly
        355                 360                 365

Thr Val Arg Ser Asn Lys Arg Glu Ile Pro Glu Val Leu Lys Asn Ser
    370                 375                 380

Arg Ser Arg Pro Val Gly Thr Ser Met Phe Cys Phe Asp Gly Pro Leu
385                 390                 395                 400

Thr Leu Val Ser Tyr Lys Pro Lys Pro Ala Lys Met Val Tyr Leu Leu
                405                 410                 415

Ser Ser Cys Asp Glu Asp Ala Ser Ile Asn Glu Ser Thr Gly Lys Pro
            420                 425                 430

Gln Met Val Met Tyr Tyr Asn Gln Thr Lys Gly Gly Val Asp Thr Leu
        435                 440                 445

Asp Gln Met Cys Ser Val Met Thr Cys Ser Arg Lys Thr Asn Arg Trp
    450                 455                 460

Pro Met Ala Leu Leu Tyr Gly Met Ile Asn Ile Ala Cys Ile Asn Ser
465                 470                 475                 480

Phe Ile Ile Tyr Ser His Asn Val Ser Ser Lys Gly Glu Lys Val Gln
                485                 490                 495

Ser Arg Lys Lys Phe Met Arg Asn Leu Tyr Met Ser Leu Thr Ser Ser
            500                 505                 510

Phe Met Arg Lys Arg Leu Glu Ala Pro Thr Leu Lys Arg Tyr Leu Arg
        515                 520                 525

Asp Asn Ile Ser Asn Ile Leu Pro Asn Glu Val Pro Gly Thr Ser Asp
```

530 535 540

Asp Ser Thr Glu Glu Pro Val Met Lys Lys Arg Thr Tyr Cys Thr Tyr
545 550 555 560

Cys Pro Ser Lys Ile Arg Arg Lys Ala Asn Ala Ser Cys Lys Lys Cys
565 570 575

Lys Lys Val Ile Cys Arg Glu His Asn Ile Asp Met Cys Gln Ser Cys
580 585 590

Phe

<210> SEQ ID NO 42
<211> LENGTH: 593
<212> TYPE: PRT
<213> ORGANISM: Artificial Sequence
<220> FEATURE:
<223> OTHER INFORMATION: Synthetic Nucleic Acid

<400> SEQUENCE: 42

Gly Ser Ser Leu Asp Asp Glu His Ile Leu Ser Ala Leu Leu Gln Ser
1 5 10 15

Asp Asp Glu Leu Val Gly Glu Asp Ser Asp Ser Glu Val Ser Asp His
20 25 30

Val Ser Glu Asp Asp Val Gln Ser Asp Thr Glu Glu Ala Phe Ile Asp
35 40 45

Glu Val His Glu Val Gln Pro Thr Ser Ser Gly Ser Glu Ile Leu Asp
50 55 60

Glu Gln Asn Val Ile Glu Gln Pro Gly Ser Ser Leu Ala Ser Asn Arg
65 70 75 80

Ile Leu Thr Leu Pro Gln Arg Thr Ile Arg Gly Lys Asn Lys His Cys
85 90 95

Trp Ser Thr Ser Lys Ser Thr Arg Arg Ser Arg Val Ser Ala Leu Asn
100 105 110

Ile Val Arg Ser Gln Arg Gly Pro Thr Arg Met Cys Arg Asn Ile Tyr
115 120 125

Asp Pro Leu Leu Cys Phe Lys Leu Phe Phe Thr Asp Glu Ile Ile Ser
130 135 140

Glu Ile Val Lys Trp Thr Asn Ala Glu Ile Ser Leu Lys Arg Arg Glu
145 150 155 160

Ser Met Thr Ser Ala Thr Phe Arg Asp Thr Asn Glu Asp Glu Ile Tyr
165 170 175

Ala Phe Phe Gly Ile Leu Val Met Thr Ala Val Arg Lys Asp Asn His
180 185 190

Met Ser Thr Asp Asp Leu Phe Asp Arg Ser Leu Ser Met Val Tyr Val
195 200 205

Ser Val Met Ser Arg Asp Arg Phe Asp Phe Leu Ile Arg Cys Leu Arg
210 215 220

Met Asp Asp Lys Ser Ile Arg Pro Thr Leu Arg Glu Asn Asp Val Phe
225 230 235 240

Thr Pro Val Arg Lys Ile Trp Asp Leu Phe Ile His Gln Cys Ile Gln
245 250 255

Asn Tyr Thr Pro Gly Ala His Leu Thr Ile Asp Glu Gln Leu Leu Gly
260 265 270

Phe Arg Gly Arg Cys Pro Phe Arg Val Tyr Ile Pro Asn Lys Pro Ser
275 280 285

Lys Tyr Gly Ile Lys Ile Leu Met Met Cys Asp Ser Gly Thr Lys Tyr
290 295 300

Met Ile Asn Gly Met Pro Tyr Leu Gly Arg Gly Thr Gln Thr Asn Gly
305 310 315 320

Val Pro Leu Gly Glu Tyr Tyr Val Lys Glu Leu Ser Lys Pro Val His
325 330 335

Gly Ser Cys Arg Asn Ile Thr Cys Asp Asn Trp Phe Thr Ser Ile Pro
340 345 350

Leu Ala Lys Asn Leu Leu Gln Glu Pro Tyr Lys Leu Thr Ile Val Gly
355 360 365

Thr Val Arg Ser Asn Lys Arg Glu Ile Pro Glu Val Leu Lys Asn Ser
370 375 380

Arg Ser Arg Pro Val Gly Thr Ser Met Phe Cys Phe Asp Gly Pro Leu
385 390 395 400

Thr Leu Val Ser Tyr Lys Pro Lys Pro Ala Lys Met Val Tyr Leu Leu
405 410 415

Ser Ser Cys Asp Glu Asp Ala Ser Ile Asn Glu Ser Thr Gly Lys Pro
420 425 430

Gln Met Val Met Tyr Tyr Asn Gln Thr Lys Gly Gly Val Asp Thr Leu
435 440 445

Asp Gln Met Cys Ser Val Met Thr Cys Ser Arg Lys Thr Asn Arg Trp
450 455 460

Pro Met Ala Leu Leu Tyr Gly Met Ile Asn Ile Ala Cys Ile Asn Ser
465 470 475 480

Phe Ile Ile Tyr Ser His Asn Val Ser Ser Lys Gly Glu Lys Val Gln
485 490 495

Ser Arg Lys Lys Phe Met Arg Asn Leu Tyr Met Ser Leu Thr Ser Ser
500 505 510

Phe Met Arg Lys Arg Leu Glu Ala Pro Thr Leu Lys Arg Tyr Leu Arg
515 520 525

Asp Asn Ile Ser Asn Ile Leu Pro Lys Glu Val Pro Gly Thr Ser Asp
530 535 540

Asp Ser Thr Glu Glu Pro Val Met Lys Lys Arg Thr Tyr Cys Thr Tyr
545 550 555 560

Cys Pro Ser Lys Ile Arg Arg Lys Ala Asn Ala Ser Cys Lys Lys Cys
565 570 575

Lys Lys Val Ile Cys Arg Glu His Asn Ile Asp Met Cys Gln Ser Cys
580 585 590

Phe

<210> SEQ ID NO 43
<211> LENGTH: 7
<212> TYPE: PRT
<213> ORGANISM: Artificial Sequence
<220> FEATURE:
<223> OTHER INFORMATION: Synthetic Nucleic Acid

<400> SEQUENCE: 43

Pro Lys Lys Lys Arg Lys Val
1 5

<210> SEQ ID NO 44
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 44
cccaagaaga agcggaaagt t 21

<210> SEQ ID NO 45
<211> LENGTH: 5
<212> TYPE: PRT
<213> ORGANISM: Artificial Sequence
<220> FEATURE:
<223> OTHER INFORMATION: Synthetic Nucleic Acid

<400> SEQUENCE: 45

Gly Gly Gly Gly Ser
1 5

<210> SEQ ID NO 46
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 46
ggcggcggag gcagc 15

<210> SEQ ID NO 47
<211> LENGTH: 605
<212> TYPE: PRT
<213> ORGANISM: Artificial Sequence
<220> FEATURE:
<223> OTHER INFORMATION: Synthetic Nucleic Acid

<400> SEQUENCE: 47

Met Ala Pro Lys Lys Lys Arg Lys Val Gly Gly Gly Gly Ser Ser Leu
1 5 10 15

Asp Asp Glu His Ile Leu Ser Ala Leu Leu Gln Ser Asp Asp Glu Leu
20 25 30

Val Gly Glu Asp Ser Asp Ser Glu Val Ser Asp His Val Ser Glu Asp
35 40 45

Asp Val Gln Ser Asp Thr Glu Glu Ala Phe Ile Asp Glu Val His Glu
50 55 60

Val Gln Pro Thr Ser Ser Gly Ser Glu Ile Leu Asp Glu Gln Asn Val
65 70 75 80

Ile Glu Gln Pro Gly Ser Ser Leu Ala Ser Asn Arg Ile Leu Thr Leu
85 90 95

Pro Gln Arg Thr Ile Arg Gly Lys Asn Lys His Cys Trp Ser Thr Ser
100 105 110

Lys Ser Thr Arg Arg Ser Arg Val Ser Ala Leu Asn Ile Val Arg Ser
115 120 125

Gln Arg Gly Pro Thr Arg Met Cys Arg Asn Ile Tyr Asp Pro Leu Leu
130 135 140

Cys Phe Lys Leu Phe Phe Thr Asp Glu Ile Ile Ser Glu Ile Val Lys
145 150 155 160

Trp Thr Asn Ala Glu Ile Ser Leu Lys Arg Arg Glu Ser Met Thr Ser
165 170 175

Ala Thr Phe Arg Asp Thr Asn Glu Asp Glu Ile Tyr Ala Phe Phe Gly
180 185 190

Ile Leu Val Met Thr Ala Val Arg Lys Asp Asn His Met Ser Thr Asp
195 200 205

Asp Leu Phe Asp Arg Ser Leu Ser Met Val Tyr Val Ser Val Met Ser
210 215 220

```
Arg Asp Arg Phe Asp Phe Leu Ile Arg Cys Leu Arg Met Asp Asp Lys
225                 230                 235                 240

Ser Ile Arg Pro Thr Leu Arg Glu Asn Asp Val Phe Thr Pro Val Arg
                245                 250                 255

Lys Ile Trp Asp Leu Phe Ile His Gln Cys Ile Gln Asn Tyr Thr Pro
            260                 265                 270

Gly Ala His Leu Thr Ile Asp Glu Gln Leu Leu Gly Phe Arg Gly Arg
        275                 280                 285

Cys Pro Phe Arg Val Tyr Ile Pro Asn Lys Pro Ser Lys Tyr Gly Ile
    290                 295                 300

Lys Ile Leu Met Met Cys Asp Ser Gly Thr Lys Tyr Met Ile Asn Gly
305                 310                 315                 320

Met Pro Tyr Leu Gly Arg Gly Thr Gln Thr Asn Gly Val Pro Leu Gly
                325                 330                 335

Glu Tyr Tyr Val Lys Glu Leu Ser Lys Pro Val His Gly Ser Cys Arg
            340                 345                 350

Asn Ile Thr Cys Asp Asn Trp Phe Thr Ser Ile Pro Leu Ala Lys Asn
        355                 360                 365

Leu Leu Gln Glu Pro Tyr Lys Leu Thr Ile Val Gly Thr Val Arg Ser
    370                 375                 380

Asn Lys Arg Glu Ile Pro Glu Val Leu Lys Asn Ser Arg Ser Arg Pro
385                 390                 395                 400

Val Gly Thr Ser Met Phe Cys Phe Asp Gly Pro Leu Thr Leu Val Ser
                405                 410                 415

Tyr Lys Pro Lys Pro Ala Lys Met Val Tyr Leu Leu Ser Ser Cys Asp
            420                 425                 430

Glu Asp Ala Ser Ile Asn Glu Ser Thr Gly Lys Pro Gln Met Val Met
        435                 440                 445

Tyr Tyr Asn Gln Thr Lys Gly Gly Val Asp Thr Leu Asp Gln Met Cys
    450                 455                 460

Ser Val Met Thr Cys Ser Arg Lys Thr Asn Arg Trp Pro Met Ala Leu
465                 470                 475                 480

Leu Tyr Gly Met Ile Asn Ile Ala Cys Ile Asn Ser Phe Ile Ile Tyr
                485                 490                 495

Ser His Asn Val Ser Ser Lys Gly Glu Lys Val Gln Ser Arg Lys Lys
            500                 505                 510

Phe Met Arg Asn Leu Tyr Met Ser Leu Thr Ser Ser Phe Met Arg Lys
        515                 520                 525

Arg Leu Glu Ala Pro Thr Leu Lys Arg Tyr Leu Arg Asp Asn Ile Ser
    530                 535                 540

Asn Ile Leu Pro Lys Glu Val Pro Gly Thr Ser Asp Asp Ser Thr Glu
545                 550                 555                 560

Glu Pro Val Met Lys Lys Arg Thr Tyr Cys Thr Tyr Cys Pro Ser Lys
                565                 570                 575

Ile Arg Arg Lys Ala Asn Ala Ser Cys Lys Lys Cys Lys Lys Val Ile
            580                 585                 590

Cys Arg Glu His Asn Ile Asp Met Cys Gln Ser Cys Phe
        595                 600                 605
```

<210> SEQ ID NO 48
<211> LENGTH: 1815
<212> TYPE: DNA
<213> ORGANISM: Artificial Sequence
<220> FEATURE:

<223> OTHER INFORMATION: Synthetic Nucleic Acid

<400> SEQUENCE: 48
atggctccca agaagaagcg gaaagttggc ggcggaggca gcagcctgga tgatgagcat 60
attctgagcg ccctgctgca gagcgacgat gaactcgtgg gcgaagatag cgacagcgag 120
gtgtccgatc acgtgtccga ggatgacgtg cagtccgata ccgaggaagc cttcatcgac 180
gaggtgcacg aagtgcagcc tacaagcagc ggcagcgaga tcctggacga gcagaatgtg 240
atcgagcagc caggatctag cctggccagc aacagaatcc tgacactgcc ccagagaacc 300
atccggggca agaacaagca ctgctggtcc accagcaaga gcaccagacg gtctagagtg 360
tctgccctga acatcgtgcg aagccagagg ggccctacca gaatgtgccg gaacatctac 420
gaccctctgc tgtgcttcaa gctgttcttc accgacgaga tcatctccga gatcgtgaag 480
tggaccaacg ccgagatcag cctgaagcgg agagaatcca tgaccagcgc caccttcaga 540
gacaccaacg aggacgagat ctacgccttc ttcggcatcc tggtcatgac agccgtgcgg 600
aaggacaacc acatgagcac cgacgacctg ttcgaccgca gcctgtctat ggtgtacgtg 660
tccgtgatga gccgggacag attcgacttc ctgatccggt gcctgcggat ggacgacaag 720
tccatcagac ccacactgcg cgagaacgac gtgttcacac ctgtgcggaa gatctgggac 780
ctgttcatcc accagtgcat ccagaactac acccctggcg ctcacctgac catcgacgaa 840
cagctgctgg gcttcagagg cagatgcccc ttcagagtgt acatccccaa caagccctct 900
aagtacggca tcaagatcct gatgatgtgc gacagcggca ccaagtacat gatcaacggc 960
atgccctacc tcggcagagg cacccaaaca aatggcgtgc cactgggcga gtactacgtg 1020
aaagaactga gcaagcctgt gcacggcagc tgcagaaaca tcacctgtga caactggttt 1080
accagcattc ccctggccaa gaacctgctg caagaaccct acaagctgac aatcgtgggc 1140
accgtgcgga gcaacaagag ggaaattccc gaggtgctga agaactctcg gagcagacct 1200
gtgggcacca gcatgttctg cttcgacgga cctctgacac tggtgtccta caagcccaag 1260
cctgccaaga tggtgtacct gctgagcagc tgtgacgagg acgccagcat caatgagagc 1320
accggcaagc cccagatggt catgtactac aaccagacca aaggcggcgt ggacaccctg 1380
gatcagatgt gcagcgtgat gacctgcagc agaaagacca acagatggcc catggctctg 1440
ctgtacggca tgatcaatat cgcctgcatc aacagcttca tcatctacag ccacaacgtg 1500
tccagcaagg gcgagaaggt gcagagccgg aagaaattca tgcggaacct gtacatgagc 1560
ctgaccagca gcttcatgag aaagcggctg gaagccccta cactgaagag atacctgcgg 1620
gacaacatca gcaacatcct gcctaaagag gtgcccggca ccagcgacga tagcacagag 1680
gaacccgtga tgaagaagag gacctactgc acctactgtc ccagcaagat ccggcggaag 1740
gccaacgcca gctgcaaaaa gtgcaagaaa gtgatctgcc gcgagcacaa catcgatatg 1800
tgccagagct gcttc 1815

<210> SEQ ID NO 49
<211> LENGTH: 603
<212> TYPE: PRT
<213> ORGANISM: Artificial Sequence
<220> FEATURE:
<223> OTHER INFORMATION: Synthetic Nucleic Acid

<400> SEQUENCE: 49

Pro Lys Lys Lys Arg Lys Val Gly Gly Gly Gly Ser Ser Leu Asp Asp
1 5 10 15

```
Glu His Ile Leu Ser Ala Leu Leu Gln Ser Asp Asp Glu Leu Val Gly
            20                  25                  30

Glu Asp Ser Asp Ser Glu Val Ser Asp His Val Ser Glu Asp Asp Val
        35                  40                  45

Gln Ser Asp Thr Glu Glu Ala Phe Ile Asp Glu Val His Glu Val Gln
    50                  55                  60

Pro Thr Ser Ser Gly Ser Glu Ile Leu Asp Glu Gln Asn Val Ile Glu
65                  70                  75                  80

Gln Pro Gly Ser Ser Leu Ala Ser Asn Arg Ile Leu Thr Leu Pro Gln
                85                  90                  95

Arg Thr Ile Arg Gly Lys Asn Lys His Cys Trp Ser Thr Ser Lys Ser
            100                 105                 110

Thr Arg Arg Ser Arg Val Ser Ala Leu Asn Ile Val Arg Ser Gln Arg
        115                 120                 125

Gly Pro Thr Arg Met Cys Arg Asn Ile Tyr Asp Pro Leu Leu Cys Phe
    130                 135                 140

Lys Leu Phe Phe Thr Asp Glu Ile Ile Ser Glu Ile Val Lys Trp Thr
145                 150                 155                 160

Asn Ala Glu Ile Ser Leu Lys Arg Arg Glu Ser Met Thr Ser Ala Thr
                165                 170                 175

Phe Arg Asp Thr Asn Glu Asp Glu Ile Tyr Ala Phe Phe Gly Ile Leu
            180                 185                 190

Val Met Thr Ala Val Arg Lys Asp Asn His Met Ser Thr Asp Asp Leu
        195                 200                 205

Phe Asp Arg Ser Leu Ser Met Val Tyr Val Ser Val Met Ser Arg Asp
    210                 215                 220

Arg Phe Asp Phe Leu Ile Arg Cys Leu Arg Met Asp Asp Lys Ser Ile
225                 230                 235                 240

Arg Pro Thr Leu Arg Glu Asn Asp Val Phe Thr Pro Val Arg Lys Ile
                245                 250                 255

Trp Asp Leu Phe Ile His Gln Cys Ile Gln Asn Tyr Thr Pro Gly Ala
            260                 265                 270

His Leu Thr Ile Asp Glu Gln Leu Leu Gly Phe Arg Gly Arg Cys Pro
        275                 280                 285

Phe Arg Val Tyr Ile Pro Asn Lys Pro Ser Lys Tyr Gly Ile Lys Ile
    290                 295                 300

Leu Met Met Cys Asp Ser Gly Thr Lys Tyr Met Ile Asn Gly Met Pro
305                 310                 315                 320

Tyr Leu Gly Arg Gly Thr Gln Thr Asn Gly Val Pro Leu Gly Glu Tyr
                325                 330                 335

Tyr Val Lys Glu Leu Ser Lys Pro Val His Gly Ser Cys Arg Asn Ile
            340                 345                 350

Thr Cys Asp Asn Trp Phe Thr Ser Ile Pro Leu Ala Lys Asn Leu Leu
        355                 360                 365

Gln Glu Pro Tyr Lys Leu Thr Ile Val Gly Thr Val Arg Ser Asn Lys
    370                 375                 380

Arg Glu Ile Pro Glu Val Leu Lys Asn Ser Arg Ser Arg Pro Val Gly
385                 390                 395                 400

Thr Ser Met Phe Cys Phe Asp Gly Pro Leu Thr Leu Val Ser Tyr Lys
                405                 410                 415

Pro Lys Pro Ala Lys Met Val Tyr Leu Leu Ser Ser Cys Asp Glu Asp
            420                 425                 430

Ala Ser Ile Asn Glu Ser Thr Gly Lys Pro Gln Met Val Met Tyr Tyr
```

```
        435                 440                 445

Asn Gln Thr Lys Gly Gly Val Asp Thr Leu Asp Gln Met Cys Ser Val
    450                 455                 460

Met Thr Cys Ser Arg Lys Thr Asn Arg Trp Pro Met Ala Leu Leu Tyr
465                 470                 475                 480

Gly Met Ile Asn Ile Ala Cys Ile Asn Ser Phe Ile Ile Tyr Ser His
                485                 490                 495

Asn Val Ser Ser Lys Gly Glu Lys Val Gln Ser Arg Lys Lys Phe Met
            500                 505                 510

Arg Asn Leu Tyr Met Ser Leu Thr Ser Ser Phe Met Arg Lys Arg Leu
        515                 520                 525

Glu Ala Pro Thr Leu Lys Arg Tyr Leu Arg Asp Asn Ile Ser Asn Ile
    530                 535                 540

Leu Pro Lys Glu Val Pro Gly Thr Ser Asp Asp Ser Thr Glu Glu Pro
545                 550                 555                 560

Val Met Lys Lys Arg Thr Tyr Cys Thr Tyr Cys Pro Ser Lys Ile Arg
                565                 570                 575

Arg Lys Ala Asn Ala Ser Cys Lys Lys Cys Lys Lys Val Ile Cys Arg
            580                 585                 590

Glu His Asn Ile Asp Met Cys Gln Ser Cys Phe
        595                 600
```

<210> SEQ ID NO 50
<211> LENGTH: 1809
<212> TYPE: DNA
<213> ORGANISM: Artificial Sequence
<220> FEATURE:
<223> OTHER INFORMATION: Synthetic Nucleic Acid

<400> SEQUENCE: 50

```
cccaagaaga agcggaaagt tggcggcgga ggcagcagcc tggatgatga gcatattctg     60

agcgccctgc tgcagagcga cgatgaactc gtgggcgaag atagcgacag cgaggtgtcc    120

gatcacgtgt ccgaggatga cgtgcagtcc gataccgagg aagccttcat cgacgaggtg    180

cacgaagtgc agcctacaag cagcggcagc gagatcctgg acgagcagaa tgtgatcgag    240

cagccaggat ctagcctggc cagcaacaga atcctgacac tgccccagag aaccatccgg    300

ggcaagaaca agcactgctg gtccaccagc aagagcacca gacggtctag agtgtctgcc    360

ctgaacatcg tgcgaagcca gaggggccct accagaatgt gccggaacat ctacgaccct    420

ctgctgtgct tcaagctgtt cttcaccgac gagatcatct ccgagatcgt gaagtggacc    480

aacgccgaga tcagcctgaa gcggagagaa tccatgacca gcgccacctt cagagacacc    540

aacgaggacg agatctacgc cttcttcggc atcctggtca tgacagccgt gcggaaggac    600

aaccacatga gcaccgacga cctgttcgac cgcagcctgt ctatggtgta cgtgtccgtg    660

atgagccggg acagattcga cttcctgatc cggtgcctgc ggatggacga caagtccatc    720

agacccacac tgcgcgagaa cgacgtgttc acacctgtgc ggaagatctg ggacctgttc    780

atccaccagt gcatccagaa ctacacccct ggcgctcacc tgaccatcga cgaacagctg    840

ctgggcttca gaggcagatg ccccttcaga gtgtacatcc ccaacaagcc ctctaagtac    900

ggcatcaaga tcctgatgat gtgcgacagc ggcaccaagt acatgatcaa cggcatgccc    960

tacctcggca gaggcaccca aacaaatggc gtgccactgg gcgagtacta cgtgaaagaa   1020

ctgagcaagc ctgtgcacgg cagctgcaga aacatcacct gtgacaactg gtttaccagc   1080

attcccctgg ccaagaacct gctgcaagaa ccctacaagc tgacaatcgt gggcaccgtg   1140
```

```
cggagcaaca agagggaaat tcccgaggtg ctgaagaact ctcggagcag acctgtgggc   1200

accagcatgt tctgcttcga cggacctctg acactggtgt cctacaagcc caagcctgcc   1260

aagatggtgt acctgctgag cagctgtgac gaggacgcca gcatcaatga gagcaccggc   1320

aagccccaga tggtcatgta ctacaaccag accaaaggcg gcgtggacac cctggatcag   1380

atgtgcagcg tgatgacctg cagcagaaag accaacagat ggcccatggc tctgctgtac   1440

ggcatgatca atatcgcctg catcaacagc ttcatcatct acagccacaa cgtgtccagc   1500

aagggcgaga aggtgcagag ccggaagaaa ttcatgcgga acctgtacat gagcctgacc   1560

agcagcttca tgagaaagcg gctggaagcc cctacactga agagatacct gcgggacaac   1620

atcagcaaca tcctgcctaa agaggtgccc ggcaccagcg acgatagcac agaggaaccc   1680

gtgatgaaga agaggaccta ctgcacctac tgtcccagca agatccggcg gaaggccaac   1740

gccagctgca aaaagtgcaa gaaagtgatc tgccgcgagc acaacatcga tatgtgccag   1800

agctgcttc                                                           1809
```

<210> SEQ ID NO 51
<211> LENGTH: 340
<212> TYPE: PRT
<213> ORGANISM: Artificial Sequence
<220> FEATURE:
<223> OTHER INFORMATION: Synthetic Nucleic Acid

<400> SEQUENCE: 51

```
Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
            20                  25                  30

Lys Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly Arg Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Arg Lys Glu Asn Tyr Val Asp Ile Leu Lys Gln
    210                 215                 220

His Leu Lys Thr Ser Val Arg Lys Leu Lys Leu Gly Arg Lys Trp Val
225                 230                 235                 240
```

Phe Gln Met Asp Asn Asp Pro Lys His Thr Ser Lys Val Val Ala Lys
245 250 255

Trp Leu Lys Asp Asn Lys Val Lys Val Leu Glu Trp Pro Ser Gln Ser
260 265 270

Pro Asp Leu Asn Pro Ile Glu Asn Leu Trp Ala Glu Leu Lys Lys Arg
275 280 285

Val Arg Ala Arg Arg Pro Thr Asn Leu Thr Gln Leu His Gln Leu Cys
290 295 300

Gln Glu Glu Trp Ala Lys Ile His Pro Thr Tyr Cys Gly Lys Leu Val
305 310 315 320

Glu Gly Tyr Pro Lys Arg Leu Thr Gln Val Lys Gln Phe Lys Gly Asn
325 330 335

Ala Thr Lys Tyr
340

<210> SEQ ID NO 52
<211> LENGTH: 339
<212> TYPE: PRT
<213> ORGANISM: Artificial Sequence
<220> FEATURE:
<223> OTHER INFORMATION: Synthetic Nucleic Acid

<400> SEQUENCE: 52

Gly Lys Ser Lys Glu Ile Ser Gln Asp Leu Arg Lys Lys Ile Val Asp
1 5 10 15

Leu His Lys Ser Gly Ser Ser Leu Gly Ala Ile Ser Lys Arg Leu Lys
20 25 30

Val Pro Arg Ser Ser Val Gln Thr Ile Val Arg Lys Tyr Lys His His
35 40 45

Gly Thr Thr Gln Pro Ser Tyr Arg Ser Gly Arg Arg Arg Val Leu Ser
50 55 60

Pro Arg Asp Glu Arg Thr Leu Val Arg Lys Val Gln Ile Asn Pro Arg
65 70 75 80

Thr Thr Ala Lys Asp Leu Val Lys Met Leu Glu Glu Thr Gly Thr Lys
85 90 95

Val Ser Ile Ser Thr Val Lys Arg Val Leu Tyr Arg His Asn Leu Lys
100 105 110

Gly Arg Ser Ala Arg Lys Lys Pro Leu Leu Gln Asn Arg His Lys Lys
115 120 125

Ala Arg Leu Arg Phe Ala Thr Ala His Gly Asp Lys Asp Arg Thr Phe
130 135 140

Trp Arg Asn Val Leu Trp Ser Asp Glu Thr Lys Ile Glu Leu Phe Gly
145 150 155 160

His Asn Asp His Arg Tyr Val Trp Arg Lys Lys Gly Glu Ala Cys Lys
165 170 175

Pro Lys Asn Thr Ile Pro Thr Val Lys His Gly Gly Gly Ser Ile Met
180 185 190

Leu Trp Gly Cys Phe Ala Ala Gly Gly Thr Gly Ala Leu His Lys Ile
195 200 205

Asp Gly Ile Met Arg Lys Glu Asn Tyr Val Asp Ile Leu Lys Gln His
210 215 220

Leu Lys Thr Ser Val Arg Lys Leu Lys Leu Gly Arg Lys Trp Val Phe
225 230 235 240

Gln Met Asp Asn Asp Pro Lys His Thr Ser Lys Val Val Ala Lys Trp
245 250 255

```
Leu Lys Asp Asn Lys Val Lys Val Leu Glu Trp Pro Ser Gln Ser Pro
            260                 265                 270

Asp Leu Asn Pro Ile Glu Asn Leu Trp Ala Glu Leu Lys Lys Arg Val
        275                 280                 285

Arg Ala Arg Arg Pro Thr Asn Leu Thr Gln Leu His Gln Leu Cys Gln
    290                 295                 300

Glu Glu Trp Ala Lys Ile His Pro Thr Tyr Cys Gly Lys Leu Val Glu
305                 310                 315                 320

Gly Tyr Pro Lys Arg Leu Thr Gln Val Lys Gln Phe Lys Gly Asn Ala
                325                 330                 335

Thr Lys Tyr


<210> SEQ ID NO 53
<211> LENGTH: 340
<212> TYPE: PRT
<213> ORGANISM: Artificial Sequence
<220> FEATURE:
<223> OTHER INFORMATION: Synthetic Nucleic Acid

<400> SEQUENCE: 53

Met Gly Lys Ser Lys Glu Ile Ser Gln Asp Leu Arg Lys Arg Ile Val
1               5                   10                  15

Asp Leu His Lys Ser Gly Ser Ser Leu Gly Ala Ile Ser Lys Arg Leu
            20                  25                  30

Ala Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly His Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Asp Ala Val Gln Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln His Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270
```

```
Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Asn Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340


<210> SEQ ID NO 54
<211> LENGTH: 339
<212> TYPE: PRT
<213> ORGANISM: Artificial Sequence
<220> FEATURE:
<223> OTHER INFORMATION: Synthetic Nucleic Acid

<400> SEQUENCE: 54

Gly Lys Ser Lys Glu Ile Ser Gln Asp Leu Arg Lys Arg Ile Val Asp
1               5                   10                  15

Leu His Lys Ser Gly Ser Ser Leu Gly Ala Ile Ser Lys Arg Leu Ala
            20                  25                  30

Val Pro Arg Ser Ser Val Gln Thr Ile Val Arg Lys Tyr Lys His His
        35                  40                  45

Gly Thr Thr Gln Pro Ser Tyr Arg Ser Gly Arg Arg Arg Val Leu Ser
    50                  55                  60

Pro Arg Asp Glu Arg Thr Leu Val Arg Lys Val Gln Ile Asn Pro Arg
65                  70                  75                  80

Thr Thr Ala Lys Asp Leu Val Lys Met Leu Glu Glu Thr Gly Thr Lys
                85                  90                  95

Val Ser Ile Ser Thr Val Lys Arg Val Leu Tyr Arg His Asn Leu Lys
            100                 105                 110

Gly His Ser Ala Arg Lys Lys Pro Leu Leu Gln Asn Arg His Lys Lys
        115                 120                 125

Ala Arg Leu Arg Phe Ala Thr Ala His Gly Asp Lys Asp Arg Thr Phe
    130                 135                 140

Trp Arg Asn Val Leu Trp Ser Asp Glu Thr Lys Ile Glu Leu Phe Gly
145                 150                 155                 160

His Asn Asp His Arg Tyr Val Trp Arg Lys Lys Gly Glu Ala Cys Lys
                165                 170                 175

Pro Lys Asn Thr Ile Pro Thr Val Lys His Gly Gly Gly Ser Ile Met
            180                 185                 190

Leu Trp Gly Cys Phe Ala Ala Gly Gly Thr Gly Ala Leu His Lys Ile
        195                 200                 205

Asp Gly Ile Met Asp Ala Val Gln Tyr Val Asp Ile Leu Lys Gln His
    210                 215                 220

Leu Lys Thr Ser Val Arg Lys Leu Lys Leu Gly Arg Lys Trp Val Phe
225                 230                 235                 240

Gln His Asp Asn Asp Pro Lys His Thr Ser Lys Val Val Ala Lys Trp
                245                 250                 255

Leu Lys Asp Asn Lys Val Lys Val Leu Glu Trp Pro Ser Gln Ser Pro
            260                 265                 270

Asp Leu Asn Pro Ile Glu Asn Leu Trp Ala Glu Leu Lys Lys Arg Val
        275                 280                 285
```

```
Arg Ala Arg Arg Pro Thr Asn Leu Thr Gln Leu His Gln Leu Cys Gln
    290                 295                 300

Glu Glu Trp Ala Lys Ile His Pro Asn Tyr Cys Gly Lys Leu Val Glu
305                 310                 315                 320

Gly Tyr Pro Lys Arg Leu Thr Gln Val Lys Gln Phe Lys Gly Asn Ala
                325                 330                 335

Thr Lys Tyr


<210> SEQ ID NO 55
<211> LENGTH: 1496
<212> TYPE: PRT
<213> ORGANISM: Artificial Sequence
<220> FEATURE:
<223> OTHER INFORMATION: Synthetic Nucleic Acid

<400> SEQUENCE: 55

Met Ser Lys Glu Gln Leu Leu Ile Gln Arg Ser Ser Ala Ala Glu Arg
1               5                   10                  15

Cys Arg Arg Tyr Arg Gln Lys Met Ser Ala Glu Gln Arg Ala Ser Asp
            20                  25                  30

Leu Glu Arg Arg Arg Arg Leu Gln Gln Asn Val Ser Glu Glu Gln Leu
        35                  40                  45

Leu Glu Lys Arg Arg Ser Glu Ala Glu Lys Gln Arg Arg His Arg Gln
    50                  55                  60

Lys Met Ser Lys Asp Gln Arg Ala Phe Glu Val Glu Arg Arg Arg Trp
65                  70                  75                  80

Arg Arg Gln Asn Met Ser Arg Glu Gln Ser Ser Thr Ser Thr Thr Asn
                85                  90                  95

Thr Gly Arg Asn Cys Leu Leu Ser Lys Asn Gly Val His Glu Asp Ala
            100                 105                 110

Ile Leu Glu His Ser Cys Gly Gly Met Thr Val Arg Cys Glu Phe Cys
        115                 120                 125

Leu Ser Leu Asn Phe Ser Asp Glu Lys Pro Ser Asp Gly Lys Phe Thr
    130                 135                 140

Arg Cys Cys Ser Lys Gly Lys Val Cys Pro Asn Asp Ile His Phe Pro
145                 150                 155                 160

Asp Tyr Pro Ala Tyr Leu Lys Arg Leu Met Thr Asn Glu Asp Ser Asp
                165                 170                 175

Ser Lys Asn Phe Met Glu Asn Ile Arg Ser Ile Asn Ser Ser Phe Ala
            180                 185                 190

Phe Ala Ser Met Gly Ala Asn Ile Ala Ser Pro Ser Gly Tyr Gly Pro
        195                 200                 205

Tyr Cys Phe Arg Ile His Gly Gln Val Tyr His Arg Thr Gly Thr Leu
    210                 215                 220

His Pro Ser Asp Gly Val Ser Arg Lys Phe Ala Gln Leu Tyr Ile Leu
225                 230                 235                 240

Asp Thr Ala Glu Ala Thr Ser Lys Arg Leu Ala Met Pro Glu Asn Gln
                245                 250                 255

Gly Cys Ser Glu Arg Leu Met Ile Asn Ile Asn Asn Leu Met His Glu
            260                 265                 270

Ile Asn Glu Leu Thr Lys Ser Tyr Lys Met Leu His Glu Val Glu Lys
        275                 280                 285

Glu Ala Gln Ser Glu Ala Ala Ala Lys Gly Ile Ala Pro Thr Glu Val
    290                 295                 300

Thr Met Ala Ile Lys Tyr Asp Arg Asn Ser Asp Pro Gly Arg Tyr Asn
```

```
305                 310                 315                 320

Ser Pro Arg Val Thr Glu Val Ala Val Ile Phe Arg Asn Glu Asp Gly
                325                 330                 335

Glu Pro Pro Phe Glu Arg Asp Leu Leu Ile His Cys Lys Pro Asp Pro
            340                 345                 350

Asn Asn Pro Asn Ala Thr Lys Met Lys Gln Ile Ser Ile Leu Phe Pro
        355                 360                 365

Thr Leu Asp Ala Met Thr Tyr Pro Ile Leu Phe Pro His Gly Glu Lys
    370                 375                 380

Gly Trp Gly Thr Asp Ile Ala Leu Arg Leu Arg Asp Asn Ser Val Ile
385                 390                 395                 400

Asp Asn Asn Thr Arg Gln Asn Val Arg Thr Arg Val Thr Gln Met Gln
                405                 410                 415

Tyr Tyr Gly Phe His Leu Ser Val Arg Asp Thr Phe Asn Pro Ile Leu
            420                 425                 430

Asn Ala Gly Lys Leu Thr Gln Gln Phe Ile Val Asp Ser Tyr Ser Lys
        435                 440                 445

Met Glu Ala Asn Arg Ile Asn Phe Ile Lys Ala Asn Gln Ser Lys Leu
    450                 455                 460

Arg Val Glu Lys Tyr Ser Gly Leu Met Asp Tyr Leu Lys Ser Arg Ser
465                 470                 475                 480

Glu Asn Asp Asn Val Pro Ile Gly Lys Met Ile Ile Leu Pro Ser Ser
                485                 490                 495

Phe Glu Gly Ser Pro Arg Asn Met Gln Gln Arg Tyr Gln Asp Ala Met
            500                 505                 510

Ala Ile Val Thr Lys Tyr Gly Lys Pro Asp Leu Phe Ile Thr Met Thr
        515                 520                 525

Cys Asn Pro Lys Trp Ala Asp Ile Thr Asn Asn Leu Gln Arg Trp Gln
    530                 535                 540

Lys Val Glu Asn Arg Pro Asp Leu Val Ala Arg Val Phe Asn Ile Lys
545                 550                 555                 560

Leu Asn Ala Leu Leu Asn Asp Ile Cys Lys Phe His Leu Phe Gly Lys
                565                 570                 575

Val Ile Ala Lys Ile His Val Ile Glu Phe Gln Lys Arg Gly Leu Pro
            580                 585                 590

His Ala His Ile Leu Leu Ile Leu Asp Ser Glu Ser Lys Leu Arg Ser
        595                 600                 605

Glu Asp Asp Ile Asp Arg Ile Val Lys Ala Glu Ile Pro Asp Glu Asp
    610                 615                 620

Gln Cys Pro Arg Leu Phe Gln Ile Val Lys Ser Asn Met Val His Gly
625                 630                 635                 640

Pro Cys Gly Ile Gln Asn Pro Asn Ser Pro Cys Met Glu Asn Gly Lys
                645                 650                 655

Cys Ser Lys Gly Tyr Pro Lys Glu Phe Gln Asn Ala Thr Ile Gly Asn
            660                 665                 670

Ile Asp Gly Tyr Pro Lys Tyr Lys Arg Arg Ser Gly Ser Thr Met Ser
        675                 680                 685

Ile Gly Asn Lys Val Val Asp Asn Thr Trp Ile Val Pro Tyr Asn Pro
    690                 695                 700

Tyr Leu Cys Leu Lys Tyr Asn Cys His Ile Asn Val Glu Val Cys Ala
705                 710                 715                 720

Ser Ile Lys Ser Val Lys Tyr Leu Phe Lys Tyr Ile Tyr Lys Gly His
                725                 730                 735
```

```
Asp Cys Ala Asn Ile Gln Ile Ser Glu Lys Asn Ile Ile Asn His Asp
            740                 745                 750

Glu Val Gln Asp Phe Ile Asp Ser Arg Tyr Val Ser Ala Pro Glu Ala
        755                 760                 765

Val Trp Arg Leu Phe Ala Met Arg Met His Asp Gln Ser His Ala Ile
    770                 775                 780

Thr Arg Leu Ala Ile His Leu Pro Asn Asp Gln Asn Leu Tyr Phe His
785                 790                 795                 800

Thr Asp Asp Phe Ala Glu Val Leu Asp Arg Ala Lys Arg His Asn Ser
                805                 810                 815

Thr Leu Met Ala Trp Phe Leu Leu Asn Arg Glu Asp Ser Asp Ala Arg
            820                 825                 830

Asn Tyr Tyr Tyr Trp Glu Ile Pro Gln His Tyr Val Phe Asn Asn Ser
        835                 840                 845

Leu Trp Thr Lys Arg Arg Lys Gly Gly Asn Lys Val Leu Gly Arg Leu
    850                 855                 860

Phe Thr Val Ser Phe Arg Glu Pro Glu Arg Tyr Tyr Leu Arg Leu Leu
865                 870                 875                 880

Leu Leu His Val Lys Gly Ala Ile Ser Phe Glu Asp Leu Arg Thr Val
                885                 890                 895

Gly Gly Val Thr Tyr Asp Thr Phe His Glu Ala Ala Lys His Arg Gly
            900                 905                 910

Leu Leu Leu Asp Asp Thr Ile Trp Lys Asp Thr Ile Asp Asp Ala Ile
        915                 920                 925

Ile Leu Asn Met Pro Lys Gln Leu Arg Gln Leu Phe Ala Tyr Ile Cys
    930                 935                 940

Val Phe Gly Cys Pro Ser Ala Ala Asp Lys Leu Trp Asp Glu Asn Lys
945                 950                 955                 960

Ser His Phe Ile Glu Asp Phe Cys Trp Lys Leu His Arg Arg Glu Gly
                965                 970                 975

Ala Cys Val Asn Cys Glu Met His Ala Leu Asn Glu Ile Gln Glu Val
            980                 985                 990

Phe Thr Leu His Gly Met Lys Cys  Ser His Phe Lys Leu  Pro Asp Tyr
        995                 1000                1005

Pro Leu  Leu Met Asn Ala Asn  Thr Cys Asp Gln Leu  Tyr Glu Gln
    1010                1015                1020

Gln Gln  Ala Glu Val Leu Ile  Asn Ser Leu Asn Asp  Glu Gln Leu
    1025                1030                1035

Ala Ala  Phe Gln Thr Ile Thr  Ser Ala Ile Glu Asp  Gln Thr Val
    1040                1045                1050

His Pro  Lys Cys Phe Phe Leu  Asp Gly Pro Gly Gly  Ser Gly Lys
    1055                1060                1065

Thr Tyr  Leu Tyr Lys Val Leu  Thr His Tyr Ile Arg  Gly Arg Gly
    1070                1075                1080

Gly Thr  Val Leu Pro Thr Ala  Ser Thr Gly Ile Ala  Ala Asn Leu
    1085                1090                1095

Leu Leu  Gly Gly Arg Thr Phe  His Ser Gln Tyr Lys  Leu Pro Ile
    1100                1105                1110

Pro Leu  Asn Glu Thr Ser Ile  Ser Arg Leu Asp Ile  Lys Ser Glu
    1115                1120                1125

Val Ala  Lys Thr Ile Lys Lys  Ala Gln Leu Leu Ile  Ile Asp Glu
    1130                1135                1140
```

```
Cys Thr  Met Ala Ser Ser His  Ala Ile Asn Ala Ile  Asp Arg Leu
    1145                 1150                 1155

Leu Arg  Glu Ile Met Asn Leu  Asn Val Ala Phe Gly  Gly Lys Val
    1160                 1165                 1170

Leu Leu  Leu Gly Gly Asp Phe  Arg Gln Cys Leu Ser  Ile Val Pro
    1175                 1180                 1185

His Ala  Met Arg Ser Ala Ile  Val Gln Thr Ser Leu  Lys Tyr Cys
    1190                 1195                 1200

Asn Val  Trp Gly Cys Phe Arg  Lys Leu Ser Leu Lys  Thr Asn Met
    1205                 1210                 1215

Arg Ser  Glu Asp Ser Ala Tyr  Ser Glu Trp Leu Val  Lys Leu Gly
    1220                 1225                 1230

Asp Gly  Lys Leu Asp Ser Ser  Phe His Leu Gly Met  Asp Ile Ile
    1235                 1240                 1245

Glu Ile  Pro His Glu Met Ile  Cys Asn Gly Ser Ile  Ile Glu Ala
    1250                 1255                 1260

Thr Phe  Gly Asn Ser Ile Ser  Ile Asp Asn Ile Lys  Asn Ile Ser
    1265                 1270                 1275

Lys Arg  Ala Ile Leu Cys Pro  Lys Asn Glu His Val  Gln Lys Leu
    1280                 1285                 1290

Asn Glu  Glu Ile Leu Asp Ile  Leu Asp Gly Asp Phe  His Thr Tyr
    1295                 1300                 1305

Leu Ser  Asp Asp Ser Ile Asp  Ser Thr Asp Asp Ala  Glu Lys Glu
    1310                 1315                 1320

Asn Phe  Pro Ile Glu Phe Leu  Asn Ser Ile Thr Pro  Ser Gly Met
    1325                 1330                 1335

Pro Cys  His Lys Leu Lys Leu  Lys Val Gly Ala Ile  Ile Met Leu
    1340                 1345                 1350

Leu Arg  Asn Leu Asn Ser Lys  Trp Gly Leu Cys Asn  Gly Thr Arg
    1355                 1360                 1365

Phe Ile  Ile Lys Arg Leu Arg  Pro Asn Ile Ile Glu  Ala Glu Val
    1370                 1375                 1380

Leu Thr  Gly Ser Ala Glu Gly  Glu Val Val Leu Ile  Pro Arg Ile
    1385                 1390                 1395

Asp Leu  Ser Pro Ser Asp Thr  Gly Leu Pro Phe Lys  Leu Ile Arg
    1400                 1405                 1410

Arg Gln  Phe Pro Val Met Pro  Ala Phe Ala Met Thr  Ile Asn Lys
    1415                 1420                 1425

Ser Gln  Gly Gln Thr Leu Asp  Arg Val Gly Ile Phe  Leu Pro Glu
    1430                 1435                 1440

Pro Val  Phe Ala His Gly Gln  Leu Tyr Val Ala Phe  Ser Arg Val
    1445                 1450                 1455

Arg Arg  Ala Cys Asp Val Lys  Val Lys Val Val Asn  Thr Ser Ser
    1460                 1465                 1470

Gln Gly  Lys Leu Val Lys His  Ser Glu Ser Val Phe  Thr Leu Asn
    1475                 1480                 1485

Val Val  Tyr Arg Glu Ile Leu  Glu
    1490                 1495
```

<210> SEQ ID NO 56
<211> LENGTH: 1495
<212> TYPE: PRT
<213> ORGANISM: Artificial Sequence
<220> FEATURE:
<223> OTHER INFORMATION: Synthetic Nucleic Acid

<400> SEQUENCE: 56

```
Ser Lys Glu Gln Leu Leu Ile Gln Arg Ser Ser Ala Ala Glu Arg Cys
1               5                   10                  15

Arg Arg Tyr Arg Gln Lys Met Ser Ala Glu Gln Arg Ala Ser Asp Leu
            20                  25                  30

Glu Arg Arg Arg Arg Leu Gln Gln Asn Val Ser Glu Glu Gln Leu Leu
        35                  40                  45

Glu Lys Arg Arg Ser Glu Ala Glu Lys Gln Arg Arg His Arg Gln Lys
    50                  55                  60

Met Ser Lys Asp Gln Arg Ala Phe Glu Val Glu Arg Arg Arg Trp Arg
65                  70                  75                  80

Arg Gln Asn Met Ser Arg Glu Gln Ser Ser Thr Ser Thr Thr Asn Thr
                85                  90                  95

Gly Arg Asn Cys Leu Leu Ser Lys Asn Gly Val His Glu Asp Ala Ile
            100                 105                 110

Leu Glu His Ser Cys Gly Gly Met Thr Val Arg Cys Glu Phe Cys Leu
        115                 120                 125

Ser Leu Asn Phe Ser Asp Glu Lys Pro Ser Asp Gly Lys Phe Thr Arg
    130                 135                 140

Cys Cys Ser Lys Gly Lys Val Cys Pro Asn Asp Ile His Phe Pro Asp
145                 150                 155                 160

Tyr Pro Ala Tyr Leu Lys Arg Leu Met Thr Asn Glu Asp Ser Asp Ser
                165                 170                 175

Lys Asn Phe Met Glu Asn Ile Arg Ser Ile Asn Ser Ser Phe Ala Phe
            180                 185                 190

Ala Ser Met Gly Ala Asn Ile Ala Ser Pro Ser Gly Tyr Gly Pro Tyr
        195                 200                 205

Cys Phe Arg Ile His Gly Gln Val Tyr His Arg Thr Gly Thr Leu His
    210                 215                 220

Pro Ser Asp Gly Val Ser Arg Lys Phe Ala Gln Leu Tyr Ile Leu Asp
225                 230                 235                 240

Thr Ala Glu Ala Thr Ser Lys Arg Leu Ala Met Pro Glu Asn Gln Gly
                245                 250                 255

Cys Ser Glu Arg Leu Met Ile Asn Ile Asn Asn Leu Met His Glu Ile
            260                 265                 270

Asn Glu Leu Thr Lys Ser Tyr Lys Met Leu His Glu Val Glu Lys Glu
        275                 280                 285

Ala Gln Ser Glu Ala Ala Ala Lys Gly Ile Ala Pro Thr Glu Val Thr
    290                 295                 300

Met Ala Ile Lys Tyr Asp Arg Asn Ser Asp Pro Gly Arg Tyr Asn Ser
305                 310                 315                 320

Pro Arg Val Thr Glu Val Ala Val Ile Phe Arg Asn Glu Asp Gly Glu
                325                 330                 335

Pro Pro Phe Glu Arg Asp Leu Leu Ile His Cys Lys Pro Asp Pro Asn
            340                 345                 350

Asn Pro Asn Ala Thr Lys Met Lys Gln Ile Ser Ile Leu Phe Pro Thr
        355                 360                 365

Leu Asp Ala Met Thr Tyr Pro Ile Leu Phe Pro His Gly Glu Lys Gly
    370                 375                 380

Trp Gly Thr Asp Ile Ala Leu Arg Leu Arg Asp Asn Ser Val Ile Asp
385                 390                 395                 400

Asn Asn Thr Arg Gln Asn Val Arg Thr Arg Val Thr Gln Met Gln Tyr
```

```
                405                 410                 415

Tyr Gly Phe His Leu Ser Val Arg Asp Thr Phe Asn Pro Ile Leu Asn
            420                 425                 430

Ala Gly Lys Leu Thr Gln Gln Phe Ile Val Asp Ser Tyr Ser Lys Met
        435                 440                 445

Glu Ala Asn Arg Ile Asn Phe Ile Lys Ala Asn Gln Ser Lys Leu Arg
    450                 455                 460

Val Glu Lys Tyr Ser Gly Leu Met Asp Tyr Leu Lys Ser Arg Ser Glu
465                 470                 475                 480

Asn Asp Asn Val Pro Ile Gly Lys Met Ile Ile Leu Pro Ser Ser Phe
                485                 490                 495

Glu Gly Ser Pro Arg Asn Met Gln Gln Arg Tyr Gln Asp Ala Met Ala
            500                 505                 510

Ile Val Thr Lys Tyr Gly Lys Pro Asp Leu Phe Ile Thr Met Thr Cys
        515                 520                 525

Asn Pro Lys Trp Ala Asp Ile Thr Asn Asn Leu Gln Arg Trp Gln Lys
    530                 535                 540

Val Glu Asn Arg Pro Asp Leu Val Ala Arg Val Phe Asn Ile Lys Leu
545                 550                 555                 560

Asn Ala Leu Leu Asn Asp Ile Cys Lys Phe His Leu Phe Gly Lys Val
                565                 570                 575

Ile Ala Lys Ile His Val Ile Glu Phe Gln Lys Arg Gly Leu Pro His
            580                 585                 590

Ala His Ile Leu Leu Ile Leu Asp Ser Glu Ser Lys Leu Arg Ser Glu
        595                 600                 605

Asp Asp Ile Asp Arg Ile Val Lys Ala Glu Ile Pro Asp Glu Asp Gln
    610                 615                 620

Cys Pro Arg Leu Phe Gln Ile Val Lys Ser Asn Met Val His Gly Pro
625                 630                 635                 640

Cys Gly Ile Gln Asn Pro Asn Ser Pro Cys Met Glu Asn Gly Lys Cys
                645                 650                 655

Ser Lys Gly Tyr Pro Lys Glu Phe Gln Asn Ala Thr Ile Gly Asn Ile
            660                 665                 670

Asp Gly Tyr Pro Lys Tyr Lys Arg Arg Ser Gly Ser Thr Met Ser Ile
        675                 680                 685

Gly Asn Lys Val Val Asp Asn Thr Trp Ile Val Pro Tyr Asn Pro Tyr
    690                 695                 700

Leu Cys Leu Lys Tyr Asn Cys His Ile Asn Val Glu Val Cys Ala Ser
705                 710                 715                 720

Ile Lys Ser Val Lys Tyr Leu Phe Lys Tyr Ile Tyr Lys Gly His Asp
                725                 730                 735

Cys Ala Asn Ile Gln Ile Ser Glu Lys Asn Ile Ile Asn His Asp Glu
            740                 745                 750

Val Gln Asp Phe Ile Asp Ser Arg Tyr Val Ser Ala Pro Glu Ala Val
        755                 760                 765

Trp Arg Leu Phe Ala Met Arg Met His Asp Gln Ser His Ala Ile Thr
    770                 775                 780

Arg Leu Ala Ile His Leu Pro Asn Asp Gln Asn Leu Tyr Phe His Thr
785                 790                 795                 800

Asp Asp Phe Ala Glu Val Leu Asp Arg Ala Lys Arg His Asn Ser Thr
                805                 810                 815

Leu Met Ala Trp Phe Leu Leu Asn Arg Glu Asp Ser Asp Ala Arg Asn
            820                 825                 830
```

```
Tyr Tyr Tyr Trp Glu Ile Pro Gln His Tyr Val Phe Asn Asn Ser Leu
        835                 840                 845

Trp Thr Lys Arg Arg Lys Gly Gly Asn Lys Val Leu Gly Arg Leu Phe
    850                 855                 860

Thr Val Ser Phe Arg Glu Pro Glu Arg Tyr Tyr Leu Arg Leu Leu Leu
865                 870                 875                 880

Leu His Val Lys Gly Ala Ile Ser Phe Glu Asp Leu Arg Thr Val Gly
                885                 890                 895

Gly Val Thr Tyr Asp Thr Phe His Glu Ala Ala Lys His Arg Gly Leu
            900                 905                 910

Leu Leu Asp Asp Thr Ile Trp Lys Asp Thr Ile Asp Asp Ala Ile Ile
        915                 920                 925

Leu Asn Met Pro Lys Gln Leu Arg Gln Leu Phe Ala Tyr Ile Cys Val
    930                 935                 940

Phe Gly Cys Pro Ser Ala Ala Asp Lys Leu Trp Asp Glu Asn Lys Ser
945                 950                 955                 960

His Phe Ile Glu Asp Phe Cys Trp Lys Leu His Arg Arg Glu Gly Ala
                965                 970                 975

Cys Val Asn Cys Glu Met His Ala Leu Asn Glu Ile Gln Glu Val Phe
            980                 985                 990

Thr Leu His Gly Met Lys Cys Ser  His Phe Lys Leu Pro  Asp Tyr Pro
        995                 1000                1005

Leu Leu  Met Asn Ala Asn Thr  Cys Asp Gln Leu Tyr  Glu Gln Gln
    1010                1015                1020

Gln Ala  Glu Val Leu Ile Asn  Ser Leu Asn Asp Glu  Gln Leu Ala
    1025                1030                1035

Ala Phe  Gln Thr Ile Thr Ser  Ala Ile Glu Asp Gln  Thr Val His
    1040                1045                1050

Pro Lys  Cys Phe Phe Leu Asp  Gly Pro Gly Gly Ser  Gly Lys Thr
    1055                1060                1065

Tyr Leu  Tyr Lys Val Leu Thr  His Tyr Ile Arg Gly  Arg Gly Gly
    1070                1075                1080

Thr Val  Leu Pro Thr Ala Ser  Thr Gly Ile Ala Ala  Asn Leu Leu
    1085                1090                1095

Leu Gly  Gly Arg Thr Phe His  Ser Gln Tyr Lys Leu  Pro Ile Pro
    1100                1105                1110

Leu Asn  Glu Thr Ser Ile Ser  Arg Leu Asp Ile Lys  Ser Glu Val
    1115                1120                1125

Ala Lys  Thr Ile Lys Lys Ala  Gln Leu Leu Ile Ile  Asp Glu Cys
    1130                1135                1140

Thr Met  Ala Ser Ser His Ala  Ile Asn Ala Ile Asp  Arg Leu Leu
    1145                1150                1155

Arg Glu  Ile Met Asn Leu Asn  Val Ala Phe Gly Gly  Lys Val Leu
    1160                1165                1170

Leu Leu  Gly Gly Asp Phe Arg  Gln Cys Leu Ser Ile  Val Pro His
    1175                1180                1185

Ala Met  Arg Ser Ala Ile Val  Gln Thr Ser Leu Lys  Tyr Cys Asn
    1190                1195                1200

Val Trp  Gly Cys Phe Arg Lys  Leu Ser Leu Lys Thr  Asn Met Arg
    1205                1210                1215

Ser Glu  Asp Ser Ala Tyr Ser  Glu Trp Leu Val Lys  Leu Gly Asp
    1220                1225                1230
```

```
Gly Lys  Leu Asp Ser Ser Phe  His Leu Gly Met Asp  Ile Ile Glu
    1235                 1240                 1245

Ile Pro  His Glu Met Ile Cys  Asn Gly Ser Ile Ile  Glu Ala Thr
    1250                 1255                 1260

Phe Gly  Asn Ser Ile Ser Ile  Asp Asn Ile Lys Asn  Ile Ser Lys
    1265                 1270                 1275

Arg Ala  Ile Leu Cys Pro Lys  Asn Glu His Val Gln  Lys Leu Asn
    1280                 1285                 1290

Glu Glu  Ile Leu Asp Ile Leu  Asp Gly Asp Phe His  Thr Tyr Leu
    1295                 1300                 1305

Ser Asp  Asp Ser Ile Asp Ser  Thr Asp Asp Ala Glu  Lys Glu Asn
    1310                 1315                 1320

Phe Pro  Ile Glu Phe Leu Asn  Ser Ile Thr Pro Ser  Gly Met Pro
    1325                 1330                 1335

Cys His  Lys Leu Lys Leu Lys  Val Gly Ala Ile Ile  Met Leu Leu
    1340                 1345                 1350

Arg Asn  Leu Asn Ser Lys Trp  Gly Leu Cys Asn Gly  Thr Arg Phe
    1355                 1360                 1365

Ile Ile  Lys Arg Leu Arg Pro  Asn Ile Ile Glu Ala  Glu Val Leu
    1370                 1375                 1380

Thr Gly  Ser Ala Glu Gly Glu  Val Val Leu Ile Pro  Arg Ile Asp
    1385                 1390                 1395

Leu Ser  Pro Ser Asp Thr Gly  Leu Pro Phe Lys Leu  Ile Arg Arg
    1400                 1405                 1410

Gln Phe  Pro Val Met Pro Ala  Phe Ala Met Thr Ile  Asn Lys Ser
    1415                 1420                 1425

Gln Gly  Gln Thr Leu Asp Arg  Val Gly Ile Phe Leu  Pro Glu Pro
    1430                 1435                 1440

Val Phe  Ala His Gly Gln Leu  Tyr Val Ala Phe Ser  Arg Val Arg
    1445                 1450                 1455

Arg Ala  Cys Asp Val Lys Val  Lys Val Val Asn Thr  Ser Ser Gln
    1460                 1465                 1470

Gly Lys  Leu Val Lys His Ser  Glu Ser Val Phe Thr  Leu Asn Val
    1475                 1480                 1485

Val Tyr  Arg Glu Ile Leu Glu
    1490                 1495
```

<210> SEQ ID NO 57
<211> LENGTH: 649
<212> TYPE: PRT
<213> ORGANISM: Artificial Sequence
<220> FEATURE:
<223> OTHER INFORMATION: Synthetic Nucleic Acid

<400> SEQUENCE: 57

```
Met Glu Glu Val Cys Asp Ser Ser Ala Ala Ala Ser Ser Thr Val Gln
1               5                   10                  15

Asn Gln Pro Gln Asp Gln Glu His Pro Trp Pro Tyr Leu Arg Glu Phe
            20                  25                  30

Phe Ser Leu Ser Gly Val Asn Lys Asp Ser Phe Lys Met Lys Cys Val
        35                  40                  45

Leu Cys Leu Pro Leu Asn Lys Glu Ile Ser Ala Phe Lys Ser Ser Pro
    50                  55                  60

Ser Asn Leu Arg Lys His Ile Glu Arg Met His Pro Asn Tyr Leu Lys
65                  70                  75                  80
```

```
Asn Tyr Ser Lys Leu Thr Ala Gln Lys Arg Lys Ile Gly Thr Ser Thr
                85                  90                  95

His Ala Ser Ser Ser Lys Gln Leu Lys Val Asp Ser Val Phe Pro Val
            100                 105                 110

Lys His Val Ser Pro Val Thr Val Asn Lys Ala Ile Leu Arg Tyr Ile
        115                 120                 125

Ile Gln Gly Leu His Pro Phe Ser Thr Val Asp Leu Pro Ser Phe Lys
    130                 135                 140

Glu Leu Ile Ser Thr Leu Gln Pro Gly Ile Ser Val Ile Thr Arg Pro
145                 150                 155                 160

Thr Leu Arg Ser Lys Ile Ala Glu Ala Ala Leu Ile Met Lys Gln Lys
                165                 170                 175

Val Thr Ala Ala Met Ser Glu Val Glu Trp Ile Ala Thr Thr Thr Asp
            180                 185                 190

Cys Trp Thr Ala Arg Arg Lys Ser Phe Ile Gly Val Thr Ala His Trp
        195                 200                 205

Ile Asn Pro Gly Ser Leu Glu Arg His Ser Ala Ala Leu Ala Cys Lys
    210                 215                 220

Arg Leu Met Gly Ser His Thr Phe Glu Val Leu Ala Ser Ala Met Asn
225                 230                 235                 240

Asp Ile His Ser Glu Tyr Glu Ile Arg Asp Lys Val Val Cys Thr Thr
                245                 250                 255

Thr Asp Ser Gly Ser Asn Phe Met Lys Ala Phe Arg Val Phe Gly Val
            260                 265                 270

Glu Asn Asn Asp Ile Glu Thr Glu Ala Arg Arg Cys Glu Ser Asp Asp
        275                 280                 285

Thr Asp Ser Glu Gly Cys Gly Glu Gly Ser Asp Gly Val Glu Phe Gln
    290                 295                 300

Asp Ala Ser Arg Val Leu Asp Gln Asp Asp Gly Phe Glu Phe Gln Leu
305                 310                 315                 320

Pro Lys His Gln Lys Cys Ala Cys His Leu Leu Asn Leu Val Ser Ser
                325                 330                 335

Val Asp Ala Gln Lys Ala Leu Ser Asn Glu His Tyr Lys Lys Leu Tyr
            340                 345                 350

Arg Ser Val Phe Gly Lys Cys Gln Ala Leu Trp Asn Lys Ser Ser Arg
        355                 360                 365

Ser Ala Leu Ala Ala Glu Ala Val Glu Ser Glu Ser Arg Leu Gln Leu
    370                 375                 380

Leu Arg Pro Asn Gln Thr Arg Trp Asn Ser Thr Phe Met Ala Val Asp
385                 390                 395                 400

Arg Ile Leu Gln Ile Cys Lys Glu Ala Gly Glu Gly Ala Leu Arg Asn
                405                 410                 415

Ile Cys Thr Ser Leu Glu Val Pro Met Phe Asn Pro Ala Glu Met Leu
            420                 425                 430

Phe Leu Thr Glu Trp Ala Asn Thr Met Arg Pro Val Ala Lys Val Leu
        435                 440                 445

Asp Ile Leu Gln Ala Glu Thr Asn Thr Gln Leu Gly Trp Leu Leu Pro
    450                 455                 460

Ser Val His Gln Leu Ser Leu Lys Leu Gln Arg Leu His His Ser Leu
465                 470                 475                 480

Arg Tyr Cys Asp Pro Leu Val Asp Ala Leu Gln Gln Gly Ile Gln Thr
                485                 490                 495

Arg Phe Lys His Met Phe Glu Asp Pro Glu Ile Ile Ala Ala Ala Ile
```

```
            500                 505                 510

Leu Leu Pro Lys Phe Arg Thr Ser Trp Thr Asn Asp Glu Thr Ile Ile
        515                 520                 525

Lys Arg Gly Met Asp Tyr Ile Arg Val His Leu Glu Pro Leu Asp His
    530                 535                 540

Lys Lys Glu Leu Ala Asn Ser Ser Ser Asp Asp Glu Asp Phe Phe Ala
545                 550                 555                 560

Ser Leu Lys Pro Thr Thr His Glu Ala Ser Lys Glu Leu Asp Gly Tyr
                565                 570                 575

Leu Ala Cys Val Ser Asp Thr Arg Glu Ser Leu Leu Thr Phe Pro Ala
            580                 585                 590

Ile Cys Ser Leu Ser Ile Lys Thr Asn Thr Pro Leu Pro Ala Ser Ala
        595                 600                 605

Ala Cys Glu Arg Leu Phe Ser Thr Ala Gly Leu Leu Phe Ser Pro Lys
    610                 615                 620

Arg Ala Arg Leu Asp Thr Asn Asn Phe Glu Asn Gln Leu Leu Leu Lys
625                 630                 635                 640

Leu Asn Leu Arg Phe Tyr Asn Phe Glu
                645


<210> SEQ ID NO 58
<211> LENGTH: 648
<212> TYPE: PRT
<213> ORGANISM: Artificial Sequence
<220> FEATURE:
<223> OTHER INFORMATION: Synthetic Nucleic Acid

<400> SEQUENCE: 58

Glu Glu Val Cys Asp Ser Ser Ala Ala Ala Ser Ser Thr Val Gln Asn
1               5                   10                  15

Gln Pro Gln Asp Gln Glu His Pro Trp Pro Tyr Leu Arg Glu Phe Phe
            20                  25                  30

Ser Leu Ser Gly Val Asn Lys Asp Ser Phe Lys Met Lys Cys Val Leu
        35                  40                  45

Cys Leu Pro Leu Asn Lys Glu Ile Ser Ala Phe Lys Ser Ser Pro Ser
    50                  55                  60

Asn Leu Arg Lys His Ile Glu Arg Met His Pro Asn Tyr Leu Lys Asn
65                  70                  75                  80

Tyr Ser Lys Leu Thr Ala Gln Lys Arg Lys Ile Gly Thr Ser Thr His
                85                  90                  95

Ala Ser Ser Ser Lys Gln Leu Lys Val Asp Ser Val Phe Pro Val Lys
            100                 105                 110

His Val Ser Pro Val Thr Val Asn Lys Ala Ile Leu Arg Tyr Ile Ile
        115                 120                 125

Gln Gly Leu His Pro Phe Ser Thr Val Asp Leu Pro Ser Phe Lys Glu
    130                 135                 140

Leu Ile Ser Thr Leu Gln Pro Gly Ile Ser Val Ile Thr Arg Pro Thr
145                 150                 155                 160

Leu Arg Ser Lys Ile Ala Glu Ala Ala Leu Ile Met Lys Gln Lys Val
                165                 170                 175

Thr Ala Ala Met Ser Glu Val Glu Trp Ile Ala Thr Thr Thr Asp Cys
            180                 185                 190

Trp Thr Ala Arg Arg Lys Ser Phe Ile Gly Val Thr Ala His Trp Ile
        195                 200                 205

Asn Pro Gly Ser Leu Glu Arg His Ser Ala Ala Leu Ala Cys Lys Arg
```

```
    210                 215                 220

Leu Met Gly Ser His Thr Phe Glu Val Leu Ala Ser Ala Met Asn Asp
225                 230                 235                 240

Ile His Ser Glu Tyr Glu Ile Arg Asp Lys Val Val Cys Thr Thr Thr
                245                 250                 255

Asp Ser Gly Ser Asn Phe Met Lys Ala Phe Arg Val Phe Gly Val Glu
            260                 265                 270

Asn Asn Asp Ile Glu Thr Glu Ala Arg Arg Cys Glu Ser Asp Asp Thr
        275                 280                 285

Asp Ser Glu Gly Cys Gly Glu Gly Ser Asp Gly Val Glu Phe Gln Asp
    290                 295                 300

Ala Ser Arg Val Leu Asp Gln Asp Asp Gly Phe Glu Phe Gln Leu Pro
305                 310                 315                 320

Lys His Gln Lys Cys Ala Cys His Leu Leu Asn Leu Val Ser Ser Val
                325                 330                 335

Asp Ala Gln Lys Ala Leu Ser Asn Glu His Tyr Lys Lys Leu Tyr Arg
            340                 345                 350

Ser Val Phe Gly Lys Cys Gln Ala Leu Trp Asn Lys Ser Ser Arg Ser
        355                 360                 365

Ala Leu Ala Ala Glu Ala Val Glu Ser Glu Ser Arg Leu Gln Leu Leu
    370                 375                 380

Arg Pro Asn Gln Thr Arg Trp Asn Ser Thr Phe Met Ala Val Asp Arg
385                 390                 395                 400

Ile Leu Gln Ile Cys Lys Glu Ala Gly Glu Gly Ala Leu Arg Asn Ile
                405                 410                 415

Cys Thr Ser Leu Glu Val Pro Met Phe Asn Pro Ala Glu Met Leu Phe
            420                 425                 430

Leu Thr Glu Trp Ala Asn Thr Met Arg Pro Val Ala Lys Val Leu Asp
        435                 440                 445

Ile Leu Gln Ala Glu Thr Asn Thr Gln Leu Gly Trp Leu Leu Pro Ser
    450                 455                 460

Val His Gln Leu Ser Leu Lys Leu Gln Arg Leu His His Ser Leu Arg
465                 470                 475                 480

Tyr Cys Asp Pro Leu Val Asp Ala Leu Gln Gln Gly Ile Gln Thr Arg
                485                 490                 495

Phe Lys His Met Phe Glu Asp Pro Glu Ile Ile Ala Ala Ala Ile Leu
            500                 505                 510

Leu Pro Lys Phe Arg Thr Ser Trp Thr Asn Asp Glu Thr Ile Ile Lys
        515                 520                 525

Arg Gly Met Asp Tyr Ile Arg Val His Leu Glu Pro Leu Asp His Lys
    530                 535                 540

Lys Glu Leu Ala Asn Ser Ser Ser Asp Asp Glu Asp Phe Phe Ala Ser
545                 550                 555                 560

Leu Lys Pro Thr Thr His Glu Ala Ser Lys Glu Leu Asp Gly Tyr Leu
                565                 570                 575

Ala Cys Val Ser Asp Thr Arg Glu Ser Leu Leu Thr Phe Pro Ala Ile
            580                 585                 590

Cys Ser Leu Ser Ile Lys Thr Asn Thr Pro Leu Pro Ala Ser Ala Ala
        595                 600                 605

Cys Glu Arg Leu Phe Ser Thr Ala Gly Leu Leu Phe Ser Pro Lys Arg
    610                 615                 620

Ala Arg Leu Asp Thr Asn Asn Phe Glu Asn Gln Leu Leu Leu Lys Leu
625                 630                 635                 640
```

```
Asn Leu Arg Phe Tyr Asn Phe Glu
                645


<210> SEQ ID NO 59
<211> LENGTH: 636
<212> TYPE: PRT
<213> ORGANISM: Artificial Sequence
<220> FEATURE:
<223> OTHER INFORMATION: Synthetic Nucleic Acid

<400> SEQUENCE: 59

Met Met Leu Asn Trp Leu Lys Ser Gly Lys Leu Glu Ser Gln Ser Gln
1               5                   10                  15

Glu Gln Ser Ser Cys Tyr Leu Glu Asn Ser Asn Cys Leu Pro Pro Thr
            20                  25                  30

Leu Asp Ser Thr Asp Ile Ile Gly Glu Glu Asn Lys Ala Gly Thr Thr
        35                  40                  45

Ser Arg Lys Lys Arg Lys Tyr Asp Glu Asp Tyr Leu Asn Phe Gly Phe
    50                  55                  60

Thr Trp Thr Gly Asp Lys Asp Glu Pro Asn Gly Leu Cys Val Ile Cys
65                  70                  75                  80

Glu Gln Val Val Asn Asn Ser Ser Leu Asn Pro Ala Lys Leu Lys Arg
                85                  90                  95

His Leu Asp Thr Lys His Pro Thr Leu Lys Gly Lys Ser Glu Tyr Phe
            100                 105                 110

Lys Arg Lys Cys Asn Glu Leu Asn Gln Lys Lys His Thr Phe Glu Arg
        115                 120                 125

Tyr Val Arg Asp Asp Asn Lys Asn Leu Leu Lys Ala Ser Tyr Leu Val
    130                 135                 140

Ser Leu Arg Ile Ala Lys Gln Gly Glu Ala Tyr Thr Ile Ala Glu Lys
145                 150                 155                 160

Leu Ile Lys Pro Cys Thr Lys Asp Leu Thr Thr Cys Val Phe Gly Glu
                165                 170                 175

Lys Phe Ala Ser Lys Val Asp Leu Val Pro Leu Ser Asp Thr Thr Ile
            180                 185                 190

Ser Arg Arg Ile Glu Asp Met Ser Tyr Phe Cys Glu Ala Val Leu Val
        195                 200                 205

Asn Arg Leu Glu Asn Ala Lys Cys Gly Phe Thr Leu Gln Met Asp Glu
    210                 215                 220

Ser Thr Asp Val Ala Gly Leu Ala Ile Leu Leu Val Phe Val Arg Tyr
225                 230                 235                 240

Ile His Glu Ser Ser Phe Glu Glu Asp Met Leu Phe Cys Lys Ala Leu
                245                 250                 255

Pro Thr Gln Thr Thr Gly Glu Glu Ile Phe Asn Leu Leu Asn Ala Tyr
            260                 265                 270

Phe Glu Lys His Ser Ile Pro Trp Asn Leu Cys Tyr His Ile Cys Thr
        275                 280                 285

Asp Gly Ala Lys Ala Met Val Gly Val Ile Lys Gly Val Ile Ala Arg
    290                 295                 300

Ile Lys Lys Leu Val Pro Asp Ile Lys Ala Ser His Cys Cys Leu His
305                 310                 315                 320

Arg His Ala Leu Ala Val Lys Arg Ile Pro Asn Ala Leu His Glu Val
                325                 330                 335

Leu Asn Asp Ala Val Lys Met Ile Asn Phe Ile Lys Ser Arg Pro Leu
            340                 345                 350
```

Asn Ala Arg Val Phe Ala Leu Leu Cys Asp Asp Leu Gly Ser Leu His
355 360 365

Lys Asn Leu Leu Leu His Thr Glu Val Arg Trp Leu Ser Arg Gly Lys
370 375 380

Val Leu Thr Arg Phe Trp Glu Leu Arg Asp Glu Ile Arg Ile Phe Phe
385 390 395 400

Asn Glu Arg Glu Phe Ala Gly Lys Leu Asn Asp Thr Ser Trp Leu Gln
405 410 415

Asn Leu Ala Tyr Ile Ala Asp Ile Phe Ser Tyr Leu Asn Glu Val Asn
420 425 430

Leu Ser Leu Gln Gly Pro Asn Ser Thr Ile Phe Lys Val Asn Ser Arg
435 440 445

Ile Asn Ser Ile Lys Ser Lys Leu Lys Leu Trp Glu Glu Cys Ile Thr
450 455 460

Lys Asn Asn Thr Glu Cys Phe Ala Asn Leu Asn Asp Phe Leu Glu Thr
465 470 475 480

Ser Asn Thr Ala Leu Asp Pro Asn Leu Lys Ser Asn Ile Leu Glu His
485 490 495

Leu Asn Gly Leu Lys Asn Thr Phe Leu Glu Tyr Phe Pro Pro Thr Cys
500 505 510

Asn Asn Ile Ser Trp Val Glu Asn Pro Phe Asn Glu Cys Gly Asn Val
515 520 525

Asp Thr Leu Pro Ile Lys Glu Arg Glu Gln Leu Ile Asp Ile Arg Thr
530 535 540

Asp Thr Thr Leu Lys Ser Ser Phe Val Pro Asp Gly Ile Gly Pro Phe
545 550 555 560

Trp Ile Lys Leu Met Asp Glu Phe Pro Glu Ile Ser Lys Arg Ala Val
565 570 575

Lys Glu Leu Met Pro Phe Val Thr Thr Tyr Leu Cys Glu Lys Ser Phe
580 585 590

Ser Val Tyr Val Ala Thr Lys Thr Lys Tyr Arg Asn Arg Leu Asp Ala
595 600 605

Glu Asp Asp Met Arg Leu Gln Leu Thr Thr Ile His Pro Asp Ile Asp
610 615 620

Asn Leu Cys Asn Asn Lys Gln Ala Gln Lys Ser His
625 630 635

<210> SEQ ID NO 60
<211> LENGTH: 635
<212> TYPE: PRT
<213> ORGANISM: Artificial Sequence
<220> FEATURE:
<223> OTHER INFORMATION: Synthetic Nucleic Acid

<400> SEQUENCE: 60

Met Leu Asn Trp Leu Lys Ser Gly Lys Leu Glu Ser Gln Ser Gln Glu
1 5 10 15

Gln Ser Ser Cys Tyr Leu Glu Asn Ser Asn Cys Leu Pro Pro Thr Leu
20 25 30

Asp Ser Thr Asp Ile Ile Gly Glu Glu Asn Lys Ala Gly Thr Thr Ser
35 40 45

Arg Lys Lys Arg Lys Tyr Asp Glu Asp Tyr Leu Asn Phe Gly Phe Thr
50 55 60

Trp Thr Gly Asp Lys Asp Glu Pro Asn Gly Leu Cys Val Ile Cys Glu
65 70 75 80

```
Gln Val Val Asn Asn Ser Ser Leu Asn Pro Ala Lys Leu Lys Arg His
                85                  90                  95

Leu Asp Thr Lys His Pro Thr Leu Lys Gly Lys Ser Glu Tyr Phe Lys
            100                 105                 110

Arg Lys Cys Asn Glu Leu Asn Gln Lys Lys His Thr Phe Glu Arg Tyr
        115                 120                 125

Val Arg Asp Asp Asn Lys Asn Leu Leu Lys Ala Ser Tyr Leu Val Ser
    130                 135                 140

Leu Arg Ile Ala Lys Gln Gly Glu Ala Tyr Thr Ile Ala Glu Lys Leu
145                 150                 155                 160

Ile Lys Pro Cys Thr Lys Asp Leu Thr Thr Cys Val Phe Gly Glu Lys
                165                 170                 175

Phe Ala Ser Lys Val Asp Leu Val Pro Leu Ser Asp Thr Thr Ile Ser
            180                 185                 190

Arg Arg Ile Glu Asp Met Ser Tyr Phe Cys Glu Ala Val Leu Val Asn
        195                 200                 205

Arg Leu Glu Asn Ala Lys Cys Gly Phe Thr Leu Gln Met Asp Glu Ser
    210                 215                 220

Thr Asp Val Ala Gly Leu Ala Ile Leu Leu Val Phe Val Arg Tyr Ile
225                 230                 235                 240

His Glu Ser Ser Phe Glu Glu Asp Met Leu Phe Cys Lys Ala Leu Pro
                245                 250                 255

Thr Gln Thr Thr Gly Glu Glu Ile Phe Asn Leu Leu Asn Ala Tyr Phe
            260                 265                 270

Glu Lys His Ser Ile Pro Trp Asn Leu Cys Tyr His Ile Cys Thr Asp
        275                 280                 285

Gly Ala Lys Ala Met Val Gly Val Ile Lys Gly Val Ile Ala Arg Ile
    290                 295                 300

Lys Lys Leu Val Pro Asp Ile Lys Ala Ser His Cys Cys Leu His Arg
305                 310                 315                 320

His Ala Leu Ala Val Lys Arg Ile Pro Asn Ala Leu His Glu Val Leu
                325                 330                 335

Asn Asp Ala Val Lys Met Ile Asn Phe Ile Lys Ser Arg Pro Leu Asn
            340                 345                 350

Ala Arg Val Phe Ala Leu Leu Cys Asp Asp Leu Gly Ser Leu His Lys
        355                 360                 365

Asn Leu Leu Leu His Thr Glu Val Arg Trp Leu Ser Arg Gly Lys Val
    370                 375                 380

Leu Thr Arg Phe Trp Glu Leu Arg Asp Glu Ile Arg Ile Phe Phe Asn
385                 390                 395                 400

Glu Arg Glu Phe Ala Gly Lys Leu Asn Asp Thr Ser Trp Leu Gln Asn
                405                 410                 415

Leu Ala Tyr Ile Ala Asp Ile Phe Ser Tyr Leu Asn Glu Val Asn Leu
            420                 425                 430

Ser Leu Gln Gly Pro Asn Ser Thr Ile Phe Lys Val Asn Ser Arg Ile
        435                 440                 445

Asn Ser Ile Lys Ser Lys Leu Lys Leu Trp Glu Glu Cys Ile Thr Lys
    450                 455                 460

Asn Asn Thr Glu Cys Phe Ala Asn Leu Asn Asp Phe Leu Glu Thr Ser
465                 470                 475                 480

Asn Thr Ala Leu Asp Pro Asn Leu Lys Ser Asn Ile Leu Glu His Leu
                485                 490                 495
```

```
Asn Gly Leu Lys Asn Thr Phe Leu Glu Tyr Phe Pro Pro Thr Cys Asn
            500                 505                 510

Asn Ile Ser Trp Val Glu Asn Pro Phe Asn Glu Cys Gly Asn Val Asp
        515                 520                 525

Thr Leu Pro Ile Lys Glu Arg Glu Gln Leu Ile Asp Ile Arg Thr Asp
    530                 535                 540

Thr Thr Leu Lys Ser Ser Phe Val Pro Asp Gly Ile Gly Pro Phe Trp
545                 550                 555                 560

Ile Lys Leu Met Asp Glu Phe Pro Glu Ile Ser Lys Arg Ala Val Lys
                565                 570                 575

Glu Leu Met Pro Phe Val Thr Thr Tyr Leu Cys Glu Lys Ser Phe Ser
            580                 585                 590

Val Tyr Val Ala Thr Lys Thr Lys Tyr Arg Asn Arg Leu Asp Ala Glu
        595                 600                 605

Asp Asp Met Arg Leu Gln Leu Thr Thr Ile His Pro Asp Ile Asp Asn
    610                 615                 620

Leu Cys Asn Asn Lys Gln Ala Gln Lys Ser His
625                 630                 635
```

<210> SEQ ID NO 61
<211> LENGTH: 239
<212> TYPE: PRT
<213> ORGANISM: Artificial Sequence
<220> FEATURE:
<223> OTHER INFORMATION: Synthetic Nucleic Acid

<400> SEQUENCE: 61

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220
```

Val Thr Ala Ala Gly Ile Thr Leu Gly Met Asp Glu Leu Tyr Lys
225 230 235

<210> SEQ ID NO 62
<211> LENGTH: 238
<212> TYPE: PRT
<213> ORGANISM: Artificial Sequence
<220> FEATURE:
<223> OTHER INFORMATION: Synthetic Nucleic Acid

<400> SEQUENCE: 62

Val Ser Lys Gly Glu Glu Leu Phe Thr Gly Val Val Pro Ile Leu Val
1 5 10 15

Glu Leu Asp Gly Asp Val Asn Gly His Lys Phe Ser Val Ser Gly Glu
20 25 30

Gly Glu Gly Asp Ala Thr Tyr Gly Lys Leu Thr Leu Lys Phe Ile Cys
35 40 45

Thr Thr Gly Lys Leu Pro Val Pro Trp Pro Thr Leu Val Thr Thr Leu
50 55 60

Thr Tyr Gly Val Gln Cys Phe Ser Arg Tyr Pro Asp His Met Lys Gln
65 70 75 80

His Asp Phe Phe Lys Ser Ala Met Pro Glu Gly Tyr Val Gln Glu Arg
85 90 95

Thr Ile Phe Phe Lys Asp Asp Gly Asn Tyr Lys Thr Arg Ala Glu Val
100 105 110

Lys Phe Glu Gly Asp Thr Leu Val Asn Arg Ile Glu Leu Lys Gly Ile
115 120 125

Asp Phe Lys Glu Asp Gly Asn Ile Leu Gly His Lys Leu Glu Tyr Asn
130 135 140

Tyr Asn Ser His Asn Val Tyr Ile Met Ala Asp Lys Gln Lys Asn Gly
145 150 155 160

Ile Lys Val Asn Phe Lys Ile Arg His Asn Ile Glu Asp Gly Ser Val
165 170 175

Gln Leu Ala Asp His Tyr Gln Gln Asn Thr Pro Ile Gly Asp Gly Pro
180 185 190

Val Leu Leu Pro Asp Asn His Tyr Leu Ser Thr Gln Ser Ala Leu Ser
195 200 205

Lys Asp Pro Asn Glu Lys Arg Asp His Met Val Leu Leu Glu Phe Val
210 215 220

Thr Ala Ala Gly Ile Thr Leu Gly Met Asp Glu Leu Tyr Lys
225 230 235

<210> SEQ ID NO 63
<211> LENGTH: 717
<212> TYPE: DNA
<213> ORGANISM: Artificial Sequence
<220> FEATURE:
<223> OTHER INFORMATION: Synthetic Nucleic Acid

<400> SEQUENCE: 63
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgtga tcacatggtc 660
ctgctggagt tcgtgaccgc cgccgggatc actctcggca tggacgagct gtacaag 717

<210> SEQ ID NO 64
<211> LENGTH: 714
<212> TYPE: DNA
<213> ORGANISM: Artificial Sequence
<220> FEATURE:
<223> OTHER INFORMATION: Synthetic Nucleic Acid

<400> SEQUENCE: 64
gtgagcaagg gcgaggagct gttcaccggg gtggtgccca tcctggtcga gctggacggc 60
gacgtaaacg gccacaagtt cagcgtgtcc ggcgagggcg agggcgatgc cacctacggc 120
aagctgaccc tgaagttcat ctgcaccacc ggcaagctgc ccgtgccctg gcccaccctc 180
gtgaccaccc tgacctacgg cgtgcagtgc ttcagccgct accccgacca catgaagcag 240
cacgacttct tcaagtccgc catgcccgaa ggctacgtcc aggagcgcac catcttcttc 300
aaggacgacg gcaactacaa gacccgcgcc gaggtgaagt tcgagggcga caccctggtg 360
aaccgcatcg agctgaaggg catcgacttc aaggaggacg gcaacatcct ggggcacaag 420
ctggagtaca actacaacag ccacaacgtc tatatcatgg ccgacaagca gaagaacggc 480
atcaaggtga acttcaagat ccgccacaac atcgaggacg gcagcgtgca gctcgccgac 540
cactaccagc agaacacccc catcggcgac ggccccgtgc tgctgcccga caaccactac 600
ctgagcaccc agtccgccct gagcaaagac cccaacgaga agcgtgatca catggtcctg 660
ctggagttcg tgaccgccgc cgggatcact ctcggcatgg acgagctgta caag 714

<210> SEQ ID NO 65
<211> LENGTH: 550
<212> TYPE: PRT
<213> ORGANISM: Artificial Sequence
<220> FEATURE:
<223> OTHER INFORMATION: Synthetic Nucleic Acid

<400> SEQUENCE: 65

Met Glu Asp Ala Lys Asn Ile Lys Lys Gly Pro Ala Pro Phe Tyr Pro
1 5 10 15

Leu Glu Asp Gly Thr Ala Gly Glu Gln Leu His Lys Ala Met Lys Arg
20 25 30

Tyr Ala Leu Val Pro Gly Thr Ile Ala Phe Thr Asp Ala His Ile Glu
35 40 45

Val Asp Ile Thr Tyr Ala Glu Tyr Phe Glu Met Ser Val Arg Leu Ala
50 55 60

Glu Ala Met Lys Arg Tyr Gly Leu Asn Thr Asn His Arg Ile Val Val
65 70 75 80

Cys Ser Glu Asn Ser Leu Gln Phe Phe Met Pro Val Leu Gly Ala Leu
85 90 95

Phe Ile Gly Val Ala Val Ala Pro Ala Asn Asp Ile Tyr Asn Glu Arg
100 105 110

Glu Leu Leu Asn Ser Met Gly Ile Ser Gln Pro Thr Val Val Phe Val

-continued

```
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540
```

```
Gly Gly Lys Ile Ala Val
545                 550


<210> SEQ ID NO 66
<211> LENGTH: 549
<212> TYPE: PRT
<213> ORGANISM: Artificial Sequence
<220> FEATURE:
<223> OTHER INFORMATION: Synthetic Nucleic Acid

<400> SEQUENCE: 66

Glu Asp Ala Lys Asn Ile Lys Lys Gly Pro Ala Pro Phe Tyr Pro Leu
1               5                   10                  15

Glu Asp Gly Thr Ala Gly Glu Gln Leu His Lys Ala Met Lys Arg Tyr
            20                  25                  30

Ala Leu Val Pro Gly Thr Ile Ala Phe Thr Asp Ala His Ile Glu Val
        35                  40                  45

Asp Ile Thr Tyr Ala Glu Tyr Phe Glu Met Ser Val Arg Leu Ala Glu
    50                  55                  60

Ala Met Lys Arg Tyr Gly Leu Asn Thr Asn His Arg Ile Val Val Cys
65                  70                  75                  80

Ser Glu Asn Ser Leu Gln Phe Phe Met Pro Val Leu Gly Ala Leu Phe
                85                  90                  95

Ile Gly Val Ala Val Ala Pro Ala Asn Asp Ile Tyr Asn Glu Arg Glu
            100                 105                 110

Leu Leu Asn Ser Met Gly Ile Ser Gln Pro Thr Val Val Phe Val Ser
        115                 120                 125

Lys Lys Gly Leu Gln Lys Ile Leu Asn Val Gln Lys Lys Leu Pro Ile
    130                 135                 140

Ile Gln Lys Ile Ile Ile Met Asp Ser Lys Thr Asp Tyr Gln Gly Phe
145                 150                 155                 160

Gln Ser Met Tyr Thr Phe Val Thr Ser His Leu Pro Pro Gly Phe Asn
                165                 170                 175

Glu Tyr Asp Phe Val Pro Glu Ser Phe Asp Arg Asp Lys Thr Ile Ala
            180                 185                 190

Leu Ile Met Asn Ser Ser Gly Ser Thr Gly Leu Pro Lys Gly Val Ala
        195                 200                 205

Leu Pro His Arg Thr Ala Cys Val Arg Phe Ser His Ala Arg Asp Pro
    210                 215                 220

Ile Phe Gly Asn Gln Ile Ile Pro Asp Thr Ala Ile Leu Ser Val Val
225                 230                 235                 240

Pro Phe His His Gly Phe Gly Met Phe Thr Thr Leu Gly Tyr Leu Ile
                245                 250                 255

Cys Gly Phe Arg Val Val Leu Met Tyr Arg Phe Glu Glu Glu Leu Phe
            260                 265                 270

Leu Arg Ser Leu Gln Asp Tyr Lys Ile Gln Ser Ala Leu Leu Val Pro
        275                 280                 285

Thr Leu Phe Ser Phe Phe Ala Lys Ser Thr Leu Ile Asp Lys Tyr Asp
    290                 295                 300

Leu Ser Asn Leu His Glu Ile Ala Ser Gly Gly Ala Pro Leu Ser Lys
305                 310                 315                 320

Glu Val Gly Glu Ala Val Ala Lys Arg Phe His Leu Pro Gly Ile Arg
                325                 330                 335

Gln Gly Tyr Gly Leu Thr Glu Thr Thr Ser Ala Ile Leu Ile Thr Pro
            340                 345                 350
```

```
Glu Gly Asp Asp Lys Pro Gly Ala Val Gly Lys Val Val Pro Phe Phe
        355                 360                 365

Glu Ala Lys Val Val Asp Leu Asp Thr Gly Lys Thr Leu Gly Val Asn
    370                 375                 380

Gln Arg Gly Glu Leu Cys Val Arg Gly Pro Met Ile Met Ser Gly Tyr
385                 390                 395                 400

Val Asn Asn Pro Glu Ala Thr Asn Ala Leu Ile Asp Lys Asp Gly Trp
                405                 410                 415

Leu His Ser Gly Asp Ile Ala Tyr Trp Asp Glu Asp Glu His Phe Phe
            420                 425                 430

Ile Val Asp Arg Leu Lys Ser Leu Ile Lys Tyr Lys Gly Tyr Gln Val
        435                 440                 445

Ala Pro Ala Glu Leu Glu Ser Ile Leu Leu Gln His Pro Asn Ile Phe
    450                 455                 460

Asp Ala Gly Val Ala Gly Leu Pro Asp Asp Asp Ala Gly Glu Leu Pro
465                 470                 475                 480

Ala Ala Val Val Val Leu Glu His Gly Lys Thr Met Thr Glu Lys Glu
                485                 490                 495

Ile Val Asp Tyr Val Ala Ser Gln Val Thr Thr Ala Lys Lys Leu Arg
            500                 505                 510

Gly Gly Val Val Phe Val Asp Glu Val Pro Lys Gly Leu Thr Gly Lys
        515                 520                 525

Leu Asp Ala Arg Lys Ile Arg Glu Ile Leu Ile Lys Ala Lys Lys Gly
    530                 535                 540

Gly Lys Ile Ala Val
545
```

<210> SEQ ID NO 67
<211> LENGTH: 1650
<212> TYPE: DNA
<213> ORGANISM: Artificial Sequence
<220> FEATURE:
<223> OTHER INFORMATION: Synthetic Nucleic Acid

<400> SEQUENCE: 67

```
atggaagatg ccaaaaacat taagaagggc ccagcgccat tctacccact cgaagacggg     60

accgccggcg agcagctgca caaagccatg aagcgctacg ccctggtgcc cggcaccatc    120

gcctttaccg acgcacatat cgaggtggac attacctacg ccgagtactt cgagatgagc    180

gttcggctgg cagaagctat gaagcgctat gggctgaata caaaccatcg gatcgtggtg    240

tgcagcgaga atagcttgca gttcttcatg cccgtgttgg gtgccctgtt catcggtgtg    300

gctgtggccc cagctaacga catctacaac gagcgcgagc tgctgaacag catgggcatc    360

agccagccca ccgtcgtatt cgtgagcaag aaagggctgc aaaagatcct caacgtgcaa    420

aagaagctac cgatcataca aaagatcatc atcatggata gcaagaccga ctaccagggc    480

ttccaaagca tgtacacctt cgtgacttcc catttgccac ccggcttcaa cgagtacgac    540

ttcgtgcccg agagcttcga ccgggacaaa accatcgccc tgatcatgaa cagtagtggc    600

agtaccggat tgcccaaggg cgtagcccta ccgcaccgca ccgcttgtgt ccgattcagt    660

catgcccgcg accccatctt cggcaaccag atcatccccg acaccgctat cctcagcgtg    720

gtgccatttc accacggctt cggcatgttc accacgctgg gctacttgat ctgcggcttt    780

cgggtcgtgc tcatgtaccg cttcgaggag gagctattct tgcgcagctt gcaagactat    840

aagattcaat ctgccctgct ggtgcccaca ctatttagct tcttcgctaa gagcactctc    900
```

atcgacaagt acgacctaag caacttgcac gagatcgcca gcggcggggc gccgctcagc 960
aaggaggtag gtgaggccgt ggccaaacgc ttccacctac caggcatccg ccagggctac 1020
ggcctgacag aaacaaccag cgccattctg atcacccccg aaggggacga caagcctggc 1080
gcagtaggca aggtggtgcc cttcttcgag gctaaggtgg tggacttgga caccggtaag 1140
acactgggtg tgaaccagcg cggcgagctg tgcgtccgtg gccccatgat catgagcggc 1200
tacgttaaca accccgaggc tacaaacgct ctcatcgaca aggacggctg gctgcacagc 1260
ggcgacatcg cctactggga cgaggacgag cacttcttca tcgtggaccg gctgaagagc 1320
ctgatcaaat acaagggcta ccaggtagcc ccagccgaac tggagagcat cctgctgcaa 1380
caccccaaca tcttcgacgc cggggtcgcc ggcctgcccg acgacgatgc cggcgagctg 1440
cccgccgcag tcgtcgtgct ggaacacggt aaaaccatga ccgagaagga gatcgtggac 1500
tatgtggcca gccaggttac aaccgccaag aagctgcgcg gtggtgttgt gttcgtggac 1560
gaggtgccta aaggactgac cggcaagttg gacgcccgca agatccgcga gattctcatt 1620
aaggccaaga agggcggcaa gatcgccgtg 1650

<210> SEQ ID NO 68
<211> LENGTH: 1647
<212> TYPE: DNA
<213> ORGANISM: Artificial Sequence
<220> FEATURE:
<223> OTHER INFORMATION: Synthetic Nucleic Acid

<400> SEQUENCE: 68
gaagatgcca aaaacattaa gaagggccca gcgccattct acccactcga agacgggacc 60
gccggcgagc agctgcacaa agccatgaag cgctacgccc tggtgcccgg caccatcgcc 120
tttaccgacg cacatatcga ggtggacatt acctacgccg agtacttcga gatgagcgtt 180
cggctggcag aagctatgaa gcgctatggg ctgaatacaa accatcggat cgtggtgtgc 240
agcgagaata gcttgcagtt cttcatgccc gtgttgggtg ccctgttcat cggtgtggct 300
gtggccccag ctaacgacat ctacaacgag cgcgagctgc tgaacagcat gggcatcagc 360
cagcccaccg tcgtattcgt gagcaagaaa gggctgcaaa agatcctcaa cgtgcaaaag 420
aagctaccga tcatacaaaa gatcatcatc atggatagca agaccgacta ccagggcttc 480
caaagcatgt acaccttcgt gacttcccat ttgccacccg gcttcaacga gtacgacttc 540
gtgcccgaga gcttcgaccg ggacaaaacc atcgccctga tcatgaacag tagtggcagt 600
accggattgc ccaagggcgt agccctaccg caccgcaccg cttgtgtccg attcagtcat 660
gcccgcgacc ccatcttcgg caaccagatc atccccgaca ccgctatcct cagcgtggtg 720
ccatttcacc acggcttcgg catgttcacc acgctgggct acttgatctg cggctttcgg 780
gtcgtgctca tgtaccgctt cgaggaggag ctattcttgc gcagcttgca agactataag 840
attcaatctg ccctgctggt gcccacacta tttagcttct tcgctaagag cactctcatc 900
gacaagtacg acctaagcaa cttgcacgag atcgccagcg gcggggcgcc gctcagcaag 960
gaggtaggtg aggccgtggc caaacgcttc cacctaccag gcatccgcca gggctacggc 1020
ctgacagaaa caaccagcgc cattctgatc acccccgaag gggacgacaa gcctggcgca 1080
gtaggcaagg tggtgccctt cttcgaggct aaggtggtgg acttggacac cggtaagaca 1140
ctgggtgtga accagcgcgg cgagctgtgc gtccgtggcc ccatgatcat gagcggctac 1200
gttaacaacc ccgaggctac aaacgctctc atcgacaagg acggctggct gcacagcggc 1260
gacatcgcct actgggacga ggacgagcac ttcttcatcg tggaccggct gaagagcctg 1320
atcaaataca agggctacca ggtagcccca gccgaactgg agagcatcct gctgcaacac 1380
cccaacatct tcgacgccgg ggtcgccggc ctgcccgacg acgatgccgg cgagctgccc 1440
gccgcagtcg tcgtgctgga acacggtaaa accatgaccg agaaggagat cgtggactat 1500
gtggccagcc aggttacaac cgccaagaag ctgcgcggtg gtgttgtgtt cgtggacgag 1560
gtgcctaaag gactgaccgg caagttggac gcccgcaaga tccgcgagat tctcattaag 1620
gccaagaagg gcggcaagat cgccgtg 1647

<210> SEQ ID NO 69
<211> LENGTH: 869
<212> TYPE: DNA
<213> ORGANISM: Artificial Sequence
<220> FEATURE:
<223> OTHER INFORMATION: Synthetic Nucleic Acid

<400> SEQUENCE: 69
tgtacattta tattggctca tgtccaatat gaccgccatg ttggcattga ttattgacta 60
gttattaata gtaatcaatt acggggtcat tagttcatag cccatatatg gagttccgcg 120
ttacataact tacggtaaat ggcccgcctg gctgaccgcc caacgacccc cgcccattga 180
cgtcaataat gacgtatgtt cccatagtaa cgccaatagg gactttccat tgacgtcaat 240
gggtggagta tttacggtaa actgcccact tggcagtaca tcaagtgtat catatgccaa 300
gtccgccccc tattgacgtc aatgacggta aatggcccgc ctggcattat gcccagtaca 360
tgaccttacg ggactttcct acttggcagt acatctacgt attagtcatc gctattacca 420
tggtgatgcg gttttggcag tacaccaatg ggcgtggata gcggtttgac tcacggggat 480
ttccaagtct ccaccccatt gacgtcaatg ggagtttgtt ttggcaccaa aatcaacggg 540
actttccaaa atgtcgtaat aaccccgccc cgttgacgca aatgggcggt aggcgtgtac 600
ggtgggaggt ctatataagc agaggtcgtt tagtgaaccg tcagatcact agtagcttta 660
ttgcggtagt ttatcacagt taaattgcta acgcagtcag tgctcgactg atcacaggta 720
agtatcaagg ttacaagaca ggtttaagga ggccaataga aactgggctt gtcgagacag 780
agaagattct tgcgtttctg ataggcacct attggtctta ctgacatcca ctttgccttt 840
ctctccacag ggtaccgaa gccgctagc 869

<210> SEQ ID NO 70
<211> LENGTH: 1866
<212> TYPE: DNA
<213> ORGANISM: Artificial Sequence
<220> FEATURE:
<223> OTHER INFORMATION: Synthetic Nucleic Acid

<400> SEQUENCE: 70
atgccggggt tttacgagat tgtgattaag gtccccagcg accttgacga gcatctgccc 60
ggcatttctg acagctttgt gaactgggtg gccgagaagg aatgggagtt gccgccagat 120
tctgacatgg atctgaatct gattgagcag gcacccctga ccgtggccga gaagctgcag 180
cgcgactttc tgacggaatg gcgccgtgtg agtaaggccc cggaggctct tttctttgtg 240
caatttgaga agggagagag ctacttccac atgcacgtgc tcgtggaaac caccggggtg 300
aaatccatgg ttttgggacg tttcctgagt cagattcgcg aaaaactgat tcagagaatt 360
taccgcggga tcgagccgac tttgccaaac tggttcgcgg tcacaaagac cagaaatggc 420
gccggaggcg ggaacaaggt ggtggatgag tgctacatcc ccaattactt gctccccaaa 480
acccagcctg agctccagtg ggcgtggact aatatggaac agtatttaag cgcctgtttg 540
aatctcacgg agcgtaaacg gttggtggcg cagcatctga cgcacgtgtc gcagacgcag 600
gagcagaaca aagagaatca gaatcccaat tctgatgcgc cggtgatcag atcaaaaact 660
tcagccaggt acatggagct ggtcgggtgg ctcgtggaca aggggattac ctcggagaag 720
cagtggatcc aggaggacca ggcctcatac atctccttca atgcggcctc caactcgcgg 780
tcccaaatca aggctgcctt ggacaatgcg ggaaagatta tgagcctgac taaaaccgcc 840
cccgactacc tggtgggcca gcagcccgtg gaggacattt ccagcaatcg gatttataaa 900
attttggaac taaacgggta cgatccccaa tatgcggctt ccgtctttct gggatgggcc 960
acgaaaaagt tcggcaagag gaacaccatc tggctgtttg ggcctgcaac taccgggaag 1020
accaacatcg cggaggccat agcccacact gtgcccttct acgggtgcgt aaactggacc 1080
aatgagaact ttcccttcaa cgactgtgtc gacaagatgg tgatctggtg ggaggagggg 1140
aagatgaccg ccaaggtcgt ggagtcggcc aaagccattc tcggaggaag caaggtgcgc 1200
gtggaccaga aatgcaagtc ctcggcccag atagacccga ctcccgtgat cgtcacctcc 1260
aacaccaaca tgtgcgccgt gattgacggg aactcaacga ccttcgaaca ccagcagccg 1320
ttgcaagacc ggatgttcaa atttgaactc acccgccgtc tggatcatga ctttgggaag 1380
gtcaccaagc aggaagtcaa agactttttc cggtgggcaa aggatcacgt ggttgaggtg 1440
gagcatgaat tctacgtcaa aaagggtgga gccaagaaaa gacccgcccc cagtgacgca 1500
gatataagtg agcccaaacg ggtgcgcgag tcagttgcgc agccatcgac gtcagacgcg 1560
gaagcttcga tcaactacgc agacaggtac caaaacaaat gttctcgtca cgtgggcatg 1620
aatctgatgc tgtttccctg cagacaatgc gagagaatga atcagaattc aaatatctgc 1680
ttcactcacg gacagaaaga ctgtttagag tgctttcccg tgtcagaatc tcaacccgtt 1740
tctgtcgtca aaaaggcgta tcagaaactg tgctacattc atcatatcat gggaaaggtg 1800
ccagacgctt gcactgcctg cgatctggtc aatgtggatt tggatgactg catctttgaa 1860
caataa 1866

<210> SEQ ID NO 71
<211> LENGTH: 2214
<212> TYPE: DNA
<213> ORGANISM: Artificial Sequence
<220> FEATURE:
<223> OTHER INFORMATION: Synthetic Nucleic Acid

<400> SEQUENCE: 71
atggctgccg atggttatct tccagattgg ctcgaggaca ctctctctga aggaataaga 60
cagtggtgga agctcaaacc tggcccacca ccaccaaagc ccgcagagcg gcataaggac 120
gacagcaggg gtcttgtgct tccgggttac aaatacctcg gacccggcaa cggactcgac 180
aagggggagc ccgtcaacgc ggcggacgca gcggccctcg agcacgacaa ggcctacgac 240
cagcagctca aagcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aacctgttaa gacggctccg 420
ggaaaaaaga ggccggtaga gcactctcct gtggagccag actcctcctc gggaaccgga 480
aaggcgggcc agcagcctgc gaggaagcga ctcaactttg gtcagactgg agacaccgac 540
tccgccgctg acccccagcc tctcggagaa ccaccagcag ccccctctgg tctgggaact 600

```
ggtacaatgg ctgcaggcgg tggcgctcca atggcagaca ataacgaagg cgccgacgga    660
gtgggtaatg cctcgggaaa ttggcattgc gattccacat ggctgggcga cagagtcatc    720
accaccagca cccgcacctg ggccttgccc acctacaata accacctcta caagcaaatc    780
tccagtgctt caacgggggc cagcaacgac aaccactact tcggctacag cacccccctgg   840
gggtactttg acttcaaccg cttccactgc cacttctcac cacgtgactg gcaaagactc    900
atcaacaaca actggggatt ccggcccaag agactcaact tcaagctctt caacatccag    960
gtcaaggagg tcacgcagaa tgaaggcacc aagaccatcg ccaataacct taccagcacg   1020
gttcaggtgt ttactgactc ggagtaccag ctgccgtacg ttctcggctc tgcccaccag   1080
ggctgcctgc ctccgttccc ggcggacgtg ttcatgattc cgcagtacgg ctacctaacg   1140
ctcaacaatg gcagccaggc gatgggtcgc tcgtccttct actgcctgga gtactttccg   1200
tcgcagatgc tgagaaccgg caacaacttc cagtttactt acaccttcga ggacgtgcct   1260
ttccacagca gctacgctca cagccagagt ttggatcgct tgatgaatcc tcttattgat   1320
cagtatctgt actacctgaa cagaacgcaa ggaacaacct ctggaacaac caaccaatca   1380
cggctgcttt ttagccaggc tgggcctcag tctatgtctt tgcaggccag aaattggcta   1440
cctgggccct gctaccggca acagagactt tcaaagactg ctaacgacaa caacaacagt   1500
aactttcctt ggacagcggc cagcaaatat catctcaatg gccgcgactc gctggtgaat   1560
ccaggaccag ctatggccag tcacaaggac gatgaagaaa aattttttccc tatgcacggc   1620
aatctaatat ttggcaaaga agggacaacg gcaagtaacg cagaattaga taatgtaatg   1680
attacggatg aagaagagat tcgtaccacc aatcctgtgg caacagagca gtatggaact   1740
gtggcaaata acttgcagag ctcaaataca gctcccacga ctagaactgt caatgatcag   1800
gggggccttac ctggcatggt gtggcaagat cgtgacgtgt accttcaagg acctatctgg   1860
gcaaagattc ctcacacgga tggacacttt catccttctc ctctgatggg cggctttggc   1920
ctgaaacatc ctccgcctca gatcctgatc aagaacacgc ctgtacctgc ggatcctcca   1980
acggccttca acaaggacaa gctgaactct ttcatcaccc agtattctac tggccaagtc   2040
agcgtggaga tcgagtggga gctgcagaag gaaaacagca agcgctggaa ccccgagatc   2100
cagtacacct ccaactacta caaatctaca agtgtggact ttgctgttaa tacagaaggc   2160
gtgtactctg aaccccgccc cattggcacc cgttacctca cccgtaatct gtaa         2214
```

<210> SEQ ID NO 72
<211> LENGTH: 1866
<212> TYPE: DNA
<213> ORGANISM: Artificial Sequence
<220> FEATURE:
<223> OTHER INFORMATION: Synthetic Nucleic Acid

<400> SEQUENCE: 72

```
atgccggggt tttacgagat tgtgattaag gtccccagcg accttgacga gcatctgccc     60
ggcatttctg acagctttgt gaactgggtg gccgagaagg aatgggagtt gccgccagat    120
tctgacatgg atctgaatct gattgagcag gcacccctga ccgtggccga gaagctgcag    180
cgcgactttc tgacggaatg gcgccgtgtg agtaaggccc cggaggccct tttctttgtg    240
caatttgaga agggagagag ctacttccac atgcacgtgc tcgtggaaac caccggggtg    300
aaatccatgg ttttgggacg tttcctgagt cagattcgcg aaaaactgat tcagagaatt    360
taccgcggga tcgagccgac tttgccaaac tggttcgcgg tcacaaagac cagaaatggc    420
gccggaggcg ggaacaaggt ggtggatgag tgctacatcc ccaattactt gctccccaaa    480
```

acccagcctg agctccagtg ggcgtggact aatatggaac agtatttaag cgcctgtttg 540
aatctcacgg agcgtaaacg gttggtggcg cagcatctga cgcacgtgtc gcagacgcag 600
gagcagaaca aagagaatca gaatcccaat tctgatgcgc cggtgatcag atcaaaaact 660
tcagccaggt acatggagct ggtcgggtgg ctcgtggaca aggggattac ctcggagaag 720
cagtggatcc aggaggacca ggcctcatac atctccttca atgcggcctc caactcgcgg 780
tcccaaatca aggctgcctt ggacaatgcg ggaaagatta tgagcctgac taaaaccgcc 840
cccgactacc tggtgggcca gcagcccgtg gaggacattt ccagcaatcg gatttataaa 900
attttggaac taaacgggta cgatccccaa tatgcggctt ccgtctttct gggatgggcc 960
acgaaaaagt tcggcaagag gaacaccatc tggctgtttg ggcctgcaac taccgggaag 1020
accaacatcg cggaggccat agcccacact gtgcccttct acgggtgcgt aaactggacc 1080
aatgagaact ttcccttcaa cgactgtgtc gacaagatgg tgatctggtg ggaggagggg 1140
aagatgaccg ccaaggtcgt ggagtcggcc aaagccattc tcggaggaag caaggtgcgc 1200
gtggaccaga aatgcaagtc ctcggcccag atagacccga ctcccgtgat cgtcacctcc 1260
aacaccaaca tgtgcgccgt gattgacggg aactcaacga ccttcgaaca ccagcagccg 1320
ttgcaagacc ggatgttcaa atttgaactc acccgccgtc tggatcatga ctttgggaag 1380
gtcaccaagc aggaagtcaa agactttttc cggtgggcaa aggatcacgt ggttgaggtg 1440
gagcatgaat tctacgtcaa aaagggtgga gccaagaaaa gacccgcccc cagtgacgca 1500
gatataagtg agcccaaacg ggtgcgcgag tcagttgcgc agccatcgac gtcagacgcg 1560
gaagcttcga tcaactacgc agacaggtac caaaacaaat gttctcgtca cgtgggcatg 1620
aatctgatgc tgtttccctg cagacaatgc gagagaatga atcagaattc aaatatctgc 1680
ttcactcacg gacagaaaga ctgtttagag tgctttcccg tgtcagaatc tcaacccgtt 1740
tctgtcgtca aaaaggcgta tcagaaactg tgctacattc atcatatcat gggaaaggtg 1800
ccagacgctt gcactgcctg cgatctggtc aatgtggatt tggatgactg catctttgaa 1860
caataa 1866

<210> SEQ ID NO 73
<211> LENGTH: 2208
<212> TYPE: DNA
<213> ORGANISM: Artificial Sequence
<220> FEATURE:
<223> OTHER INFORMATION: Synthetic Nucleic Acid

<400> SEQUENCE: 73
atggctgccg atggttatct tccagattgg ctcgaggaca ctctctctga aggaataaga 60
cagtggtgga agctcaaacc tggcccacca ccaccaaagc ccgcagagcg gcataaggac 120
gacagcaggg gtcttgtgct tcctgggtac aagtacctcg gacccttcaa cggactcgac 180
aagggagagc cggtcaacga ggcagacgcc gcggccctcg agcacgacaa agcctacgac 240
cggcagctcg acagcggaga caacccgtac ctcaagtaca accacgccga cgcggagttt 300
caggagcgcc ttaaagaaga tacgtctttt gggggcaacc tcggacgagc agtcttccag 360
gcgaaaaaga gggttcttga acctctgggc ctggttgagg aacctgttaa gacggctccg 420
ggaaaaaaga ggccggtaga gcactctcct gtggagccag actcctcctc gggaaccggc 480
aagacaggcc agcagcccgc taaaaagaga ctcaattttg gtcagactgg cgactcagag 540
tcagtcccag accctcaacc tctcggagaa ccaccagcag ccccctctgg tctgggaact 600
aatacgatgg ctacaggcag tggcgcacca atggcagaca ataacgaggg tgccgatgga 660
gtgggtaatt cctcaggaaa ttggcattgc gattcccaat ggctgggcga cagagtcatc 720
accaccagca cccgaacctg ggccctgccc acctacaaca accatctcta caagcaaatc 780
tccagccaat caggagcttc aaacgacaac cactactttg gctacagcac cccttggggg 840
tattttgact ttaacagatt ccactgccac ttctcaccac gtgactggca gcgactcatt 900
aacaacaact ggggattccg gcccaagaaa ctcagcttca agctcttcaa catccaagtt 960
aaagaggtca cgcagaacga tggcacgacg actattgcca ataaccttac cagcacggtt 1020
caagtgttta ctgactcgga gtaccagctc ccgtacgtcc tcggctcggc gcatcaagga 1080
tgcctcccgc cgttcccagc agacgtcttc atggtgccac agtatggata cctcaccctg 1140
aacaacggga gtcaggcagt aggacgctct tcattttact gcctggagta ctttccttct 1200
cagatgctgc gtaccggaaa caactttacc ttcagctaca cttttgagga cgttcctttc 1260
cacagcagct acgctcacag ccagagtctg gaccgtctca tgaatcctct catcgaccag 1320
tacctgtatt acttgagcag aacaaacact ccaagtggaa ccaccacgca gtcaaggctt 1380
cagttttctc aggccggagc gagtgacatt cgggaccagt ctaggaactg gcttcctgga 1440
ccctgttacc gccagcagcg agtatcaaag acatctgcgg ataacaacaa cagtgaatac 1500
tcgtgggctg gagctaccaa gtaccacctc aatggcagag actctctggt gaatccgggc 1560
ccggccatgg caagccacaa ggacgatgaa gaaaagtttt ttcctcagag cggggttctc 1620
atctttggga agcaaggctc agagaaaaca aatgtggaca ttgaaaaggt catgattaca 1680
gacgaagagg aaatcaggac aaccaatccc gtggctacgg agcagtatgg ttctgtatct 1740
accaacctcc agagaggcaa cagacaagca gctaccgcag atgtcgacac acaaggcgtt 1800
cttccaggca tggtatggca ggacagagat gtgtaccttc agggacccat ctgggcaaag 1860
attccacaca cggacggaca ttttcacccc tctcccctca tgggtggatt cggacttaaa 1920
caccctcctc cacagattct catcaagaac accccggtac ctgcgaatcc ttcgaccacc 1980
ttcagtgcgg caaagtttgc ttccttcatc acacagtact caacgggaca ggtcagcgtg 2040
gagatcgagt gggagctgca gaaggaaaac agcaaacgct ggaatcccga aattcagtac 2100
acttccaact acaacaagtc tgttaatgtg gactttactg tggacactaa tggcgtgtat 2160
tcagagcctc gccccattgg caccagatac ctgactcgta atctgtaa 2208

<210> SEQ ID NO 74
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 74
atgatttaaa tcaggt 16

<210> SEQ ID NO 75
<211> LENGTH: 5336
<212> TYPE: DNA
<213> ORGANISM: Artificial Sequence
<220> FEATURE:
<223> OTHER INFORMATION: Synthetic Nucleic Acid

<400> SEQUENCE: 75
ggtacccaac tccatgctta acagtcccca ggtacagccc accctgcgtc gcaaccagga 60
acagctctac agcttcctgg agcgccactc gccctacttc cgcagccaca gtgcgcagat 120

```
taggagcgcc acttcttttt gtcacttgaa aaacatgtaa aaataatgta ctaggagaca    180
ctttcaataa aggcaaatgt ttttatttgt acactctcgg gtgattattt accccccacc    240
cttgccgtct gcgccgttta aaaatcaaag ggttctgcc gcgcatcgct atgcgccact    300
ggcagggaca cgttgcgata ctggtgttta gtgctccact taaactcagg cacaaccatc    360
cgcggcagct cggtgaagtt ttcactccac aggctgcgca ccatcaccaa cgcgtttagc    420
aggtcgggcg ccgatatctt gaagtcgcag ttggggcctc cgccctgcgc gcgcgagttg    480
cgatacacag ggttgcagca ctggaacact atcagcgccg ggtggtgcac gctggccagc    540
acgctcttgt cggagatcag atccgcgtcc aggtcctccg cgttgctcag ggcgaacgga    600
gtcaactttg gtagctgcct tcccaaaaag ggtgcatgcc caggctttga gttgcactcg    660
caccgtagtg gcatcagaag gtgaccgtgc ccggtctggg cgttaggata cagcgcctgc    720
atgaaagcct tgatctgctt aaaagccacc tgagcctttg cgccttcaga gaagaacatg    780
ccgcaagact tgccggaaaa ctgattggcc ggacaggccg cgtcatgcac gcagcacctt    840
gcgtcggtgt tggagatctg caccacattt cggccccacc ggttcttcac gatcttggcc    900
ttgctagact gctccttcag cgcgcgctgc ccgttttcgc tcgtcacatc catttcaatc    960
acgtgctcct tatttatcat aatgctcccg tgtagacact taagctcgcc ttcgatctca   1020
gcgcagcggt gcagccacaa cgcgcagccc gtgggctcgt ggtgcttgta ggttacctct   1080
gcaaacgact gcaggtacgc ctgcaggaat cgccccatca tcgtcacaaa ggtcttgttg   1140
ctggtgaagg tcagctgcaa cccgcggtgc tcctcgttta gccaggtctt gcatacggcc   1200
gccagagctt ccacttggtc aggcagtagc ttgaagtttg cctttagatc gttatccacg   1260
tggtacttgt ccatcaacgc gcgcgcagcc tccatgccct tctcccacgc agacacgatc   1320
ggcaggctca gcgggtttat caccgtgctt tcactttccg cttcactgga ctcttccttt   1380
tcctcttgcg tccgcatacc ccgcgccact gggtcgtctt cattcagccg ccgcaccgtg   1440
cgcttacctc ccttgccgtg cttgattagc accggtgggt tgctgaaacc caccatttgt   1500
agcgccacat cttctctttc ttcctcgctg tccacgatca cctctgggga tggcgggcgc   1560
tcgggcttgg gagaggggcg cttctttttc tttttggacg caatggccaa atccgccgtc   1620
gaggtcgatg gccgcgggct gggtgtgcgc ggcaccagcg catcttgtga cgagtcttct   1680
tcgtcctcgg actcgagacg ccgcctcagc cgcttttttg ggggcgcgcg gggaggcggc   1740
ggcgacggcg acggggacga cacgtcctcc atggttggtg gacgtcgcgc cgcaccgcgt   1800
ccgcgctcgg gggtggtttc gcgctgctcc tcttcccgac tggccatttc cttctcctat   1860
aggcagaaaa agatcatgga gtcagtcgag aaggaggaca gcctaaccgc cccctttgag   1920
ttcgccacca ccgcctccac cgatgccgcc aacgcgccta ccaccttccc cgtcgaggca   1980
cccccgcttg aggaggagga agtgattatc gagcaggacc caggttttgt aagcgaagac   2040
gacgaggatc gctcagtacc aacagaggat aaaaagcaag accaggacga cgcagaggca   2100
aacgaggaac aagtcgggcg gggggaccaa aggcatggcg actacctaga tgtgggagac   2160
gacgtgctgt tgaagcatct gcagcgccag tgcgccatta tctgcgacgc gttgcaagag   2220
cgcagcgatg tgcccctcgc catagcggat gtcagccttg cctacgaacg ccacctgttc   2280
tcaccgcgcg taccccccaa acgccaagaa aacggcacat gcgagcccaa cccgcgcctc   2340
aacttctacc ccgtatttgc cgtgccagag gtgcttgcca cctatcacat ctttttccaa   2400
aactgcaaga taccccctatc ctgccgtgcc aaccgcagcc gagcggacaa gcagctggcc   2460
```

ttgcggcagg gcgctgtcat acctgatatc gcctcgctcg acgaagtgcc aaaaatcttt 2520
gagggtcttg gacgcgacga gaaacgcgcg gcaaacgctc tgcaacaaga aaacagcgaa 2580
aatgaaagtc actgtggagt gctggtggaa cttgagggtg acaacgcgcg cctagccgtg 2640
ctgaaacgca gcatcgaggt cacccacttt gcctacccgg cacttaacct accccccaag 2700
gttatgagca cagtcatgag cgagctgatc gtgcgccgtg cacgacccct ggagagggat 2760
gcaaacttgc aagaacaaac cgaggagggc ctacccgcag ttggcgatga gcagctggcg 2820
cgctggcttg agacgcgcga gcctgccgac ttggaggagc gacgcaagct aatgatggcc 2880
gcagtgcttg ttaccgtgga gcttgagtgc atgcagcggt tctttgctga cccggagatg 2940
cagcgcaagc tagaggaaac gttgcactac acctttcgcc agggctacgt gcgccaggcc 3000
tgcaaaattt ccaacgtgga gctctgcaac ctggtctcct accttggaat tttgcacgaa 3060
aaccgcctcg ggcaaaacgt gcttcattcc acgctcaagg gcgaggcgcg ccgcgactac 3120
gtccgcgact gcgtttactt atttctgtgc tacacctggc aaacggccat gggcgtgtgg 3180
cagcaatgcc tggaggagcg caacctaaag gagctgcaga agctgctaaa gcaaaacttg 3240
aaggacctat ggacggcctt caacgagcgc tccgtggccg cgcacctggc ggacattatc 3300
ttccccgaac gcctgcttaa aaccctgcaa cagggtctgc cagacttcac cagtcaaagc 3360
atgttgcaaa actttaggaa ctttatccta gagcgttcag gaattctgcc cgccacctgc 3420
tgtgcgcttc ctagcgactt tgtgcccatt aagtaccgtg aatgccctcc gccgctttgg 3480
ggtcactgct accttctgca gctagccaac taccttgcct accactccga catcatggaa 3540
gacgtgagcg gtgacggcct actggagtgt cactgtcgct gcaacctatg caccccgcac 3600
cgctccctgg tctgcaattc gcaactgctt agcgaaagtc aaattatcgg tacctttgag 3660
ctgcagggtc cctcgcctga cgaaaagtcc gcggctccgg ggttgaaact cactccgggg 3720
ctgtggacgt cggcttacct tcgcaaattt gtacctgagg actaccacgc ccacgagatt 3780
aggttctacg aagaccaatc ccgcccgcca aatgcggagc ttaccgcctg cgtcattacc 3840
cagggccaca tccttggcca attgcaagcc atcaacaaag cccgccaaga gtttctgcta 3900
cgaaagggac gggggggttta cctggacccc cagtccggcg aggagctcaa cccaatcccc 3960
ccgccgccgc agccctatca gcagccgcgg gcccttgctt cccaggatgg cacccaaaaa 4020
gaagctgcag ctgccgccgc cgccacccac ggacgaggag gaatactggg acagtcaggc 4080
agaggaggtt ttggacgagg aggaggagat gatggaagac tgggacagcc tagacgaagc 4140
ttccgaggcc gaagaggtgt cagacgaaac accgtcaccc tcggtcgcat tcccctcgcc 4200
ggcgccccag aaattggcaa ccgttcccag catcgctaca acctccgctc ctcaggcgcc 4260
gccggcactg cctgttcgcc gacccaaccg tagatgggac accactggaa ccagggccgg 4320
taagtctaag cagccgccgc cgttagccca agagcaacaa cagcgccaag gctaccgctc 4380
gtggcgcggg cacaagaacg ccatagttgc ttgcttgcaa gactgtgggg gcaacatctc 4440
cttcgcccgc cgctttcttc tctaccatca cggcgtggcc ttcccccgta acatcctgca 4500
ttactaccgt catctctaca gcccctactg caccggcggc agcggcagcg gcagcaacag 4560
cagcggtcac acagaagcaa aggcgaccgg atagcaagac tctgacaaag cccaagaaat 4620
ccacagcggc ggcagcagca ggaggaggag cgctgcgtct ggcgcccaac gaacccgtat 4680
cgacccgcga gcttagaaat aggatttttc ccactctgta tgctatattt caacaaagca 4740
ggggccaaga acaagagctg aaaataaaaa acaggtctct gcgctccctc acccgcagct 4800
gcctgtatca caaaagcgaa gatcagcttc ggcgcacgct ggaagacgcg gaggctctct 4860
tcagcaaata ctgcgcgctg actcttaagg actagtttcg cgccctttct caaatttaag 4920
cgcgaaaact acgtcatctc cagcggccac acccggcgcc agcacctgtc gtcagcgcca 4980
ttatgagcaa ggaaattccc acgccctaca tgtggagtta ccagccacaa atgggacttg 5040
cggctggagc tgcccaagac tactcaaccc gaataaacta catgagcgcg ggaccccaca 5100
tgatatcccg ggtcaacgga atccgcgccc accgaaaccg aattctcctc gaacaggcgg 5160
ctattaccac cacacctcgt aataacctta atccccgtag ttggcccgct gccctggtgt 5220
accaggaaag tcccgctccc accactgtgg tacttcccag agacgcccag gccgaagttc 5280
agatgactaa ctcaggggcg cagcttgcgg gcggctttcg tcacagggtg cggtcg 5336

<210> SEQ ID NO 76
<211> LENGTH: 3944
<212> TYPE: DNA
<213> ORGANISM: Artificial Sequence
<220> FEATURE:
<223> OTHER INFORMATION: Synthetic Nucleic Acid

<400> SEQUENCE: 76
cccgggcgtt ttagggcgga gtaacttgca tgtattggga attgtagttt ttttaaaatg 60
ggaagtgacg tatcgtggga aaacggaagt gaagatttga ggaagttgtg ggtttttttgg 120 ctttcgtttc tgggcgtagg ttcgcgtgcg gttttctggg tgtttttttgt ggactttaac 180 cgttacgtca tttttttagtc ctatatatac tcgctctgta cttggccctt tttacactgt 240
gactgattga gctggtgccg tgtcgagtgg tgttttttaa taggtttttt tactggtaag 300
gctgactgtt atggctgccg ctgtggaagc gctgtatgtt gttctggagc gggagggtgc 360
tattttgcct aggcaggagg gtttttcagg tgtttatgtg tttttctctc ctattaattt 420
tgttatacct cctatggggg ctgtaatgtt gtctctacgc ctgcgggtat gtattccccc 480
gggctatttc ggtcgctttt tagcactgac cgatgttaac caacctgatg tgtttaccga 540
gtcttacatt atgactccgg acatgaccga ggaactgtcg gtggtgcttt ttaatcacgg 600
tgaccagttt ttttacggtc acgccggcat ggccgtagtc cgtcttatgc ttataagggt 660
tgtttttcct gttgtaagac aggcttctaa tgtttaaatg tttttttttt tgttatttta 720
ttttgtgttt aatgcaggaa cccgcagaca tgtttgagag aaaaatggtg tctttttctg 780
tggtggttcc ggaacttacc tgcctttatc tgcatgagca tgactacgat gtgcttgctt 840
ttttgcgcga ggctttgcct gattttttga gcagcacctt gcattttata tcgccgccca 900
tgcaacaagc ttacataggg gctacgctgg ttagcatagc tccgagtatg cgtgtcataa 960
tcagtgtggg ttcttttgtc atggttcctg gcggggaagt ggccgcgctg gtccgtgcag 1020
acctgcacga ttatgttcag ctggccctgc gaagggacct acgggatcgc ggtatttttg 1080
ttaatgttcc gcttttgaat cttatacagg tctgtgagga acctgaattt ttgcaatcat 1140
gattcgctgc ttgaggctga aggtggaggg cgctctggag cagattttta caatggccgg 1200
acttaatatt cgggatttgc ttagagacat attgataagg tggcgagatg aaaattattt 1260
gggcatggtt gaaggtgctg gaatgtttat agaggagatt caccctgaag ggtttagcct 1320
ttacgtccac ttggacgtga gggcagtttg ccttttggaa gccattgtgc aacatcttac 1380
aaatgccatt atctgttctt tggctgtaga gtttgaccac gccaccggag gggagcgcgt 1440
tcacttaata gatcttcatt ttgaggtttt ggataatctt ttggaataaa aaaaaaaaaa 1500
catggttctt ccagctcttc ccgctcctcc cgtgtgtgac tcgcagaacg aatgtgtagg 1560

-continued

```
ttggctgggt gtggcttatt ctgcggtggt ggatgttatc agggcagcgg cgcatgaagg   1620
agtttacata gaacccgaag ccagggggcg cctggatgct ttgagagagt ggatatacta   1680
caactactac acagagcgag ctaagcgacg agaccggaga cgcagatctg tttgtcacgc   1740
ccgcacctgg ttttgcttca ggaaatatga ctacgtccgg cgttccattt ggcatgacac   1800
tacgaccaac acgatctcgg ttgtctcggc gcactccgta cagtagggat cgcctacctc   1860
cttttgagac agagacccgc gctaccatac tggaggatca tccgctgctg cccgaatgta   1920
acactttgac aatgcacaac gtgagttacg tgcgaggtct tccctgcagt gtgggattta   1980
cgctgattca ggaatgggtt gttccctggg atatggttct gacgcgggag gagcttgtaa   2040
tcctgaggaa gtgtatgcac gtgtgcctgt gttgtgccaa cattgatatc atgacgagca   2100
tgatgatcca tggttacgag tcctgggctc tccactgtca ttgttccagt cccggttccc   2160
tgcagtgcat agccggcggg caggttttgg ccagctggtt taggatggtg gtggatggcg   2220
ccatgtttaa tcagaggttt atatggtacc gggaggtggt gaattacaac atgccaaaag   2280
aggtaatgtt tatgtccagc gtgtttatga ggggtcgcca cttaatctac ctgcgcttgt   2340
ggtatgatgg ccacgtgggt tctgtggtcc ccgccatgag ctttggatac agcgccttgc   2400
actgtgggat tttgaacaat attgtggtgc tgtgctgcag ttactgtgct gatttaagtg   2460
agatcagggt gcgctgctgt gcccggagga caaggcgtct catgctgcgg gcggtgcgaa   2520
tcatcgctga ggagaccact gccatgttgt attcctgcag gacggagcgg cggcggcagc   2580
agtttattcg cgcgctgctg cagcaccacc gccctatcct gatgcacgat tatgactcta   2640
cccccatgta ggcgtggact tccccttcgc cgcccgttga gcaaccgcaa gttggacagc   2700
agcctgtggc tcagcagctg gacagcgaca tgaacttaag cgagctgccc ggggagttta   2760
ttaatatcac tgatgagcgt ttggctcgac aggaaaccgt gtggaatata acacctaaga   2820
atatgtctgt tacccatgat atgatgcttt ttaaggccag ccggggagaa aggactgtgt   2880
actctgtgtg ttgggaggga ggtggcaggt tgaatactag ggttctgtga gtttgattaa   2940
ggtacggtga tcaatataag ctatgtggtg gtggggctat actactgaat gaaaaatgac   3000
ttgaaatttt ctgcaattga aaaataaaca cgttgaaaca taacatgcaa caggttcacg   3060
attctttatt cctgggcaat gtaggagaag gtgtaagagt tggtagcaaa agtttcagtg   3120
gtgtattttc cactttccca ggaccatgta aaagacatag agtaagtgct tacctcgcta   3180
gtttctgtgg attcactaga atcgatgtag gatgttgccc ctcctgacgc ggtaggagaa   3240
ggggagggtg ccctgcatgt ctgccgctgc tcttgctctt gccgctgctg aggagggggg   3300
cgcatctgcc gcagcaccgg atgcatctgg gaaaagcaaa aaaggggctc gtccctgttt   3360
ccggaggaat ttgcaagcgg ggtcttgcat gacggggagg caaacccccg ttcgccgcag   3420
tccggccggc ccgagactcg aaccgggggt cctgcgactc aacccttgga aaataaccct   3480
ccggctacag ggagcgagcc acttaatgct ttcgctttcc agcctaaccg cttacgccgc   3540
gcgcggccag tggccaaaaa agctagcgca gcagccgccg cgcctggaag gaagccaaaa   3600
ggagcgctcc cccgttgtct gacgtcgcac acctgggttc gacacgcggg cggtaaccgc   3660
atggatcacg gcggacggcc ggatccgggg ttcgaacccc ggtcgtccgc catgataccc   3720
ttgcgaattt atccaccaga ccacggaaga gtgcccgctt acaggctctc cttttgcacg   3780
gtctagagcg tcaacgactg cgcacgcctc accggccaga gcgtcccgac catggagcac   3840
tttttgccgc tgcgcaacat ctggaaccgc gtccgcgact ttccgcgcgc ctccaccacc   3900
gccgccggca tcacctggat gtccaggtac atctacggat tacg                    3944
```

<210> SEQ ID NO 77
<211> LENGTH: 77
<212> TYPE: DNA
<213> ORGANISM: Artificial Sequence
<220> FEATURE:
<223> OTHER INFORMATION: Synthetic Nucleic Acid

<400> SEQUENCE: 77
cccagggatg tacgtcccta acccgctagg gggcagcacc caggcctgca ctgccgcctg 60
ccggcagggg tccagtc 77

<210> SEQ ID NO 78
<211> LENGTH: 77
<212> TYPE: DNA
<213> ORGANISM: Artificial Sequence
<220> FEATURE:
<223> OTHER INFORMATION: Synthetic Nucleic Acid

<400> SEQUENCE: 78
gactggaccc ctgccggcag gcggcagtgc aggcctgggt gctgccccct agcgggttag 60
ggacgtacat ccctggg 77

<210> SEQ ID NO 79
<211> LENGTH: 190
<212> TYPE: DNA
<213> ORGANISM: Artificial Sequence
<220> FEATURE:
<223> OTHER INFORMATION: Synthetic Nucleic Acid

<400> SEQUENCE: 79
gtgcgggcca ggcccccgag ggccttatcg gccccagagg cgcttgctgt cgggccgggc 60
gctcccggca cgggcgggcg gaggggtggc gcccgcctgg ggaccgcaga ttacaagagc 120
acctcctccc ccaaccccag gaggccccgc tccccaggcc tcggccggcg cggacccctg 180
gttgccccgg 190

<210> SEQ ID NO 80
<211> LENGTH: 190
<212> TYPE: DNA
<213> ORGANISM: Artificial Sequence
<220> FEATURE:
<223> OTHER INFORMATION: Synthetic Nucleic Acid

<400> SEQUENCE: 80
ccggggcaac caggggtccg cgccggccga ggcctgggga gcggggcctc ctggggttgg 60
gggaggaggt gctcttgtaa tctgcggtcc ccaggcgggc gccacccctc cgcccgcccg 120
tgccgggagc gcccggcccg acagcaagcg cctctggggc cgataaggcc ctcgggggcc 180
tggcccgcac 190

<210> SEQ ID NO 81
<211> LENGTH: 353
<212> TYPE: PRT
<213> ORGANISM: Artificial Sequence
<220> FEATURE:
<223> OTHER INFORMATION: Synthetic Nucleic Acid

<400> SEQUENCE: 81

Leu Phe Asn Leu Arg Ile Leu Leu Asn Asn Ala Ala Phe Arg Asn Gly
1 5 10 15

His Asn Phe Met Val Arg Asn Phe Arg Cys Gly Gln Pro Leu Gln Asn

```
            20                  25                  30

Lys Val Gln Leu Lys Gly Arg Asp Leu Leu Thr Leu Lys Asn Phe Thr
        35                  40                  45

Gly Glu Glu Ile Lys Tyr Met Leu Trp Leu Ser Ala Asp Leu Lys Phe
    50                  55                  60

Arg Ile Lys Gln Lys Gly Glu Tyr Leu Pro Leu Leu Gln Gly Lys Ser
65                  70                  75                  80

Leu Gly Met Ile Phe Glu Lys Arg Ser Thr Arg Thr Arg Leu Ser Thr
                85                  90                  95

Glu Thr Gly Phe Ala Leu Leu Gly Gly His Pro Cys Phe Leu Thr Thr
            100                 105                 110

Gln Asp Ile His Leu Gly Val Asn Glu Ser Leu Thr Asp Thr Ala Arg
        115                 120                 125

Val Leu Ser Ser Met Ala Asp Ala Val Leu Ala Arg Val Tyr Lys Gln
    130                 135                 140

Ser Asp Leu Asp Thr Leu Ala Lys Glu Ala Ser Ile Pro Ile Ile Asn
145                 150                 155                 160

Gly Leu Ser Asp Leu Tyr His Pro Ile Gln Ile Leu Ala Asp Tyr Leu
                165                 170                 175

Thr Leu Gln Glu His Tyr Ser Ser Leu Lys Gly Leu Thr Leu Ser Trp
            180                 185                 190

Ile Gly Asp Gly Asn Asn Ile Leu His Ser Ile Met Met Ser Ala Ala
        195                 200                 205

Lys Phe Gly Met His Leu Gln Ala Ala Thr Pro Lys Gly Tyr Glu Pro
    210                 215                 220

Asp Ala Ser Val Thr Lys Leu Ala Glu Gln Tyr Ala Lys Glu Asn Gly
225                 230                 235                 240

Thr Lys Leu Leu Leu Thr Asn Asp Pro Leu Glu Ala Ala His Gly Gly
                245                 250                 255

Asn Val Leu Ile Thr Asp Thr Trp Ile Ser Met Gly Gln Glu Glu Glu
            260                 265                 270

Lys Lys Lys Arg Leu Gln Ala Phe Gln Gly Tyr Gln Val Thr Met Lys
        275                 280                 285

Thr Ala Lys Val Ala Ala Ser Asp Trp Thr Phe Leu His Cys Leu Pro
    290                 295                 300

Arg Lys Pro Glu Glu Val Asp Asp Glu Val Phe Tyr Ser Pro Arg Ser
305                 310                 315                 320

Leu Val Phe Pro Glu Ala Glu Asn Arg Lys Trp Thr Ile Met Ala Val
                325                 330                 335

Met Val Ser Leu Leu Thr Asp Tyr Ser Pro Gln Leu Gln Lys Pro Lys
            340                 345                 350

Phe
```

<210> SEQ ID NO 82
<211> LENGTH: 1059
<212> TYPE: DNA
<213> ORGANISM: Artificial Sequence
<220> FEATURE:
<223> OTHER INFORMATION: Synthetic Nucleic Acid

<400> SEQUENCE: 82

```
ctgttcaacc tgcgcatcct gctgaacaac gccgccttca gaaacggcca caacttcatg      60

gttcgaaact tcagatgcgg ccagcctctc cagaacaagg tgcagctgaa aggcagggac     120

ctgctgaccc tgaagaactt caccggcgaa gagatcaagt acatgctgtg gctgtccgcc     180
```

```
gacctgaagt tcagaatcaa gcagaagggc gagtacctgc ctctgctcca gggaaagtct    240

ctgggcatga tcttcgagaa gcggagcacc agaaccagac tgagcaccga gacaggcttt    300

gccctgctcg gaggacaccc ctgctttctg acaacccagg acatccacct gggcgtgaac    360

gagagcctga ccgatacagc cagagtgctg tcctctatgg ccgatgccgt gctggctaga    420

gtgtataagc agagcgacct ggacaccctg gctaaagagg ccagcattcc catcatcaac    480

ggcctgtccg acctgtatca ccccatccag atcctggccg actacctgac actgcaagag    540

cactacagca gcctgaaggg actgaccctg tcttggatcg gcgacggcaa caacatcctg    600

cacagcatta tgatgagcgc cgccaagttc ggaatgcacc tccaggccgc tacacccaag    660

ggctatgaac ctgatgccag cgtgacaaag ctggccgagc agtacgccaa agagaacggc    720

acaaagctgc tgctgaccaa cgatcccctg gaagctgctc acggcggcaa tgtgctgatc    780

accgatacct ggatcagcat gggccaagag gaagagaaga agaagcggct gcaagccttc    840

cagggctacc aagtgaccat gaagacagcc aaggtggccg ccagcgattg gacctttctg    900

cactgcctgc ctcggaagcc tgaagaggtg gacgacgagg tgttctacag ccctagaagc    960

ctggtgttcc ccgaggccga gaacagaaag tggaccatca tggctgtgat ggtgtctctg   1020

ctgaccgact actcccctca gctccagaag cctaagttc                          1059
```

<210> SEQ ID NO 83
<211> LENGTH: 1059
<212> TYPE: DNA
<213> ORGANISM: Artificial Sequence
<220> FEATURE:
<223> OTHER INFORMATION: Synthetic Nucleic Acid

<400> SEQUENCE: 83

```
ctgttcaacc tgcgaatcct gctgaacaat gccgcttttc ggaacgggca caatttcatg     60

gtgaggaact ttcgctgcgg acagcccctc cagaacaagg tccagctgaa gggcagggac    120

ctgctgaccc tgaaaaattt cacaggggag gaaatcaagt acatgctgtg gctgtcagcc    180

gatctgaagt tccggatcaa gcagaagggc gaatatctgc ctctgctcca gggcaaaagc    240

ctggggatga tcttcgaaaa gcgcagtact cggaccagac tgtcaacaga gactggattc    300

gcactgctgg gaggacaccc atgttttctg accacacagg acattcatct gggagtgaac    360

gagtccctga ccgacacagc acgcgtcctg agctccatgg ctgatgcagt gctggctcga    420

gtctacaaac agtctgacct ggataccctg gccaaggaag cttctatccc aatcattaat    480

ggcctgagtg acctgtatca ccccatccag attctggccg attacctgac cctccaggag    540

cattattcta gtctgaaagg gctgacactg agctggattg gggacggaaa caatatcctg    600

cactccatta tgatgagcgc cgccaagttt ggaatgcacc tccaggctgc aaccccaaaa    660

ggctacgaac ccgatgcctc cgtgacaaag ctggcagaac agtatgccaa agagaacggc    720

actaagctgc tgctcaccaa tgaccctctg gaggccgctc acggaggcaa cgtgctgatc    780

actgatacct ggattagtat gggacaggag gaagagaaga agaagcggct ccaggccttc    840

cagggctacc aggtgacaat gaaaactgct aaggtcgcag ccagcgactg gacctttctg    900

cattgcctgc ccagaaagcc tgaagaggtg gacgatgagg tcttctactc acccagaagc    960

ctggtgtttc ctgaagctga gaataggaag tggacaatca tggcagtgat ggtcagcctg   1020

ctgactgatt attcccctca gctccagaaa ccaaagttc                          1059
```

<210> SEQ ID NO 84

<211> LENGTH: 394
<212> TYPE: PRT
<213> ORGANISM: Artificial Sequence
<220> FEATURE:
<223> OTHER INFORMATION: Synthetic Nucleic Acid

<400> SEQUENCE: 84

Gly Val Gln Val Glu Thr Ile Ser Pro Gly Asp Gly Arg Thr Phe Pro
1 5 10 15

Lys Arg Gly Gln Thr Cys Val Val His Tyr Thr Gly Met Leu Glu Asp
20 25 30

Gly Lys Lys Val Asp Ser Ser Arg Asp Arg Asn Lys Pro Phe Lys Phe
35 40 45

Met Leu Gly Lys Gln Glu Val Ile Arg Gly Trp Glu Glu Gly Val Ala
50 55 60

Gln Met Ser Val Gly Gln Arg Ala Lys Leu Thr Ile Ser Pro Asp Tyr
65 70 75 80

Ala Tyr Gly Ala Thr Gly His Pro Gly Ile Ile Pro Pro His Ala Thr
85 90 95

Leu Val Phe Asp Val Glu Leu Leu Lys Leu Glu Gly Gly Gly Gly Ser
100 105 110

Gly Phe Gly Asp Val Gly Ala Leu Glu Ser Leu Arg Gly Asn Ala Asp
115 120 125

Leu Ala Tyr Ile Leu Ser Met Glu Pro Cys Gly His Cys Leu Ile Ile
130 135 140

Asn Asn Val Asn Phe Cys Arg Glu Ser Gly Leu Arg Thr Arg Thr Gly
145 150 155 160

Ser Asn Ile Asp Cys Glu Lys Leu Arg Arg Arg Phe Ser Ser Leu His
165 170 175

Phe Met Val Glu Val Lys Gly Asp Leu Thr Ala Lys Lys Met Val Leu
180 185 190

Ala Leu Leu Glu Leu Ala Gln Gln Asp His Gly Ala Leu Asp Cys Cys
195 200 205

Val Val Val Ile Leu Ser His Gly Cys Gln Ala Ser His Leu Gln Phe
210 215 220

Pro Gly Ala Val Tyr Gly Thr Asp Gly Cys Pro Val Ser Val Glu Lys
225 230 235 240

Ile Val Asn Ile Phe Asn Gly Thr Ser Cys Pro Ser Leu Gly Gly Lys
245 250 255

Pro Lys Leu Phe Phe Ile Gln Ala Cys Gly Gly Glu Gln Lys Asp His
260 265 270

Gly Phe Glu Val Ala Ser Thr Ser Pro Glu Asp Glu Ser Pro Gly Ser
275 280 285

Asn Pro Glu Pro Asp Ala Thr Pro Phe Gln Glu Gly Leu Arg Thr Phe
290 295 300

Asp Gln Leu Asp Ala Ile Ser Ser Leu Pro Thr Pro Ser Asp Ile Phe
305 310 315 320

Val Ser Tyr Ser Thr Phe Pro Gly Phe Val Ser Trp Arg Asp Pro Lys
325 330 335

Ser Gly Ser Trp Tyr Val Glu Thr Leu Asp Asp Ile Phe Glu Gln Trp
340 345 350

Ala His Ser Glu Asp Leu Gln Ser Leu Leu Leu Arg Val Ala Asn Ala
355 360 365

Val Ser Val Lys Gly Ile Tyr Lys Gln Met Pro Gly Cys Phe Asn Phe
370 375 380

Leu Arg Lys Lys Leu Phe Phe Lys Thr Ser
385 390

<210> SEQ ID NO 85
<211> LENGTH: 1182
<212> TYPE: DNA
<213> ORGANISM: Artificial Sequence
<220> FEATURE:
<223> OTHER INFORMATION: Synthetic Nucleic Acid

<400> SEQUENCE: 85
ggggtccagg tggaaacaat ctctccgggg gatgggcgga cattccctaa aaggggccag 60
acctgcgtgg tgcattacac cggcatgctg gaagatggca agaaggtgga cagcagccgg 120
gacagaaaca agcccttcaa gttcatgctg ggcaagcaag aagtgatcag aggctgggaa 180
gagggcgtcg cccagatgtc tgttggacag agagccaagc tgacaatcag ccccgattac 240
gcctatggcg ccacaggaca ccctggcatc attcctccac atgccacact ggtgttcgac 300
gtggaactgc tgaagctgga aggcggcgga ggatctggct ttggagatgt gggagccctg 360
gaaagcctga gaggcaatgc cgatctggcc tacatcctga gcatggaacc ttgcggccac 420
tgcctgatta tcaacaacgt gaacttctgt agagagagcg gcctgcggac cagaaccggc 480
agcaatatcg attgcgagaa gctgcggcgg agattcagca gcctgcactt catggtggaa 540
gtgaagggcg acctgaccgc caagaaaatg gtgctggctc tgctggaact ggcccagcaa 600
gatcatggcg ccctggattg ctgtgtggtc gtgatcctgt ctcacggctg tcaggccagc 660
caccttcaat tccctggcgc cgtgtatggc acagatggct gtcctgtgtc cgtggaaaag 720
atcgtgaaca tcttcaacgg caccagctgt cctagcctcg gcggaaagcc caagctgttc 780
ttcatccaag cctgtggcgg cgagcagaag gatcacggat ttgaggtggc cagcacaagc 840
cccgaggatg agtctcctgg aagcaaccct gagcctgacg ccacaccttt ccaagagggc 900
ctgagaacct tcgaccagct ggacgctatc agctccctgc ctacacctag cgacatcttc 960
gtgtcctaca gcacattccc cggctttgtg tcttggcggg accctaagtc tggctcttgg 1020
tacgtggaaa ccctggacga catctttgag cagtgggctc acagcgagga cctccagtct 1080
ctgctgctga gagtggccaa tgccgtgtcc gtgaagggca tctacaagca gatgcctggc 1140
tgcttcaact tcctgcggaa gaagctgttt ttcaagacca gc 1182

<210> SEQ ID NO 86
<211> LENGTH: 309
<212> TYPE: DNA
<213> ORGANISM: Artificial Sequence
<220> FEATURE:
<223> OTHER INFORMATION: Synthetic Nucleic Acid

<400> SEQUENCE: 86
gatatctata acaagaaaat atatatataa taagttatca cgtaagtaga acatgaaata 60
acaatataat tatcgtatga gttaaatctt aaaagtcacg taaaagataa tcatgcgtca 120
ttttgactca cgcggtcgtt atagttcaaa atcagtgaca cttaccgcat tgacaagcac 180
gcctcacggg agctccaagc ggcgactgag atgtcctaaa tgcacagcga cggattcgcg 240
ctatttagaa agagagagca atatttcaag aatgcatgcg tcaattttac gcagactatc 300
tttctaggg 309

<210> SEQ ID NO 87
<211> LENGTH: 35

<212> TYPE: DNA
<213> ORGANISM: Artificial Sequence
<220> FEATURE:
<223> OTHER INFORMATION: Synthetic Nucleic Acid

<400> SEQUENCE: 87
ccctagaaag atagtctgcg taaaattgac gcatg 35

<210> SEQ ID NO 88
<211> LENGTH: 63
<212> TYPE: DNA
<213> ORGANISM: Artificial Sequence
<220> FEATURE:
<223> OTHER INFORMATION: Synthetic Nucleic Acid

<400> SEQUENCE: 88
ccctagaaag ataatcatat tgtgacgtac gttaaagata atcatgcgta aaattgacgc 60
atg 63

<210> SEQ ID NO 89
<211> LENGTH: 64
<212> TYPE: DNA
<213> ORGANISM: Artificial Sequence
<220> FEATURE:
<223> OTHER INFORMATION: Synthetic Nucleic Acid

<400> SEQUENCE: 89
ccctagaaag ataatcatat tgtgacgtac gttaaagata atcatgcgta aaattgacgc 60
atgc 64

<210> SEQ ID NO 90
<211> LENGTH: 237
<212> TYPE: DNA
<213> ORGANISM: Artificial Sequence
<220> FEATURE:
<223> OTHER INFORMATION: Synthetic Nucleic Acid

<400> SEQUENCE: 90
ccctagaaag ataatcatat tgtgacgtac gttaaagata atcatgtgta aaattgacgc 60
atgtgtttta tcggtctgta tatcgaggtt tatttattaa tttgaataga tattaagttt 120
tattatattt acacttacat actaataata aattcaacaa acaatttatt tatgtttatt 180
tatttattaa aaaaaacaaa aactcaaaat ttcttctata aagtaacaaa actttta 237

<210> SEQ ID NO 91
<211> LENGTH: 94
<212> TYPE: DNA
<213> ORGANISM: Artificial Sequence
<220> FEATURE:
<223> OTHER INFORMATION: Synthetic Nucleic Acid

<400> SEQUENCE: 91
ggtaccgtgc acgtcgactc tagacgcgta gaggggcgga agggacgtta ggagggaggc 60
agggaggcag ggaggcaggg aggaacggag ggag 94

<210> SEQ ID NO 92
<211> LENGTH: 94
<212> TYPE: DNA
<213> ORGANISM: Artificial Sequence
<220> FEATURE:
<223> OTHER INFORMATION: Synthetic Nucleic Acid

<400> SEQUENCE: 92
ctccctccgt tcctccctgc ctccctgcct ccctgcctcc ctcctaacgt cccttccgcc 60
cctctacgcg tctagagtcg acgtgcacgg tacc 94

<210> SEQ ID NO 93
<211> LENGTH: 119
<212> TYPE: DNA
<213> ORGANISM: Artificial Sequence
<220> FEATURE:
<223> OTHER INFORMATION: Synthetic Nucleic Acid

<400> SEQUENCE: 93
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcct 119

<210> SEQ ID NO 94
<211> LENGTH: 133
<212> TYPE: DNA
<213> ORGANISM: Artificial Sequence
<220> FEATURE:
<223> OTHER INFORMATION: Synthetic Nucleic Acid

<400> SEQUENCE: 94
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag ctg 133

<210> SEQ ID NO 95
<211> LENGTH: 238
<212> TYPE: DNA
<213> ORGANISM: Artificial Sequence
<220> FEATURE:
<223> OTHER INFORMATION: Synthetic Nucleic Acid

<400> SEQUENCE: 95
ccctagaaag ataatcatat tgtgacgtac gttaaagata atcatgcgta aaattgacgc 60
atgtgtttta tcggtctgta tatcgaggtt tatttattaa tttgaataga tattaagttt 120
tattatattt acacttacat actaataata aattcaacaa acaatttatt tatgtttatt 180
tatttattaa aaaaaaacaa aaactcaaaa tttcttctat aaagtaacaa aactttta 238

<210> SEQ ID NO 96
<211> LENGTH: 309
<212> TYPE: DNA
<213> ORGANISM: Artificial Sequence
<220> FEATURE:
<223> OTHER INFORMATION: Synthetic Nucleic Acid

<400> SEQUENCE: 96
gatatctata acaagaaaat atatatataa taagttatca cgtaagtaga acatgaaata 60
acaatataat tatcgtatga gttaaatctt aaaagtcacg taaaagataa tcatgcgtca 120
ttttgactca cgcggtcgtt atagttcaaa atcagtgaca cttaccgcat tgacaagcac 180
gcctcacggg agctccaagc ggcgactgag atgtcctaaa tgcacagcga cggattcgcg 240
ctatttagaa agagagagca atatttcaag aatgcatgcg tcaattttac gcagactatc 300
tttctaggg 309

<210> SEQ ID NO 97
<211> LENGTH: 122
<212> TYPE: DNA
<213> ORGANISM: Artificial Sequence
<220> FEATURE:
<223> OTHER INFORMATION: Synthetic Nucleic Acid

<400> SEQUENCE: 97
taagatacat tgatgagttt ggacaaacca caactagaat gcagtgaaaa aaatgcttta 60
tttgtgaaat ttgtgatgct attgctttat ttgtaaccat tataagctgc aataaacaag 120
tt 122

<210> SEQ ID NO 98
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 98
aagctgcaat aaacaagtta 20

<210> SEQ ID NO 99
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 99
ctgcgcatgc gcttg 15

<210> SEQ ID NO 100
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 100
gtaatcatgg tcatagctgt t 21

<210> SEQ ID NO 101
<211> LENGTH: 18
<212> TYPE: DNA
<213> ORGANISM: Artificial Sequence
<220> FEATURE:
<223> OTHER INFORMATION: Synthetic Nucleic Acid

<400> SEQUENCE: 101
agctagcctt aagggcgc 18

<210> SEQ ID NO 102
<211> LENGTH: 34
<212> TYPE: DNA
<213> ORGANISM: Artificial Sequence
<220> FEATURE:
<223> OTHER INFORMATION: Synthetic Nucleic Acid

<400> SEQUENCE: 102
acagtgtaca tcatgaccat ggtctagagt agac 34

<210> SEQ ID NO 103
<211> LENGTH: 977
<212> TYPE: DNA
<213> ORGANISM: Artificial Sequence
<220> FEATURE:
<223> OTHER INFORMATION: Synthetic Nucleic Acid

<400> SEQUENCE: 103
acagtgtaca tcatgaccat ggtctagagt agacgataac cacactgacg ctaagacatc 60
gttatttttt tagacacttt accctctgtt attatccccg ccgggaatgg ctacccggat 120
catatacacc gacgtgccaa gttcccgccc tgtctcctta tttccgctcg gtgcaagatt 180
acagacgtcc gaagtgtatt agagtagacg catcagtatc acttgtgtcc ttaaaccgac 240
aggagaagtg ctagtacgct gtgtaaagga tcctgaatat aatataggac accgtctatt 300
atatgtatat aggaaactta tgtcgtattt gggcggacca ccaatccgat tccaaacccc 360
ggttggaacg tgtcggatcg acactcgccc aaaatgaaat ttaggctctt aaatgcaaaa 420
tctggttcgt aaattcagtc gggatagaga cagttaacgg ttgcttgtct ccatgaccta 480
cacatggtgc agggtgtctt ggggatacca gattgttata taacggtgat caaacaagta 540
gttccaaaag aaatatacag aagatccaca gctaggccat atcctttaag agttagttat 600
cacagcaacc tcgctaactg gcgtagagcg taagccgcgg ttcgcaggtc ataccacttt 660
atgattagtc cttgtcgaat gtgtacctac taaccctaac cgggtaaggc tgataaatgc 720
cttcacgtag ccaagtgtat tgaggaatct cccggccggg ggtaccgtct cgggctcccg 780
ttgcagttac ttacgatggt ctaaggtgca cctcccttca catggttttc cgcaacggaa 840
cccctcctgc tcacctttaa agggggcaat ttcaaatcca tgatagctca ttcatgtctg 900
cgatcagtac ctgttagaca atactaggcg catttccccg atttaatagt atttatactg 960
ggactcaggg ccacttt 977

<210> SEQ ID NO 104
<211> LENGTH: 4599
<212> TYPE: DNA
<213> ORGANISM: Artificial Sequence
<220> FEATURE:
<223> OTHER INFORMATION: Synthetic Nucleic Acid

<400> SEQUENCE: 104
cagctgcgcg ctcgctcgct cactgaggcc gcccgggcgt cgggcgacct ttggtcgccc 60
ggcctcagtg agcgagcgag cgcgcagaga gggagtggcc aactccatca ctaggggttc 120
ctgcggccgc gaagactctt aaccctagaa agataatcat attgtgacgt acgttaaaga 180
taatcatgcg taaaattgac gcatgtgttt tatcggtctg tatatcgagg tttatttatt 240
aatttgaata gatattaagt tttattatat ttacacttac atactaataa taaattcaac 300
aaacaattta tttatgttta tttatttatt aaaaaaaaac aaaaactcaa aatttcttct 360
ataaagtaac aaaactttta tcaaatacct gcagcccggg ggatgcagag ggacagcccc 420
cccccaaagc ccccagggat gtaattacgt ccctcccccg ctagggggca gcagcgagcc 480
gcccggggct ccgctccggt ccggcgctcc ccccgcatcc ccgagccggc agcgtgcggg 540
gacagcccgg gcacggggaa ggtggcacgg gatcgctttc ctctgaacgc ttctcgctgc 600
tctttgagcc tgcagacacc tgggggggata cggggaaaag ttgactgtgc ctttcgatcg 660
agtactccta ggcgcgtgtt tgctgcttgc aatgtttgcc cattttaggg tggacacagg 720
acgctgtggt ttctgagcca gggggcgact cagatcccag ccagtggact tagcccctgt 780
ttgctcctcc gataactggg gtgaccttgg ttaatattca ccagcagcct cccccgttgc 840
ccctctggat ccactgctta aatacggacg aggacagggc cctgtctcct cagcttcagg 900
caccaccact gacctgggac agtgaatcgc aaagcttatt ggacgtcgct tagcggtacc 960
gccaccatgc tgttcaacct gcgcatcctg ctgaacaacg ccgccttcag aaacggccac 1020

```
aacttcatgg ttcgaaactt cagatgcggc cagcctctcc agaacaaggt gcagctgaaa   1080
ggcagggacc tgctgaccct gaagaacttc accggcgaag agatcaagta catgctgtgg   1140
ctgtccgccg acctgaagtt cagaatcaag cagaagggcg agtacctgcc tctgctccag   1200
ggaaagtctc tgggcatgat cttcgagaag cggagcacca gaaccagact gagcaccgag   1260
acaggctttg ccctgctcgg aggacacccc tgctttctga caacccagga catccacctg   1320
ggcgtgaacg agagcctgac cgatacagcc agagtgctgt cctctatggc cgatgccgtg   1380
ctggctagag tgtataagca gagcgacctg gacaccctgg ctaaagaggc cagcattccc   1440
atcatcaacg gcctgtccga cctgtatcac cccatccaga tcctggccga ctacctgaca   1500
ctgcaagagc actacagcag cctgaaggga ctgaccctgt cttggatcgg cgacggcaac   1560
aacatcctgc acagcattat gatgagcgcc gccaagttcg gaatgcacct ccaggccgct   1620
acacccaagg gctatgaacc tgatgccagc gtgacaaagc tggccgagca gtacgccaaa   1680
gagaacggca caaagctgct gctgaccaac gatcccctgg aagctgctca cggcggcaat   1740
gtgctgatca ccgatacctg gatcagcatg ggccaagagg aagagaagaa gaagcggctg   1800
caagccttcc agggctacca agtgaccatg aagacagcca aggtggccgc cagcgattgg   1860
acctttctgc actgcctgcc tcggaagcct gaagaggtgg acgacgaggt gttctacagc   1920
cctagaagcc tggtgttccc cgaggccgag aacagaaagt ggaccatcat ggctgtgatg   1980
gtgtctctgc tgaccgacta ctcccctcag ctccagaagc ctaagttcta aacactagtt   2040
ctatagtgtc acctaaattc cctttagtga gggttaatgg ccgtaggccg ccagaattgg   2100
gtccagacat gataagatac attgatgagt ttggacaaac cacaactaga atgcagtgaa   2160
aaaaatgctt tatttgtgaa atttgtgatg ctattgcttt atttgtaacc attataagct   2220
gcaataaaca agttaacaac aacaattgca ttcattttat gtttcaggtt cagggggagg   2280
tgtgggaggt tttttcggac tctaggacct gcgcatgcgc ttggcgtaat catggtcata   2340
gctgtttcct gttttccccg tatcccccca ggtgtctgca ggctcaaaga gcagcgagaa   2400
gcgttcagag gaaagcgatc ccgtgccacc ttccccgtgc ccgggctgtc cccgcacgct   2460
gccggctcgg ggatgcgggg ggagcgccgg accggagcgg agccccgggc ggctcgctgc   2520
tgcccccctag cgggggaggg acgtaattac atccctgggg gctttggggg ggggctgtcc   2580
ctctcaccgc ggtggagctc cagcttttgt tcgaattggg gcccccccctc gagggtatcg   2640
atgatatcta taacaagaaa atatatatat aataagttat cacgtaagta gaacatgaaa   2700
taacaatata attatcgtat gagttaaatc ttaaaagtca cgtaaaagat aatcatgcgt   2760
cattttgact cacgcggtcg ttatagttca aaatcagtga cacttaccgc attgacaagc   2820
acgcctcacg ggagctccaa gcggcgactg agatgtccta aatgcacagc gacggattcg   2880
cgctatttag aaagagagag caatatttca agaatgcatg cgtcaatttt acgcagacta   2940
tctttctagg gttaatctag ctagccttaa gggcgcacag tgtacatcat gaccatggtc   3000
tagagtagac gataaccaca ctgacgctaa gacatcgtta ttttttttaga cactttaccc   3060
tctgttatta tccccgccgg gaatggctac ccggatcata tacaccgacg tgccaagttc   3120
ccgccctgtc tccttatttc cgctcggtgc aagattacag acgtccgaag tgtattagag   3180
tagacgcatc agtatcactt gtgtccttaa accgacagga gaagtgctag tacgctgtgt   3240
aaaggatcct gaatataata taggacaccg tctattatat gtatatagga aacttatgtc   3300
gtatttgggc ggaccaccaa tccgattcca aaccccggtt ggaacgtgtc ggatcgacac   3360
```

```
tcgcccaaaa tgaaatttag gctcttaaat gcaaaatctg gttcgtaaat tcagtcggga   3420

tagagacagt taacggttgc ttgtctccat gacctacaca tggtgcaggg tgtcttgggg   3480

ataccagatt gttatataac ggtgatcaaa caagtagttc caaaagaaat atacagaaga   3540

tccacagcta ggccatatcc tttaagagtt agttatcaca gcaacctcgc taactggcgt   3600

agagcgtaag ccgcggttcg caggtcatac cactttatga ttagtccttg tcgaatgtgt   3660

acctactaac cctaaccggg taaggctgat aaatgccttc acgtagccaa gtgtattgag   3720

gaatctcccg gccgggggta ccgtctcggg ctcccgttgc agttacttac gatggtctaa   3780

ggtgcacctc ccttcacatg gttttccgca acggaacccc tcctgctcac ctttaaaggg   3840

ggcaatttca aatccatgat agctcattca tgtctgcgat cagtacctgt tagacaatac   3900

taggcgcatt tccccgattt aatagtattt atactgggac tcagggccac tttgggcgcc   3960

tcgagacctt gcggccgcag gaacccctag tgatggagtt ggccactccc tctctgcgcg   4020

ctcgctcgct cactgaggcc gggcgaccaa aggtcgcccg acgcccgggc tttgcccggg   4080

cggcctcagt gagcgagcga gcgcgcagct gcctgcaggt ctagctagcc cgcctaatga   4140

gcgggctttt ttttggcttg ttgtccacaa ccgttaaacc ttaaaagctt taaaagcctt   4200

atatattctt ttttttctta taaaacttaa aaccttagag gctatttaag ttgctgattt   4260

atattaattt tattgttcaa acatgagagc ttagtacgtg aaacatgaga gcttagtacg   4320

ttagccatga gagcttagta cgttagccat gagggtttag ttcgttaaac atgagagctt   4380

agtacgttaa acatgagagc ttagtacgta ctatcaacag gttgaactgc tgatccacgt   4440

tgtggtagaa ttggtaaaga gagtcgtgta aaatatcgag ttcgcacatc ttgttgtctg   4500

attattgatt tttggcgaaa ccatttgatc atatgacaag atgtgtatct accttaactt   4560

aatgattttg ataaaaatca ttacctaggt tcctgcagg                          4599
```

<210> SEQ ID NO 105
<211> LENGTH: 182
<212> TYPE: DNA
<213> ORGANISM: Artificial Sequence
<220> FEATURE:
<223> OTHER INFORMATION: Synthetic Nucleic Acid

<400> SEQUENCE: 105

```
ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctacgta gccatgctct    180

ag                                                                   182
```

<210> SEQ ID NO 106
<211> LENGTH: 178
<212> TYPE: DNA
<213> ORGANISM: Artificial Sequence
<220> FEATURE:
<223> OTHER INFORMATION: Synthetic Nucleic Acid

<400> SEQUENCE: 106

```
agcatggcta cgtagataag tagcatggcg ggttaatcat taactacaag gaacccctag     60

tgatggagtt ggccactccc tctctgcgcg ctcgctcgct cactgaggcc gggcgaccaa    120

aggtcgcccg acgcccgggc tttgcccggg cggcctcagt gagcgagcga gcgcgcag      178
```

<210> SEQ ID NO 107
<211> LENGTH: 256

<212> TYPE: DNA
<213> ORGANISM: Artificial Sequence
<220> FEATURE:
<223> OTHER INFORMATION: Synthetic Nucleic Acid

<400> SEQUENCE: 107
gcgcgtgttt gctgcttgca atgtttgccc attttagggt ggacacagga cgctgtggtt 60
tctgagccag gggcgactc agatcccagc cagtggactt agcccctgtt tgctcctccg 120
ataactgggg tgaccttggt taatattcac cagcagcctc cccgttgcc cctctggatc 180 cactgcttaa atacggatat ccgaggacag ggccctgtct cctcagcttc aggcaccacc 240
actgacctgg gacagt 256

<210> SEQ ID NO 108
<211> LENGTH: 139
<212> TYPE: DNA
<213> ORGANISM: Artificial Sequence
<220> FEATURE:
<223> OTHER INFORMATION: Synthetic Nucleic Acid

<400> SEQUENCE: 108
tgtttattgc agcttataat ggttacaaat aaagcaatag catcacaaat ttcacaaata 60
aagcattttt ttcactgcat tctagttgtg gtttgtccaa actcatcaat gtatcttatc 120
atgtctggcg ctagcagca 139

<210> SEQ ID NO 109
<211> LENGTH: 1906
<212> TYPE: DNA
<213> ORGANISM: Artificial Sequence
<220> FEATURE:
<223> OTHER INFORMATION: Synthetic Nucleic Acid

<400> SEQUENCE: 109
cctcgcagga ggcctggccg gcctccggat tacttccggt gcaggcgtca gctgcatctt 60
gctggccagc tcggaggact gtccccgtaa ctcccgtccg ctgtgtatca acacagctct 120
agccaaattg ttgaccgaac gacggggttc gattgtttca ttcctcacat ccaacacttg 180
agtagtacaa tgccttgtct aagtgcgctt gggacccagt ctattttgtt tgtgtgcaca 240
agacgatact cctcgatcac gcaccaagcg caggctggcc ctaacgacgt ggtattctcg 300
tattggagag ccccagattg cataaggcac tcatcacctg cgtttatgac gctggacgcc 360
tgcgtatgtt gcaggactcc tatgatgtcg cttgcctgat gcgttgttat gtgattgagg 420
tttagtactt ggcaatatca ttagatggaa ctaatacgcg gtctaatcgt tacaggtttc 480
cgacgattga gaagtatcac ctgattctcg ggagcgactt gtaacactac tacacttatt 540
gatttggtac tcctatgtgt tgctatcttg actccgtaaa tcgccgtgat acactctctt 600
cgtttctcgg caatctatgg ctctaaacta tacacaggca ttctaagaat aatctgacct 660
gtccctgtag tactggtagg ttactaccag tacggcgaca atgtgggagc tacggcgtgg 720
tagaaccggg tacagacaca gtccctgatc ccgatagtaa cactgtgccc gtagcagtga 780
taatcattgc gcctcaacct gaggaagata agggaggcag tatatcgtgc tattccctct 840
attctcccac atgcgtatgg cctgaggtca atgttcaggt acatgccgta atatgaggtt 900
ttacgtagcc gatcacgaaa aggttgctaa atacttctcg tcatatccca gctcattgtt 960
gggattatcg ctaaacaggc taagttctaa tgcccgtggg catggcctca cgatctatgg 1020
tgatacagac agcccgattt agcaatgctt cagagcacag tggtaaatat tggttgatac 1080
gtagaaccat gatcactgct caattcgtga tgaagttgtt caatatacct agaagccact 1140
caaggattct ctctgagtca ctaatagagg tggtagagtg tttggaagcc ggttccacac 1200
agatttagag tgtcacctaa ttgccgttta tctaaggaat tacgacagga gataccgaag 1260
taattaggct attgcagaga tacaggctag gtgaggtgga gggtgtcttg cggtcttcgt 1320
ccagccgcct tgaaagcggg gttttttca agcatcgctg cgtcattgcg tggtcgagac 1380
ttatgcgccc tacgaagttc gtctgaagta gtccaggaaa gacctacttt gcagttatct 1440
tcgcattccc acactcacca ctacaactac tcttccctca atttcccggt tagtttcgct 1500
aagctccgac cttgggttac tgtgttgcat ccgactcgct gcggctttct agtacgctgt 1560
actgtttcat tcttctgtag gtctggttcc gtaagtccga atttccaggc cgtggtctag 1620
tcctaattat tttctgtccc ggtagctata tttagccgag ggtttgtcca tttgcccggc 1680
gtagagcgcc gcgtttgcga acatttgcgc ccgtaatacg tagggacacc gtcgggtaat 1740
ggatggcaaa agccgaaaac ggcgtcttcc ggcgcttgga ttcagcgctc ttgagccata 1800
aaccgcgttg cttctttggt taattcgtat taatgatcct aagcgccagc ttattcgtta 1860
agaggcacta ggcgcgccgc ggcatgcgat cgccagcatg gctacg 1906

<210> SEQ ID NO 110
<211> LENGTH: 7302
<212> TYPE: DNA
<213> ORGANISM: Artificial Sequence
<220> FEATURE:
<223> OTHER INFORMATION: Synthetic Nucleic Acid

<400> SEQUENCE: 110
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt ggagatcggt acttcgcgaa 420
tgcgtcgaga tggtaccacc ggtactgcgc gctcgctcgc tcactgaggc cgcccgggca 480
aagcccgggc gtcgggcgac ctttggtcgc ccggcctcag tgagcgagcg agcgcgcaga 540
gagggagtgg ccaactccat cactaggggt tccttgtagt taatgattaa cccgccatgc 600
tacttatcta cgtagccatg ctctagctta agcctaggcg cgtgtttgct gcttgcaatg 660
tttgcccatt ttagggtgga cacaggacgc tgtggtttct gagccagggg gcgactcaga 720
tcccagccag tggacttagc ccctgtttgc tcctccgata actggggtga ccttggttaa 780
tattcaccag cagcctcccc cgttgcccct ctggatccac tgcttaaata cggatatccg 840
aggacagggc cctgtctcct cagcttcagg caccaccact gacctgggac agtgaatcgc 900
aagaattcac gcgtcaattg ctcgaggcca ccatggctcc caagaagaag cggaaagttg 960
gcggcggagg cagcagcctg gatgatgagc atattctgag cgccctgctg cagagcgacg 1020
atgaactcgt gggcgaagat agcgacagcg aggtgtccga tcacgtgtcc gaggatgacg 1080
tgcagtccga taccgaggaa gccttcatcg acgaggtgca cgaagtgcag cctacaagca 1140
gcggcagcga gatcctggac gagcagaatg tgatcgagca gccaggatct agcctggcca 1200
gcaacagaat cctgacactg ccccagagaa ccatccgggg caagaacaag cactgctggt 1260

```
ccaccagcaa gagcaccaga cggtctagag tgtctgccct gaacatcgtg cgaagccaga   1320
ggggccctac cagaatgtgc cggaacatct acgaccctct gctgtgcttc aagctgttct   1380
tcaccgacga gatcatctcc gagatcgtga agtggaccaa cgccgagatc agcctgaagc   1440
ggagagaatc catgaccagc gccaccttca gagacaccaa cgaggacgag atctacgcct   1500
tcttcggcat cctggtcatg acagccgtgc ggaaggacaa ccacatgagc accgacgacc   1560
tgttcgaccg cagcctgtct atggtgtacg tgtccgtgat gagccgggac agattcgact   1620
tcctgatccg gtgcctgcgg atggacgaca agtccatcag acccacactg cgcgagaacg   1680
acgtgttcac acctgtgcgg aagatctggg acctgttcat ccaccagtgc atccagaact   1740
acacccctgg cgctcacctg accatcgacg aacagctgct gggcttcaga ggcagatgcc   1800
ccttcagagt gtacatcccc aacaagccct ctaagtacgg catcaagatc ctgatgatgt   1860
gcgacagcgg caccaagtac atgatcaacg gcatgcccta cctcggcaga ggcacccaaa   1920
caaatggcgt gccactgggc gagtactacg tgaaagaact gagcaagcct gtgcacggca   1980
gctgcagaaa catcacctgt gacaactggt ttaccagcat tcccctggcc aagaacctgc   2040
tgcaagaacc ctacaagctg acaatcgtgg gcaccgtgcg gagcaacaag agggaaattc   2100
ccgaggtgct gaagaactct cggagcagac ctgtgggcac cagcatgttc tgcttcgacg   2160
gacctctgac actggtgtcc tacaagccca agcctgccaa gatggtgtac ctgctgagca   2220
gctgtgacga ggacgccagc atcaatgaga gcaccggcaa gccccagatg gtcatgtact   2280
acaaccagac caaaggcggc gtggacaccc tggatcagat gtgcagcgtg atgacctgca   2340
gcagaaagac caacagatgg cccatggctc tgctgtacgg catgatcaat atcgcctgca   2400
tcaacagctt catcatctac agccacaacg tgtccagcaa gggcgagaag gtgcagagcc   2460
ggaagaaatt catgcggaac ctgtacatga gcctgaccag cagcttcatg agaaagcggc   2520
tggaagcccc tacactgaag agatacctgc gggacaacat cagcaacatc ctgcctaaag   2580
aggtgcccgg caccagcgac gatagcacag aggaacccgt gatgaagaag aggacctact   2640
gcacctactg tcccagcaag atccggcgga aggccaacgc cagctgcaaa aagtgcaaga   2700
aagtgatctg ccgcgagcac aacatcgata tgtgccagag ctgcttctga tgagatgcat   2760
tcgaagcggc cgcgagctca agcttgcaat tccgataact tgtttattgc agcttataat   2820
ggttacaaat aaagcaatag catcacaaat ttcacaaata aagcattttt ttcactgcat   2880
tctagttgtg gtttgtccaa actcatcaat gtatcttatc atgtctggcg ctagcagcac   2940
ctcgcaggag gcctggccgg cctccggatt acttccggtg caggcgtcag ctgcatcttg   3000
ctggccagct cggaggactg tccccgtaac tcccgtccgc tgtgtatcaa cacagctcta   3060
gccaaattgt tgaccgaacg acggggttcg attgtttcat tcctcacatc caacacttga   3120
gtagtacaat gccttgtcta agtgcgcttg ggacccagtc tattttgttt gtgtgcacaa   3180
gacgatactc ctcgatcacg caccaagcgc aggctggccc taacgacgtg gtattctcgt   3240
attggagagc cccagattgc ataaggcact catcacctgc gtttatgacg ctggacgcct   3300
gcgtatgttg caggactcct atgatgtcgc ttgcctgatg cgttgttatg tgattgaggt   3360
ttagtacttg gcaatatcat tagatggaac taatacgcgg tctaatcgtt acaggtttcc   3420
gacgattgag aagtatcacc tgattctcgg gagcgacttg taacactact acacttattg   3480
atttggtact cctatgtgtt gctatcttga ctccgtaaat cgccgtgata cactctcttc   3540
gtttctcggc aatctatggc tctaaactat acacaggcat tctaagaata atctgacctg   3600
```

```
tccctgtagt actggtaggt tactaccagt acggcgacaa tgtgggagct acggcgtggt   3660
agaaccgggt acagacacag tccctgatcc cgatagtaac actgtgcccg tagcagtgat   3720
aatcattgcg cctcaacctg aggaagataa gggaggcagt atatcgtgct attccctcta   3780
ttctcccaca tgcgtatggc ctgaggtcaa tgttcaggta catgccgtaa tatgaggttt   3840
tacgtagccg atcacgaaaa ggttgctaaa tacttctcgt catatcccag ctcattgttg   3900
ggattatcgc taaacaggct aagttctaat gcccgtgggc atggcctcac gatctatggt   3960
gatacagaca gcccgattta gcaatgcttc agagcacagt ggtaaatatt ggttgatacg   4020
tagaaccatg atcactgctc aattcgtgat gaagttgttc aatataccta gaagccactc   4080
aaggattctc tctgagtcac taatagaggt ggtagagtgt ttggaagccg gttccacaca   4140
gatttagagt gtcacctaat tgccgtttat ctaaggaatt acgacaggag ataccgaagt   4200
aattaggcta ttgcagagat acaggctagg tgaggtggag ggtgtcttgc ggtcttcgtc   4260
cagccgcctt gaaagcgggg tttttttcaa gcatcgctgc gtcattgcgt ggtcgagact   4320
tatgcgccct acgaagttcg tctgaagtag tccaggaaag acctactttg cagttatctt   4380
cgcattccca cactcaccac tacaactact cttccctcaa tttcccggtt agtttcgcta   4440
agctccgacc ttgggttact gtgttgcatc cgactcgctg cggctttcta gtacgctgta   4500
ctgtttcatt cttctgtagg tctggttccg taagtccgaa tttccaggcc gtggtctagt   4560
cctaattatt ttctgtcccg gtagctatat ttagccgagg gtttgtccat ttgcccggcg   4620
tagagcgccg cgtttgcgaa catttgcgcc cgtaatacgt agggacaccg tcgggtaatg   4680
gatggcaaaa gccgaaaacg gcgtcttccg gcgcttggat tcagcgctct tgagccataa   4740
accgcgttgc ttctttggtt aattcgtatt aatgatccta agcgccagct tattcgttaa   4800
gaggcactag gcgcgccgcg gcatgcgatc gccagcatgg ctacgtagat aagtagcatg   4860
gcgggttaat cattaactac aaggaacccc tagtgatgga gttggccact ccctctctgc   4920
gcgctcgctc gctcactgag gccgggcgac caaaggtcgc ccgacgcccg ggctttgccc   4980
gggcggcctc agtgagcgag cgagcgcgca gactagtgtc gacatcggat gccgggaccg   5040
acgagtgcag aggcgtgcaa gcgagcttgg cgtaatcatg gtcatagctg tttcctgtgt   5100
gaaattgtta tccgctcaca attccacaca acatacgagc cggaagcata aagtgtaaag   5160
cctggggtgc ctaatgagtg agctaactca cattaattgc gttgcgctca ctgcccgctt   5220
tccagtcggg aaacctgtcg tgccagctgc attaatgaat cggccaacgc gcggggagag   5280
gcggtttgcg tattgggcgc tcttccgctt cctcgctcac tgactcgctg cgctcggtcg   5340
ttcggctgcg gcgagcggta tcagctcact caaaggcggt aatacggtta tccacagaat   5400
caggggataa cgcaggaaag aacatgtgag caaaaggcca gcaaaaggcc aggaaccgta   5460
aaaaggccgc gttgctggcg tttttccata ggctccgccc ccctgacgag catcacaaaa   5520
atcgacgctc aagtcagagg tggcgaaacc cgacaggact ataaagatac caggcgtttc   5580
cccctggaag ctccctcgtg cgctctcctg ttccgaccct gccgcttacc ggatacctgt   5640
ccgcctttct cccttcggga agcgtggcgc tttctcatag ctcacgctgt aggtatctca   5700
gttcggtgta ggtcgttcgc tccaagctgg gctgtgtgca cgaacccccc gttcagcccg   5760
accgctgcgc cttatccggt aactatcgtc ttgagtccaa cccggtaaga cacgacttat   5820
cgccactggc agcagccact ggtaacagga ttagcagagc gaggtatgta ggcggtgcta   5880
cagagttctt gaagtggtgg cctaactacg gctacactag aagaacagta tttggtatct   5940
gcgctctgct gaagccagtt accttcggaa aaagagttgg tagctcttga tccggcaaac   6000
```

aaaccaccgc tggtagcggt ggtttttttg tttgcaagca gcagattacg cgcagaaaaa 6060
aaggatctca agaagatcct ttgatctttt ctacggggtc tgacgctcag tggaacgaaa 6120
actcacgtta agggattttg gtcatgagat tatcaaaaag gatcttcacc tagatccttt 6180
taaattaaaa atgaagtttt aaatcaatct aaagtatata tgagtaaact tggtctgaca 6240
gttaccaatg cttaatcagt gaggcaccta tctcagcgat ctgtctattt cgttcatcca 6300
tagttgcctg actccccgtc gtgtagataa ctacgatacg ggagggctta ccatctggcc 6360
ccagtgctgc aatgataccg cgagacccac gctcaccggc tccagattta tcagcaataa 6420
accagccagc cggaagggcc gagcgcagaa gtggtcctgc aactttatcc gcctccatcc 6480
agtctattaa ttgttgccgg gaagctagag taagtagttc gccagttaat agtttgcgca 6540
acgttgttgc cattgctaca ggcatcgtgg tgtcacgctc gtcgtttggt atggcttcat 6600
tcagctccgg ttcccaacga tcaaggcgag ttacatgatc ccccatgttg tgcaaaaaag 6660
cggttagctc cttcggtcct ccgatcgttg tcagaagtaa gttggccgca gtgttatcac 6720
tcatggttat ggcagcactg cataattctc ttactgtcat gccatccgta agatgctttt 6780
ctgtgactgg tgagtactca accaagtcat tctgagaata gtgtatgcgg cgaccgagtt 6840
gctcttgccc ggcgtcaata cgggataata ccgcgccaca tagcagaact ttaaaagtgc 6900
tcatcattgg aaaacgttct tcggggcgaa aactctcaag gatcttaccg ctgttgagat 6960
ccagttcgat gtaacccact cgtgcaccca actgatcttc agcatctttt actttcacca 7020
gcgtttctgg gtgagcaaaa acaggaaggc aaaatgccgc aaaaaaggga ataagggcga 7080
cacggaaatg ttgaatactc atactcttcc tttttcaata ttattgaagc atttatcagg 7140
gttattgtct catgagcgga tacatatttg aatgtattta gaaaaataaa caaatagggg 7200
ttccgcgcac atttccccga aaagtgccac ctgacgtcta agaaaccatt attatcatga 7260
cattaaccta taaaaatagg cgtatcacga ggccctttcg tc 7302

<210> SEQ ID NO 111
<211> LENGTH: 2256
<212> TYPE: DNA
<213> ORGANISM: Artificial Sequence
<220> FEATURE:
<223> OTHER INFORMATION: Synthetic Nucleic Acid

<400> SEQUENCE: 111
atgctgcggg ccaagaatca actgttcctg ctgtcccctc actacctgcg gcaagtgaaa 60
gagagcagcg gcagcagact gatccagcag agactgctgc atcagcagca gccactgcac 120
cctgaatggg ccgctctggc taagaagcag ctcaagggca agaaccccga ggacctgatc 180
tggcacacac cagagggcat cagcatcaag cccctgtact ccaagcggga cacaatggat 240
ctgcccgagg aactgcctgg cgtgaagcct tttacaagag gcccctatcc taccatgtat 300
accttcagac cctggaccat ccggcagtac gccggctttt ctaccgtgga agagagcaac 360
aagttctaca aggacaacat caaggccggc cagcagggac tgagcgtggc atttgatctg 420
gctacccaca ggggctacga cagcgacaac cctagagtgc ggggagatgt tggaatggcc 480
ggcgtggcaa tcgacacagt ggaagatacc aagatcctgt tcgacggcat ccctctggaa 540
aagatgagcg tgtccatgac catgaacggc gctgtgatcc ccgtgctggc taactttatt 600
gtgaccggcg aggaacaggg cgtgcccaaa gaaaagctga ccggcaccat ccagaacgac 660
atcctgaaag agttcatggt tcgaaacacc tacatcttcc cacctgagcc gagcatgaag 720

```
atcattgccg acatcttcga gtacaccgcc aagcacatgc ccaagttcaa cagcatctcc     780

atcagcggct accacatgca agaggctggc gccgatgcca tcctggaact ggcttataca     840

ctggccgacg gcctggaata ctccagaaca ggactgcaag ccggcctgac catcgatgag     900

tttgcccccta gactgagctt cttctggggc atcggcatga acttctacat ggaaatcgcc     960

aagatgagag ccggcagacg gctgtgggct cacctgatcg agaagatgtt ccagcctaag    1020

aacagcaaga gcctgctcct gagagcccac tgtcagacaa gtggctggtc cctgactgag    1080

caggacccct acaacaacat cgtgcgcaca gccatcgaag ctatggccgc cgtgtttggc    1140

ggaacacaga gcctgcacac caacagcttt gacgaggctc tgggcctgcc taccgtgaag    1200

tctgccagaa tcgcccggaa cacccagatc atcatccaag aggaaagcgg catccccaag    1260

gtggcagatc cttggggcgg cagctacatg atggaatgcc tgaccaacga cgtgtacgac    1320

gccgctctga agctgatcaa cgagatcgaa gagatgggcg gcatggctaa ggctgtggcc    1380

gagggaatcc ccaagctgag aatcgaggaa tgcgccgcca gacggcaggc cagaattgat    1440

agcggaagcg aagtgatcgt gggcgtgaac aagtaccagc tcgaaaaaga ggacgccgtc    1500

gaggtcctgg ctatcgacaa taccagcgtg cggaaccggc agattgagaa gctgaagaag    1560

atcaagagca gccgcgatca ggccctggcc gaaagatgtc ttgctgccct gacagagtgt    1620

gccgccagcg gcgacggaaa tattctggct ctggccgtgg atgccagccg ggctagatgt    1680

accgtgggcg agattacaga cgccctgaag aaggtgttcg gcgagcacaa ggccaacgac    1740

agaatggtgt ctggcgccta cagacaagag tttggcgaga gcaaagagat caccagcgcc    1800

atcaagcggg tccacaagtt catggaaaga gaaggcaggc ggcccagact gctggtggct    1860

aagatgggac aagacggcca tgacagaggc gccaaagtga tcgccacagg ctttgccgat    1920

ctgggcttcg acgtggacat cggccctctg tttcagaccc ctagagaggt ggcacagcag    1980

gccgttgatg ccgatgttca cgctgtgggc gtgtctacac tggctgccgg acacaagaca    2040

ctggtgcccg aactgatcaa agagctgaac agcctgggca gacccgacat ccttgtgatg    2100

tgtggcggag tgatcccacc gcaggactac gagttcctgt ttgaagtggg cgtgtccaac    2160

gtgttcggcc ctggcacaag aatccctaaa gccgccgtgc aggttctgga cgacatcgag    2220

aagtgcctgg aaaaaaagca gcagagcgtg ggatcc                              2256
```

<210> SEQ ID NO 112
<211> LENGTH: 2253
<212> TYPE: DNA
<213> ORGANISM: Artificial Sequence
<220> FEATURE:
<223> OTHER INFORMATION: Synthetic Nucleic Acid

<400> SEQUENCE: 112

```
ctgcgggcca agaatcaact gttcctgctg tcccctcact acctgcggca agtgaaagag      60

agcagcggca gcagactgat ccagcagaga ctgctgcatc agcagcagcc actgcaccct     120

gaatgggccg ctctggctaa gaagcagctc aagggcaaga accccgagga cctgatctgg     180

cacacaccag agggcatcag catcaagccc ctgtactcca agcgggacac aatggatctg     240

cccgaggaac tgcctggcgt gaagcctttt acaagaggcc cctatcctac catgtatacc     300

ttcagaccct ggaccatccg gcagtacgcc ggcttttcta ccgtggaaga gagcaacaag     360

ttctacaagg acaacatcaa ggccggccag cagggactga gcgtggcatt tgatctggct     420

acccacaggg gctacgacag cgacaaccct agagtgcggg gagatgttgg aatggccggc     480

gtggcaatcg acacagtgga agataccaag atcctgttcg acggcatccc tctggaaaag     540
```

atgagcgtgt ccatgaccat gaacggcgct gtgatccccg tgctggctaa ctttattgtg 600
accggcgagg aacagggcgt gcccaaagaa aagctgaccg gcaccatcca gaacgacatc 660
ctgaaagagt tcatggttcg aaacacctac atcttcccac ctgagccgag catgaagatc 720
attgccgaca tcttcgagta caccgccaag cacatgccca agttcaacag catctccatc 780
agcggctacc acatgcaaga ggctggcgcc gatgccatcc tggaactggc ttatacactg 840
gccgacggcc tggaatactc cagaacagga ctgcaagccg gcctgaccat cgatgagttt 900
gcccctagac tgagcttctt ctggggcatc ggcatgaact tctacatgga aatcgccaag 960
atgagagccg gcagacggct gtgggctcac ctgatcgaga agatgttcca gcctaagaac 1020
agcaagagcc tgctcctgag agcccactgt cagacaagtg gctggtccct gactgagcag 1080 gaccccctaca acaacatcgt gcgcacagcc atcgaagcta tggccgccgt gtttggcgga 1140
acacagagcc tgcacaccaa cagctttgac gaggctctgg gcctgcctac cgtgaagtct 1200
gccagaatcg cccggaacac ccagatcatc atccaagagg aaagcggcat ccccaaggtg 1260
gcagatcctt ggggcggcag ctacatgatg gaatgcctga ccaacgacgt gtacgacgcc 1320
gctctgaagc tgatcaacga gatcgaagag atgggcggca tggctaaggc tgtggccgag 1380
ggaatcccca agctgagaat cgaggaatgc gccgccagac ggcaggccag aattgatagc 1440
ggaagcgaag tgatcgtggg cgtgaacaag taccagctcg aaaaagagga cgccgtcgag 1500
gtcctggcta tcgacaatac cagcgtgcgg aaccggcaga ttgagaagct gaagaagatc 1560
aagagcagcc gcgatcaggc cctggccgaa agatgtcttg ctgccctgac agagtgtgcc 1620
gccagcggcg acggaaatat tctggctctg gccgtggatg ccagccgggc tagatgtacc 1680
gtgggcgaga ttacagacgc cctgaagaag gtgttcggcg agcacaaggc caacgacaga 1740
atggtgtctg gcgcctacag acaagagttt ggcgagagca aagagatcac cagcgccatc 1800
aagcgggtcc acaagttcat ggaaagagaa ggcaggcggc ccagactgct ggtggctaag 1860
atgggacaag acggccatga cagaggcgcc aaagtgatcg ccacaggctt tgccgatctg 1920
ggcttcgacg tggacatcgg ccctctgttt cagacccta gagaggtggc acagcaggcc 1980
gttgatgccg atgttcacgc tgtgggcgtg tctacactgg ctgccggaca caagacactg 2040
gtgcccgaac tgatcaaaga gctgaacagc ctgggcagac ccgacatcct tgtgatgtgt 2100
ggcggagtga tcccaccgca ggactacgag ttcctgtttg aagtgggcgt gtccaacgtg 2160
ttcggccctg gcacaagaat ccctaaagcc gccgtgcagg ttctggacga catcgagaag 2220
tgcctggaaa aaaagcagca gagcgtggga tcc 2253

<210> SEQ ID NO 113
<211> LENGTH: 2250
<212> TYPE: DNA
<213> ORGANISM: Artificial Sequence
<220> FEATURE:
<223> OTHER INFORMATION: Synthetic Nucleic Acid

<400> SEQUENCE: 113
atgctgcggg ccaagaatca actgttcctg ctgtcccctc actacctgcg gcaagtgaaa 60
gagagcagcg gcagcagact gatccagcag agactgctgc atcagcagca gccactgcac 120
cctgaatggg ccgctctggc taagaagcag ctcaagggca agaaccccga ggacctgatc 180
tggcacacac cagagggcat cagcatcaag cccctgtact ccaagcggga cacaatggat 240
ctgcccgagg aactgcctgg cgtgaagcct tttacaagag gcccctatcc taccatgtat 300
accttcagac cctggaccat ccggcagtac gccggctttt ctaccgtgga agagagcaac 360
aagttctaca aggacaacat caaggccggc cagcagggac tgagcgtggc atttgatctg 420
gctacccaca ggggctacga cagcgacaac cctagagtgc ggggagatgt tggaatggcc 480
ggcgtggcaa tcgacacagt ggaagatacc aagatcctgt tcgacggcat ccctctggaa 540
aagatgagcg tgtccatgac catgaacggc gctgtgatcc ccgtgctggc taactttatt 600
gtgaccggcg aggaacaggg cgtgcccaaa gaaaagctga ccggcaccat ccagaacgac 660
atcctgaaag agttcatggt tcgaaacacc tacatcttcc cacctgagcc gagcatgaag 720
atcattgccg acatcttcga gtacaccgcc aagcacatgc ccaagttcaa cagcatctcc 780
atcagcggct accacatgca agaggctggc gccgatgcca tcctggaact ggcttataca 840
ctggccgacg gcctggaata ctccagaaca ggactgcaag ccggcctgac catcgatgag 900 tttgcccccta gactgagctt cttctggggc atcggcatga acttctacat ggaaatcgcc 960
aagatgagag ccggcagacg gctgtgggct cacctgatcg agaagatgtt ccagcctaag 1020
aacagcaaga gcctgctcct gagagcccac tgtcagacaa gtggctggtc cctgactgag 1080
caggacccct acaacaacat cgtgcgcaca gccatcgaag ctatggccgc cgtgtttggc 1140
ggaacacaga gcctgcacac caacagcttt gacgaggctc tgggcctgcc taccgtgaag 1200
tctgccagaa tcgcccggaa cacccagatc atcatccaag aggaaagcgg catccccaag 1260
gtggcagatc cttggggcgg cagctacatg atggaatgcc tgaccaacga cgtgtacgac 1320
gccgctctga agctgatcaa cgagatcgaa gagatgggcg gcatggctaa ggctgtggcc 1380
gagggaatcc ccaagctgag aatcgaggaa tgcgccgcca gacggcaggc cagaattgat 1440
agcggaagcg aagtgatcgt gggcgtgaac aagtaccagc tcgaaaaaga ggacgccgtc 1500
gaggtcctgg ctatcgacaa taccagcgtg cggaaccggc agattgagaa gctgaagaag 1560
atcaagagca gccgcgatca ggccctggcc gaaagatgtc ttgctgccct gacagagtgt 1620
gccgccagcg gcgacggaaa tattctggct ctggccgtgg atgccagccg ggctagatgt 1680
accgtgggcg agattacaga cgccctgaag aaggtgttcg gcgagcacaa ggccaacgac 1740
agaatggtgt ctggcgccta cagacaagag tttggcgaga gcaaagagat caccagcgcc 1800
atcaagcggg tccacaagtt catggaaaga gaaggcaggc ggcccagact gctggtggct 1860
aagatgggac aagacggcca tgacagaggc gccaaagtga tcgccacagg ctttgccgat 1920
ctgggcttcg acgtggacat cggccctctg tttcagaccc ctagagaggt ggcacagcag 1980
gccgttgatg ccgatgttca cgctgtgggc atctctacac tggctgccgg acacaagaca 2040
ctggtgcccg aactgatcaa agagctgaac agcctgggca gacccgacat ccttgtgatg 2100
tgtggcggag tgatcccacc gcaggactac gagttcctgt ttgaagtggg cgtgtccaac 2160
gtgttcggcc ctggcacaag aatccctaaa gccgccgtgc aggttctgga cgacatcgag 2220
aagtgcctgg aaaaaaagca gcagagcgtg 2250

<210> SEQ ID NO 114
<211> LENGTH: 2247
<212> TYPE: DNA
<213> ORGANISM: Artificial Sequence
<220> FEATURE:
<223> OTHER INFORMATION: Synthetic Nucleic Acid

<400> SEQUENCE: 114
ctgcgggcca agaatcaact gttcctgctg tcccctcact acctgcggca agtgaaagag 60
agcagcggca gcagactgat ccagcagaga ctgctgcatc agcagcagcc actgcaccct 120

```
gaatgggccg ctctggctaa gaagcagctc aagggcaaga accccgagga cctgatctgg    180
cacacaccag agggcatcag catcaagccc ctgtactcca agcgggacac aatggatctg    240
cccgaggaac tgcctggcgt gaagcctttt acaagaggcc cctatcctac catgtatacc    300
ttcagaccct ggaccatccg gcagtacgcc ggcttttcta ccgtggaaga gagcaacaag    360
ttctacaagg acaacatcaa ggccggccag cagggactga gcgtggcatt tgatctggct    420
acccacaggg gctacgacag cgacaaccct agagtgcggg gagatgttgg aatggccggc    480
gtggcaatcg acacagtgga agataccaag atcctgttcg acggcatccc tctggaaaag    540
atgagcgtgt ccatgaccat gaacggcgct gtgatccccg tgctggctaa ctttattgtg    600
accggcgagg aacagggcgt gcccaaagaa aagctgaccg gcaccatcca gaacgacatc    660
ctgaaagagt tcatggttcg aaacacctac atcttcccac ctgagccgag catgaagatc    720
attgccgaca tcttcgagta caccgccaag cacatgccca agttcaacag catctccatc    780
agcggctacc acatgcaaga ggctggcgcc gatgccatcc tggaactggc ttatacactg    840
gccgacggcc tggaatactc cagaacagga ctgcaagccg gcctgaccat cgatgagttt    900
gcccctagac tgagcttctt ctggggcatc ggcatgaact tctacatgga aatcgccaag    960
atgagagccg gcagacggct gtgggctcac ctgatcgaga agatgttcca gcctaagaac   1020
agcaagagcc tgctcctgag agcccactgt cagacaagtg gctggtccct gactgagcag   1080
gacccctaca acaacatcgt gcgcacagcc atcgaagcta tggccgccgt gtttggcgga   1140
acacagagcc tgcacaccaa cagctttgac gaggctctgg gcctgcctac cgtgaagtct   1200
gccagaatcg cccggaacac ccagatcatc atccaagagg aaagcggcat ccccaaggtg   1260
gcagatcctt ggggcggcag ctacatgatg gaatgcctga ccaacgacgt gtacgacgcc   1320
gctctgaagc tgatcaacga gatcgaagag atgggcggca tggctaaggc tgtggccgag   1380
ggaatcccca agctgagaat cgaggaatgc gccgccagac ggcaggccag aattgatagc   1440
ggaagcgaag tgatcgtggg cgtgaacaag taccagctcg aaaaagagga cgccgtcgag   1500
gtcctggcta tcgacaatac cagcgtgcgg aaccggcaga ttgagaagct gaagaagatc   1560
aagagcagcc gcgatcaggc cctggccgaa agatgtcttg ctgccctgac agagtgtgcc   1620
gccagcggcg acggaaatat tctggctctg gccgtggatg ccagccgggc tagatgtacc   1680
gtgggcgaga ttacagacgc cctgaagaag gtgttcggcg agcacaaggc caacgacaga   1740
atggtgtctg gcgcctacag acaagagttt ggcgagagca aagagatcac cagcgccatc   1800
aagcgggtcc acaagttcat ggaaagagaa ggcaggcggc ccagactgct ggtggctaag   1860
atgggacaag acggccatga cagaggcgcc aaagtgatcg ccacaggctt tgccgatctg   1920
ggcttcgacg tggacatcgg ccctctgttt cagacccccta gagaggtggc acagcaggcc   1980
gttgatgccg atgttcacgc tgtgggcatc tctacactgg ctgccggaca caagacactg   2040
gtgcccgaac tgatcaaaga gctgaacagc ctgggcagac ccgacatcct tgtgatgtgt   2100
ggcggagtga tcccaccgca ggactacgag ttcctgtttg aagtgggcgt gtccaacgtg   2160
ttcggccctg gcacaagaat ccctaaagcc gccgtgcagg ttctggacga catcgagaag   2220
tgcctggaaa aaaagcagca gagcgtg                                       2247
```

<210> SEQ ID NO 115
<211> LENGTH: 2253
<212> TYPE: DNA
<213> ORGANISM: Artificial Sequence
<220> FEATURE:

<223> OTHER INFORMATION: Synthetic Nucleic Acid

<400> SEQUENCE: 115

```
atgctgagag ccaaaaacca gctgttcctg ctgagccccc actatctgag acaggtcaaa     60
gaaagttccg ggagtagact gatccagcag agactgctgc accagcagca gccactgcat    120
cctgagtggg ccgctctggc caagaaacag ctgaagggca aaaacccaga agacctgatc    180
tggcacactc cagaggggat ttcaatcaag cccctgtaca gcaaaaggga cactatggat    240
ctgccagagg aactgccagg agtgaagcct ttcacccgcg gaccttaccc aactatgtat    300
acctttcgac cctggacaat tcggcagtac gccggcttca gtactgtgga ggaatcaaac    360
aagttttata aggacaacat caaggctgga cagcagggcc tgagtgtggc attcgatctg    420
gccacacatc gcggctatga ctcagataat cccagagtca ggggggacgt gggaatggca    480
ggagtcgcta tcgacacagt ggaagatact aagattctgt tcgatggaat ccctctggag    540
aaaatgtctg tgagtatgac aatgaacggc gctgtcattc ccgtgctggc aaacttcatc    600
gtcactggcg aggaacaggg ggtgcctaag gaaaaactga ccggcacaat tcagaacgac    660
atcctgaagg agttcatggt gcggaatact tacatttttc cccctgaacc atccatgaaa    720
atcattgccg atatcttcga gtacaccgct aagcacatgc ccaagttcaa ctcaattagc    780
atctccgggt atcatatgca ggaagcagga gccgacgcta ttctggagct ggcttacacc    840
ctggcagatg gcctggaata ttctcgaacc ggactgcagg caggcctgac aatcgacgag    900
ttcgctccta gactgagttt cttttgggga attggcatga acttttacat ggagatcgcc    960
aagatgaggg ctggccggag actgtgggca cacctgatcg agaagatgtt ccagcctaag   1020
aactctaaga gtctgctgct gcgggcccat tgccagacat ccggctggtc tctgactgaa   1080
caggacccat ataacaatat tgtcagaacc gcaatcgagg caatggcagc cgtgttcgga   1140
ggaacccaga gcctgcacac aaactccttt gatgaggccc tggggctgcc taccgtgaag   1200
tctgctagga ttgcacgcaa tacacagatc attatccagg aggaatccgg aatcccaaag   1260
gtggccgatc cctggggagg ctcttacatg atggagtgcc tgacaaacga cgtgtatgat   1320
gctgcactga agctgattaa tgaaatcgag gaaatggggg gaatggcaaa ggccgtggct   1380
gagggcattc caaaactgag gatcgaggaa tgtgcagcta ggcgccaggc acgaattgac   1440
tcaggaagcg aagtgatcgt cggggtgaat aagtaccagc tggagaaaga agacgcagtc   1500
gaagtgctgg ccatcgataa cacaagcgtg cgcaatcgac agattgagaa gctgaagaaa   1560
atcaaaagct cccgcgatca ggcactggcc gaacgatgcc tggcagccct gactgagtgt   1620
gctgcaagcg gggacggaaa cattctggct ctggcagtcg atgcctcccg ggctagatgc   1680
actgtgggg aaatcaccga cgccctgaag aaagtcttcg gagagcacaa ggccaatgat   1740
cggatggtga gcggcgctta tagacaggag ttcggggaat ctaaagagat taccagtgcc   1800
atcaagaggg tgcacaagtt catggagaga gaagggcgac ggcccaggct gctggtggca   1860
aagatgggac aggacggaca tgatcgcgga gcaaaagtca ttgccaccgg gttcgctgac   1920
ctgggatttg acgtggatat cggccctctg ttccagacac cacgagaggt cgcacagcag   1980
gcagtcgacg ctgatgtgca cgcagtcgga gtgtccactc tggcagctgg ccataagacc   2040
ctggtgcctg aactgatcaa agagctgaac tctctgggca gaccagacat cctggtcatg   2100
tgcggcggcg tgatcccacc ccaggattac gaattcctgt ttgaggtcgg ggtgagcaac   2160
gtgttcggac caggaaccag gatccctaag gccgcagtgc aggtcctgga tgatattgaa   2220
aagtgtctgg aaaagaaaca gcagtcagtg taa                                2253
```

<210> SEQ ID NO 116
<211> LENGTH: 2250
<212> TYPE: DNA
<213> ORGANISM: Artificial Sequence
<220> FEATURE:
<223> OTHER INFORMATION: Synthetic Nucleic Acid

<400> SEQUENCE: 116
ctgagagcca aaaaccagct gttcctgctg agcccccact atctgagaca ggtcaaagaa 60
agttccggga gtagactgat ccagcagaga ctgctgcacc agcagcagcc actgcatcct 120
gagtgggccg ctctggccaa gaaacagctg aagggcaaaa acccagaaga cctgatctgg 180
cacactccag aggggatttc aatcaagccc ctgtacagca aaagggacac tatggatctg 240
ccagaggaac tgccaggagt gaagcctttc acccgcggac cttacccaac tatgtatacc 300
tttcgaccct ggacaattcg gcagtacgcc ggcttcagta ctgtggagga atcaaacaag 360
ttttataagg acaacatcaa ggctggacag cagggcctga gtgtggcatt cgatctggcc 420
acacatcgcg gctatgactc agataatccc agagtcaggg gggacgtggg aatggcagga 480
gtcgctatcg acacagtgga agatactaag attctgttcg atggaatccc tctggagaaa 540
atgtctgtga gtatgacaat gaacggcgct gtcattcccg tgctggcaaa cttcatcgtc 600
actggcgagg aacagggggt gcctaaggaa aaactgaccg gcacaattca gaacgacatc 660
ctgaaggagt tcatggtgcg gaatacttac atttttcccc ctgaaccatc catgaaaatc 720
attgccgata tcttcgagta caccgctaag cacatgccca agttcaactc aattagcatc 780
tccgggtatc atatgcagga agcaggagcc gacgctattc tggagctggc ttacaccctg 840
gcagatggcc tggaatattc tcgaaccgga ctgcaggcag gcctgacaat cgacgagttc 900
gctcctagac tgagtttctt ttggggaatt ggcatgaact tttacatgga gatcgccaag 960
atgagggctg gccggagact gtgggcacac ctgatcgaga agatgttcca gcctaagaac 1020
tctaagagtc tgctgctgcg ggcccattgc cagacatccg gctggtctct gactgaacag 1080
gacccatata acaatattgt cagaaccgca atcgaggcaa tggcagccgt gttcggagga 1140
acccagagcc tgcacacaaa ctcctttgat gaggccctgg ggctgcctac cgtgaagtct 1200
gctaggattg cacgcaatac acagatcatt atccaggagg aatccggaat cccaaaggtg 1260
gccgatccct ggggaggctc ttacatgatg gagtgcctga caaacgacgt gtatgatgct 1320
gcactgaagc tgattaatga aatcgaggaa atggggggaa tggcaaaggc cgtggctgag 1380
ggcattccaa aactgaggat cgaggaatgt gcagctaggc gccaggcacg aattgactca 1440
ggaagcgaag tgatcgtcgg ggtgaataag taccagctgg agaaagaaga cgcagtcgaa 1500
gtgctggcca tcgataacac aagcgtgcgc aatcgacaga ttgagaagct gaagaaaatc 1560
aaaagctccc gcgatcaggc actggccgaa cgatgcctgg cagccctgac tgagtgtgct 1620
gcaagcgggg acggaaacat tctggctctg gcagtcgatg cctcccgggc tagatgcact 1680
gtgggggaaa tcaccgacgc cctgaagaaa gtcttcggag agcacaaggc caatgatcgg 1740
atggtgagcg gcgcttatag acaggagttc ggggaatcta aagagattac cagtgccatc 1800
aagagggtgc acaagttcat ggagagagaa gggcgacggc ccaggctgct ggtggcaaag 1860
atgggacagg acggacatga tcgcggagca aaagtcattg ccaccgggtt cgctgacctg 1920
ggatttgacg tggatatcgg ccctctgttc cagacaccac gagaggtcgc acagcaggca 1980
gtcgacgctg atgtgcacgc agtcggagtg tccactctgg cagctggcca taagaccctg 2040
gtgcctgaac tgatcaaaga gctgaactct ctgggcagac cagacatcct ggtcatgtgc 2100
ggcggcgtga tcccacccca ggattacgaa ttcctgtttg aggtcggggt gagcaacgtg 2160
ttcggaccag gaaccaggat ccctaaggcc gcagtgcagg tcctggatga tattgaaaag 2220
tgtctggaaa agaaacagca gtcagtgtaa 2250

<210> SEQ ID NO 117
<211> LENGTH: 2253
<212> TYPE: DNA
<213> ORGANISM: Artificial Sequence
<220> FEATURE:
<223> OTHER INFORMATION: Synthetic Nucleic Acid

<400> SEQUENCE: 117
atgttaagag ctaagaatca gctttttta ctttcacctc attacctgag gcaggtaaaa 60
gaatcatcag gctccaggct catacagcaa cgacttctac accagcaaca gccccttcac 120
ccagaatggg ctgccctggc taaaaagcag ctgaaaggca aaaacccaga agacctaata 180
tggcacaccc cggaagggat ctctataaaa cccttgtatt ccaagagaga tactatggac 240
ttacctgaag aacttccagg agtgaagcca ttcacacgtg gaccatatcc taccatgtat 300
acctttaggc cctggaccat ccgccagtat gctggtttta gtactgtgga agaaagcaat 360
aagttctata aggacaacat taaggctggt cagcagggat tatcagttgc ctttgatctg 420
gcgacacatc gtggctatga ttcagacaac cctcgagttc gtggtgatgt tggaatggct 480
ggagttgcta ttgacactgt ggaagatacc aaaattcttt ttgatggaat tcctttagaa 540
aaaatgtcag tttccatgac tatgaatgga gcagttattc cagttcttgc aaattttata 600
gtaactggag aagaacaagg tgtacctaaa gagaagctta ctggtaccat ccaaaatgat 660
atactaaagg aatttatggt tcgaaataca tacatttttc ctccagaacc atccatgaaa 720
attattgctg acatatttga atatacagca aagcacatgc caaaatttaa ttcaatttca 780
attagtggat accatatgca ggaagcaggg gctgatgcca ttctggagct ggcctatact 840
ttagcagatg gattggagta ctctagaact ggactccagg ctggcctgac aattgatgaa 900
tttgcaccaa ggttgtcttt cttctgggga attggaatga atttctatat ggaaatagca 960
aagatgagag ctggtagaag actctgggct cacttaatag agaaaatgtt tcagcctaaa 1020
aactcaaaat ctcttcttct aagagcacac tgtcagacat ctggatggtc acttactgag 1080
caggatccct acaataatat tgtccgtact gcaatagaag caatggcagc agtatttgga 1140
gggactcagt ctttgcacac aaattctttt gatgaagctt tgggtttgcc aactgtgaaa 1200
agtgctcgaa ttgccaggaa cacacaaatc atcattcaag aagaatctgg gattcccaaa 1260
gtggctgatc cttggggagg ttcttacatg atggaatgtc tcacaaatga tgtttatgat 1320
gctgctttaa agctcattaa tgaaattgaa gaaatgggtg gaatggccaa agctgtagct 1380
gagggaatac ctaaacttcg aattgaagaa tgtgctgccc gaagacaagc tagaatagat 1440
tctggttctg aagtaattgt tggagtaaat aagtaccagt tggaaaaaga agacgctgta 1500
gaagttctgg caattgataa tacttcagtg cgaaacaggc agattgaaaa acttaagaag 1560
atcaaatcca gcagggatca agctttggct gaacgttgtc ttgctgcact aaccgaatgt 1620
gctgctagcg gagatggaaa tatcctggct cttgcagtgg atgcatctcg ggcaagatgt 1680
acagtgggag aaatcacaga tgccctgaaa aaggtatttg gtgaacataa agcgaatgat 1740
cgaatggtga gtggagcata tcgccaggaa tttggagaaa gtaaagagat aacatctgct 1800
atcaagaggg ttcataaatt catggaacgt gaaggtcgca gacctcgtct tcttgtagca 1860
aaaatgggac aagatggcca tgacagagga gcaaaagtta ttgctacagg atttgctgat 1920
cttggttttg atgtggacat aggccctctt ttccagactc ctcgtgaagt ggcccagcag 1980
gctgtggatg cggatgtgca tgctgtgggc ataagcaccc tcgctgctgg tcataaaacc 2040
ctagttcctg aactcatcaa agaacttaac tcccttggac ggccagatat tcttgtcatg 2100
tgtggagggg tgataccacc tcaggattat gaatttctgt ttgaagttgg tgtttccaat 2160
gtatttggtc ctgggactcg aattccaaag gctgccgttc aggtgcttga tgatattgag 2220
aagtgtttgg aaaagaagca gcaatctgta taa 2253

<210> SEQ ID NO 118
<211> LENGTH: 2250
<212> TYPE: DNA
<213> ORGANISM: Artificial Sequence
<220> FEATURE:
<223> OTHER INFORMATION: Synthetic Nucleic Acid

<400> SEQUENCE: 118
ttaagagcta agaatcagct ttttttactt tcacctcatt acctgaggca ggtaaaagaa 60
tcatcaggct ccaggctcat acagcaacga cttctacacc agcaacagcc ccttcaccca 120
gaatgggctg ccctggctaa aaagcagctg aaaggcaaaa acccagaaga cctaatatgg 180
cacaccccgg aagggatctc tataaaaccc ttgtattcca agagagatac tatggactta 240
cctgaagaac ttccaggagt gaagccattc acacgtggac catatcctac catgtatacc 300
tttaggccct ggaccatccg ccagtatgct ggttttagta ctgtggaaga aagcaataag 360
ttctataagg acaacattaa ggctggtcag cagggattat cagttgcctt tgatctggcg 420
acacatcgtg gctatgattc agacaaccct cgagttcgtg gtgatgttgg aatggctgga 480
gttgctattg acactgtgga agataccaaa attcttttttg atggaattcc tttagaaaaa 540
atgtcagttt ccatgactat gaatggagca gttattccag ttcttgcaaa ttttatagta 600
actggagaag aacaaggtgt acctaaagag aagcttactg gtaccatcca aaatgatata 660
ctaaaggaat ttatggttcg aaatacatac atttttcctc cagaaccatc catgaaaatt 720
attgctgaca tatttgaata tacagcaaag cacatgccaa aatttaattc aatttcaatt 780
agtggatacc atatgcagga agcaggggct gatgccattc tggagctggc ctatacttta 840
gcagatggat tggagtactc tagaactgga ctccaggctg gcctgacaat tgatgaattt 900
gcaccaaggt tgtctttctt ctggggaatt ggaatgaatt tctatatgga aatagcaaag 960
atgagagctg gtagaagact ctgggctcac ttaatagaga aaatgtttca gcctaaaaac 1020
tcaaaatctc ttcttctaag agcacactgt cagacatctg gatggtcact tactgagcag 1080
gatccctaca ataatattgt ccgtactgca atagaagcaa tggcagcagt atttggaggg 1140
actcagtctt tgcacacaaa ttcttttgat gaagctttgg gtttgccaac tgtgaaaagt 1200
gctcgaattg ccaggaacac acaaatcatc attcaagaag aatctgggat tcccaaagtg 1260
gctgatcctt ggggaggttc ttacatgatg gaatgtctca caaatgatgt ttatgatgct 1320
gctttaaagc tcattaatga aattgaagaa atgggtggaa tggccaaagc tgtagctgag 1380
ggaataccta aacttcgaat tgaagaatgt gctgcccgaa gacaagctag aatagattct 1440
ggttctgaag taattgttgg agtaaataag taccagttgg aaaaagaaga cgctgtagaa 1500
gttctggcaa ttgataatac ttcagtgcga aacaggcaga ttgaaaaact taagaagatc 1560
aaatccagca gggatcaagc tttggctgaa cgttgtcttg ctgcactaac cgaatgtgct 1620
gctagcggag atggaaatat cctggctctt gcagtggatg catctcgggc aagatgtaca 1680
gtgggagaaa tcacagatgc cctgaaaaag gtatttggtg aacataaagc gaatgatcga 1740
atggtgagtg gagcatatcg ccaggaattt ggagaaagta aagagataac atctgctatc 1800
aagagggttc ataaattcat ggaacgtgaa ggtcgcagac ctcgtcttct tgtagcaaaa 1860
atgggacaag atggccatga cagaggagca aaagttattg ctacaggatt tgctgatctt 1920
ggttttgatg tggacatagg ccctcttttc cagactcctc gtgaagtggc ccagcaggct 1980
gtggatgcgg atgtgcatgc tgtgggcata agcaccctcg ctgctggtca taaaacccta 2040
gttcctgaac tcatcaaaga acttaactcc cttggacggc cagatattct tgtcatgtgt 2100
ggaggggtga taccacctca ggattatgaa tttctgtttg aagttggtgt ttccaatgta 2160
tttggtcctg ggactcgaat tccaaaggct gccgttcagg tgcttgatga tattgagaag 2220
tgtttggaaa agaagcagca atctgtataa 2250

<210> SEQ ID NO 119
<211> LENGTH: 2250
<212> TYPE: DNA
<213> ORGANISM: Artificial Sequence
<220> FEATURE:
<223> OTHER INFORMATION: Synthetic Nucleic Acid

<400> SEQUENCE: 119
atgctgcggg ccaagaacca gctgttcctg ctgagccctc actacctgcg gcaggtgaag 60
gagagcagcg gcagccggct gatccagcag cggctgctgc accagcagca gcccctgcac 120
cccgagtggg ccgccctggc caagaagcag ctgaagggca agaaccccga ggacctgatc 180
tggcacacgc ccgagggcat cagcatcaag cccctgtaca gcaagcggga caccatggac 240
ctgcccgagg agctgcccgg cgtgaagccc ttcacccggg gcccctaccc caccatgtac 300
accttccggc cctggaccat ccggcagtac gccggcttca gcaccgtgga ggagagcaac 360
aagttctaca aggacaacat caaggccggc cagcagggcc tgagcgtggc cttcgacctg 420
gccacccacc ggggctacga cagcgacaac ccacgggtgc ggggcgacgt gggcatggcc 480
ggcgtggcca tcgacaccgt ggaggacacc aagatcctgt tcgacggcat ccctctggag 540
aagatgagcg tgagcatgac catgaacggc gccgtgatcc ccgtgctggc caacttcatc 600
gtgaccggcg aggagcaggg cgtgcccaag gagaagctga ccggcaccat ccagaacgac 660
atcctgaagg agttcatggt gcggaacacc tacatcttcc ctcccgagcc cagcatgaag 720
atcatcgccg acatcttcga gtacaccgcc aagcacatgc ccaagttcaa cagcatcagc 780
atcagcggct accacatgca ggaggccggc gccgacgcca tcctggagct ggcctacacc 840
ctggccgacg gcctggagta cagccggacc ggcctgcagg ccggcctgac catcgacgag 900
ttcgcgcccc ggctgagctt cttctggggc atcggcatga acttctacat ggagatcgcc 960
aagatgcggg ccggccggcg gctgtgggcc cacctgatcg agaagatgtt ccagcccaag 1020
aacagcaaga gcctgctgct gcgggcccac tgccagacca gcggctggag cctgaccgag 1080
caggacccct acaacaacat cgtgcggacc gccatcgagg ccatggccgc cgtgttcggc 1140
ggcacccaga gcctgcacac caacagcttc gacgaggccc tgggcctgcc caccgtgaag 1200
agcgcccgga tcgcccggaa cacccagatc atcatccagg aggagagcgg catccccaag 1260
gtggccgacc cctggggcgg cagctacatg atggagtgcc tgaccaacga cgtgtacgac 1320
gccgccctga agctgatcaa cgagatcgag gagatgggcg gcatggccaa ggccgtggcc 1380
gagggcatcc ccaagctgcg gatcgaggag tgcgccgccc ggcggcaggc ccggatcgac 1440
agcggcagcg aggtgatcgt gggcgtgaac aagtaccagc tggagaagga ggacgccgtg 1500
gaggtgctgg ccatcgacaa caccagcgtg cggaaccggc agatcgagaa gctgaagaag 1560
atcaagagca gccgggacca ggccctggcc gagcggtgcc tggccgccct gaccgagtgc 1620
gccgccagcg gcgacggcaa catcctggcc ctggccgtgg acgccagccg ggcccggtgc 1680
accgtgggcg agatcaccga cgccctgaag aaggtgttcg gcgagcacaa ggccaacgac 1740
cggatggtga gcggcgccta ccggcaggag ttcggcgaga gcaaggagat caccagcgcc 1800
atcaagcggg tgcacaagtt catggagcgg gagggccggc ggccccggct gctggtggcc 1860
aagatgggcc aggacggcca cgaccggggc gccaaggtga tcgccaccgg cttcgccgac 1920
ctgggcttcg acgtggacat cggccccactg ttccagacgc cccgggaggt ggcccagcag 1980
gccgtggacg ccgacgtgca cgccgtgggc gtgagcaccc tggccgccgg ccacaagacc 2040
ctggtgcccg agctgatcaa ggagctgaac agcctgggcc ggcccgacat cctggtgatg 2100
tgcggcggcg tgatcccgcc ccaggactac gagttcctgt tcgaggtggg cgtgagcaac 2160
gtgttcggcc ccggcacccg gatccccaag gccgccgtgc aggtgctgga cgacatcgag 2220
aagtgcctgg agaagaagca gcagagcgtg 2250

<210> SEQ ID NO 120
<211> LENGTH: 2247
<212> TYPE: DNA
<213> ORGANISM: Artificial Sequence
<220> FEATURE:
<223> OTHER INFORMATION: Synthetic Nucleic Acid

<400> SEQUENCE: 120
ctgcgggcca agaaccagct gttcctgctg agccctcact acctgcggca ggtgaaggag 60
agcagcggca gccggctgat ccagcagcgg ctgctgcacc agcagcagcc cctgcacccc 120
gagtgggccg ccctggccaa gaagcagctg aagggcaaga accccgagga cctgatctgg 180
cacacgcccg agggcatcag catcaagccc ctgtacagca agcgggacac catggacctg 240
cccgaggagc tgcccggcgt gaagcccttc acccggggcc cctaccccac catgtacacc 300
ttccggccct ggaccatccg gcagtacgcc ggcttcagca ccgtggagga gagcaacaag 360
ttctacaagg acaacatcaa ggccggccag cagggcctga gcgtggcctt cgacctggcc 420
acccaccggg gctacgacag cgacaaccca cgggtgcggg gcgacgtggg catggccggc 480
gtggccatcg acaccgtgga ggacaccaag atcctgttcg acggcatccc tctggagaag 540
atgagcgtga gcatgaccat gaacggcgcc gtgatccccg tgctggccaa cttcatcgtg 600
accggcgagg agcagggcgt gcccaaggag aagctgaccg gcaccatcca gaacgacatc 660
ctgaaggagt tcatggtgcg gaacacctac atcttccctc ccgagcccag catgaagatc 720
atcgccgaca tcttcgagta caccgccaag cacatgccca agttcaacag catcagcatc 780
agcggctacc acatgcagga ggccggcgcc gacgccatcc tggagctggc ctacaccctg 840
gccgacggcc tggagtacag ccggaccggc ctgcaggccg gcctgaccat cgacgagttc 900
gcgccccggc tgagcttctt ctggggcatc ggcatgaact tctacatgga gatcgccaag 960
atgcgggccg gccggcggct gtgggcccac ctgatcgaga agatgttcca gcccaagaac 1020
agcaagagcc tgctgctgcg ggcccactgc cagaccagcg gctggagcct gaccgagcag 1080
gacccctaca acaacatcgt gcggaccgcc atcgaggcca tggccgccgt gttcggcggc 1140
acccagagcc tgcacaccaa cagcttcgac gaggccctgg gcctgcccac cgtgaagagc 1200
gcccggatcg cccggaacac ccagatcatc atccaggagg agagcggcat ccccaaggtg 1260
gccgacccct ggggcggcag ctacatgatg gagtgcctga ccaacgacgt gtacgacgcc 1320
gccctgaagc tgatcaacga gatcgaggag atgggcggca tggccaaggc cgtggccgag 1380
ggcatcccca agctgcggat cgaggagtgc gccgcccggc ggcaggcccg gatcgacagc 1440
ggcagcgagg tgatcgtggg cgtgaacaag taccagctgg agaaggagga cgccgtggag 1500
gtgctggcca tcgacaacac cagcgtgcgg aaccggcaga tcgagaagct gaagaagatc 1560
aagagcagcc gggaccaggc cctggccgag cggtgcctgg ccgccctgac cgagtgcgcc 1620
gccagcggcg acggcaacat cctggccctg gccgtggacg ccagccgggc ccggtgcacc 1680
gtgggcgaga tcaccgacgc cctgaagaag gtgttcggcg agcacaaggc caacgaccgg 1740
atggtgagcg gcgcctaccg gcaggagttc ggcgagagca aggagatcac cagcgccatc 1800
aagcgggtgc acaagttcat ggagcgggag ggccggcggc cccggctgct ggtggccaag 1860
atgggccagg acggccacga ccggggcgcc aaggtgatcg ccaccggctt cgccgacctg 1920
ggcttcgacg tggacatcgg cccactgttc cagacgcccc gggaggtggc ccagcaggcc 1980
gtggacgccg acgtgcacgc cgtgggcgtg agcaccctgg ccgccggcca caagaccctg 2040
gtgcccgagc tgatcaagga gctgaacagc ctgggccggc ccgacatcct ggtgatgtgc 2100
ggcggcgtga tcccgcccca ggactacgag ttcctgttcg aggtgggcgt gagcaacgtg 2160
ttcggccccg gcacccggat ccccaaggcc gccgtgcagg tgctggacga catcgagaag 2220
tgcctggaga agaagcagca gagcgtg 2247

<210> SEQ ID NO 121
<211> LENGTH: 750
<212> TYPE: PRT
<213> ORGANISM: Artificial Sequence
<220> FEATURE:
<223> OTHER INFORMATION: Synthetic Nucleic Acid

<400> SEQUENCE: 121

Met Leu Arg Ala Lys Asn Gln Leu Phe Leu Leu Ser Pro His Tyr Leu
1 5 10 15

Arg Gln Val Lys Glu Ser Ser Gly Ser Arg Leu Ile Gln Gln Arg Leu
20 25 30

Leu His Gln Gln Gln Pro Leu His Pro Glu Trp Ala Ala Leu Ala Lys
35 40 45

Lys Gln Leu Lys Gly Lys Asn Pro Glu Asp Leu Ile Trp His Thr Pro
50 55 60

Glu Gly Ile Ser Ile Lys Pro Leu Tyr Ser Lys Arg Asp Thr Met Asp
65 70 75 80

Leu Pro Glu Glu Leu Pro Gly Val Lys Pro Phe Thr Arg Gly Pro Tyr
85 90 95

Pro Thr Met Tyr Thr Phe Arg Pro Trp Thr Ile Arg Gln Tyr Ala Gly
100 105 110

Phe Ser Thr Val Glu Glu Ser Asn Lys Phe Tyr Lys Asp Asn Ile Lys
115 120 125

Ala Gly Gln Gln Gly Leu Ser Val Ala Phe Asp Leu Ala Thr His Arg
130 135 140

Gly Tyr Asp Ser Asp Asn Pro Arg Val Arg Gly Asp Val Gly Met Ala
145 150 155 160

Gly Val Ala Ile Asp Thr Val Glu Asp Thr Lys Ile Leu Phe Asp Gly
165 170 175

```
Ile Pro Leu Glu Lys Met Ser Val Ser Met Thr Met Asn Gly Ala Val
            180                 185                 190

Ile Pro Val Leu Ala Asn Phe Ile Val Thr Gly Glu Glu Gln Gly Val
        195                 200                 205

Pro Lys Glu Lys Leu Thr Gly Thr Ile Gln Asn Asp Ile Leu Lys Glu
    210                 215                 220

Phe Met Val Arg Asn Thr Tyr Ile Phe Pro Pro Glu Pro Ser Met Lys
225                 230                 235                 240

Ile Ile Ala Asp Ile Phe Glu Tyr Thr Ala Lys His Met Pro Lys Phe
                245                 250                 255

Asn Ser Ile Ser Ile Ser Gly Tyr His Met Gln Glu Ala Gly Ala Asp
            260                 265                 270

Ala Ile Leu Glu Leu Ala Tyr Thr Leu Ala Asp Gly Leu Glu Tyr Ser
        275                 280                 285

Arg Thr Gly Leu Gln Ala Gly Leu Thr Ile Asp Glu Phe Ala Pro Arg
    290                 295                 300

Leu Ser Phe Phe Trp Gly Ile Gly Met Asn Phe Tyr Met Glu Ile Ala
305                 310                 315                 320

Lys Met Arg Ala Gly Arg Arg Leu Trp Ala His Leu Ile Glu Lys Met
                325                 330                 335

Phe Gln Pro Lys Asn Ser Lys Ser Leu Leu Leu Arg Ala His Cys Gln
            340                 345                 350

Thr Ser Gly Trp Ser Leu Thr Glu Gln Asp Pro Tyr Asn Asn Ile Val
        355                 360                 365

Arg Thr Ala Ile Glu Ala Met Ala Ala Val Phe Gly Gly Thr Gln Ser
    370                 375                 380

Leu His Thr Asn Ser Phe Asp Glu Ala Leu Gly Leu Pro Thr Val Lys
385                 390                 395                 400

Ser Ala Arg Ile Ala Arg Asn Thr Gln Ile Ile Ile Gln Glu Glu Ser
                405                 410                 415

Gly Ile Pro Lys Val Ala Asp Pro Trp Gly Gly Ser Tyr Met Met Glu
            420                 425                 430

Cys Leu Thr Asn Asp Val Tyr Asp Ala Ala Leu Lys Leu Ile Asn Glu
        435                 440                 445

Ile Glu Glu Met Gly Gly Met Ala Lys Ala Val Ala Glu Gly Ile Pro
    450                 455                 460

Lys Leu Arg Ile Glu Glu Cys Ala Ala Arg Arg Gln Ala Arg Ile Asp
465                 470                 475                 480

Ser Gly Ser Glu Val Ile Val Gly Val Asn Lys Tyr Gln Leu Glu Lys
                485                 490                 495

Glu Asp Ala Val Glu Val Leu Ala Ile Asp Asn Thr Ser Val Arg Asn
            500                 505                 510

Arg Gln Ile Glu Lys Leu Lys Lys Ile Lys Ser Ser Arg Asp Gln Ala
        515                 520                 525

Leu Ala Glu Arg Cys Leu Ala Ala Leu Thr Glu Cys Ala Ala Ser Gly
    530                 535                 540

Asp Gly Asn Ile Leu Ala Leu Ala Val Asp Ala Ser Arg Ala Arg Cys
545                 550                 555                 560

Thr Val Gly Glu Ile Thr Asp Ala Leu Lys Lys Val Phe Gly Glu His
                565                 570                 575

Lys Ala Asn Asp Arg Met Val Ser Gly Ala Tyr Arg Gln Glu Phe Gly
            580                 585                 590

Glu Ser Lys Glu Ile Thr Ser Ala Ile Lys Arg Val His Lys Phe Met
```

```
        595                 600                 605

Glu Arg Glu Gly Arg Arg Pro Arg Leu Leu Val Ala Lys Met Gly Gln
    610                 615                 620

Asp Gly His Asp Arg Gly Ala Lys Val Ile Ala Thr Gly Phe Ala Asp
625                 630                 635                 640

Leu Gly Phe Asp Val Asp Ile Gly Pro Leu Phe Gln Thr Pro Arg Glu
                645                 650                 655

Val Ala Gln Gln Ala Val Asp Ala Asp Val His Ala Val Gly Val Ser
            660                 665                 670

Thr Leu Ala Ala Gly His Lys Thr Leu Val Pro Glu Leu Ile Lys Glu
        675                 680                 685

Leu Asn Ser Leu Gly Arg Pro Asp Ile Leu Val Met Cys Gly Gly Val
    690                 695                 700

Ile Pro Pro Gln Asp Tyr Glu Phe Leu Phe Glu Val Gly Val Ser Asn
705                 710                 715                 720

Val Phe Gly Pro Gly Thr Arg Ile Pro Lys Ala Ala Val Gln Val Leu
                725                 730                 735

Asp Asp Ile Glu Lys Cys Leu Glu Lys Lys Gln Gln Ser Val
            740                 745                 750


<210> SEQ ID NO 122
<211> LENGTH: 749
<212> TYPE: PRT
<213> ORGANISM: Artificial Sequence
<220> FEATURE:
<223> OTHER INFORMATION: Synthetic Nucleic Acid

<400> SEQUENCE: 122

Leu Arg Ala Lys Asn Gln Leu Phe Leu Leu Ser Pro His Tyr Leu Arg
1               5                   10                  15

Gln Val Lys Glu Ser Ser Gly Ser Arg Leu Ile Gln Gln Arg Leu Leu
            20                  25                  30

His Gln Gln Gln Pro Leu His Pro Glu Trp Ala Ala Leu Ala Lys Lys
        35                  40                  45

Gln Leu Lys Gly Lys Asn Pro Glu Asp Leu Ile Trp His Thr Pro Glu
    50                  55                  60

Gly Ile Ser Ile Lys Pro Leu Tyr Ser Lys Arg Asp Thr Met Asp Leu
65                  70                  75                  80

Pro Glu Glu Leu Pro Gly Val Lys Pro Phe Thr Arg Gly Pro Tyr Pro
                85                  90                  95

Thr Met Tyr Thr Phe Arg Pro Trp Thr Ile Arg Gln Tyr Ala Gly Phe
            100                 105                 110

Ser Thr Val Glu Glu Ser Asn Lys Phe Tyr Lys Asp Asn Ile Lys Ala
        115                 120                 125

Gly Gln Gln Gly Leu Ser Val Ala Phe Asp Leu Ala Thr His Arg Gly
    130                 135                 140

Tyr Asp Ser Asp Asn Pro Arg Val Arg Gly Asp Val Gly Met Ala Gly
145                 150                 155                 160

Val Ala Ile Asp Thr Val Glu Asp Thr Lys Ile Leu Phe Asp Gly Ile
                165                 170                 175

Pro Leu Glu Lys Met Ser Val Ser Met Thr Met Asn Gly Ala Val Ile
            180                 185                 190

Pro Val Leu Ala Asn Phe Ile Val Thr Gly Glu Glu Gln Gly Val Pro
        195                 200                 205

Lys Glu Lys Leu Thr Gly Thr Ile Gln Asn Asp Ile Leu Lys Glu Phe
```

```
    210                 215                 220

Met Val Arg Asn Thr Tyr Ile Phe Pro Pro Glu Pro Ser Met Lys Ile
225                 230                 235                 240

Ile Ala Asp Ile Phe Glu Tyr Thr Ala Lys His Met Pro Lys Phe Asn
                245                 250                 255

Ser Ile Ser Ile Ser Gly Tyr His Met Gln Glu Ala Gly Ala Asp Ala
            260                 265                 270

Ile Leu Glu Leu Ala Tyr Thr Leu Ala Asp Gly Leu Glu Tyr Ser Arg
        275                 280                 285

Thr Gly Leu Gln Ala Gly Leu Thr Ile Asp Glu Phe Ala Pro Arg Leu
    290                 295                 300

Ser Phe Phe Trp Gly Ile Gly Met Asn Phe Tyr Met Glu Ile Ala Lys
305                 310                 315                 320

Met Arg Ala Gly Arg Arg Leu Trp Ala His Leu Ile Glu Lys Met Phe
                325                 330                 335

Gln Pro Lys Asn Ser Lys Ser Leu Leu Leu Arg Ala His Cys Gln Thr
            340                 345                 350

Ser Gly Trp Ser Leu Thr Glu Gln Asp Pro Tyr Asn Asn Ile Val Arg
        355                 360                 365

Thr Ala Ile Glu Ala Met Ala Ala Val Phe Gly Gly Thr Gln Ser Leu
    370                 375                 380

His Thr Asn Ser Phe Asp Glu Ala Leu Gly Leu Pro Thr Val Lys Ser
385                 390                 395                 400

Ala Arg Ile Ala Arg Asn Thr Gln Ile Ile Ile Gln Glu Glu Ser Gly
                405                 410                 415

Ile Pro Lys Val Ala Asp Pro Trp Gly Gly Ser Tyr Met Met Glu Cys
            420                 425                 430

Leu Thr Asn Asp Val Tyr Asp Ala Ala Leu Lys Leu Ile Asn Glu Ile
        435                 440                 445

Glu Glu Met Gly Gly Met Ala Lys Ala Val Ala Glu Gly Ile Pro Lys
    450                 455                 460

Leu Arg Ile Glu Glu Cys Ala Ala Arg Arg Gln Ala Arg Ile Asp Ser
465                 470                 475                 480

Gly Ser Glu Val Ile Val Gly Val Asn Lys Tyr Gln Leu Glu Lys Glu
                485                 490                 495

Asp Ala Val Glu Val Leu Ala Ile Asp Asn Thr Ser Val Arg Asn Arg
            500                 505                 510

Gln Ile Glu Lys Leu Lys Lys Ile Lys Ser Ser Arg Asp Gln Ala Leu
        515                 520                 525

Ala Glu Arg Cys Leu Ala Ala Leu Thr Glu Cys Ala Ala Ser Gly Asp
    530                 535                 540

Gly Asn Ile Leu Ala Leu Ala Val Asp Ala Ser Arg Ala Arg Cys Thr
545                 550                 555                 560

Val Gly Glu Ile Thr Asp Ala Leu Lys Lys Val Phe Gly Glu His Lys
                565                 570                 575

Ala Asn Asp Arg Met Val Ser Gly Ala Tyr Arg Gln Glu Phe Gly Glu
            580                 585                 590

Ser Lys Glu Ile Thr Ser Ala Ile Lys Arg Val His Lys Phe Met Glu
        595                 600                 605

Arg Glu Gly Arg Arg Pro Arg Leu Leu Val Ala Lys Met Gly Gln Asp
    610                 615                 620

Gly His Asp Arg Gly Ala Lys Val Ile Ala Thr Gly Phe Ala Asp Leu
625                 630                 635                 640
```

-continued

Gly Phe Asp Val Asp Ile Gly Pro Leu Phe Gln Thr Pro Arg Glu Val
645 650 655

Ala Gln Gln Ala Val Asp Ala Asp Val His Ala Val Gly Val Ser Thr
660 665 670

Leu Ala Ala Gly His Lys Thr Leu Val Pro Glu Leu Ile Lys Glu Leu
675 680 685

Asn Ser Leu Gly Arg Pro Asp Ile Leu Val Met Cys Gly Gly Val Ile
690 695 700

Pro Pro Gln Asp Tyr Glu Phe Leu Phe Glu Val Gly Val Ser Asn Val
705 710 715 720

Phe Gly Pro Gly Thr Arg Ile Pro Lys Ala Ala Val Gln Val Leu Asp
725 730 735

Asp Ile Glu Lys Cys Leu Glu Lys Lys Gln Gln Ser Val
740 745

<210> SEQ ID NO 123
<211> LENGTH: 354
<212> TYPE: PRT
<213> ORGANISM: Artificial Sequence
<220> FEATURE:
<223> OTHER INFORMATION: Synthetic Sequence

<400> SEQUENCE: 123

Met Leu Ser Asn Leu Arg Ile Leu Leu Asn Asn Ala Ala Leu Arg Lys
1 5 10 15

Gly His Thr Ser Val Val Arg His Phe Trp Cys Gly Lys Pro Val Gln
20 25 30

Asn Lys Val Gln Leu Lys Gly Arg Asp Leu Leu Thr Leu Lys Asn Phe
35 40 45

Thr Gly Glu Glu Ile Lys Tyr Met Leu Trp Leu Ser Ala Asp Leu Lys
50 55 60

Phe Arg Ile Lys Gln Lys Gly Glu Tyr Leu Pro Leu Leu Gln Gly Lys
65 70 75 80

Ser Leu Gly Met Ile Phe Glu Lys Arg Ser Thr Arg Thr Arg Leu Ser
85 90 95

Thr Glu Thr Gly Phe Ala Leu Leu Gly Gly His Pro Cys Phe Leu Thr
100 105 110

Thr Gln Asp Ile His Leu Gly Val Asn Glu Ser Leu Thr Asp Thr Ala
115 120 125

Arg Val Leu Ser Ser Met Ala Asp Ala Val Leu Ala Arg Val Tyr Lys
130 135 140

Gln Ser Asp Leu Asp Thr Leu Ala Lys Glu Ala Ser Ile Pro Ile Ile
145 150 155 160

Asn Gly Leu Ser Asp Leu Tyr His Pro Ile Gln Ile Leu Ala Asp Tyr
165 170 175

Leu Thr Leu Gln Glu His Tyr Ser Ser Leu Lys Gly Leu Thr Leu Ser
180 185 190

Trp Ile Gly Asp Gly Asn Asn Ile Leu His Ser Ile Met Met Ser Ala
195 200 205

Ala Lys Phe Gly Met His Leu Gln Ala Ala Thr Pro Lys Gly Tyr Glu
210 215 220

Pro Asp Ala Ser Val Thr Lys Leu Ala Glu Gln Tyr Ala Lys Glu Asn
225 230 235 240

Gly Thr Lys Leu Leu Leu Thr Asn Asp Pro Leu Glu Ala Ala His Gly
245 250 255

Gly Asn Val Leu Ile Thr Asp Thr Trp Ile Ser Met Gly Gln Glu Glu
260 265 270

Glu Lys Lys Lys Arg Leu Gln Ala Phe Gln Gly Tyr Gln Val Thr Met
275 280 285

Lys Thr Ala Lys Val Ala Ala Ser Asp Trp Thr Phe Leu His Cys Leu
290 295 300

Pro Arg Lys Pro Glu Glu Val Asp Asp Glu Val Phe Tyr Ser Pro Arg
305 310 315 320

Ser Leu Val Phe Pro Glu Ala Glu Asn Arg Lys Trp Thr Ile Met Ala
325 330 335

Val Met Val Ser Leu Leu Thr Asp Tyr Ser Pro Gln Leu Gln Lys Pro
340 345 350

Lys Phe

<210> SEQ ID NO 124
<211> LENGTH: 353
<212> TYPE: PRT
<213> ORGANISM: Artificial Sequence
<220> FEATURE:
<223> OTHER INFORMATION: Synthetic Sequence

<400> SEQUENCE: 124

Leu Ser Asn Leu Arg Ile Leu Leu Asn Asn Ala Ala Leu Arg Lys Gly
1 5 10 15

His Thr Ser Val Val Arg His Phe Trp Cys Gly Lys Pro Val Gln Asn
20 25 30

Lys Val Gln Leu Lys Gly Arg Asp Leu Leu Thr Leu Lys Asn Phe Thr
35 40 45

Gly Glu Glu Ile Lys Tyr Met Leu Trp Leu Ser Ala Asp Leu Lys Phe
50 55 60

Arg Ile Lys Gln Lys Gly Glu Tyr Leu Pro Leu Leu Gln Gly Lys Ser
65 70 75 80

Leu Gly Met Ile Phe Glu Lys Arg Ser Thr Arg Thr Arg Leu Ser Thr
85 90 95

Glu Thr Gly Phe Ala Leu Leu Gly Gly His Pro Cys Phe Leu Thr Thr
100 105 110

Gln Asp Ile His Leu Gly Val Asn Glu Ser Leu Thr Asp Thr Ala Arg
115 120 125

Val Leu Ser Ser Met Ala Asp Ala Val Leu Ala Arg Val Tyr Lys Gln
130 135 140

Ser Asp Leu Asp Thr Leu Ala Lys Glu Ala Ser Ile Pro Ile Ile Asn
145 150 155 160

Gly Leu Ser Asp Leu Tyr His Pro Ile Gln Ile Leu Ala Asp Tyr Leu
165 170 175

Thr Leu Gln Glu His Tyr Ser Ser Leu Lys Gly Leu Thr Leu Ser Trp
180 185 190

Ile Gly Asp Gly Asn Asn Ile Leu His Ser Ile Met Met Ser Ala Ala
195 200 205

Lys Phe Gly Met His Leu Gln Ala Ala Thr Pro Lys Gly Tyr Glu Pro
210 215 220

Asp Ala Ser Val Thr Lys Leu Ala Glu Gln Tyr Ala Lys Glu Asn Gly
225 230 235 240

Thr Lys Leu Leu Leu Thr Asn Asp Pro Leu Glu Ala Ala His Gly Gly
245 250 255

```
Asn Val Leu Ile Thr Asp Thr Trp Ile Ser Met Gly Gln Glu Glu Glu
            260                 265                 270

Lys Lys Lys Arg Leu Gln Ala Phe Gln Gly Tyr Gln Val Thr Met Lys
        275                 280                 285

Thr Ala Lys Val Ala Ala Ser Asp Trp Thr Phe Leu His Cys Leu Pro
    290                 295                 300

Arg Lys Pro Glu Glu Val Asp Asp Glu Val Phe Tyr Ser Pro Arg Ser
305                 310                 315                 320

Leu Val Phe Pro Glu Ala Glu Asn Arg Lys Trp Thr Ile Met Ala Val
                325                 330                 335

Met Val Ser Leu Leu Thr Asp Tyr Ser Pro Gln Leu Gln Lys Pro Lys
            340                 345                 350

Phe
```

<210> SEQ ID NO 125
<211> LENGTH: 175
<212> TYPE: DNA
<213> ORGANISM: Artificial Sequence
<220> FEATURE:
<223> OTHER INFORMATION: Synthetic Construct

<400> SEQUENCE: 125

```
tgttttatcg gtctgtatat cgaggtttat ttattaattt gaatagatat taagttttat     60

tatatttaca cttacatact aataataaat tcaacaaaca atttatttat gtttatttat    120

ttattaaaaa aaaacaaaaa ctcaaaattt cttctataaa gtaacaaaac tttta         175
```

<210> SEQ ID NO 126
<211> LENGTH: 255
<212> TYPE: DNA
<213> ORGANISM: Artificial Sequence
<220> FEATURE:
<223> OTHER INFORMATION: Synthetic Sequence

<400> SEQUENCE: 126

```
tgtttgctgc ttgcaatgtt tgcccatttt agggtggaca caggacgctg tggtttctga     60

gccagggggc gactcagatc ccagccagtg gacttagccc ctgtttgctc ctccgataac    120

tggggtgacc ttggttaata ttcaccagca gcctcccccg ttgcccctct ggatccactg    180

cttaaatacg gacgaggaca gggccctgtc tcctcagctt caggcaccac cactgacctg    240

ggacagtgaa tcgca                                                     255
```

<210> SEQ ID NO 127
<211> LENGTH: 141
<212> TYPE: DNA
<213> ORGANISM: Artificial Sequence
<220> FEATURE:
<223> OTHER INFORMATION: Synthetic Sequence

<400> SEQUENCE: 127

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc t                                              141
```

<210> SEQ ID NO 128
<211> LENGTH: 122
<212> TYPE: DNA
<213> ORGANISM: Artificial Sequence
<220> FEATURE:
<223> OTHER INFORMATION: Synthetic Sequence

<400> SEQUENCE: 128
taagatacat tgatgagttt ggacaaacca caactagaat gcagtgaaaa aaatgcttta 60
tttgtgaaat ttgtgatgct attgctttat ttgtaaccat tataagctgc aataaacaag 120
tt 122

<210> SEQ ID NO 129
<211> LENGTH: 1445
<212> TYPE: DNA
<213> ORGANISM: Artificial Sequence
<220> FEATURE:
<223> OTHER INFORMATION: Synthetic Sequence

<400> SEQUENCE: 129
tttcctggac tacttcagac gaacttcgta gggcgcataa gtctcgacca cgcaatgacg 60
cagcgatgct tgaaaaaaac accgctttca aggcggctgg acgaagaccg caagacaccc 120
tccacctcac ctagcctgta tctctgcaat agcctaatta cttcggaatc tcctgtcgta 180
attccttaga taaacggcaa ttaggtgaca ctctaaatct gtgtggaacc ggcttccaaa 240
cactctacca cctctattag tgacacagag agaatccttg agtggcttct aggtatattg 300
aacaacttca tcacgaattg agcagtgatc atggttctac gtatcaacca atattaacca 360
ctgtgctctg tagcattgct aaatcgggct gtctgtttca ccatagatcg tgaggccatg 420
cccacgggca ttagaactta gcctgtttag cgataatccc aacaatgagc tgggatatga 480
cgagaagtat ttagcaacct tttcgtgatc ggctacgtaa aacctcatat tacggcatgt 540
acctgatcat tgacctcagg ccatacgcat gtgggagaat agagggaata gcacgatata 600
ctgcctccct tatcttcctc aggttgaggc gcaatgatta tcactgctac gggcacagtg 660
ttactatcgg gatcagggac tgtgtctgta cccggttcta ccacgccgta gctcccacat 720
tgtcgccgta ctggtagtaa cctaccagta ctacagggac aggtcagatt attcttagaa 780
tgcctgtgta tagtttagag ccatagattg ccgagaaacg aagagagtgt atcacggcga 840
tttacggagt caagatagca acacatagga gtaccaaatc aataagtgta gtagagttac 900
aagtcgctcc cgagaatcag gtgatacttc tcaatcgtcg gaaacctgta acgattagac 960
cgcgtattag ttccatctaa tgatattgcc aagtactaaa cctcaatcac ataacaacgc 1020
atcaggctag cgacatcata ggagtcctgc aacatacgca ggcgtccagc gtcataaacg 1080
caggtgatga gtgccttatg caatctgggg cacaccaata cgagaatacc acgtcgttag 1140
ggccagcctg cgcttggtac gtgatcgagg agtatcgtct tgtgcacaca aacaaaatag 1200
actgggtccc aagcgcactt agacaaggca ttgtactact caagtgttgg atgtgaggaa 1260
tgatacaatc gaaccccgtc gttcggtcaa caatttggct agagctgtgt tgatacacag 1320
cggacgggag ttacggggac agtcctccga gctggccagc aagatgcagc tgacgcctgc 1380
accggaagta atccggaggc cggccaggcc tcctgcgagg gggcgcctcg agaccttgcg 1440
gccgc 1445

<210> SEQ ID NO 130
<211> LENGTH: 1445
<212> TYPE: DNA
<213> ORGANISM: Artificial Sequence
<220> FEATURE:
<223> OTHER INFORMATION: Synthetic Sequence

<400> SEQUENCE: 130

```
tttcctggac tacttcagac gaacttcgta gggcgcataa gtctcgacca cgcaatgacg     60

cagcgatgct tgaaaaaaac cccgctttca aggcggctgg acgaagaccg caagacaccc    120

tccacctcac ctagcctgta tctctgcaat agcctaatta cttcggaatc tcctgtcgta    180

attccttaga taaacggcaa ttaggtgaca ctctaaatct gtgtggaacc ggcttccaaa    240

cactctacca cctctattag tgacacagag agaatccttg agtggcttct aggtatattg    300

aacaacttca tcacgaattg agcagtgatc atggttctac gtatcaacca atattaacca    360

ctgtgctctg tagcattgct aaatcgggct gtctgtttca ccatagatcg tgaggccatg    420

cccacgggca ttagaactta gcctgtttag cgataatccc aacaatgagc tgggatatga    480

cgagaagtat ttagcaacct tttcgtgatc ggctacgtaa aacctcatat tacggcatgt    540

acctgatcat tgacctcagg ccatacgcat gtgggagaat agagggaata gcacgatata    600

ctgcctccct tatcttcctc aggttgaggc gcaatgatta tcactgctac gggcacagtg    660

ttactatcgg gatcagggac tgtgtctgta cccggttcta ccacgccgta gctcccacat    720

tgtcgccgta ctggtagtaa cctaccagta ctacagggac aggtcagatt attcttagaa    780

tgcctgtgta tagtttagag ccatagattg ccgagaaacg aagagagtgt atcacggcga    840

tttacggagt caagatagca acacatagga gtaccaaatc aataagtgta gtagagttac    900

aagtcgctcc cgagaatcag gtgatacttc tcaatcgtcg gaaacctgta acgattagac    960

cgcgtattag ttccatctaa tgatattgcc aagtactaaa cctcaatcac ataacaacgc   1020

atcaggctag cgacatcata ggagtcctgc aacatacgca ggcgtccagc gtcataaacg   1080

caggtgatga gtgccttatg caatctgggg cacaccaata cgagaatacc acgtcgttag   1140

ggccagcctg cgcttggtac gtgatcgagg agtatcgtct tgtgcacaca aacaaaatag   1200

actgggtccc aagcgcactt agacaaggca ttgtactact caagtgttgg atgtgaggaa   1260

tgatacaatc gaaccccgtc gttcggtcaa caatttggct agagctgtgt tgatacacag   1320

cggacgggag ttacggggac agtcctccga gctggccagc aagatgcagc tgacgcctgc   1380

accggaagta atccggaggc cggccaggcc tcctgcgagg gggcgcctcg agaccttgcg   1440

gccgc                                                                1445
```

```
<210> SEQ ID NO 131
<211> LENGTH: 927
<212> TYPE: DNA
<213> ORGANISM: Artificial Sequence
<220> FEATURE:
<223> OTHER INFORMATION: Synthetic Sequence

<400> SEQUENCE: 131

tttcctgtcg acggaggcat gtacctgatc attgacctca ggccatacgc atgtgggaga     60

atagagggaa tagcacgata tactgcctcc cttatcttcc tcaggttgag gcgcaatgat    120

tatcactgct acgggcacag tgttactatc gggatcaggg actgtgtctg tacccggttc    180

taccacgccg tagctcccac attgtcgccg tactggtagt aacctaccag tactacaggg    240

acaggtcaga ttattcttag aatgcctgtg tatagtttag agccatagat tgccgagaaa    300

cgaagagagt gtatcacggc gatttacgga gtcaagatag caacacatag gagtaccaaa    360

tcaataagtg tagtagagtt acaagtcgct cccgagaatc aggtgatact tctcaatcgt    420

cggaaacctg taacgattag accgcgtatt agttccatct aatgatattg ccaagtacta    480

aacctcaatc acataacaac gcatcaggct agcgacatca taggagtcct gcaacatacg    540

caggcgtcca gcgtcataaa cgcaggtgat gagtgcctta tgcaatctgg ggcacaccaa    600
```

tacgagaata ccacgtcgtt agggccagcc tgcgcttggt acgtgatcga ggagtatcgt 660
cttgtgcaca caaacaaaat agactgggtc ccaagcgcac ttagacaagg cattgtacta 720
ctcaagtgtt ggatgtgagg aatgatacaa tcgaaccccg tcgttcggtc aacaatttgg 780
ctagagctgt gttgatacac agcggacggg agttacgggg acagtcctcc gagctggcca 840
gcaagatgca gctgacgcct gcaccggaag taatccggag gccggccagg cctcctgcga 900
gggggcgcct cgagaccttg cggccgc 927

<210> SEQ ID NO 132
<211> LENGTH: 435
<212> TYPE: DNA
<213> ORGANISM: Artificial Sequence
<220> FEATURE:
<223> OTHER INFORMATION: Synthetic Sequence

<400> SEQUENCE: 132
aaacattgca agcagcaaac agcaaacaca cagccctccc tgcctgctga ccttggagct 60
ggggcagagg tcagagacct ctctgggccc atgccacctc caacatccac tcgacccctt 120
ggaatttcgg tggagaggag cagaggttgt cctggcgtgg tttaggtagt gtgagagggg 180
aatgactcct ttcggtaagt gcagtggaag ctgtacactg cccaggcaaa gcgtccgggc 240
agcgtaggcg ggcgactcag atcccagcca gtggacttag cccctgtttg ctcctccgat 300
aactggggtg accttggtta atattcacca gcagcctccc ccgttgcccc tctggatcca 360
ctgcttaaat acggacgagg acagggccct gtctcctcag cttcaggcac caccactgac 420
ctgggacagt gaatc 435

<210> SEQ ID NO 133
<211> LENGTH: 717
<212> TYPE: DNA
<213> ORGANISM: Artificial Sequence
<220> FEATURE:
<223> OTHER INFORMATION: Synthetic Sequence

<400> SEQUENCE: 133
atggtttcca agggcgaaga actgtttacc ggcgtggtgc ccatcctggt ggaactggat 60
ggcgacgtta acggacacaa gttcagcgtc agcggagaag gcgaaggcga cgccacatac 120
ggaaagctga cactgaagtt tatctgcacc accggcaagc tgcccgtgcc ttggcctaca 180
ctggtcacca cactgacata cggcgtgcag tgcttcagca gataccccga ccacatgaag 240
cagcacgatt tcttcaagag cgccatgcct gagggctacg tgcaagagcg gaccatcttc 300
ttcaaggacg acgggaacta caagaccaga gccgaagtga agttcgaggg cgacaccctc 360
gtgaaccgga tcgagctgaa gggcatcgac ttcaaagagg acggaaacat cctgggccac 420
aaacttgagt acaactacaa cagccacaac gtctacatca tggccgacaa gcagaaaaac 480
ggcatcaaag tgaacttcaa gatccggcac aacatcgagg acggctctgt gcagctggct 540
gaccactacc agcagaacac acccatcgga gatggccctg tgctgctgcc cgataaccac 600
tacctgagca cacagagcgc cctgagcaag gaccccaacg agaagaggga tcacatggtg 660
ctgctggaat ttgtgaccgc tgccggcatc accctcggca tggatgaact gtacaag 717

<210> SEQ ID NO 134
<211> LENGTH: 628
<212> TYPE: DNA
<213> ORGANISM: Artificial Sequence
<220> FEATURE:

<223> OTHER INFORMATION: Synthetic Sequence

<400> SEQUENCE: 134
atggtcttta ccctggaaga tttcgtcggc gactggcggc agacagccgg ctataatctg 60
gaccaggtgc tggaacaagg cggagtgtcc agcctgttcc agaatctggg agtgtccgtg 120
acacccatcc agcggattgt gctgtctggc gagaacggcc tgaagatcga catccacgtg 180
atcatccctt acgagggcct gagcggcgat cagatgggac agatcgagaa gattttcaag 240
gtggtgtacc ccgtggacga ccaccacttc aaagtgatcc tgcactacgg caccctggtc 300
atcgatggcg tgacccctaa catgatcgac tacttcggca gaccctacga gggaatcgcc 360
gtgttcgacg gcaagaaaat caccgtgacc ggcacactgt ggaacgggaa caagatcatc 420
gacgagcggc tgatcaaccc cgatggcagc ctgctgttca gagtgaccat taacggcgtg 480
acaggctggc ggctgtgcga aaggattctg gcctgatgat ctagagatct catatgcctt 540
taattaaaca ctagttctat agtgtcacct aaattccctt tagtgagggt taatggccgt 600
aggccgccag aattgggtcc agacatga 628

<210> SEQ ID NO 135
<211> LENGTH: 63
<212> TYPE: DNA
<213> ORGANISM: Artificial Sequence
<220> FEATURE:
<223> OTHER INFORMATION: Synthetic Sequence

<400> SEQUENCE: 135
ggatccggag aaggacgggg aagcctgctt acatgcggag atgtggagga gaatcctggt 60
ccc 63

<210> SEQ ID NO 136
<211> LENGTH: 122
<212> TYPE: DNA
<213> ORGANISM: Artificial Sequence
<220> FEATURE:
<223> OTHER INFORMATION: Synthetic Sequence

<400> SEQUENCE: 136
aacttgttta ttgcagctta taatggttac aaataaagca atagcatcac aaatttcaca 60
aataaagcat ttttttcact gcattctagt tgtggtttgt ccaaactcat caatgtatct 120
ta 122

<210> SEQ ID NO 137
<211> LENGTH: 1906
<212> TYPE: DNA
<213> ORGANISM: Artificial Sequence
<220> FEATURE:
<223> OTHER INFORMATION: Synthetic Sequence

<400> SEQUENCE: 137
cctcgcagga ggcctggccg gcctccggat tacttccggt gcaggcgtca gctgcatctt 60
gctggccagc tcggaggact gtccccgtaa ctcccgtccg ctgtgtatca acacagctct 120
agccaaattg ttgaccgaac gacggggttc gattgtatca ttcctcacat ccaacacttg 180
agtagtacaa tgccttgtct aagtgcgctt gggacccagt ctattttgtt tgtgtgcaca 240
agacgatact cctcgatcac gtaccaagcg caggctggcc ctaacgacgt ggtattctcg 300
tattggtgtg ccccagattg cataaggcac tcatcacctg cgtttatgac gctggacgcc 360
tgcgtatgtt gcaggactcc tatgatgtcg ctagcctgat gcgttgttat gtgattgagg 420
tttagtactt ggcaatatca ttagatggaa ctaatacgcg gtctaatcgt tacaggtttc 480
cgacgattga gaagtatcac ctgattctcg ggagcgactt gtaactctac tacacttatt 540
gatttggtac tcctatgtgt tgctatcttg actccgtaaa tcgccgtgat acactctctt 600
cgtttctcgg caatctatgg ctctaaacta tacacaggca ttctaagaat aatctgacct 660
gtccctgtag tactggtagg ttactaccag tacggcgaca atgtgggagc tacggcgtgg 720
tagaaccggg tacagacaca gtccctgatc ccgatagtaa cactgtgccc gtagcagtga 780
taatcattgc gcctcaacct gaggaagata agggaggcag tatatcgtgc tattccctct 840
attctcccac atgcgtatgg cctgaggtca atgatcaggt acatgccgta atatgaggtt 900
ttacgtagcc gatcacgaaa aggttgctaa atacttctcg tcatatccca gctcattgtt 960
gggattatcg ctaaacaggc taagttctaa tgcccgtggg catggcctca cgatctatgg 1020
tgaaacagac agcccgattt agcaatgcta cagagcacag tggttaatat tggttgatac 1080
gtagaaccat gatcactgct caattcgtga tgaagttgtt caatatacct agaagccact 1140
caaggattct ctctgtgtca ctaatagagg tggtagagtg tttggaagcc ggttccacac 1200
agatttagag tgtcacctaa ttgccgttta tctaaggaat tacgacagga gattccgaag 1260
taattaggct attgcagaga tacaggctag gtgaggtgga gggtgtcttg cggtcttcgt 1320
ccagccgcct tgaaagcggg gttttttca agcatcgctg cgtcattgcg tggtcgagac 1380
ttatgcgccc tacgaagttc gtctgaagta gtccaggaaa gacctacttt gcagttatct 1440
tcgcattccc acactcacca ctacaactac tcttccctca atttcccggt tagtttcgct 1500
aagctccgac cttgggttac tgtgttgcat ccgactcgct gcggctttct agtacgctgt 1560
actgtttcat tcttctgtag gtctggttcc gtaagtccga atttccaggc cgtggtctag 1620
tcctaattat tttctgtccc ggtagctata tttagccgag ggtttgtcca tttgcccggc 1680
gtagagcgcc gcgtttgcga acatttgcgc ccgtaatacg tagggacacc gtcgggtaat 1740
ggatggcaaa agccgaaaac ggcgtcttcc ggcgcttgga ttcagcgctc ttgagccata 1800
aaccgcgttg cttctttggt taattcgtat taatgatcct aagcgccagc ttattcgtta 1860
agaggcacta ggcgcgccgc ggcatgcgat cgccagcatg gctacg 1906

<210> SEQ ID NO 138
<211> LENGTH: 4596
<212> TYPE: DNA
<213> ORGANISM: Artificial Sequence
<220> FEATURE:
<223> OTHER INFORMATION: Synthetic Sequence

<400> SEQUENCE: 138
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcga agactcttaa ccctagaaag ataatcatat tgtgacgtac 180
gttaaagata atcatgcgta aaattgacgc atgtgtttta tcggtctgta tatcgaggtt 240
tatttattaa tttgaataga tattaagttt tattatattt acacttacat actaataata 300
aattcaacaa acaatttatt tatgtttatt tatttattaa aaaaaaacaa aaactcaaaa 360
tttcttctat aaagtaacaa aacttttatc aaatacctgc agcccggggg atgcagaggg 420
acagcccccc cccaaagccc ccagggatgt aattacgtcc ctcccccgct agggggcagc 480
agcgagccgc ccggggctcc gctccggtcc ggcgctcccc ccgcatcccc gagccggcag 540

-continued

```
cgtgcgggga cagcccgggc acggggaagg tggcacggga tcgctttcct ctgaacgctt    600
ctcgctgctc tttgagcctg cagacacctg gggggatacg gggaaaagtt gactgtgcct    660
ttcgatcgag tactcctagg cgcgtgtttg ctgcttgcaa tgtttgccca ttttagggtg    720
gacacaggac gctgtggttt ctgagccagg gggcgactca gatcccagcc agtggactta    780
gcccctgttt gctcctccga taactggggt gaccttggtt aatattcacc agcagcctcc    840
cccgttgccc ctctggatcc actgcttaaa tacggacgag gacagggccc tgtctcctca    900
gcttcaggca ccaccactga cctgggacag tgaatcgcaa agcttattgg acgtcgctta    960
gcggtaccgc caccatgctg ttcaacctgc gcatcctgct gaacaacgcc gccttcagaa   1020
acggccacaa cttcatggtt cgaaacttca gatgcggcca gcctctccag aacaaggtgc   1080
agctgaaagg cagggacctg ctgaccctga agaacttcac cggcgaagag atcaagtaca   1140
tgctgtggct gtccgccgac ctgaagttca gaatcaagca gaagggcgag tacctgcctc   1200
tgctccaggg aaagtctctg ggcatgatct tcgagaagcg gagcaccaga accagactga   1260
gcaccgagac aggctttgcc ctgctcggag gacacccctg ctttctgaca acccaggaca   1320
tccacctggg cgtgaacgag agcctgaccg atacagccag agtgctgtcc tctatggccg   1380
atgccgtgct ggctagagtg tataagcaga gcgacctgga caccctggct aaagaggcca   1440
gcattcccat catcaacggc ctgtccgacc tgtatcaccc catccagatc ctggccgact   1500
acctgacact gcaagagcac tacagcagcc tgaagggact gaccctgtct tggatcggcg   1560
acggcaacaa catcctgcac agcattatga tgagcgccgc caagttcgga atgcacctcc   1620
aggccgctac acccaagggc tatgaacctg atgccagcgt gacaaagctg gccgagcagt   1680
acgccaaaga gaacggcaca aagctgctgc tgaccaacga tcccctggaa gctgctcacg   1740
gcggcaatgt gctgatcacc gatacctgga tcagcatggg ccaagaggaa gagaagaaga   1800
agcggctgca agccttccag ggctaccaag tgaccatgaa gacagccaag gtggccgcca   1860
gcgattggac ctttctgcac tgcctgcctc ggaagcctga agaggtggac gacgaggtgt   1920
tctacagccc tagaagcctg gtgttccccg aggccgagaa cagaaagtgg accatcatgg   1980
ctgtgatggt gtctctgctg accgactact cccctcagct ccagaagcct aagttctaat   2040
gaagatctca tatgccttta attaaacact agttctatag tgtcacctaa attcccttta   2100
gtgagggtta atggccgtag gccgccagaa ttgggtccag acatgataag atacattgat   2160
gagtttggac aaaccacaac tagaatgcag tgaaaaaaat gctttatttg tgaaatttgt   2220
gatgctattg ctttatttgt aaccattata agctgcaata aacaagttaa caacaacaat   2280
tgcattcatt ttatgtttca ggttcagggg gaggtgtggg aggtttttc ggactctagg    2340
acctgcgcat gcgcttggcg taatcatggt catagctgtt tcctgttttc cccgtatccc   2400
cccaggtgtc tgcaggctca aagagcagcg agaagcgttc agaggaaagc gatcccgtgc   2460
caccttcccc gtgcccgggc tgtccccgca cgctgccggc tcggggatgc ggggggagcg   2520
ccggaccgga gcggagcccc gggcggctcg ctgctgcccc ctagcggggg agggacgtaa   2580
ttacatccct gggggctttg gggggggct gtccctctca ccgcggtgga gctccagctt    2640
ttgttcgaat tggggccccc cctcgagggt atcgatgata tctataacaa gaaaatatat   2700
atataataag ttatcacgta agtagaacat gaaataacaa tataattatc gtatgagtta   2760
aatcttaaaa gtcacgtaaa agataatcat gcgtcatttt gactcacgcg gtcgttatag   2820
ttcaaaatca gtgacactta ccgcattgac aagcacgcct cacgggagct ccaagcggcg   2880
actgagatgt cctaaatgca cagcgacgga ttcgcgctat ttagaaagag agagcaatat   2940
```

```
ttcaagaatg catgcgtcaa ttttacgcag actatctttc tagggttaat ctagctagcc   3000

ttaagggcgc tttcctggac tacttcagac gaacttcgta gggcgcataa gtctcgacca   3060

cgcaatgacg cagcgatgct tgaaaaaaac accgctttca aggcggctgg acgaagaccg   3120

caagacaccc tccacctcac ctagcctgta tctctgcaat agcctaatta cttcggaatc   3180

tcctgtcgta attccttaga taaacggcaa ttaggtgaca ctctaaatct gtgtggaacc   3240

ggcttccaaa cactctacca cctctattag tgacacagag agaatccttg agtggcttct   3300

aggtatattg aacaacttca tcacgaattg agcagtgatc atggttctac gtatcaacca   3360

atattaacca ctgtgctctg tagcattgct aaatcgggct gtctgtttca ccatagatcg   3420

tgaggccatg cccacgggca ttagaactta gcctgtttag cgataatccc aacaatgagc   3480

tgggatatga cgagaagtat ttagcaacct tttcgtgatc ggctacgtaa aacctcatat   3540

tacggcatgt acctgatcat tgacctcagg ccatacgcat gtgggagaat agagggaata   3600

gcacgatata ctgcctccct tatcttcctc aggttgaggc gcaatgatta tcactgctac   3660

gggcacagtg ttactatcgg gatcagggac tgtgtctgta cccggttcta ccacgccgta   3720

gctcccacat tgtcgccgta ctggtagtaa cctaccagta ctacagggac aggtcagatt   3780

attcttagaa tgcctgtgta tagtttagag ccatagattg ccgagaaacg aagagagtgt   3840

atcacggcga tttacggagt caagatagca acacatagga gtaccaaatc aataagtgta   3900

gtagagttac aagtcgctcc cgagaatcag gtgatacttc tcaatcgtcg gaaacctgta   3960

acgattagac cgcgtattag ttccatctaa tgatattgcc aagtactaaa cctcaatcac   4020

ataacaacgc atcaggctag cgacatcata ggagtcctgc aacatacgca ggcgtccagc   4080

gtcataaacg caggtgatga gtgccttatg caatctgggg cacaccaata cgagaatacc   4140

acgtcgttag ggccagcctg cgcttggtac gtgatcgagg agtatcgtct tgtgcacaca   4200

aacaaaatag actgggtccc aagcgcactt agacaaggca ttgtactact caagtgttgg   4260

atgtgaggaa tgatacaatc gaaccccgtc gttcggtcaa caatttggct agagctgtgt   4320

tgatacacag cggacgggag ttacggggac agtcctccga gctggccagc aagatgcagc   4380

tgacgcctgc accggaagta atccggaggc cggccaggcc tcctgcgagg gggcgcctcg   4440

agaccttgcg gccgcaggaa cccctagtga tggagttggc cactccctct ctgcgcgctc   4500

gctcgctcac tgaggccggg cgaccaaagg tcgcccgacg cccgggcttt gcccgggcgg   4560

cctcagtgag cgagcgagcg cgcagctgcc tgcagg                             4596
```

<210> SEQ ID NO 139
<211> LENGTH: 4790
<212> TYPE: DNA
<213> ORGANISM: Artificial Sequence
<220> FEATURE:
<223> OTHER INFORMATION: Synthetic Sequence

<400> SEQUENCE: 139

```
cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct gcggccgcga agactcttaa ccctagaaag ataatcatat tgtgacgtac    180

gttaaagata atcatgcgta aaattgacgc atgtgtttta tcggtctgta tatcgaggtt    240

tatttattaa tttgaataga tattaagttt tattatattt acacttacat actaataata    300

aattcaacaa acaatttatt tatgtttatt tatttattaa aaaaaaacaa aaactcaaaa    360
```

```
tttcttctat aaagtaacaa aacttttatc aaatacctgc agcccggggg atgcagaggg    420
acagcccccc cccaaagccc ccagggatgt aattacgtcc ctcccccgct agggggcagc    480
agcgagccgc ccggggctcc gctccggtcc ggcgctcccc ccgcatcccc gagccggcag    540
cgtgcgggga cagcccgggc acggggaagg tggcacggga tcgctttcct ctgaacgctt    600
ctcgctgctc tttgagcctg cagacacctg gggggatacg gggaaaagtt gactgtgcct    660
ttcgatcgag tactcctagg cgcgccccta aaatgggcaa acattgcaag cagcaaacag    720
caaacacaca gccctccctg cctgctgacc ttggagctgg ggcagaggtc agagacctct    780
ctgggcccat gccacctcca acatccactc gaccccttgg aatttcggtg gagaggagca    840
gaggttgtcc tggcgtggtt taggtagtgt gagaggggaa tgactccttt cggtaagtgc    900
agtggaagct gtacactgcc caggcaaagc gtccgggcag cgtaggcggg cgactcagat    960
cccagccagt ggacttagcc cctgtttgct cctccgataa ctggggtgac cttggttaat   1020
attcaccagc agcctccccc gttgcccctc tggatccact gcttaaatac ggacgaggac   1080
agggccctgt ctcctcagct tcaggcacca ccactgacct gggacagtga atcaagctta   1140
ttggacgtcg cttagcggta ccgccaccat gctgttcaac ctgcgcatcc tgctgaacaa   1200
cgccgccttc agaaacggcc acaacttcat ggttcgaaac ttcagatgcg gccagcctct   1260
ccagaacaag gtgcagctga aaggcaggga cctgctgacc ctgaagaact tcaccggcga   1320
agagatcaag tacatgctgt ggctgtccgc cgacctgaag ttcagaatca agcagaaggg   1380
cgagtacctg cctctgctcc agggaaagtc tctgggcatg atcttcgaga agcggagcac   1440
cagaaccaga ctgagcaccg agacaggctt tgccctgctc ggaggacacc cctgctttct   1500
gacaacccag gacatccacc tgggcgtgaa cgagagcctg accgatacag ccagagtgct   1560
gtcctctatg gccgatgccg tgctggctag agtgtataag cagagcgacc tggacaccct   1620
ggctaaagag gccagcattc ccatcatcaa cggcctgtcc gacctgtatc accccatcca   1680
gatcctggcc gactacctga cactgcaaga gcactacagc agcctgaagg gactgaccct   1740
gtcttggatc ggcgacggca acaacatcct gcacagcatt atgatgagcg ccgccaagtt   1800
cggaatgcac ctccaggccg ctacacccaa gggctatgaa cctgatgcca gcgtgacaaa   1860
gctggccgag cagtacgcca aagagaacgg cacaaagctg ctgctgacca acgatcccct   1920
ggaagctgct cacggcggca atgtgctgat caccgatacc tggatcagca tgggccaaga   1980
ggaagagaag aagaagcggc tgcaagcctt ccagggctac caagtgacca tgaagacagc   2040
caaggtggcc gccagcgatt ggacctttct gcactgcctg cctcggaagc ctgaagaggt   2100
ggacgacgag gtgttctaca gccctagaag cctggtgttc cccgaggccg agaacagaaa   2160
gtggaccatc atggctgtga tggtgtctct gctgaccgac tactcccctc agctccagaa   2220
gcctaagttc taatgaagat ctcatatgcc tttaattaaa cactagttct atagtgtcac   2280
ctaaattccc tttagtgagg gttaatggcc gtaggccgcc agaattgggt ccagacatga   2340
taagatacat tgatgagttt ggacaaacca caactagaat gcagtgaaaa aaatgcttta   2400
tttgtgaaat ttgtgatgct attgctttat ttgtaaccat tataagctgc aataaacaag   2460
ttaacaacaa caattgcatt cattttatgt ttcaggttca gggggaggtg tgggaggttt   2520
tttcggactc taggacctgc gcatgcgctt ggcgtaatca tggtcatagc tgtttcctgt   2580
tttccccgta tccccccagg tgtctgcagg ctcaaagagc agcgagaagc gttcagagga   2640
aagcgatccc gtgccacctt ccccgtgccc gggctgtccc cgcacgctgc cggctcgggg   2700
atgcgggggg agcgccggac cggagcggag ccccgggcgg ctcgctgctg ccccctagcg   2760
```

```
ggggagggac gtaattacat ccctgggggc tttggggggg ggctgtccct ctcaccgcgg   2820
tggagctcca gcttttgttc gaattggggc ccccctcga gggtatcgat gatatctata   2880
acaagaaaat atatatataa taagttatca cgtaagtaga acatgaaata acaatataat   2940
tatcgtatga gttaaatctt aaaagtcacg taaaagataa tcatgcgtca ttttgactca   3000
cgcggtcgtt atagttcaaa atcagtgaca cttaccgcat tgacaagcac gcctcacggg   3060
agctccaagc ggcgactgag atgtcctaaa tgcacagcga cggattcgcg ctatttagaa   3120
agagagagca atatttcaag aatgcatgcg tcaattttac gcagactatc tttctagggt   3180
taatctagct agccttaagg gcgctttcct ggactacttc agacgaactt cgtagggcgc   3240
ataagtctcg accacgcaat gacgcagcga tgcttgaaaa aaaccccgct ttcaaggcgg   3300
ctggacgaag accgcaagac accctccacc tcacctagcc tgtatctctg caatagccta   3360
attacttcgg aatctcctgt cgtaattcct tagataaacg gcaattaggt gacactctaa   3420
atctgtgtgg aaccggcttc caaacactct accacctcta ttagtgacac agagagaatc   3480
cttgagtggc ttctaggtat attgaacaac ttcatcacga attgagcagt gatcatggtt   3540
ctacgtatca accaatatta accactgtgc tctgtagcat tgctaaatcg ggctgtctgt   3600
ttcaccatag atcgtgaggc catgcccacg ggcattagaa cttagcctgt ttagcgataa   3660
tcccaacaat gagctgggat atgacgagaa gtatttagca accttttcgt gatcggctac   3720
gtaaaacctc atattacggc atgtacctga tcattgacct caggccatac gcatgtggga   3780
gaatagaggg aatagcacga tatactgcct cccttatctt cctcaggttg aggcgcaatg   3840
attatcactg ctacgggcac agtgttacta tcgggatcag ggactgtgtc tgtacccggt   3900
tctaccacgc cgtagctccc acattgtcgc cgtactggta gtaacctacc agtactacag   3960
ggacaggtca gattattctt agaatgcctg tgtatagttt agagccatag attgccgaga   4020
aacgaagaga gtgtatcacg gcgatttacg gagtcaagat agcaacacat aggagtacca   4080
aatcaataag tgtagtagag ttacaagtcg ctcccgagaa tcaggtgata cttctcaatc   4140
gtcggaaacc tgtaacgatt agaccgcgta ttagttccat ctaatgatat tgccaagtac   4200
taaacctcaa tcacataaca acgcatcagg ctagcgacat cataggagtc ctgcaacata   4260
cgcaggcgtc cagcgtcata aacgcaggtg atgagtgcct tatgcaatct ggggcacacc   4320
aatacgagaa taccacgtcg ttagggccag cctgcgcttg gtacgtgatc gaggagtatc   4380
gtcttgtgca cacaaacaaa atagactggg tcccaagcgc acttagacaa ggcattgtac   4440
tactcaagtg ttggatgtga ggaatgatac aatcgaaccc cgtcgttcgg tcaacaattt   4500
ggctagagct gtgttgatac acagcggacg ggagttacgg ggacagtcct ccgagctggc   4560
cagcaagatg cagctgacgc ctgcaccgga agtaatccgg aggccggcca ggcctcctgc   4620
gagggggcgc ctcgagacct tgcggccgca ggaaccccta gtgatggagt tggccactcc   4680
ctctctgcgc gctcgctcgc tcactgaggc cgggcgacca aaggtcgccc gacgcccggg   4740
ctttgcccgg gcggcctcag tgagcgagcg agcgcgcagc tgcctgcagg              4790
```

<210> SEQ ID NO 140
<211> LENGTH: 4700
<212> TYPE: DNA
<213> ORGANISM: Artificial Sequence
<220> FEATURE:
<223> OTHER INFORMATION: Synthetic Sequence

<400> SEQUENCE: 140

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgcga agactcttaa ccctagaaag ataatcatat tgtgacgtac    180
gttaaagata atcatgcgta aaattgacgc atgtgtttta tcggtctgta tatcgaggtt    240
tatttattaa tttgaataga tattaagttt tattatattt acacttacat actaataata    300
aattcaacaa acaatttatt tatgtttatt tatttattaa aaaaaaacaa aaactcaaaa    360
tttcttctat aaagtaacaa aacttttatc aaatacctgc agcccggggg atgcagaggg    420
acagcccccc cccaaagccc ccagggatgt aattacgtcc ctcccccgct agggggcagc    480
agcgagccgc ccggggctcc gctccggtcc ggcgctcccc ccgcatcccc gagccggcag    540
cgtgcgggga cagcccgggc acggggaagg tggcacggga tcgctttcct ctgaacgctt    600
ctcgctgctc tttgagcctg cagacacctg gggggatacg gggaaaagtt gactgtgcct    660
ttcgatcgag tactcctagg agctagcagg ttaattttta aaaagcagtc aaaagtccaa    720
gtggcccttg gcagcattta ctctctctgt ttgctctggt taataatctc aggagcacaa    780
acattccaga tccaggttaa tttttaaaaa gcagtcaaaa gtccaagtgg cccttggcag    840
catttactct ctctgtttgc tctggttaat aatctcagga gcacaaacat tccagatccg    900
gcgcgccagg gctggaagct acctttgaca tcatttcctc tgcgaatgca tgtataattt    960
ctacagaacc tattagaaag gatcacccag cctctgcttt tgtacaactt tcccttaaaa   1020
aactgccaat tccactgctg tttggcccaa tagtgagaac tttttcctgc tgcctcttgg   1080
tgcttttgcc tatggcccct attctgcctg ctgaagacac tcttgccagc atggacttaa   1140
acccctccag ctctgacaat cctctttctc ttttgtttta catgaagggt ctggcagcca   1200
aagcaatcac tcaaagttca aaccttatca ttttttgctt tgttcctctt ggccttggtt   1260
ttgtacatca gctttgaaaa taccatccca gggttaatgc tggggttaat ttataactaa   1320
gagtgctcta gttttgcaat acaggacatg ctataaaaat ggaaagatgt tgctttctga   1380
gagactgcag aagttggtcg tgaggcactg ggcaggtaag tatcaaggtt acaagacagg   1440
tttaaggaga ccaatagaaa ctgggcttgt cgagacagag aagactcttg cgtttctgat   1500
aggcacctat tggtcttact gacatccact ttgcctttct ctccacaggt gtccagtggc   1560
aaagcttatt ggacgtcgct tagcggtacc gccaccatgc tgttcaacct gcgcatcctg   1620
ctgaacaacg ccgccttcag aaacggccac aacttcatgg ttcgaaactt cagatgcggc   1680
cagcctctcc agaacaaggt gcagctgaaa ggcagggacc tgctgaccct gaagaacttc   1740
accggcgaag agatcaagta catgctgtgg ctgtccgccg acctgaagtt cagaatcaag   1800
cagaagggcg agtacctgcc tctgctccag ggaaagtctc tgggcatgat cttcgagaag   1860
cggagcacca gaaccagact gagcaccgag acaggctttg ccctgctcgg aggacacccc   1920
tgctttctga caacccagga catccacctg ggcgtgaacg agagcctgac cgatacagcc   1980
agagtgctgt cctctatggc cgatgccgtg ctggctagag tgtataagca gagcgacctg   2040
gacaccctgg ctaaagaggc cagcattccc atcatcaacg gcctgtccga cctgtatcac   2100
cccatccaga tcctggccga ctacctgaca ctgcaagagc actacagcag cctgaaggga   2160
ctgaccctgt cttggatcgg cgacggcaac aacatcctgc acagcattat gatgagcgcc   2220
gccaagttcg gaatgcacct ccaggccgct acacccaagg gctatgaacc tgatgccagc   2280
gtgacaaagc tggccgagca gtacgccaaa gagaacggca caaagctgct gctgaccaac   2340
gatcccctgg aagctgctca cggcggcaat gtgctgatca ccgatacctg gatcagcatg   2400
```

```
ggccaagagg aagagaagaa gaagcggctg caagccttcc agggctacca agtgaccatg   2460
aagacagcca aggtggccgc cagcgattgg acctttctgc actgcctgcc tcggaagcct   2520
gaagaggtgg acgacgaggt gttctacagc cctagaagcc tggtgttccc cgaggccgag   2580
aacagaaagt ggaccatcat ggctgtgatg gtgtctctgc tgaccgacta ctcccctcag   2640
ctccagaagc ctaagttcta atgaagatct catatgcctt taattaaaca ctagttctat   2700
agtgtcacct aaattccctt tagtgagggt taatggccgt aggccgccag aattgggtcc   2760
agacatgata agatacattg atgagtttgg acaaaccaca actagaatgc agtgaaaaaa   2820
atgctttatt tgtgaaattt gtgatgctat tgctttattt gtaaccatta taagctgcaa   2880
taaacaagtt aacaacaaca attgcattca ttttatgttt caggttcagg gggaggtgtg   2940
ggaggttttt tcggactcta ggacctgcgc atgcgcttgg cgtaatcatg gtcatagctg   3000
tttcctgttt tccccgtatc cccccaggtg tctgcaggct caaagagcag cgagaagcgt   3060
tcagaggaaa gcgatcccgt gccaccttcc ccgtgcccgg gctgtccccg cacgctgccg   3120
gctcggggat gcggggggag cgccggaccg gagcggagcc ccgggcggct cgctgctgcc   3180
ccctagcggg ggagggacgt aattacatcc ctgggggctt tggggggggg ctgtccctct   3240
caccgcggtg gagctccagc ttttgttcga attggggccc cccctcgagg gtatcgatga   3300
tatctataac aagaaaatat atatataata agttatcacg taagtagaac atgaaataac   3360
aatataatta tcgtatgagt taaatcttaa aagtcacgta aaagataatc atgcgtcatt   3420
ttgactcacg cggtcgttat agttcaaaat cagtgacact taccgcattg acaagcacgc   3480
ctcacgggag ctccaagcgg cgactgagat gtcctaaatg cacagcgacg gattcgcgct   3540
atttagaaag agagagcaat atttcaagaa tgcatgcgtc aattttacgc agactatctt   3600
tctagggtta atctagctag ccttaagggc gctttcctgt cgacggaggc atgtacctga   3660
tcattgacct caggccatac gcatgtggga gaatagaggg aatagcacga tatactgcct   3720
cccttatctt cctcaggttg aggcgcaatg attatcactg ctacgggcac agtgttacta   3780
tcgggatcag ggactgtgtc tgtacccggt tctaccacgc cgtagctccc acattgtcgc   3840
cgtactggta gtaacctacc agtactacag ggacaggtca gattattctt agaatgcctg   3900
tgtatagttt agagccatag attgccgaga aacgaagaga gtgtatcacg gcgatttacg   3960
gagtcaagat agcaacacat aggagtacca aatcaataag tgtagtagag ttacaagtcg   4020
ctcccgagaa tcaggtgata cttctcaatc gtcggaaacc tgtaacgatt agaccgcgta   4080
ttagttccat ctaatgatat tgccaagtac taaacctcaa tcacataaca acgcatcagg   4140
ctagcgacat cataggagtc ctgcaacata cgcaggcgtc cagcgtcata aacgcaggtg   4200
atgagtgcct tatgcaatct ggggcacacc aatacgagaa taccacgtcg ttagggccag   4260
cctgcgcttg gtacgtgatc gaggagtatc gtcttgtgca cacaaacaaa atagactggg   4320
tcccaagcgc acttagacaa ggcattgtac tactcaagtg ttggatgtga ggaatgatac   4380
aatcgaaccc cgtcgttcgg tcaacaattt ggctagagct gtgttgatac acagcggacg   4440
ggagttacgg ggacagtcct ccgagctggc cagcaagatg cagctgacgc ctgcaccgga   4500
agtaatccgg aggccggcca ggcctcctgc gagggggcgc ctcgagacct tgcggccgca   4560
ggaaccccta gtgatggagt tggccactcc ctctctgcgc gctcgctcgc tcactgaggc   4620
cgggcgacca aaggtcgccc gacgcccggg ctttgcccgg gcggcctcag tgagcgagcg   4680
agcgcgcagc tgcctgcagg                                               4700
```

<210> SEQ ID NO 141
<211> LENGTH: 4531
<212> TYPE: DNA
<213> ORGANISM: Artificial Sequence
<220> FEATURE:
<223> OTHER INFORMATION: Synthetic Sequence

<400> SEQUENCE: 141
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcga agactcttaa ccctagaaag ataatcatat tgtgacgtac 180
gttaaagata atcatgcgta aaattgacgc atgtgtttta tcggtctgta tatcgaggtt 240
tatttattaa tttgaataga tattaagttt tattatattt acacttacat actaataata 300
aattcaacaa acaatttatt tatgtttatt tatttattaa aaaaaaacaa aaactcaaaa 360
tttcttctat aaagtaacaa aacttttatc aaatacctgc agcccggggg atgcagaggg 420
acagcccccc cccaaagccc ccagggatgt aattacgtcc ctcccccgct agggggcagc 480
agcgagccgc ccggggctcc gctccggtcc ggcgctcccc ccgcatcccc gagccggcag 540
cgtgcgggga cagcccgggc acggggaagg tggcacggga tcgctttcct ctgaacgctt 600
ctcgctgctc tttgagcctg cagacacctg gggggatacg gggaaaagtt gactgtgcct 660
ttcgatcgag tactcctagg cgcgtgtttg ctgcttgcaa tgtttgccca ttttagggtg 720
gacacaggac gctgtggttt ctgagccagg gggcgactca gatcccagcc agtggactta 780
gcccctgttt gctcctccga taactggggt gaccttggtt aatattcacc agcagcctcc 840
cccgttgccc ctctggatcc actgcttaaa tacggacgag gacagggccc tgtctcctca 900
gcttcaggca ccaccactga cctgggacag tgaatcgcaa agcttattgg acgtcgctta 960
gcggtaccgc caccatgctg ttcaacctgc gcatcctgct gaacaacgcc gccttcagaa 1020
acggccacaa cttcatggtt cgaaacttca gatgcggcca gcctctccag aacaaggtgc 1080
agctgaaagg cagggacctg ctgaccctga agaacttcac cggcgaagag atcaagtaca 1140
tgctgtggct gtccgccgac ctgaagttca gaatcaagca gaagggcgag tacctgcctc 1200
tgctccaggg aaagtctctg ggcatgatct tcgagaagcg gagcaccaga accagactga 1260
gcaccgagac aggctttgcc ctgctcggag gacacccctg ctttctgaca acccaggaca 1320
tccacctggg cgtgaacgag agcctgaccg atacagccag agtgctgtcc tctatggccg 1380
atgccgtgct ggctagagtg tataagcaga gcgacctgga caccctggct aaagaggcca 1440
gcattcccat catcaacggc ctgtccgacc tgtatcaccc catccagatc ctggccgact 1500
acctgacact gcaagagcac tacagcagcc tgaagggact gaccctgtct tggatcggcg 1560
acggcaacaa catcctgcac agcattatga tgagcgccgc caagttcgga atgcacctcc 1620
aggccgctac acccaagggc tatgaacctg atgccagcgt gacaaagctg gccgagcagt 1680
acgccaaaga gaacggcaca aagctgctgc tgaccaacga tcccctggaa gctgctcacg 1740
gcggcaatgt gctgatcacc gatacctgga tcagcatggg ccaagaggaa gagaagaaga 1800
agcggctgca agccttccag ggctaccaag tgaccatgaa gacagccaag gtggccgcca 1860
gcgattggac ctttctgcac tgcctgcctc ggaagcctga agaggtggac gacgaggtgt 1920
tctacagccc tagaagcctg gtgttccccg aggccgagaa cagaaagtgg accatcatgg 1980
ctgtgatggt gtctctgctg accgactact cccctcagct ccagaagcct aagttcggat 2040
ccggcgaagg cagaggctca ctgcttactt gtggcgacgt ggaggagaac cccggaccta 2100
tggtttccaa gggcgaagaa ctgtttaccg gcgtggtgcc catcctggtg gaactggatg 2160
gcgacgttaa cggacacaag ttcagcgtca gcggagaagg cgaaggcgac gccacatacg 2220
gaaagctgac actgaagttt atctgcacca ccggcaagct gcccgtgcct tggcctacac 2280
tggtcaccac actgacatac ggcgtgcagt gcttcagcag ataccccgac cacatgaagc 2340
agcacgattt cttcaagagc gccatgcctg agggctacgt gcaagagcgg accatcttct 2400
tcaaggacga cgggaactac aagaccagag ccgaagtgaa gttcgagggc gacaccctcg 2460
tgaaccggat cgagctgaag ggcatcgact tcaaagagga cggaaacatc ctgggccaca 2520
aacttgagta caactacaac agccacaacg tctacatcat ggccgacaag cagaaaaacg 2580
gcatcaaagt gaacttcaag atccggcaca acatcgagga cggctctgtg cagctggctg 2640
accactacca gcagaacaca cccatcggag atggccctgt gctgctgccc gataaccact 2700
acctgagcac acagagcgcc ctgagcaagg accccaacga gaagagggat cacatggtgc 2760
tgctggaatt tgtgaccgct gccggcatca ccctcggcat ggatgaactg tacaagggct 2820
ccggagaagg acggggaagc ctgcttacat gcggagatgt ggaggagaat cctggtccca 2880
tggtctttac cctggaagat ttcgtcggcg actggcggca gacagccggc tataatctgg 2940
accaggtgct ggaacaaggc ggagtgtcca gcctgttcca gaatctggga gtgtccgtga 3000
cacccatcca gcggattgtg ctgtctggcg agaacggcct gaagatcgac atccacgtga 3060
tcatccctta cgagggcctg agcggcgatc agatgggaca gatcgagaag attttcaagg 3120
tggtgtaccc cgtggacgac caccacttca aagtgatcct gcactacggc accctggtca 3180
tcgatggcgt gacccctaac atgatcgact acttcggcag accctacgag ggaatcgccg 3240
tgttcgacgg caagaaaatc accgtgaccg gcacactgtg gaacgggaac aagatcatcg 3300
acgagcggct gatcaacccc gatggcagcc tgctgttcag agtgaccatt aacggcgtga 3360
caggctggcg gctgtgcgaa aggattctgg cctgatgatc tagagatctc atatgccttt 3420
aattaaacac tagttctata gtgtcaccta aattcccttt agtgagggtt aatggccgta 3480
ggccgccaga attgggtcca gacatgataa gatacattga tgagtttgga caaaccacaa 3540
ctagaatgca gtgaaaaaaa tgctttattt gtgaaatttg tgatgctatt gctttatttg 3600
taaccattat aagctgcaat aaacaagtta acaacaacaa ttgcattcat tttatgtttc 3660
aggttcaggg ggaggtgtgg gaggtttttt cggactctag gacctgcgca tgcgcttggc 3720
gtaatcatgg tcatagctgt ttcctgtttt ccccgtatcc ccccaggtgt ctgcaggctc 3780
aaagagcagc gagaagcgtt cagaggaaag cgatcccgtg ccaccttccc cgtgcccggg 3840
ctgtccccgc acgctgccgg ctcggggatg cggggggagc gccggaccgg agcggagccc 3900
cgggcggctc gctgctgccc cctagcgggg gagggacgta attacatccc tgggggcttt 3960
gggggggggc tgtccctctc accgcggtgg agctccagct tttgttcgaa ttggggcccc 4020
ccctcgaggg tatcgatgat atctataaca agaaaatata tatataataa gttatcacgt 4080
aagtagaaca tgaaataaca atataattat cgtatgagtt aaatcttaaa agtcacgtaa 4140
aagataatca tgcgtcattt tgactcacgc ggtcgttata gttcaaaatc agtgacactt 4200
accgcattga caagcacgcc tcacgggagc tccaagcggc gactgagatg tcctaaatgc 4260
acagcgacgg attcgcgcta tttagaaaga gagagcaata tttcaagaat gcatgcgtca 4320
attttacgca gactatcttt ctagggttaa tctagctagc cttaagggcg cctcgagacc 4380
ttgcggccgc aggaacccct agtgatggag ttggccactc cctctctgcg cgctcgctcg 4440
ctcactgagg ccgggcgacc aaaggtcgcc cgacgcccgg gctttgcccg ggcggcctca 4500
gtgagcgagc gagcgcgcag ctgcctgcag g 4531

<210> SEQ ID NO 142
<211> LENGTH: 4725
<212> TYPE: DNA
<213> ORGANISM: Artificial Sequence
<220> FEATURE:
<223> OTHER INFORMATION: Synthetic Sequence

<400> SEQUENCE: 142
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcga agactcttaa ccctagaaag ataatcatat tgtgacgtac 180
gttaaagata atcatgcgta aaattgacgc atgtgtttta tcggtctgta tatcgaggtt 240
tatttattaa tttgaataga tattaagttt tattatattt acacttacat actaataata 300
aattcaacaa acaatttatt tatgtttatt tatttattaa aaaaaaacaa aaactcaaaa 360
tttcttctat aaagtaacaa aacttttatc aaatacctgc agcccggggg atgcagaggg 420
acagcccccc cccaaagccc ccagggatgt aattacgtcc ctcccccgct agggggcagc 480
agcgagccgc ccggggctcc gctccggtcc ggcgctcccc ccgcatcccc gagccggcag 540
cgtgcgggga cagcccgggc acggggaagg tggcacggga tcgctttcct ctgaacgctt 600
ctcgctgctc tttgagcctg cagacacctg gggggatacg gggaaaagtt gactgtgcct 660
ttcgatcgag tactcctagg cgcgccccta aaatgggcaa acattgcaag cagcaaacag 720
caaacacaca gccctccctg cctgctgacc ttggagctgg ggcagaggtc agagacctct 780
ctgggcccat gccacctcca acatccactc gaccccttgg aatttcggtg gagaggagca 840
gaggttgtcc tggcgtggtt taggtagtgt gagaggggaa tgactccttt cggtaagtgc 900
agtggaagct gtacactgcc caggcaaagc gtccgggcag cgtaggcggg cgactcagat 960
cccagccagt ggacttagcc cctgtttgct cctccgataa ctggggtgac cttggttaat 1020
attcaccagc agcctccccc gttgcccctc tggatccact gcttaaatac ggacgaggac 1080
agggccctgt ctcctcagct tcaggcacca ccactgacct gggacagtga atcaagctta 1140
ttggacgtcg cttagcggta ccgccaccat gctgttcaac ctgcgcatcc tgctgaacaa 1200
cgccgccttc agaaacggcc acaacttcat ggttcgaaac ttcagatgcg gccagcctct 1260
ccagaacaag gtgcagctga aggcaggga cctgctgacc ctgaagaact tcaccggcga 1320
agagatcaag tacatgctgt ggctgtccgc cgacctgaag ttcagaatca agcagaaggg 1380
cgagtacctg cctctgctcc agggaaagtc tctgggcatg atcttcgaga agcggagcac 1440
cagaaccaga ctgagcaccg agacaggctt tgccctgctc ggaggacacc cctgctttct 1500
gacaacccag gacatccacc tgggcgtgaa cgagagcctg accgatacag ccagagtgct 1560
gtcctctatg gccgatgccg tgctggctag agtgtataag cagagcgacc tggacaccct 1620
ggctaaagag gccagcattc ccatcatcaa cggcctgtcc gacctgtatc accccatcca 1680
gatcctggcc gactacctga cactgcaaga gcactacagc agcctgaagg gactgaccct 1740
gtcttggatc ggcgacggca acaacatcct gcacagcatt atgatgagcg ccgccaagtt 1800
cggaatgcac ctccaggccg ctacacccaa gggctatgaa cctgatgcca gcgtgacaaa 1860
gctggccgag cagtacgcca aagagaacgg cacaaagctg ctgctgacca acgatcccct 1920
ggaagctgct cacggcggca atgtgctgat caccgatacc tggatcagca tgggccaaga 1980

```
ggaagagaag aagaagcggc tgcaagcctt ccagggctac caagtgacca tgaagacagc   2040
caaggtggcc gccagcgatt ggacctttct gcactgcctg cctcggaagc ctgaagaggt   2100
ggacgacgag gtgttctaca gccctagaag cctggtgttc cccgaggccg agaacagaaa   2160
gtggaccatc atggctgtga tggtgtctct gctgaccgac tactcccctc agctccagaa   2220
gcctaagttc ggatccggcg aaggcagagg ctcactgctt acttgtggcg acgtggagga   2280
gaaccccgga cctatggttt ccaagggcga agaactgttt accggcgtgg tgcccatcct   2340
ggtggaactg gatggcgacg ttaacggaca caagttcagc gtcagcggag aaggcgaagg   2400
cgacgccaca tacggaaagc tgacactgaa gtttatctgc accaccggca agctgcccgt   2460
gccttggcct acactggtca ccacactgac atacggcgtg cagtgcttca gcagataccc   2520
cgaccacatg aagcagcacg atttcttcaa gagcgccatg cctgagggct acgtgcaaga   2580
gcggaccatc ttcttcaagg acgacgggaa ctacaagacc agagccgaag tgaagttcga   2640
gggcgacacc ctcgtgaacc ggatcgagct gaagggcatc gacttcaaag aggacggaaa   2700
catcctgggc cacaaacttg agtacaacta caacagccac aacgtctaca tcatggccga   2760
caagcagaaa aacggcatca aagtgaactt caagatccgg cacaacatcg aggacggctc   2820
tgtgcagctg gctgaccact accagcagaa cacacccatc ggagatggcc ctgtgctgct   2880
gcccgataac cactacctga gcacacagag cgccctgagc aaggacccca acgagaagag   2940
ggatcacatg gtgctgctgg aatttgtgac cgctgccggc atcaccctcg gcatggatga   3000
actgtacaag ggctccggag aaggacgggg aagcctgctt acatgcggag atgtggagga   3060
gaatcctggt cccatggtct ttaccctgga agatttcgtc ggcgactggc ggcagacagc   3120
cggctataat ctggaccagg tgctggaaca aggcggagtg tccagcctgt tccagaatct   3180
gggagtgtcc gtgacaccca tccagcggat tgtgctgtct ggcgagaacg gcctgaagat   3240
cgacatccac gtgatcatcc cttacgaggg cctgagcggc gatcagatgg gacagatcga   3300
gaagattttc aaggtggtgt accccgtgga cgaccaccac ttcaaagtga tcctgcacta   3360
cggcaccctg gtcatcgatg gcgtgacccc taacatgatc gactacttcg gcagacccta   3420
cgagggaatc gccgtgttcg acggcaagaa aatcaccgtg accggcacac tgtggaacgg   3480
gaacaagatc atcgacgagc ggctgatcaa ccccgatggc agcctgctgt tcagagtgac   3540
cattaacggc gtgacaggct ggcggctgtg cgaaaggatt ctggcctgat gatctagaga   3600
tctcatatgc ctttaattaa acactagttc tatagtgtca cctaaattcc ctttagtgag   3660
ggttaatggc cgtaggccgc cagaattggg tccagacatg ataagataca ttgatgagtt   3720
tggacaaacc acaactagaa tgcagtgaaa aaaatgcttt atttgtgaaa tttgtgatgc   3780
tattgcttta tttgtaacca ttataagctg caataaacaa gttaacaaca acaattgcat   3840
tcattttatg tttcaggttc agggggaggt gtgggaggtt ttttcggact ctaggacctg   3900
cgcatgcgct tggcgtaatc atggtcatag ctgtttcctg ttttccccgt atcccccccag   3960
gtgtctgcag gctcaaagag cagcgagaag cgttcagagg aaagcgatcc cgtgccacct   4020
tccccgtgcc cgggctgtcc ccgcacgctg ccggctcggg gatgcggggg gagcgccgga   4080
ccggagcgga gccccgggcg gctcgctgct gccccctagc gggggaggga cgtaattaca   4140
tccctggggg ctttgggggg gggctgtccc tctcaccgcg gtggagctcc agcttttgtt   4200
cgaattgggg ccccccctcg agggtatcga tgatatctat aacaagaaaa tatatatata   4260
ataagttatc acgtaagtag aacatgaaat aacaatataa ttatcgtatg agttaaatct   4320
```

taaaagtcac gtaaaagata atcatgcgtc attttgactc acgcggtcgt tatagttcaa 4380
aatcagtgac acttaccgca ttgacaagca cgcctcacgg gagctccaag cggcgactga 4440
gatgtcctaa atgcacagcg acggattcgc gctatttaga aagagagagc aatatttcaa 4500
gaatgcatgc gtcaatttta cgcagactat ctttctaggg ttaatctagc tagccttaag 4560
ggcgcctcga gaccttgcgg ccgcaggaac ccctagtgat ggagttggcc actccctctc 4620
tgcgcgctcg ctcgctcact gaggccgggc gaccaaaggt cgcccgacgc ccgggctttg 4680
cccgggcggc ctcagtgagc gagcgagcgc gcagctgcct gcagg 4725

<210> SEQ ID NO 143
<211> LENGTH: 4363
<212> TYPE: DNA
<213> ORGANISM: Artificial Sequence
<220> FEATURE:
<223> OTHER INFORMATION: Synthetic Sequence

<400> SEQUENCE: 143
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcga agactcttaa ccctagaaag ataatcatat tgtgacgtac 180
gttaaagata atcatgcgta aaattgacgc atgtgtttta tcggtctgta tatcgaggtt 240
tatttattaa tttgaataga tattaagttt tattatattt acacttacat actaataata 300
aattcaacaa acaatttatt tatgtttatt tatttattaa aaaaaaacaa aaactcaaaa 360
tttcttctat aaagtaacaa aacttttatc aaatacctgc agcccggggg atgcagaggg 420
acagcccccc cccaaagccc ccagggatgt aattacgtcc ctcccccgct agggggcagc 480
agcgagccgc ccggggctcc gctccggtcc ggcgctcccc ccgcatcccc gagccggcag 540
cgtgcgggga cagcccgggc acggggaagg tggcacggga tcgctttcct ctgaacgctt 600
ctcgctgctc tttgagcctg cagacacctg gggggatacg gggaaaagtt gactgtgcct 660
ttcgatcgag tactcctagg agctagcagg ttaattttta aaaagcagtc aaaagtccaa 720
gtggcccttg gcagcattta ctctctctgt ttgctctggt taataatctc aggagcacaa 780
acattccaga tccaggttaa tttttaaaaa gcagtcaaaa gtccaagtgg cccttggcag 840
catttactct ctctgtttgc tctggttaat aatctcagga gcacaaacat tccagatccg 900
gcgcgccagg gctggaagct acctttgaca tcatttcctc tgcgaatgca tgtataattt 960
ctacagaacc tattagaaag gatcacccag cctctgcttt tgtacaactt tcccttaaaa 1020
aactgccaat tccactgctg tttggcccaa tagtgagaac tttttcctgc tgcctcttgg 1080
tgcttttgcc tatggcccct attctgcctg ctgaagacac tcttgccagc atggacttaa 1140
acccctccag ctctgacaat cctctttctc ttttgtttta catgaagggt ctggcagcca 1200
aagcaatcac tcaaagttca aaccttatca ttttttgctt tgttcctctt ggccttggtt 1260
ttgtacatca gctttgaaaa taccatccca gggttaatgc tggggttaat ttataactaa 1320
gagtgctcta gttttgcaat acaggacatg ctataaaaat ggaaagatgt tgctttctga 1380
gagactgcag aagttggtcg tgaggcactg ggcaggtaag tatcaaggtt acaagacagg 1440
tttaaggaga ccaatagaaa ctgggcttgt cgagacagag aagactcttg cgtttctgat 1500
aggcacctat tggtcttact gacatccact ttgcctttct ctccacaggt gaagcttatt 1560
ggacgtcgct tagcggtacc gccaccatgc tgttcaacct gcgcatcctg ctgaacaacg 1620
ccgccttcag aaacggccac aacttcatgg ttcgaaactt cagatgcggc cagcctctcc 1680

```
agaacaaggt gcagctgaaa ggcagggacc tgctgaccct gaagaacttc accggcgaag   1740
agatcaagta catgctgtgg ctgtccgccg acctgaagtt cagaatcaag cagaagggcg   1800
agtacctgcc tctgctccag ggaaagtctc tgggcatgat cttcgagaag cggagcacca   1860
gaaccagact gagcaccgag acaggctttg ccctgctcgg aggacacccc tgctttctga   1920
caacccagga catccacctg ggcgtgaacg agagcctgac cgatacagcc agagtgctgt   1980
cctctatggc cgatgccgtg ctggctagag tgtataagca gagcgacctg gacaccctgg   2040
ctaaagaggc cagcattccc atcatcaacg gcctgtccga cctgtatcac cccatccaga   2100
tcctggccga ctacctgaca ctgcaagagc actacagcag cctgaaggga ctgaccctgt   2160
cttggatcgg cgacggcaac aacatcctgc acagcattat gatgagcgcc gccaagttcg   2220
gaatgcacct ccaggccgct acacccaagg gctatgaacc tgatgccagc gtgacaaagc   2280
tggccgagca gtacgccaaa gagaacggca caaagctgct gctgaccaac gatcccctgg   2340
aagctgctca cggcggcaat gtgctgatca ccgatacctg gatcagcatg ggccaagagg   2400
aagagaagaa gaagcggctg caagccttcc agggctacca agtgaccatg aagacagcca   2460
aggtggccgc cagcgattgg acctttctgc actgcctgcc tcggaagcct gaagaggtgg   2520
acgacgaggt gttctacagc cctagaagcc tggtgttccc cgaggccgag aacagaaagt   2580
ggaccatcat ggctgtgatg gtgtctctgc tgaccgacta ctcccctcag ctccagaagc   2640
ctaagttcgg atccggagaa ggacggggaa gcctgcttac atgcggagat gtggaggaga   2700
atcctggtcc catggtcttt accctggaag atttcgtcgg cgactggcgg cagacagccg   2760
gctataatct ggaccaggtg ctggaacaag gcggagtgtc cagcctgttc cagaatctgg   2820
gagtgtccgt gacacccatc cagcggattg tgctgtctgg cgagaacggc ctgaagatcg   2880
acatccacgt gatcatccct tacgagggcc tgagcggcga tcagatggga cagatcgaga   2940
agattttcaa ggtggtgtac cccgtggacg accaccactt caaagtgatc ctgcactacg   3000
gcaccctggt catcgatggc gtgaccccta acatgatcga ctacttcggc agaccctacg   3060
agggaatcgc cgtgttcgac ggcaagaaaa tcaccgtgac cggcacactg tggaacggga   3120
acaagatcat cgacgagcgg ctgatcaacc ccgatggcag cctgctgttc agagtgacca   3180
ttaacggcgt gacaggctgg cggctgtgcg aaaggattct ggcctgatga tctagagatc   3240
tcatatgcct ttaattaaac actagttcta tagtgtcacc taaattccct ttagtgaggg   3300
ttaatggccg taggccgcca gaattgggtc cagacatgat aagatacatt gatgagtttg   3360
gacaaaccac aactagaatg cagtgaaaaa aatgctttat ttgtgaaatt tgtgatgcta   3420
ttgctttatt tgtaaccatt ataagctgca ataaacaagt taacaacaac aattgcattc   3480
attttatgtt tcaggttcag ggggaggtgt gggaggtttt ttcggactct aggacctgcg   3540
catgcgcttg gcgtaatcat ggtcatagct gtttcctgtt ttccccgtat ccccccaggt   3600
gtctgcaggc tcaaagagca gcgagaagcg ttcagaggaa agcgatcccg tgccaccttc   3660
cccgtgcccg ggctgtcccc gcacgctgcc ggctcgggga tgcgggggga gcgccggacc   3720
ggagcggagc cccgggcggc tcgctgctgc cccctagcgg gggagggacg taattacatc   3780
cctgggggct ttgggggggg gctgtccctc tcaccgcggt ggagctccag cttttgttcg   3840
aattggggcc ccccctcgag ggtatcgatg atatctataa caagaaaata tatatataat   3900
aagttatcac gtaagtagaa catgaaataa caatataatt atcgtatgag ttaaatctta   3960
aaagtcacgt aaaagataat catgcgtcat tttgactcac gcggtcgtta tagttcaaaa   4020
```

tcagtgacac ttaccgcatt gacaagcacg cctcacggga gctccaagcg gcgactgaga 4080
tgtcctaaat gcacagcgac ggattcgcgc tatttagaaa gagagagcaa tatttcaaga 4140
atgcatgcgt caattttacg cagactatct ttctagggtt aatctagcta gccttaaggg 4200
cgcctcgaga ccttgcggcc gcaggaaccc ctagtgatgg agttggccac tccctctctg 4260
cgcgctcgct cgctcactga ggccgggcga ccaaaggtcg cccgacgccc gggctttgcc 4320
cgggcggcct cagtgagcga gcgagcgcgc agctgcctgc agg 4363

<210> SEQ ID NO 144
<211> LENGTH: 4651
<212> TYPE: DNA
<213> ORGANISM: Artificial Sequence
<220> FEATURE:
<223> OTHER INFORMATION: Synthetic Sequence

<400> SEQUENCE: 144
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tatcgatggc gcgcctccag atatcataca ctcgagcaac 180
tttgtataga aaagttggcg cgtgtttgct gcttgcaatg tttgcccatt ttagggtgga 240
cacaggacgc tgtggtttct gagccagggg gcgactcaga tcccagccag tggacttagc 300
ccctgtttgc tcctccgata actggggtga ccttggttaa tattcaccag cagcctcccc 360
cgttgcccct ctggatccac tgcttaaata cggacgagga cagggccctg tctcctcagc 420
ttcaggcacc accactgacc tgggacagtg aatcgcaaga attcacgcgt caattgctcg 480
aggccaccat ggctcccaag aagaagcgga aagttggcgg cggaggcagc agcctggatg 540
atgagcatat tctgagcgcc ctgctgcaga gcgacgatga actcgtgggc gaagatagcg 600
acagcgaggt gtccgatcac gtgtccgagg atgacgtgca gtccgatacc gaggaagcct 660
tcatcgacga ggtgcacgaa gtgcagccta caagcagcgg cagcgagatc ctggacgagc 720
agaatgtgat cgagcagcca ggatctagcc tggccagcaa cagaatcctg acactgcccc 780
agagaaccat ccggggcaag aacaagcact gctggtccac cagcaagagc accagacggt 840
ctagagtgtc tgccctgaac atcgtgcgaa gccagagggg ccctaccaga atgtgccgga 900
acatctacga ccctctgctg tgcttcaagc tgttcttcac cgacgagatc atctccgaga 960
tcgtgaagtg gaccaacgcc gagatcagcc tgaagcggag agaatccatg accagcgcca 1020
ccttcagaga caccaacgag gacgagatct acgccttctt cggcatcctg gtcatgacag 1080
ccgtgcggaa ggacaaccac atgagcaccg acgacctgtt cgaccgcagc ctgtctatgg 1140
tgtacgtgtc cgtgatgagc cgggacagat tcgacttcct gatccggtgc ctgcggatgg 1200
acgacaagtc catcagaccc acactgcgcg agaacgacgt gttcacacct gtgcggaaga 1260
tctgggacct gttcatccac cagtgcatcc agaactacac ccctggcgct cacctgacca 1320
tcgacgaaca gctgctgggc ttcagaggca gatgcccctt cagagtgtac atccccaaca 1380
agccctctaa gtacggcatc aagatcctga tgatgtgcga cagcggcacc aagtacatga 1440
tcaacggcat gccctacctc ggcagaggca cccaaacaaa tggcgtgcca ctgggcgagt 1500
actacgtgaa agaactgagc aagcctgtgc acggcagctg cagaaacatc acctgtgaca 1560
actggtttac cagcattccc ctggccaaga acctgctgca agaaccctac aagctgacaa 1620
tcgtgggcac cgtgcggagc aacaagaggg aaattcccga ggtgctgaag aactctcgga 1680
gcagacctgt gggcaccagc atgttctgct tcgacggacc tctgacactg gtgtcctaca 1740

```
agcccaagcc tgccaagatg gtgtacctgc tgagcagctg tgacgaggac gccagcatca   1800
atgagagcac cggcaagccc cagatggtca tgtactacaa ccagaccaaa ggcggcgtgg   1860
acaccctgga tcagatgtgc agcgtgatga cctgcagcag aaagaccaac agatggccca   1920
tggctctgct gtacggcatg atcaatatcg cctgcatcaa cagcttcatc atctacagcc   1980
acaacgtgtc cagcaagggc gagaaggtgc agagccggaa gaaattcatg cggaacctgt   2040
acatgagcct gaccagcagc ttcatgagaa agcggctgga agcccctaca ctgaagagat   2100
acctgcggga caacatcagc aacatcctgc ctaaagaggt gcccggcacc agcgacgata   2160
gcacagagga acccgtgatg aagaagagga cctactgcac ctactgtccc agcaagatcc   2220
ggcggaaggc caacgccagc tgcaaaaagt gcaagaaagt gatctgccgc gagcacaaca   2280
tcgatatgtg ccagagctgc ttctgatgag atgcattcga agcggccgcg agctcaagct   2340
tgcaattccg ataacttgtt tattgcagct tataatggtt acaaataaag caatagcatc   2400
acaaatttca caaataaagc atttttttca ctgcattcta gttgtggttt gtccaaactc   2460
atcaatgtat cttatcatgt ctggcgctag cagcacaagt ttgtacaaaa aagcaggctc   2520
ctcgcaggag gcctggccgg cctccggatt acttccggtg caggcgtcag ctgcatcttg   2580
ctggccagct cggaggactg tccccgtaac tcccgtccgc tgtgtatcaa cacagctcta   2640
gccaaattgt tgaccgaacg acggggttcg attgtatcat tcctcacatc caacacttga   2700
gtagtacaat gccttgtcta agtgcgcttg ggacccagtc tattttgttt gtgtgcacaa   2760
gacgatactc ctcgatcacg taccaagcgc aggctggccc taacgacgtg gtattctcgt   2820
attggtgtgc cccagattgc ataaggcact catcacctgc gtttatgacg ctggacgcct   2880
gcgtatgttg caggactcct atgatgtcgc tagcctgatg cgttgttatg tgattgaggt   2940
ttagtacttg gcaatatcat tagatggaac taatacgcgg tctaatcgtt acaggtttcc   3000
gacgattgag aagtatcacc tgattctcgg gagcgacttg taactctact acacttattg   3060
atttggtact cctatgtgtt gctatcttga ctccgtaaat cgccgtgata cactctcttc   3120
gtttctcggc aatctatggc tctaaactat acacaggcat tctaagaata atctgacctg   3180
tccctgtagt actggtaggt tactaccagt acggcgacaa tgtgggagct acggcgtggt   3240
agaaccgggt acagacacag tccctgatcc cgatagtaac actgtgcccg tagcagtgat   3300
aatcattgcg cctcaacctg aggaagataa gggaggcagt atatcgtgct attccctcta   3360
ttctcccaca tgcgtatggc ctgaggtcaa tgatcaggta catgccgtaa tatgaggttt   3420
tacgtagccg atcacgaaaa ggttgctaaa tacttctcgt catatcccag ctcattgttg   3480
ggattatcgc taaacaggct aagttctaat gcccgtgggc atggcctcac gatctatggt   3540
gaaacagaca gcccgattta gcaatgctac agagcacagt ggttaatatt ggttgatacg   3600
tagaaccatg atcactgctc aattcgtgat gaagttgttc aatataccta gaagccactc   3660
aaggattctc tctgtgtcac taatagaggt ggtagagtgt ttggaagccg gttccacaca   3720
gatttagagt gtcacctaat tgccgtttat ctaaggaatt acgacaggag attccgaagt   3780
aattaggcta ttgcagagat acaggctagg tgaggtggag ggtgtcttgc ggtcttcgtc   3840
cagccgcctt gaaagcgggg ttttttttcaa gcatcgctgc gtcattgcgt ggtcgagact   3900
tatgcgccct acgaagttcg tctgaagtag tccaggaaag acctactttg cagttatctt   3960
cgcattccca cactcaccac tacaactact cttccctcaa tttcccggtt agtttcgcta   4020
agctccgacc ttgggttact gtgttgcatc cgactcgctg cggctttcta gtacgctgta   4080
```

ctgtttcatt cttctgtagg tctggttccg taagtccgaa tttccaggcc gtggtctagt 4140
cctaattatt ttctgtcccg gtagctatat ttagccgagg gtttgtccat ttgcccggcg 4200
tagagcgccg cgtttgcgaa catttgcgcc cgtaatacgt agggacaccg tcgggtaatg 4260
gatggcaaaa gccgaaaacg gcgtcttccg gcgcttggat tcagcgctct tgagccataa 4320
accgcgttgc ttctttggtt aattcgtatt aatgatccta agcgccagct tattcgttaa 4380
gaggcactag gcgcgccgcg gcatgcgatc gccagcatgg ctacgaccca gctttcttgt 4440
acaaagtggt gatggccggc cgcttcgagt taattaatcc aaccggttac cgcctaggat 4500
cgatagatct aggaacccct agtgatggag ttggccactc cctctctgcg cgctcgctcg 4560
ctcactgagg ccgggcgacc aaaggtcgcc cgacgcccgg gctttgcccg ggcggcctca 4620
gtgagcgagc gagcgcgcag ctgcctgcag g 4651

<210> SEQ ID NO 145
<211> LENGTH: 689
<212> TYPE: DNA
<213> ORGANISM: Artificial Sequence
<220> FEATURE:
<223> OTHER INFORMATION: Synthetic Sequence

<400> SEQUENCE: 145
cgaaccatgg gaattgtacc gcgggggagg ctgctggtga atattaacca aggtcacccc 60
agttatcgga ggagcaaaca ggggctaagt ccaccggggg aggctgctgg tgaatattaa 120
ccaaggtcac cccagttatc ggaggagcaa acaggggcta agtccaccgg gggaggctgc 180
tggtgaatat taaccaaggt caccccagtt atcggaggag caaacagggg ctaagtccac 240
ggatcccact gggaggatgt tgagtaagat ggaaaactac tgatgaccct tgcagagaca 300
gagtattagg acatgtttga acaggggccg ggcgatcagc aggtagctct agaggatccc 360
cgtctgtctg cacatttcgt agagcgagtg ttccgatact ctaatctccc taggcaaggt 420
tcatatttgt gtaggttact tattctcctt ttgttgacta agtcaataat cagaatcagc 480
aggtttggag tcagcttggc agggatcagc agcctgggtt ggaaggaggg ggtataaaag 540
ccccttcacc aggagaagcc gtcacacaga tccacaagct cctgaagagg taagggttta 600
agggatggtt ggttggtggg gtattaatgt ttaattacct ggagcacctg cctgaaatca 660
ctttttttca ggttggacgc gtcgccacc 689

<210> SEQ ID NO 146
<211> LENGTH: 336
<212> TYPE: DNA
<213> ORGANISM: Artificial Sequence
<220> FEATURE:
<223> OTHER INFORMATION: Synthetic Sequence

<400> SEQUENCE: 146
gtctgtctgc acatttcgta gagcgagtgt tccgatactc taatctccct aggcaaggtt 60
catattgact taggttactt attctccttt tgttgactaa gtcaataatc agaatcagca 120
ggtttggagt cagcttggca gggatcagca gcctgggttg gaaggagggg gtataaaagc 180
cccttcacca ggagaagccg tcacacagat ccacaagctc ctgctagcag gtaagtgccg 240
tgtgtggttc ccgcgggcct ggcctcttta cgggttatgg cccttgcgtg ccttgaatta 300
ctgacactga catccacttt ttctttttct ccacag 336

COMPOSITIONS AND METHODS FOR THE TREATMENT OF METABOLIC LIVER DISORDERS

CROSS REFERENCE TO RELATED APPLICATIONS

This application is a U.S. National Phase application, filed under U.S.C. § 371, of International Application No. PCT/US2021/020929, filed Mar. 4, 2021, which claims priority to, and the benefit of, U.S. Provisional Application No. 62/985,047, filed on Mar. 4, 2020, and U.S. Provisional Application No. 63/121,488, filed on Dec. 4, 2020. The contents of each of the aforementioned patent applications are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Sep. 2, 2022, is named "POTH-058_N01US_SeqList.txt" and is about 337,828 bytes in size

BACKGROUND

Inherited metabolic disorders, also known as inborn errors of metabolism, are medical conditions caused by genetic defects most commonly inherited from both parents. Proper metabolism requires a complex set of chemical reactions that cells and organisms use to transform food and other nutrients into essential compounds and energy. These chemical reactions are also used as to breakdown and remove substances that are not needed, including substances that are toxic. The genetic defects that cause inherited metabolic disorders often result in a deficiency in the activity of a particular enzyme within one or more metabolic pathways. This deficiency can result in the accumulation of substances that are potentially toxic, as well as limit a subject's ability to synthesize essential compounds. There are hundreds of inherited metabolic disorders that have been characterized, including those that primarily affect the liver. Inherited metabolic disorders of the liver include urea cycle disorders (UCDs) and methylmalonic acidemia (MMA).

Urea cycle disorders (UCDs) result from genetic mutations which result in defects in the metabolism of nitrogen produced by the breakdown of proteins as well as other nitrogen-containing molecules. UCDs are commonly caused by the severe deficiency or total absence of activity of any of the first four enzymes in the urea cycle, namely Carbamoylphosphate Synthetase I (CPSI), Ornithine Transcarbamylase (OTC), Argininosuccinate Synthetase Deficiency (ASS) and Argininosuccinate Lyase Deficiency (ASL), or the cofactor producer N-Acetylglutamate Synthetase (NAGS), leading to accumulation of ammonia and other precursor metabolites. UCDs are usually diagnosed in neonates, but late-onset UCDs have been reported. UCDs can result in brain damage, cognitive defects and even death. In fact, it is hypothesized that up to 20% of sudden infant death syndrome (SIDS) cases may be attributed to a hereditary metabolic disorder such as a UCD.

Current treatments of UCDs are focused on the acute control of hyperammonemia—a common symptom of UCDs. Hyperammonemia is highly neurotoxic, requiring intensive care intervention including veno-venous hemofiltration. Long-term treatment of UCDs currently relies on alternative pathway therapy, stringent dietary protein restriction, supplementation with urea cycle intermediates and the strict avoidance of catabolism. Patients with UCDs often require liver transplantation. However, the prevention of recurring hyperammonemia prior to liver transplantation can be difficult. Thus, there is a need in the art for improved compositions and methods for the treatment of UCDs.

Other metabolic disorders affecting the liver include the autosomal recessive disorder methylmalonic acidemia (MMA) (also called methylmalonic aciduria). MMA disrupts normal amino acid metabolism. The inherited forms of methylmalonic acidemia cause defects in the metabolic pathway that regulate conversion of methylmalonyl-coenzyme A (CoA) into succinyl-CoA by the enzyme methylmalonyl-CoA mutase. The result of this condition is the inability to properly digest specific fats and proteins, which in turn leads to a buildup of a toxic level of methylmalonic acid in the blood. Isolated methylmalonic acidemia is caused by changes in one of five genes: MMUT, MMAA, MMAB, MMADHC, or MCEE. Methylmalonic acidemia with homocystinuria is caused by mutations in the MMADHC, LMBRD1 and ABCD4 genes.

There is no specific treatment for methylmalonic acidemia. Treatment is currently limited to managing the symptoms and include aggressive treatment of decompensation events, special protein managed diet, vitamin B12 supplementation for the vitamin B12 responsive subtypes, medications such as carnitine, and avoidance of stressors (such as fasting or illness) that can lead to a decompensation event. Liver or kidney transplantation (or both) have been shown to help some patients. These transplants provide the body with new cells that help breakdown methylmalonic acid normally.

Previous attempts at developing gene therapies for the treatment of inherited metabolic disorders, including inherited metabolic disorders of the liver, have suffered from the inability to produce long-term expression of the delivered transgene in the target tissues. This problem is particularly pronounced in rapidly dividing tissues, such as the juvenile liver. Existing gene therapy vectors, such as AAV vectors, suffer from a lack of integration into the host's genome, resulting in only short-term expression of the delivered transgene. The compositions and methods of the present disclosure provide a solution to this long felt-need in the art by providing transposon/transposase-based AAV vectors that yield long-term expression of the delivered transgene in targeted tissues.

SUMMARY

The present disclosure provides an adeno-associated virus (AAV) piggyBac transposon polynucleotide comprising in the 5' to 3' direction: a) a first AAV ITR sequence comprising the nucleic acid sequence of SEQ ID NO: 3; b) a first piggyBac ITR sequence comprising the nucleic acid sequence of SEQ ID NO: 125; c) a first insulator sequence comprising the nucleic acid sequence of SEQ ID NO: 7; d) at least one promoter sequence comprising the nucleic acid sequence of SEQ ID NO: 126; e) at least one transgene sequence comprising the nucleic acid sequence of SEQ ID NO: 22; f) a polyA sequence comprising the nucleic acid sequence of SEQ ID NO: 97; g) a second insulator sequence comprising the nucleic acid sequence of SEQ ID NO: 8; h) a second piggyBac ITR sequence comprising the nucleic acid sequence of SEQ ID NO: 96; i) at least one DNA spacer sequence comprising the nucleic acid sequence of SEQ ID NO: 129; and j) a second AAV ITR sequence comprising the nucleic acid sequence of SEQ ID NO: 4.

The present disclosure provides an AAV piggyBac transposon polynucleotide, wherein the AAV piggyBac transposon polynucleotide comprises the nucleic acid sequence of SEQ ID NO: 138.

The present disclosure provides an AAV piggyBac transposon polynucleotide comprising in the 5' to 3' direction: a) a first AAV ITR sequence comprising the nucleic acid sequence of SEQ ID NO: 3; b) a first piggyBac ITR sequence comprising the nucleic acid sequence of SEQ ID NO: 125; c) a first insulator sequence comprising the nucleic acid sequence of SEQ ID NO: 7; d) at least one promoter sequence comprising the nucleic acid sequence of SEQ ID NO: 132; e) at least one transgene sequence comprising the nucleic acid sequence of SEQ ID NO: 22; f) a polyA sequence comprising the nucleic acid sequence of SEQ ID NO: 97; g) a second insulator sequence comprising the nucleic acid sequence of SEQ ID NO: 8; h) a second piggyBac ITR sequence comprising the nucleic acid sequence of SEQ ID NO: 96; i) at least one DNA spacer sequence comprising the nucleic acid sequence of SEQ ID NO: 130; and j) a second AAV ITR sequence comprising the nucleic acid sequence of SEQ ID NO: 4.

The present disclosure provides an AAV piggyBac transposon polynucleotide, wherein the AAV piggyBac transposon polynucleotide comprises the nucleic acid sequence of SEQ ID NO: 139.

The present disclosure provides an adeno-associated virus (AAV) piggyBac transposon polynucleotide comprising in the 5' to 3' direction: a) a first AAV ITR sequence comprising the nucleic acid sequence of SEQ ID NO: 3; b) a first piggyBac ITR sequence comprising the nucleic acid sequence of SEQ ID NO: 125; c) a first insulator sequence comprising the nucleic acid sequence of SEQ ID NO: 7; d) at least one promoter sequence comprising the nucleic acid sequence of SEQ ID NO: 13; e) at least one transgene sequence comprising the nucleic acid sequence of SEQ ID NO: 22; f) a polyA sequence comprising the nucleic acid sequence of SEQ ID NO: 97; g) a second insulator sequence comprising the nucleic acid sequence of SEQ ID NO: 8; h) a second piggyBac ITR sequence comprising the nucleic acid sequence of SEQ ID NO: 96; i) at least one DNA spacer sequence comprising the nucleic acid sequence of SEQ ID NO: 131; and j) a second AAV ITR sequence comprising the nucleic acid sequence of SEQ ID NO: 4.

The present disclosure provides an AAV piggyBac transposon polynucleotide, wherein the AAV piggyBac transposon polynucleotide comprises the nucleic acid sequence of SEQ ID NO: 140.

The present disclosure provides an AAV transposase polynucleotide comprising in the 5' to 3' direction: a) a first AAV ITR sequence comprising the nucleic acid sequence of SEQ ID NO: 127; b) at least one promoter sequence at least one promoter sequence comprising the nucleic acid sequence of SEQ ID NO: 126; c) at least one transposase sequence comprising the nucleic acid sequence of SEQ ID NO: 48; d) a polyA sequence comprising the nucleic acid sequences of SEQ ID NO: 136; e) at least one DNA spacer sequence comprising the nucleic acid sequences of SEQ ID NO: 137; and f) a second AAV ITR sequence comprising the nucleic acid sequences of SEQ ID NO: 4.

The present disclosure provides an AAV transposase polynucleotide, wherein the AAV transposase polynucleotide comprises the nucleic acid sequence of SEQ ID NO: 144.

The present disclosure provides a vector comprising at least one of the AAV piggyBac transposon polynucleotides of the present disclosure. In some aspects, the vector can be a viral vector. In some aspects, a viral vector can be an AAV viral vector. In some aspects, an AAV viral vector can be an AAV1, AAV2, AAV3, AAV4, AAV5, AAV6, AAV7, AAV8, AAV9, AAV10 or AAV11 viral vector. In some aspects, an AAV viral vector can be an AAV-KP-1 or AAV-NP59 viral vector. In some aspects, an AAV viral vector can be an AAV-KP-1 viral vector.

The present disclosure provides a composition comprising at least one vector of the present disclosure.

The present disclosure provides methods of treating at least one metabolic liver disorder (MLD) in a subject in need thereof comprising administering to the subject at least one therapeutically effective dose of the polynucleotide, vector or composition of the presented disclosure.

The present disclosure provides methods of treating at least one MLD in a subject in need thereof, the method comprising administering to the subject: a) an AAV piggyBac transposon polynucleotide of the present disclosure, or a vector or composition comprising an AAV piggyBac transposon polynucleotide of the present disclosure; and b) an AAV transposase polynucleotide of the present disclosure, or a vector or composition comprising an AAV transposase polynucleotide of the present disclosure.

The present disclosure provides uses of the polynucleotide, vector or composition of the present disclosure for the treatment of at least one MLD in a subject in need thereof, wherein the polynucleotide, vector or composition is for administration to the subject in at least one therapeutically effective amount.

The present disclosure provides the combination of: a) an AAV piggyBac transposon polynucleotide of the present disclosure, or a vector or composition comprising an AAV piggyBac transposon polynucleotide of the present disclosure; and b) an AAV transposase polynucleotide of the present disclosure, or a vector or composition comprising an AAV transposase polynucleotide of the present disclosure for use in the treatment of at least one MLD in a subject in need thereof.

In some aspects, an at least one MLD is N-Acetylglutamate Synthetase (NAGS) Deficiency, Carbamoylphosphate Synthetase I Deficiency (CPSI Deficiency), Ornithine Transcarbamylase (OTC) Deficiency, Argininosuccinate Synthetase Deficiency (ASSD) (Citrullinemia I), Citrin Deficiency (Citrullinemia II), Argininosuccinate Lyase Deficiency (Argininosuccinic Aciduria), Arginase Deficiency (Hyperargininemia), Ornithine Translocase Deficiency (HHH Syndrome), methylmalonic acidemia (MMA), progressive familial intrahepatic cholestasis type 1 (PFIC1), progressive familial intrahepatic cholestasis type 1 (PFIC2), progressive familial intrahepatic cholestasis type 1 (PFIC3) or any combination thereof. In some aspects, an MLD is OTC deficiency.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms “a,” “an,” and “the” are understood to be singular or plural and the term “or” is understood to be inclusive. By way of example, “an element” means one or more element. Throughout the specification the word “comprising,” or variations such as “comprises” or “comprising,” will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

DETAILED DESCRIPTION

Figure 1:
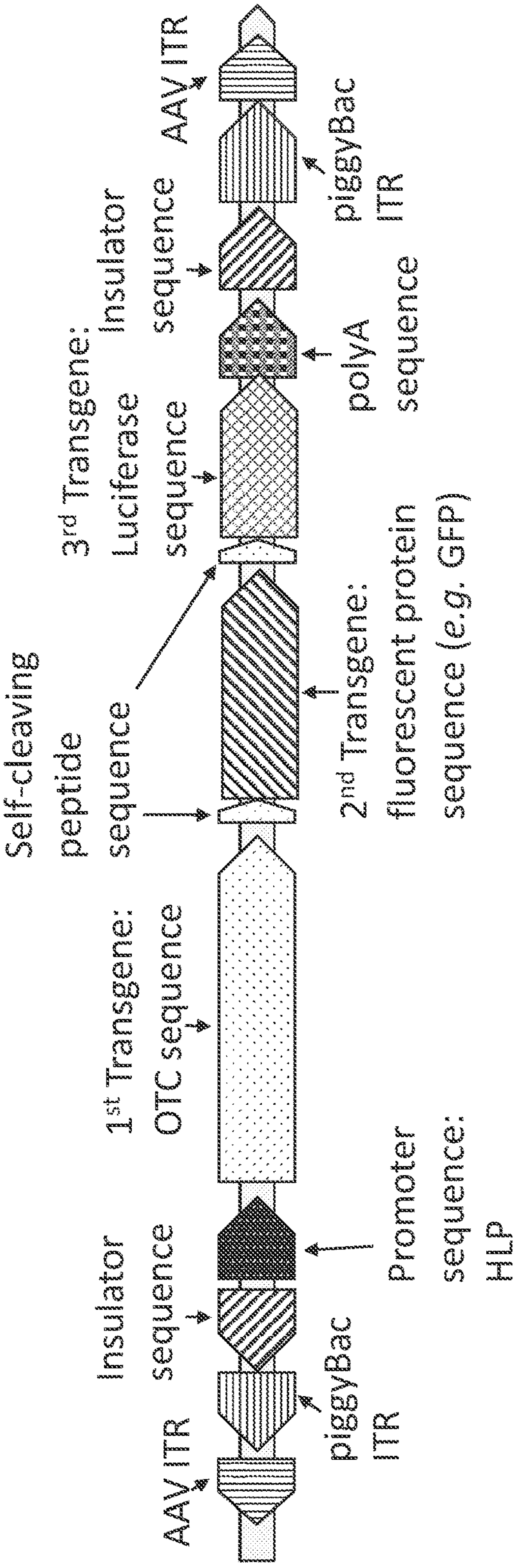
FIG. 1 is a schematic of an exemplary AAV piggyBac transposon polynucleotide of the present disclosure.

The present disclosure provides for compositions and methods for the treatment of metabolic liver disorders, including, but not limited to, urea cycle disorders (UCDs). The compositions and methods are described in further detail herein.

Compositions of Disclosure

Adeno-Associated Virus (AAV) piggyBac Transposon Polynucleotides

The present disclosure provides compositions comprising adeno-associated virus (AAV) piggyBac transposon polynucleotides.

In some aspects an AAV piggyBac transposon polynucleotide can comprise at least one AAV inverted terminal repeat (ITR) sequence. In some aspects, an AAV piggyBac transposon polynucleotide can comprise at least one piggyBac ITR sequence. In some aspects, an AAV piggyBac transposon polynucleotide can comprise at least one insulator sequence. In some aspects an AAV piggyBac transposon polynucleotide can comprise at least one promoter sequence. In some aspects, an AAV piggyBac transposon polynucleotide can comprise at least one transgene sequence. In some aspects, an AAV piggyBac transposon polynucleotide can comprise at least one polyA sequence. In some aspects, an AAV piggyBac transposon polynucleotide can comprise at least one self-cleaving peptide sequence. In some aspects, an AAV piggyBac transposon polynucleotide can comprise at least one DNA spacer sequence. In some aspects, an AAV piggyBac transposon polynucleotide can comprise at least one Int6F sequence. In some aspects, an AAV piggyBac transposon polynucleotide can comprise at least one Int6P1 sequence. In some aspects, an AAV piggyBac transposon polynucleotide can comprise at least one Int6R sequence. In some aspects, an AAV piggyBac transposon polynucleotide can comprise at least one JctR sequence. In some aspects, an AAV piggyBac transposon polynucleotide can comprise at least one MCS sequence.

An AAV piggyBac transposon polynucleotide can comprise a first AAV ITR sequence, a first piggyBac ITR sequence, a first insulator sequence, a second insulator sequence, a second piggyBac ITR sequence, and a second AAV ITR sequence.

In some aspects, an AAV piggyBac transposon polynucleotide can comprise in the 5' to 3' direction a first AAV ITR sequence, a first piggyBac ITR sequence, a first insulator sequence, a second insulator sequence, a second piggyBac ITR sequence, and a second AAV ITR sequence.

In some aspects, an AAV piggyBac transposon polynucleotide can comprise a first AAV ITR sequence, followed by a first piggyBac ITR sequence, followed by a first insulator sequence, followed by a second insulator sequence, followed by a second piggyBac ITR sequence, and followed by a second AAV ITR sequence.

An AAV piggyBac transposon polynucleotide can comprise a first AAV ITR sequence, a first piggyBac ITR sequence, a first insulator sequence, a second insulator sequence, a second piggyBac ITR sequence, and a second AAV ITR sequence, wherein between the first insulator sequence and the second insulator sequence there is any combination of at least one promoter sequence, at least one transgene sequence, at least one self-cleaving peptide sequence, and at least one polyA sequence.

In some aspects, an AAV piggyBac transposon polynucleotide can comprise in the 5' to 3' direction a first AAV ITR sequence, a first piggyBac ITR sequence, a first insulator sequence, a second insulator sequence, a second piggyBac ITR sequence, and a second AAV ITR sequence, wherein between the first insulator sequence and the second insulator sequence there is any combination of at least one promoter sequence, at least one transgene sequence, at least one self-cleaving peptide sequence, and at least one polyA sequence.

In some aspects, an AAV piggyBac transposon polynucleotide can comprise a first AAV ITR sequence, followed by a first piggyBac ITR sequence, followed by a first insulator sequence, followed by a second insulator sequence, followed by a second piggyBac ITR sequence, and followed by a second AAV ITR sequence, wherein between the first insulator sequence and the second insulator sequence there is any combination of at least one promoter sequence, at least one transgene sequence, at least one self-cleaving peptide sequence, and at least one polyA sequence.

An AAV piggyBac transposon polynucleotide can comprise a first AAV ITR sequence, a first piggyBac ITR sequence, a first insulator sequence, at least one promoter sequence, at least one transgene sequence, a polyA sequence, a second insulator sequence, a second piggyBac ITR sequence, and a second AAV ITR sequence.

In some aspects, an AAV piggyBac transposon polynucleotide can comprise in the 5' to 3' direction a first AAV ITR sequence, a first piggyBac ITR sequence, a first insulator sequence, at least one promoter sequence, at least one transgene sequence, a polyA sequence, a second insulator sequence, a second piggyBac ITR sequence, and a second AAV ITR sequence.

In some aspects, an AAV piggyBac transposon polynucleotide can comprise a first AAV ITR sequence, followed by a first piggyBac ITR sequence, followed by a first insulator sequence, followed by at least one promoter sequence, followed by at least one transgene sequence, followed by a polyA sequence, followed by a second insulator sequence, followed by a second piggyBac ITR sequence, and followed by a second AAV ITR sequence.

Figure 2:
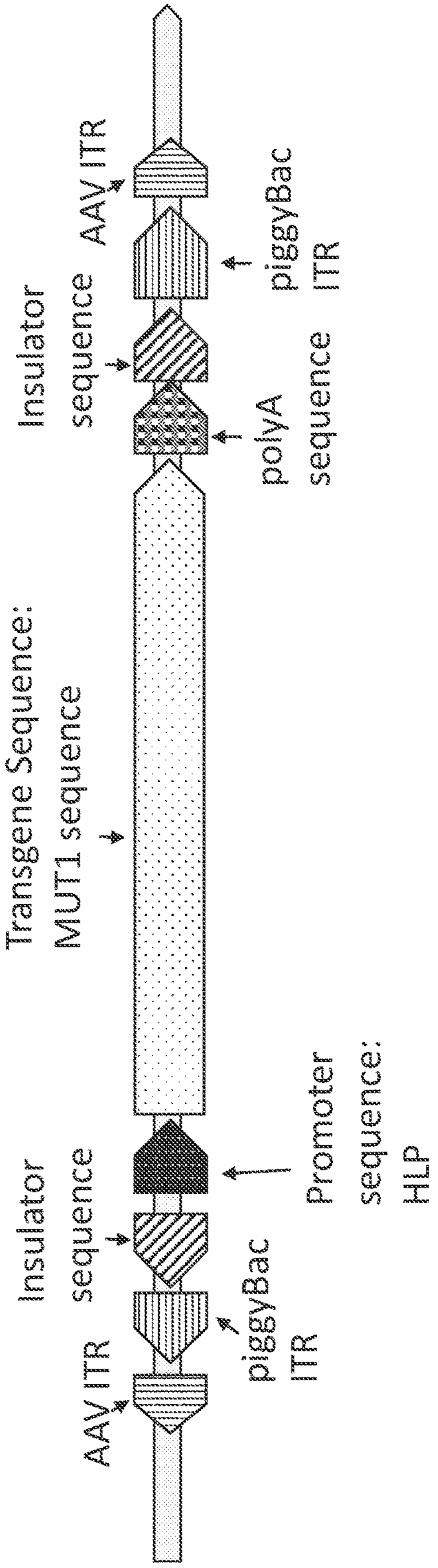
FIG. 2 is a schematic of an exemplary AAV piggyBac transposon polynucleotide of the present disclosure.

In a non-limiting example of the preceding AAV piggyBac transposon polynucleotides, the at least one promoter sequence can comprise a hybrid liver promoter (HLP) and the at least one transgene sequence can comprise a nucleic acid sequence that encodes for a methylmalonyl-CoA mutase (MUT1) polypeptide. This non-limiting example of an AAV piggyBac transposon polynucleotide is shown in FIG. 2.

An AAV piggyBac transposon polynucleotide can comprise a first AAV ITR sequence, a first piggyBac ITR sequence, a first insulator sequence, at least one promoter sequence, at least one transgene sequence, a polyA sequence, a second insulator sequence, a second piggyBac ITR sequence, at least one DNA spacer sequence and a second AAV ITR sequence.

In some aspects, an AAV piggyBac transposon polynucleotide can comprise in the 5' to 3' direction a first AAV ITR sequence, a first piggyBac ITR sequence, a first insulator sequence, at least one promoter sequence, at least one transgene sequence, a polyA sequence, a second insulator sequence, a second piggyBac ITR sequence, at least one DNA spacer sequence and a second AAV ITR sequence.

In some aspects, an AAV piggyBac transposon polynucleotide can comprise a first AAV ITR sequence, followed by a first piggyBac ITR sequence, followed by a first insulator sequence, followed by at least one promoter sequence, followed by at least one transgene sequence, followed by a polyA sequence, followed by a second insulator sequence, followed by a second piggyBac ITR sequence, followed by at least one DNA spacer sequence and followed by a second AAV ITR sequence.

Figure 3A:
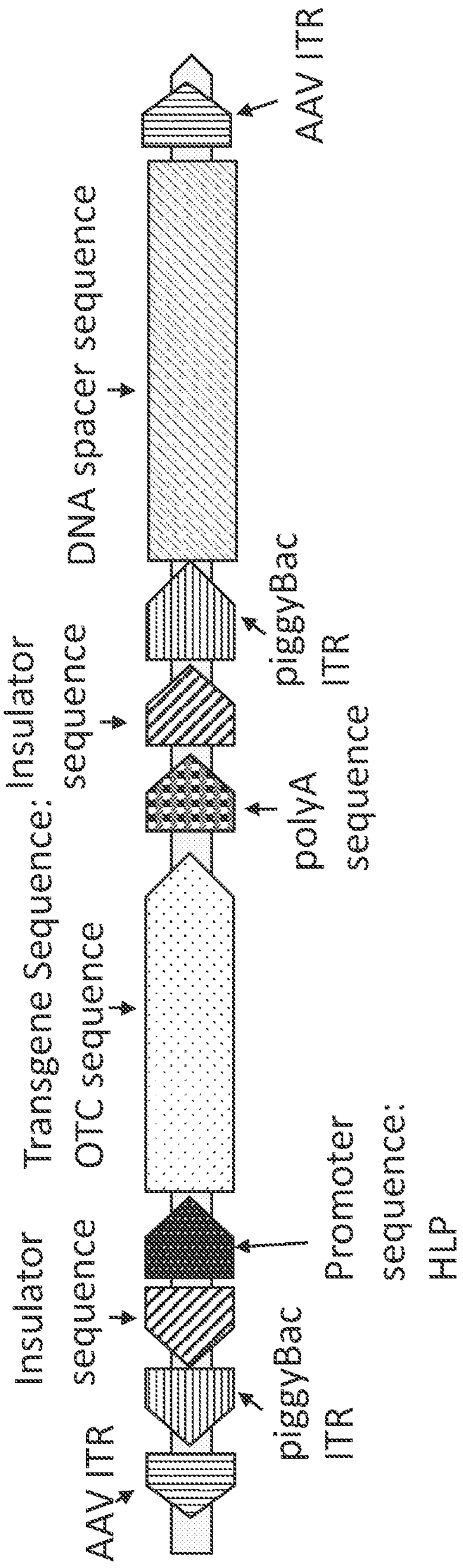
FIG. 3A is a schematic of an exemplary AAV piggyBac transposon polynucleotide of the present disclosure.

In a non-limiting example of the preceding AAV piggyBac transposon polynucleotides, the at least one promoter sequence can comprise a hybrid liver promoter (HLP) and the at least one transgene sequence can comprise a nucleic acid sequence that encodes for an ornithine transcarbamylase (OTC) polypeptide. This non-limiting example of an AAV piggyBac transposon polynucleotide is shown in FIG. 3A.

In some aspects, an AAV piggyBac transposon polynucleotide can comprise in between a second piggyBac ITR sequence and a second AAV ITR sequence, at least one DNA spacer sequence.

An AAV piggyBac transposon polynucleotide can comprise a first AAV ITR sequence, a first piggyBac ITR sequence, a first insulator sequence, at least one promoter sequence, at least one transgene sequence, a polyA sequence, a second insulator sequence, a second piggyBac ITR sequence, a second AAV ITR sequence and at least one DNA spacer sequence.

In some aspects, an AAV piggyBac transposon polynucleotide can comprise in the 5' to 3' direction a first AAV ITR sequence, a first piggyBac ITR sequence, a first insulator sequence, at least one promoter sequence, at least one transgene sequence, a polyA sequence, a second insulator sequence, a second piggyBac ITR sequence, a second AAV ITR sequence and at least one DNA spacer sequence.

In some aspects, an AAV piggyBac transposon polynucleotide can comprise a first AAV ITR sequence, followed by a first piggyBac ITR sequence, followed by a first insulator sequence, followed by at least one promoter sequence, followed by at least one transgene sequence, followed by a polyA sequence, followed by a second insulator sequence, followed by a second piggyBac ITR sequence, followed by a second AAV ITR sequence and followed by at least one DNA spacer sequence.

Figure 3B:
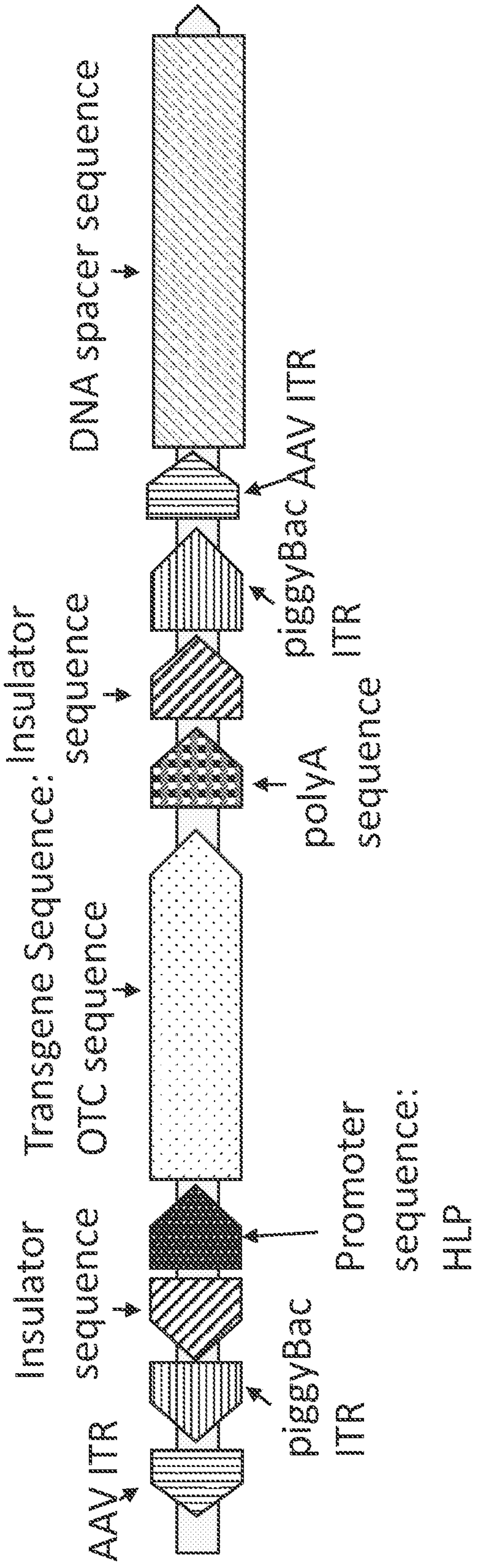
FIG. 3B is a schematic of an exemplary AAV piggyBac transposon polynucleotide of the present disclosure.

In a non-limiting example of the preceding AAV piggyBac transposon polynucleotides, the at least one promoter sequence can comprise a hybrid liver promoter (HLP) and the at least one transgene sequence can comprise a nucleic acid sequence that encodes for an ornithine transcarbamylase (OTC) polypeptide. This non-limiting example of an AAV piggyBac transposon polynucleotide is shown in FIG. 3B.

In some aspects, an AAV piggyBac transposon polynucleotide can comprise after a second AAV ITR sequence, at least one DNA spacer. A non-limiting example of an AAV piggyBac transposon polynucleotide with at least one DNA spacer following a second AAV ITR sequence is shown in FIG. 3B An AAV piggyBac transposon polynucleotide can comprise a first AAV ITR sequence, a first piggyBac ITR sequence, a first insulator sequence, at least one promoter sequence, a first transgene sequence, at least one self-cleaving peptide sequence, an at least second transgene sequence, a polyA sequence, a second insulator sequence, a second piggyBac ITR sequence, and a second AAV ITR sequence.

In some aspects, an AAV piggyBac transposon polynucleotide can comprise in the 5' to 3' direction a first AAV ITR sequence, a first piggyBac ITR sequence, a first insulator sequence, at least one promoter sequence, a first transgene sequence, at least one self-cleaving peptide sequence, an at least second transgene sequence, a polyA sequence, a second insulator sequence, a second piggyBac ITR sequence, and a second AAV ITR sequence.

In some aspects, an AAV piggyBac transposon polynucleotide can comprise a first AAV ITR sequence, followed by a first piggyBac ITR sequence, followed by a first insulator sequence, followed by at least one promoter sequence, followed by a first transgene sequence, followed by at least one self-cleaving peptide sequence, followed by an at least second transgene sequence, followed by a polyA sequence, followed by a second insulator sequence, followed by a second piggyBac ITR sequence, and followed by a second AAV ITR sequence.

Figure 5:
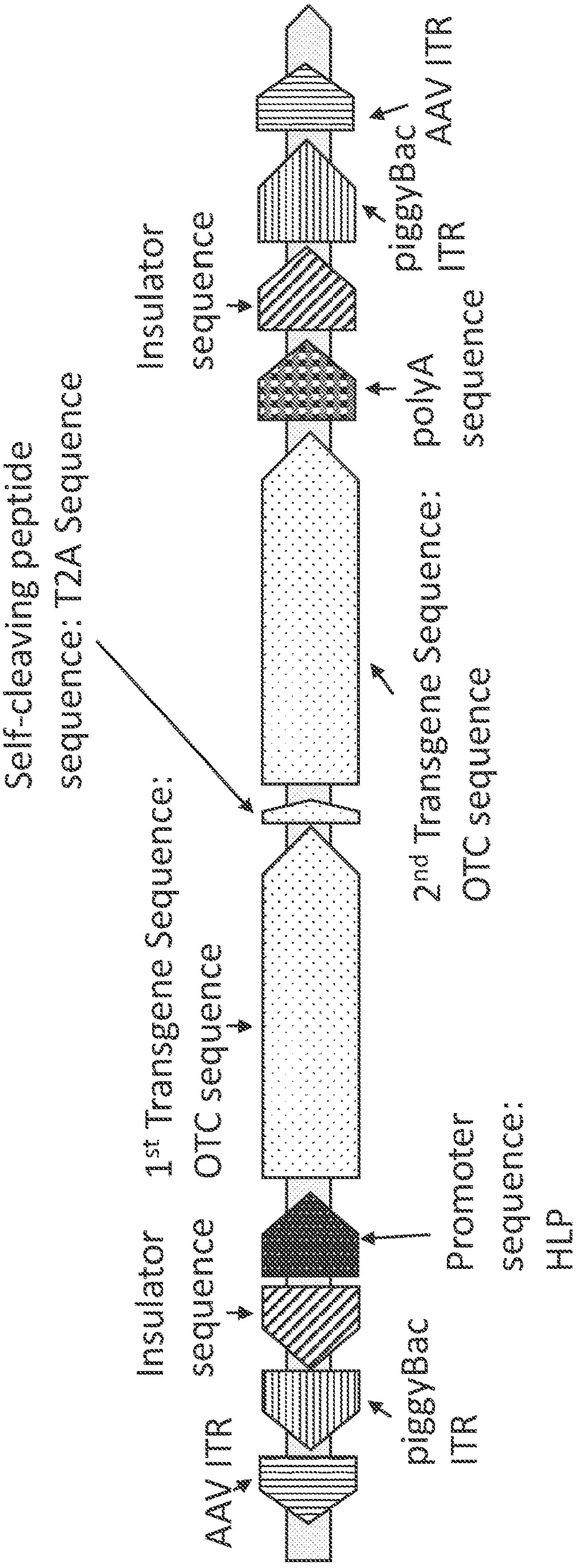
FIG. 5 is a schematic of an exemplary AAV piggyBac transposon polynucleotide of the present disclosure.

In a non-limiting example of the preceding AAV piggyBac transposon polynucleotides, the at least one promoter sequence can comprise a hybrid liver promoter (HLP), the first transgene sequence can comprise a nucleic acid sequence that encodes for an ornithine transcarbamylase (OTC) polypeptide, the at least one self-cleaving peptide sequence can comprise that encodes for a T2A peptide and the at least second transgene sequence can comprise a nucleic acid sequence that encodes for an ornithine transcarbamylase (OTC) polypeptide. This non-limiting example of an AAV piggyBac transposon polynucleotide is shown in FIG. 5.

Figure 8:
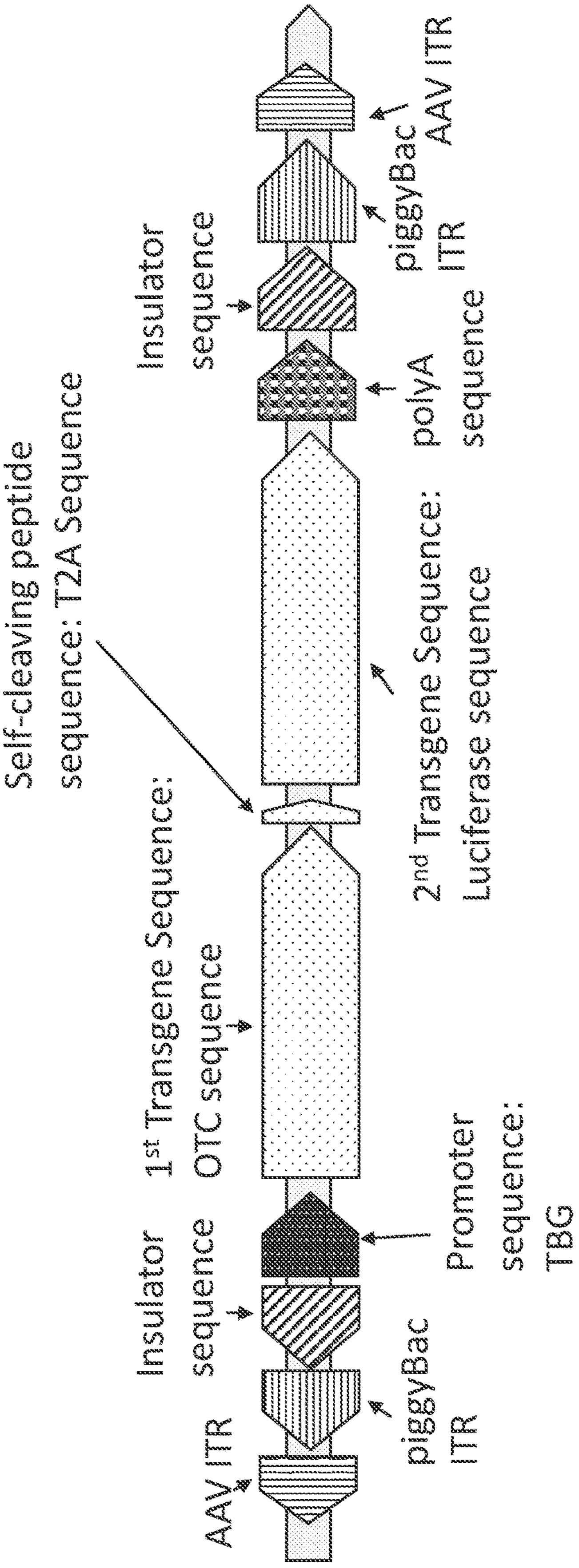
FIG. 8 is a schematic of an exemplary AAV piggyBac transposon polynucleotide of the present disclosure.

In another non-limiting example of the preceding AAV piggyBac transposon polynucleotides the at least one promoter sequence can comprise a thyroxine binding globulin (TBG) promoter, the first transgene sequence can comprise a nucleic acid sequence that encodes for an ornithine transcarbamylase (OTC) polypeptide, the at least one self-cleaving peptide sequence can comprise that encodes for a T2A peptide and the at least second transgene sequence can comprise a luciferase sequence (e.g. NanoLuc). This non-limiting example of an AAV piggyBac transposon polynucleotide is shown in FIG. 8.

Figure 7:
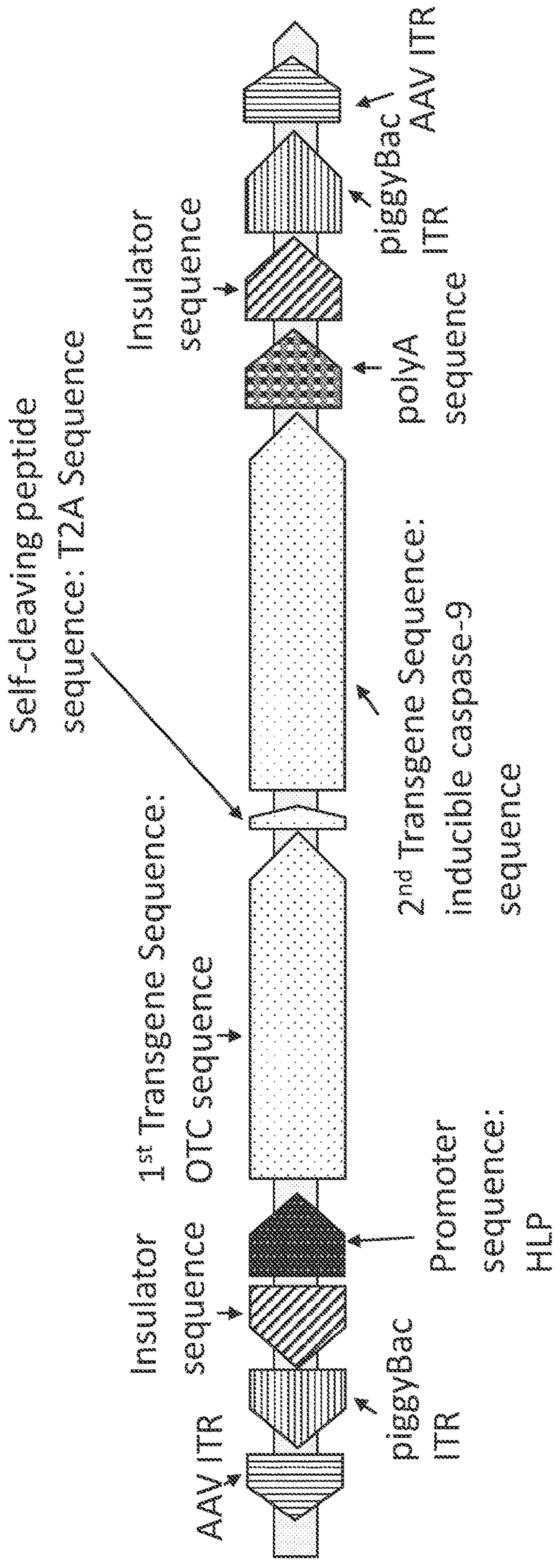
FIG. 7 is a schematic of an exemplary AAV piggyBac transposon polynucleotide of the present disclosure.

In a non-limiting of the preceding AAV piggyBac transposon polynucleotides, the at least one promoter sequence can comprise a hybrid liver promoter (HLP), the first transgene sequence can comprise a nucleic acid sequence that encodes for an ornithine transcarbamylase (OTC) polypeptide, the at least one self-cleaving peptide sequence can comprise that encodes for a T2A peptide and the at least second transgene sequence can comprise a nucleic acid sequence that encodes for an inducible caspase-9 (iCAS9) polypeptide. This non-limiting example of an AAV piggyBac transposon polynucleotide is shown in FIG. 7.

An AAV piggyBac transposon polynucleotide can comprise a first AAV ITR sequence, a first piggyBac ITR sequence, a first insulator sequence, a first promoter sequence, a first transgene sequence, at least a second promoter sequence, an at least second transgene sequence, a polyA sequence, a second insulator sequence, a second piggyBac ITR sequence, and a second AAV ITR sequence.

An AAV piggyBac transposon polynucleotide can comprise in the 5' to 3' direction a first AAV ITR sequence, a first piggyBac ITR sequence, a first insulator sequence, a first promoter sequence, a first transgene sequence, an at least a second promoter sequence, an at least second transgene sequence, a polyA sequence, a second insulator sequence, a second piggyBac ITR sequence, and a second AAV ITR sequence.

An AAV piggyBac transposon polynucleotide can comprise a first AAV ITR sequence, followed by a first piggyBac ITR sequence, followed by a first insulator sequence, followed by a first promoter sequence, followed by a first transgene sequence, followed by an at least a second promoter sequence, followed by an at least second transgene sequence, followed by a polyA sequence, followed by a second insulator sequence, followed by a second piggyBac ITR sequence and followed by a second AAV ITR sequence.

Figure 6:
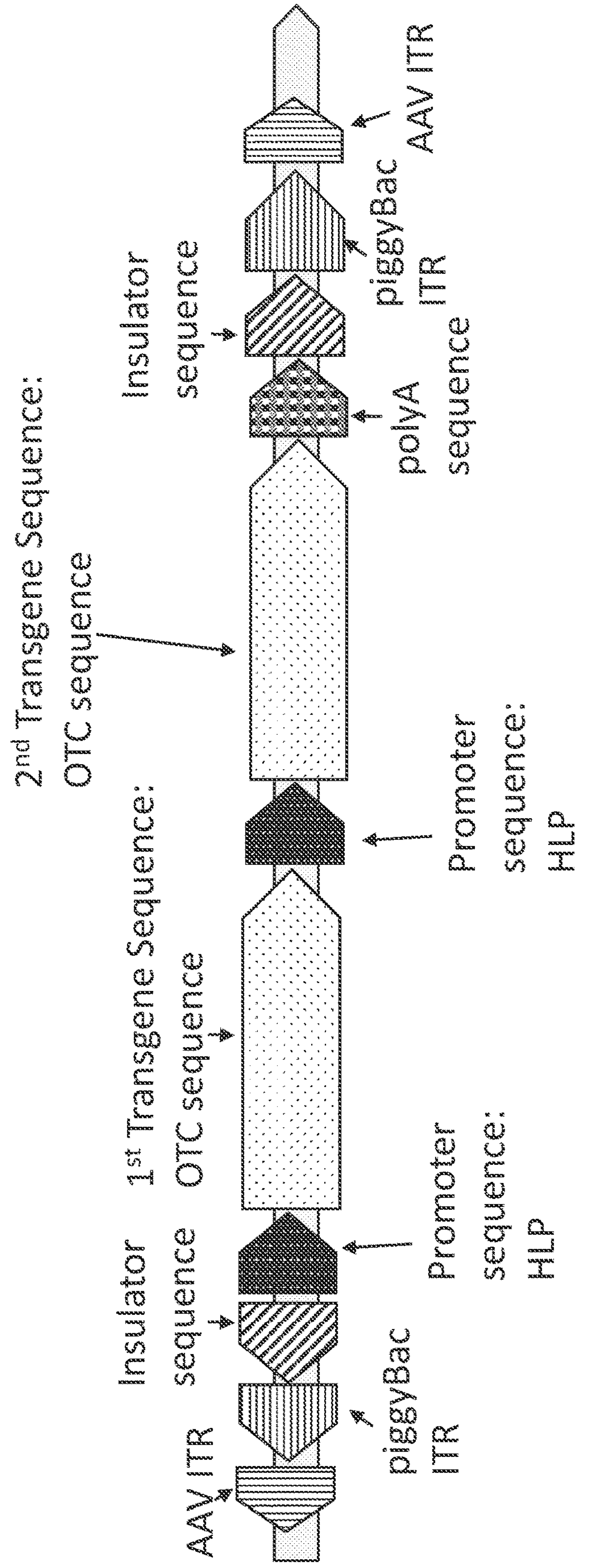
FIG. 6 is a schematic of an exemplary AAV piggyBac transposon polynucleotide of the present disclosure.

In a non-limiting example of the preceding AAV piggyBac transposon polynucleotides, the first promoter sequence can comprise a hybrid liver promoter (HLP), the first transgene sequence can comprise a nucleic acid sequence that encodes for an ornithine transcarbamylase (OTC) polypeptide, the at least second promoter sequence can comprise a HLP and the at least second transgene sequence can comprise a nucleic acid sequence that encodes for an ornithine transcarbamylase (OTC) polypeptide. This non-limiting example of an AAV piggyBac transposon polynucleotide is shown in FIG. 6.

In some aspects, an AAV piggyBac transposon polynucleotide can comprise more than one transgene sequence. In some aspects wherein the AAV piggyBac transposon polynucleotide comprises more than one transgene sequence, individual transgene sequences can be separated by a self-cleaving peptide sequence. In some aspects wherein the AAV piggyBac transposon polynucleotide comprises more than one self-cleaving peptide sequence, the self-cleaving peptide sequences can be the same or can be different.

In some aspects, an AAV piggyBac transposon polynucleotide can comprise more than one transgene sequence. In some aspects wherein the AAV piggyBac transposon polynucleotide comprises more than one transgene sequence, the AAV piggyBac transposon may comprise multiple copies of a nucleic acid sequence that encodes for the same polypeptide. In a non-limiting example, an AAV piggyBac transposon polynucleotide can comprise a first transgene sequence and a second transgene sequence, wherein the first transgene sequence and the second transgene sequence comprise a nucleic acid that encodes of an ornithine transcarbamylase (OTC) polypeptide.

In some aspects, an AAV piggyBac transposon polynucleotide can comprise more than one promoter sequence. In some aspects wherein the AAV piggyBac transposon polynucleotide comprises more than one promoter sequence, the promoter sequences can be the same or the promoter sequences can be different.

In some aspects, an AAV piggyBac transposon polynucleotide can comprise a first AAV ITR sequence, a first piggyBac ITR sequence, a first insulator sequence, at least one promoter sequence, a first transgene sequence, a first self-cleaving peptide sequence, a second transgene sequence, an at least second self-cleaving peptide sequence, at least a third transgene sequence, a polyA sequence, a second insulator sequence and a second AAV ITR sequence.

In some aspects, an AAV piggyBac transposon polynucleotide can comprise in the 5' to 3' direction a first AAV ITR sequence, a first piggyBac ITR sequence, a first insulator sequence, at least one promoter sequence, a first transgene sequence, a first self-cleaving peptide sequence, a second transgene sequence, an at least second self-cleaving peptide sequence, at least a third transgene sequence, a polyA sequence, a second insulator sequence and a second AAV ITR sequence.

In some aspects, an AAV piggyBac transposon polynucleotide can comprise a first AAV ITR sequence, followed by a first piggyBac ITR sequence, followed by a first insulator sequence, followed by at least one promoter sequence, followed by a first transgene sequence, followed by a first self-cleaving peptide sequence, followed by a second transgene sequence, followed by an at least second self-cleaving peptide sequence, followed by at least a third transgene sequence, followed by a polyA sequence, followed by a second insulator sequence and followed by a second AAV ITR sequence.

In some aspects, an AAV piggyBac transposon polynucleotide can comprise a first AAV ITR sequence, a first piggyBac ITR sequence, a first insulator sequence, at least one promoter sequence, a first transgene sequence, a first self-cleaving peptide sequence, a second transgene sequence, an at least second self-cleaving peptide sequence, at least a third transgene sequence, a polyA sequence, a second insulator sequence, a second piggyBac ITR sequence and a second AAV ITR sequence.

In some aspects, an AAV piggyBac transposon polynucleotide can comprise in the 5' to 3' direction a first AAV ITR sequence, a first piggyBac ITR sequence, a first insulator sequence, at least one promoter sequence, a first transgene sequence, a first self-cleaving peptide sequence, a second transgene sequence, an at least second self-cleaving peptide sequence, at least a third transgene sequence, a polyA sequence, a second insulator sequence, a second piggyBac ITR sequence and a second AAV ITR sequence.

In some aspects, an AAV piggyBac transposon polynucleotide can comprise a first AAV ITR sequence, followed by a first piggyBac ITR sequence, followed by a first insulator sequence, followed by at least one promoter sequence, followed by a first transgene sequence, followed by a first self-cleaving peptide sequence, followed by a second transgene sequence, followed by an at least second self-cleaving peptide sequence, followed by at least a third transgene sequence, followed by a polyA sequence, followed by a second insulator sequence, followed by a second piggyBac ITR sequence and followed by a second AAV ITR sequence In a non-limiting example of the preceding AAV piggyBac transposon polynucleotide, the at least one promoter sequence can comprise a hybrid liver promoter (HLP), the first transgene sequence can comprise a nucleic acid sequence that encodes for an ornithine transcarbamylase (OTC) polypeptide, the second transgene sequence can comprise a fluorescent protein sequence (e.g. GFP or eGFP) and the at least third transgene sequence can comprise a luciferase sequence (e.g. NanoLuc). In this non-limiting example, both of the first self-cleaving peptide sequence and the at least second self-cleaving peptide sequence can comprise a can comprise a nucleic acid sequence that encodes for a T2A peptide or a GSG-T2A peptide. This non-limiting example of an AAV piggyBac transposon polynucleotide is shown in FIG. 1.

Figure 9:
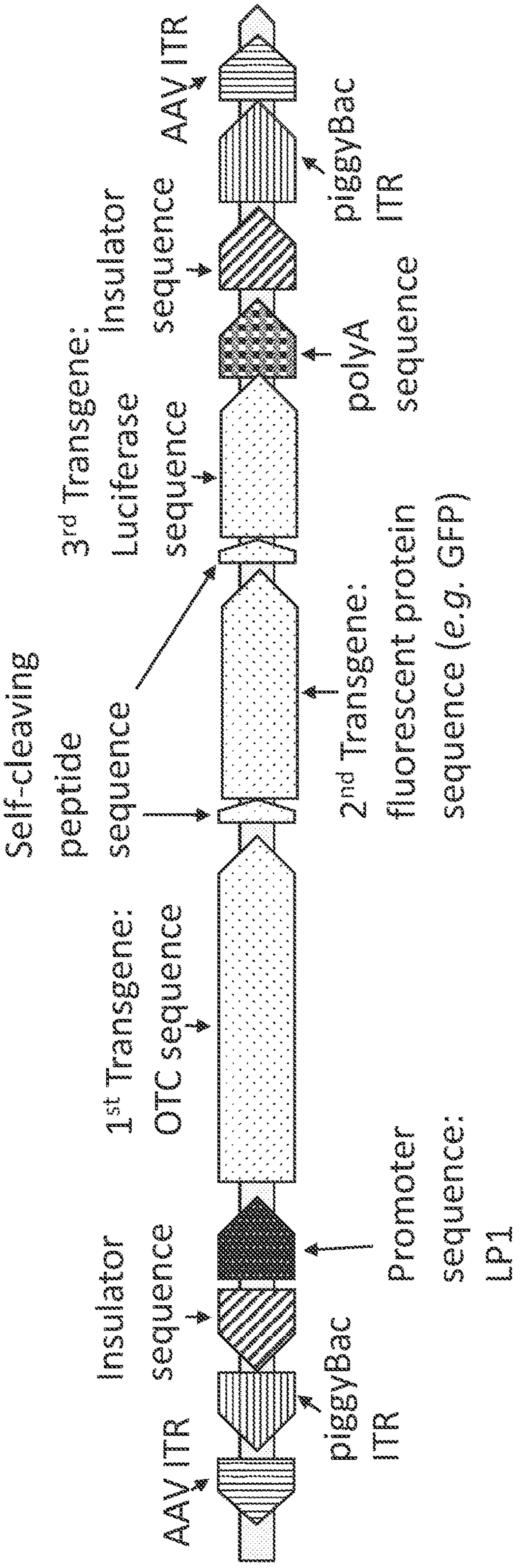
FIG. 9 is a schematic of an exemplary AAV piggyBac transposon polynucleotide of the present disclosure.

In another non-limiting example of the preceding AAV piggyBac transposon polynucleotide, the at least one promoter sequence can comprise a LP1 promoter, the first transgene sequence can comprise a nucleic acid sequence that encodes for an ornithine transcarbamylase (OTC) polypeptide, the second transgene sequence can comprise a fluorescent protein sequence (e.g. GFP or eGFP) and the at least third transgene sequence can comprise a luciferase sequence (e.g. NanoLuc). In this non-limiting example, both of the first self-cleaving peptide sequence and the at least second self-cleaving peptide sequence can comprise a can comprise a nucleic acid sequence that encodes for a T2A peptide or a GSG-T2A peptide. This non-limiting example of an AAV piggyBac transposon polynucleotide is shown in FIG. 9.

In some aspects, an AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to the sequence put forth in SEQ ID NO: 104.

AAV ITR Sequences

In some aspects, an AAV ITR sequence can comprise any AAV ITR sequence known in the art. In some aspects, an AAV ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs: 1-4, 93-94, 105-106 and 127.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 1 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 2.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 3 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 4.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 93 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 94.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 105 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 106.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 127 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 4.

Piggybac ITR Sequences

In some aspects, a piggyBac ITR sequence can comprise any piggyBac ITR sequence known in the art. In some aspects, a piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs: 5-6, 86-90, 95-96 and 125.

In some aspects, a first piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 5 and a second piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 6.

In some aspects, a first piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 6 and a second piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 5.

In some aspects, a first piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 95 and a second piggy-Bac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 96.

In some aspects, a first piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 125 and a second piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 96.

In some aspects of the methods of the present disclosure, a piggyBac ITR sequence, such as a first piggyBac ITR sequence and/or a second piggyBac ITR sequence in an AAV piggyBac transposon can comprise, consist essentially of, or consist of a Sleeping Beauty transposon ITR, a Helraiser transposon ITR, a Tol2 transposon ITR, a TcBuster transposon ITR or any combination thereof.

In some aspects, a piggyBac ITR sequence of the present disclosure can be flanked on either or both ends by at least one of the following sequences: 5'-CTAA-3', 5'-TTAG-3', 5'-ATAA-3', 5'-TCAA-3', 5'AGTT-3', 5'-ATTA-3', 5'-GTTA-3', 5'-TTGA-3', 5'-TTTA-3', 5'-TTAC-3', 5'-ACTA-3', 5'-AGGG-3', 5'-CTAG-3', 5'-TGAA-3', 5'-AGGT-3', 5'-ATCA-3', 5'-CTCC-3', 5'-TAAA-3', 5'-TCTC-3', 5'TGAA-3', 5'-AAAT-3', 5'-AATC-3', 5'-ACAA-3', 5'-ACAT-3', 5'-ACTC-3', 5'-AGTG-3', 5'-ATAG-3', 5'-CAAA-3', 5'-CACA-3', 5'-CATA-3', 5'-CCAG-3', 5'-CCCA-3', 5'-CGTA-3', 5'-GTCC-3', 5'-TAAG-3', 5'-TCTA-3', 5'-TGAG-3', 5'-TGTT-3', 5'-TTCA-3'5'-TTCT-3' and 5'-TTTT-3'. In some aspects, a piggyBac ITR sequence can be flanked by 5'-TTAA-3'. Thus, any AAV transposase polynucleotide, AAV piggyBac transposon polynucleotide and/or any liver nanoplasmid of the present disclosure can further comprise any one of: 5'-CTAA-3', 5'-TTAG-3', 5'-ATAA-3', 5'-TCAA-3', 5'AGTT-3', 5'-ATTA-3', 5'-GTTA-3', 5'-TTGA-3', 5'-TTTA-3', 5'-TTAC-3', 5'-ACTA-3', 5'-AGGG-3', 5'-CTAG-3', 5'-TGAA-3', 5'-AGGT-3', 5'-ATCA-3', 5'-CTCC-3', 5'-TAAA-3', 5'-TCTC-3', 5'TGAA-3', 5'-AAAT-3', 5'-AATC-3', 5'-ACAA-3', 5'-ACAT-3', 5'-ACTC-3', 5'-AGTG-3', 5'-ATAG-3', 5'-CAAA-3', 5'-CACA-3', 5'-CATA-3', 5'-CCAG-3', 5'-CCCA-3', 5'-CGTA-3', 5'-GTCC-3', 5'-TAAG-3', 5'-TCTA-3', 5'-TGAG-3', 5'-TGTT-3', 5'-TTCA-3'5'-TTCT-3' and 5'-TTTT-3' flanking a piggyBac ITR sequence.

Insulator Sequences

In some aspects, an insulator sequence can comprise any insulator sequence known in the art. In some aspects, an insulator sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs: 7-8, 77-80 and 91-92.

In some aspects, a first insulator sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 7 and a second insulator sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any SEQ ID NO: 8.

In some aspects, a first insulator sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 77 and a second insulator sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any SEQ ID NO: 78.

In some aspects, a first insulator sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 79 and a second insulator sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any SEQ ID NO: 80.

In some aspects, a first insulator sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 91 and a second insulator sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any SEQ ID NO: 92.

Promoter Sequences

In some aspects, a promoter sequence can comprise any promoter sequence known in the art. In some aspects, a promoter sequence can comprise any liver-specific promoter sequence known in the art.

In some aspects, a promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs: 9-16, 69, 107, 126, 132, 145 and 146.

In some aspects, a promoter sequence can comprise a hybrid liver promoter (HLP). An HLP can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 9, 107 or 126.

In some aspects, a promoter sequence can comprise an LP1 promoter. An LP1 promoter can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 10 or 132.

In some aspects, a promoter sequence can comprise a leukocyte-specific expression of the pp52 (LSP1) long promoter. An LSP1 long promoter can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 11.

In some aspects, a promoter sequence can comprise a thyroxine binding globulin (TBG) promoter. A TBG promoter can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 12.

In some aspects, a promoter sequence can comprise a wTBG promoter. A wTBG promoter can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 13.

In some aspects, a promoter sequence can comprise a hepatic combinatorial bundle (HCB) promoter. An HCB promoter can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 14.

In some aspects, a promoter sequence can comprise a 2×ApoE-hAAT promoter. An 2×ApoE-hAAT promoter can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 15.

In some aspects, a promoter sequence can comprise a leukocyte-specific expression of the pp52 (LSP1) plus chimeric intron promoter. An LSP1 plus chimeric intron promoter can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 16.

In some aspects, a promoter sequence can comprise a cytomegalovirus (CMV) promoter. A CMV promoter can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 69.

In some aspects, a promoter sequence can comprise a TTR promoter. A TTR promoter can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 145.

In some aspects, a promoter sequence can comprise a TTRm promoter. A TTRm promoter can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 146.

Transgene Sequences

In some aspects, a transgene sequence can comprise a nucleic acid sequence that encodes for a methylmalonyl-CoA mutase (MUT1) polypeptide. In some aspects, a transgene sequence can comprise a nucleic acid sequence that encodes for a MUT1 polypeptide, wherein the MUT1 polypeptide comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 17, 18, 121 or 122. In some aspects, a nucleic acid sequence that encodes for a MUT1 polypeptide can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs: 19, 20 or 111-120.

In some aspects, a transgene sequence can comprise a nucleic acid sequence that encodes for an ornithine transcarbamylase (OTC) polypeptide. In some aspects, a transgene sequence can comprise a nucleic acid sequence that encodes for an OTC polypeptide, wherein the OTC polypeptide comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 21, 81, 123 or 124. In some aspects, a nucleic acid sequence that encodes for an OTC polypeptide can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs: 22, 23, 82 and 83.

In some aspects, a transgene sequence can comprise a nucleic acid sequence that encodes for an iCAS9 polypeptide. In some aspects, a transgene sequence can comprise a nucleic acid sequence that encodes for an iCAS9 polypeptide, wherein the iCAS9 polypeptide comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 24 or 84. In some aspects, a nucleic acid sequence that encodes for an iCAS9 polypeptide can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs: 25 or 85.

In some aspects, a transgene sequence can be codon optimized according to methods known in the art.

In some aspects, the nucleic acid sequence encoding a polypeptide (e.g. OTC, MUT1, etc.) can be a codon optimized nucleic acid sequence that encodes for the polypeptide. A codon optimized nucleic acid sequence encoding a polypeptide can comprise, consist essentially of, or consist of a nucleic acid sequence that is no more than 65%, 70%, 75%, 80%, 85%, 90%, 95%, 96%, 97%, 98%, 99% (or any percentage in between) identical to the wildtype human nucleic acid sequence encoding the polypeptide.

SEQ ID NOs: 19, 20, 22, 23, 82 and 83 are unique codon optimized nucleic acid sequences that can be included in the polynucleotides, vectors and compositions of the present disclosure.

In some aspects, a codon optimized nucleic acid sequence encoding a polypeptide, such as those put forth in SEQ ID NOs: 19, 20, 22, 23, 82 and 83, can comprise no donor splice sites. In some aspects, a codon optimized nucleic acid sequence encoding a polypeptide can comprise no more than about one, or about two, or about three, or about four, or about five, or about six, or about seven, or about eight, or about nine, or about ten donor splice sites. In some aspects, a codon optimized nucleic acid sequence encoding a polypeptide comprises at least one, or at least two, or at least three, or at least four, or at least five, or at least six, or at least seven, or at least eight, or at least nine, or at least ten fewer donor splice sites as compared to the wildtype human nucleic acid sequence encoding the polypeptide. Without wishing to be bound by theory, the removal of donor splice sites in the codon optimized nucleic acid sequence can unexpectedly and unpredictably increase expression of the polypeptide in vivo, as cryptic splicing is prevented. Moreover, cryptic splicing may vary between different subjects, meaning that the expression level of the polypeptide comprising donor splice sites may unpredictably vary between different subjects.

In some aspects, a codon optimized nucleic acid sequence encoding a polypeptide, such as those put forth in SEQ ID NOs: 19, 20, 22, 23, 82 and 83, can have a GC content that differs from the GC content of the wildtype human nucleic acid sequence encoding the polypeptide. In some aspects, the GC content of a codon optimized nucleic acid sequence encoding a polypeptide is more evenly distributed across the entire nucleic acid sequence, as compared to the wildtype human nucleic acid sequence encoding the polypeptide. Without wishing to be bound by theory, by more evenly distributing the GC content across the entire nucleic acid sequence, the codon optimized nucleic acid sequence exhibits a more uniform melting temperature ("Tm") across the length of the transcript. The uniformity of melting temperature results unexpectedly in increased expression of the codon optimized nucleic acid in a human subject, as transcription and/or translation of the nucleic acid sequence occurs with less stalling of the polymerase and/or ribosome.

In some aspects, the codon optimized nucleic acid sequence encoding a polypeptide, such as those put forth in SEQ ID NOs: 19, 20, 22, 23, 82 and 83, exhibits at least 5%, at least 10%, at least 20%, at least 30%, at least 50%, at least 75%, at least 100%, at least 200%, at least 300%, at least 500%, or at least 1000% increased expression in a human subject relative to a wild-type or non-codon optimized nucleic acid sequence encoding the polypeptide.

In some aspects, an at least one transgene sequence can be operatively linked to at least one promoter sequence present in the same polynucleotide.

PolyA Sequences

In some aspects, a polyA sequence can comprise any polyA sequence known in the art. Non-limiting examples of polyA sequences include, but are not limited to, SV40 polyA sequences In some aspects, polyA sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs: 26-27, 97, 108, 128 and 136.

Self-Cleaving Peptide Sequence

In some aspects, a self-cleaving peptide sequence can comprise any self-cleaving peptide sequence known in the art. In some aspects, a self-cleaving peptide sequence can comprise an 2A self-cleaving peptide sequence known in the art. Non-limiting examples of self-cleaving peptides include a T2A peptide, GSG-T2A peptide, an E2A peptide, a GSG-E2A peptide, an F2A peptide, a GSG-F2A peptide, a P2A peptide, or a GSG-P2A peptide.

In some aspects, a self-cleaving peptide sequence can comprise a nucleic acid sequence that encodes for a T2A peptide. In some aspects, a self-cleaving peptide sequence comprise a nucleic acid sequence that encodes for a T2A peptide, wherein the T2A peptide comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 28.

In some aspects, a self-cleaving peptide sequence can comprise a nucleic acid sequence that encodes for a GSG-T2A peptide. In some aspects, a self-cleaving peptide sequence comprise a nucleic acid sequence that encodes for a GSG-T2A peptide, wherein the GSG-T2A peptide comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 29. In some aspects, a nucleic acid sequence that encodes for a GSG-T2A peptide can comprise, consist essentially of or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs: 30-32 and 135.

In some aspects, a self-cleaving peptide sequence can comprise a nucleic acid sequence that encodes for an E2A peptide. In some aspects, a self-cleaving peptide sequence comprise a nucleic acid sequence that encodes for an E2A peptide, wherein the E2A peptide comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 33.

In some aspects, a self-cleaving peptide sequence can comprise a nucleic acid sequence that encodes for a GSG-E2A peptide. In some aspects, a self-cleaving peptide sequence comprise a nucleic acid sequence that encodes for a GSG-E2A peptide, wherein the GSG-E2A peptide comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 34.

In some aspects, a self-cleaving peptide sequence can comprise a nucleic acid sequence that encodes for a F2A peptide. In some aspects, a self-cleaving peptide sequence comprise a nucleic acid sequence that encodes for a F2A peptide, wherein the F2A peptide comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 35.

In some aspects, a self-cleaving peptide sequence can comprise a nucleic acid sequence that encodes for a GSG-F2A peptide. In some aspects, a self-cleaving peptide sequence comprise a nucleic acid sequence that encodes for a GSG-F2A peptide, wherein the GSG-F2A peptide comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 36.

In some aspects, a self-cleaving peptide sequence can comprise a nucleic acid sequence that encodes for a P2A peptide. In some aspects, a self-cleaving peptide sequence comprise a nucleic acid sequence that encodes for a P2A peptide, wherein the P2A peptide comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 37.

In some aspects, a self-cleaving peptide sequence can comprise a nucleic acid sequence that encodes for a GSG-P2A peptide. In some aspects, a self-cleaving peptide sequence comprise a nucleic acid sequence that encodes for a GSG-P2A peptide, wherein the GSG-P2A peptide comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 38.

DNA Spacer Sequences

In some aspects, a DNA spacer sequence can comprise, consist essentially of or consist of a nucleic acid sequence at least 65%, 70%, 75%, 80%, 85%, 90%, 95%, 96%, 97%, 98%, 99% or 100% (or any percentage in between) identical to any one of the nucleic acid sequence put forth in SEQ ID NOs: 103, 109, 129-131 and 137.

DNA spacer sequences can be located at any position within an AAV piggyBac transposon polynucleotide or an AAV piggyBac transposase polynucleotide.

Int6F Sequences

In some aspects, an Int6F sequence can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 98. In some aspects, an Int6F sequence can be located between a polyA sequence and a second insulator sequence.

Int6P1 Sequences

In some aspects, an Int6P1 sequence can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 99. In some aspects, an IntP1 sequence can be located between a polyA sequence and a second insulator sequence.

Int6R Sequences

In some aspects, an Int6R sequence can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 100. In some aspects, an Int6R sequence can be located between a polyA sequence and a second insulator sequence.

JctR Sequences

In some aspects, a JctR sequence can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 101. In some aspects, a JctR sequence can be located between a second piggyBac ITR sequence and a second AAV ITR sequence.

In some aspects, an AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 138.

In some aspects, an AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 139.

In some aspects, an AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 140.

In some aspects, an AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 141.

In some aspects, an AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 142.

In some aspects, an AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 143.

MCS Sequences

In some aspects, a MCS sequence can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 102. In some aspects, an MCS sequence can be located between a second piggyBac ITR sequence and a second AAV ITR sequence.

AAV Transposase Polynucleotides

The present disclosure provides compositions comprising AAV transposase polynucleotides.

In some aspects an AAV transposase polynucleotide can comprise at least one AAV inverted terminal repeat (ITR) sequence. In some aspects an AAV transposase polynucleotide can comprise at least one promoter sequence. In some aspects, an AAV transposase polynucleotide can comprise at least one transposase sequence. In some aspects, an AAV transposon polynucleotide can comprise at least one polyA sequence. In some aspects, an AAV transposon polynucleotide can comprise at least one DNA spacer sequence.

In some aspects, an AAV transposase polynucleotide can comprise a first AAV ITR sequence, at least one promoter sequence, at least one transposase sequence, a polyA sequence and a second AAV ITR sequence.

In some aspects, an AAV transposase polynucleotide can comprise in the 5' to 3' direction a first AAV ITR sequence, at least one promoter sequence, at least one transposase sequence, a polyA sequence and a second AAV ITR sequence.

In some aspects, an AAV transposase polynucleotide can comprise a first AAV ITR sequence, followed by at least one promoter sequence, followed by at least one transposase sequence, followed by a polyA sequence and followed by a second AAV ITR sequence.

In some aspects, an AAV transposase polynucleotide can comprise a first AAV ITR sequence, at least one promoter sequence, at least one transposase sequence, a polyA sequence, at least one DNA spacer sequence and a second AAV ITR sequence.

In some aspects, an AAV transposase polynucleotide can comprise in the 5' to 3' direction a first AAV ITR sequence, at least one promoter sequence, at least one transposase sequence, a polyA sequence, at least one DNA spacer sequence and a second AAV ITR sequence.

In some aspects, an AAV transposase polynucleotide can comprise a first AAV ITR sequence, followed by at least one promoter sequence, followed by at least one transposase sequence, followed by a polyA sequence, followed by at least one DNA spacer sequence and followed by a second AAV ITR sequence.

In a non-limiting example of the preceding AAV transposase polynucleotides, the at least one promoter sequence can comprise a hybrid liver promoter (HLP) and the at least one transposase sequence can comprise a nucleic acid sequence encoding a Super piggyBac™ (SPB) transposase polypeptide. This non-limiting example of an AAV piggyBac transposon polynucleotide is shown in FIG. 4A.

Figure 4A:
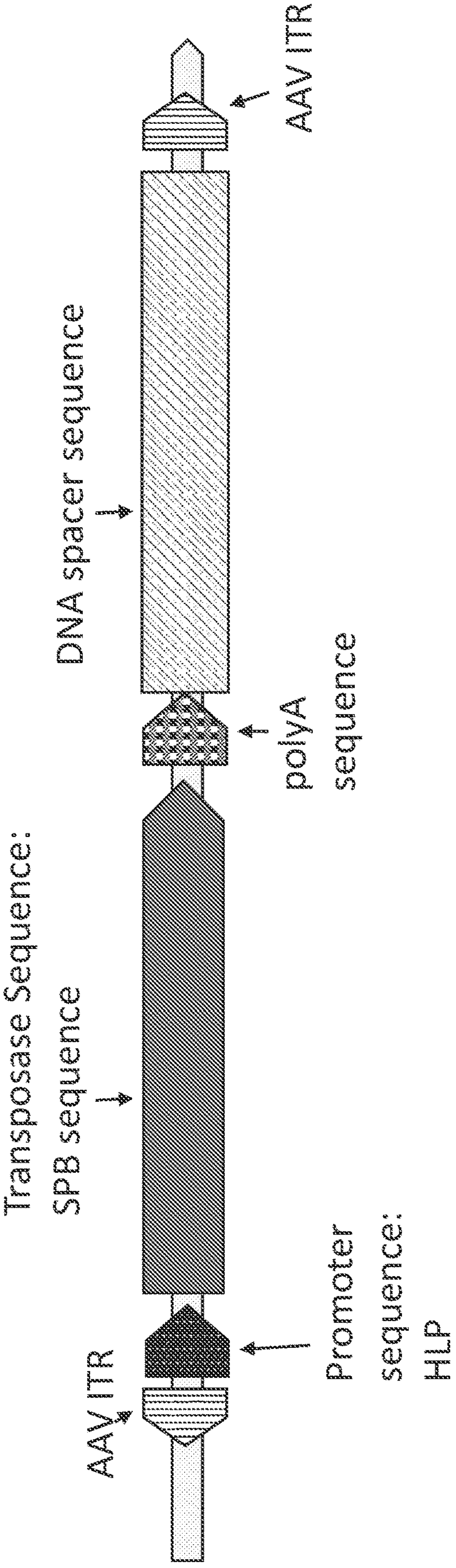
FIG. 4A is a schematic of an exemplary AAV transposase polynucleotide of the present disclosure.

In some aspects, an AAV transposase polynucleotide can comprise, in between a polyA sequence and a second AAV ITR sequence, at least one DNA spacer sequence, as is shown in the non-limiting example presented in FIG. 4A.

In some aspects, an AAV transposase polynucleotide can comprise a first AAV ITR sequence, at least one promoter sequence, at least one transposase sequence, a polyA sequence, a second AAV ITR sequence and at least one DNA spacer sequence.

In some aspects, an AAV transposase polynucleotide can comprise in the 5' to 3' direction a first AAV ITR sequence, at least one promoter sequence, at least one transposase sequence, a polyA sequence, a second AAV ITR sequence and at least one DNA spacer sequence.

In some aspects, an AAV transposase polynucleotide can comprise a first AAV ITR sequence, followed by at least one promoter sequence, followed by at least one transposase sequence, followed by a polyA sequence, followed by a second AAV ITR sequence and followed by at least one DNA spacer sequence.

In a non-limiting example of the preceding AAV transposase polynucleotides, the at least one promoter sequence can comprise a hybrid liver promoter (HLP) and the at least one transposase sequence can comprise a nucleic acid sequence encoding a Super piggyBac™ (SPB) transposase polypeptide. This non-limiting example of an AAV piggyBac transposon polynucleotide is shown in FIG. 4B.

Figure 4B:
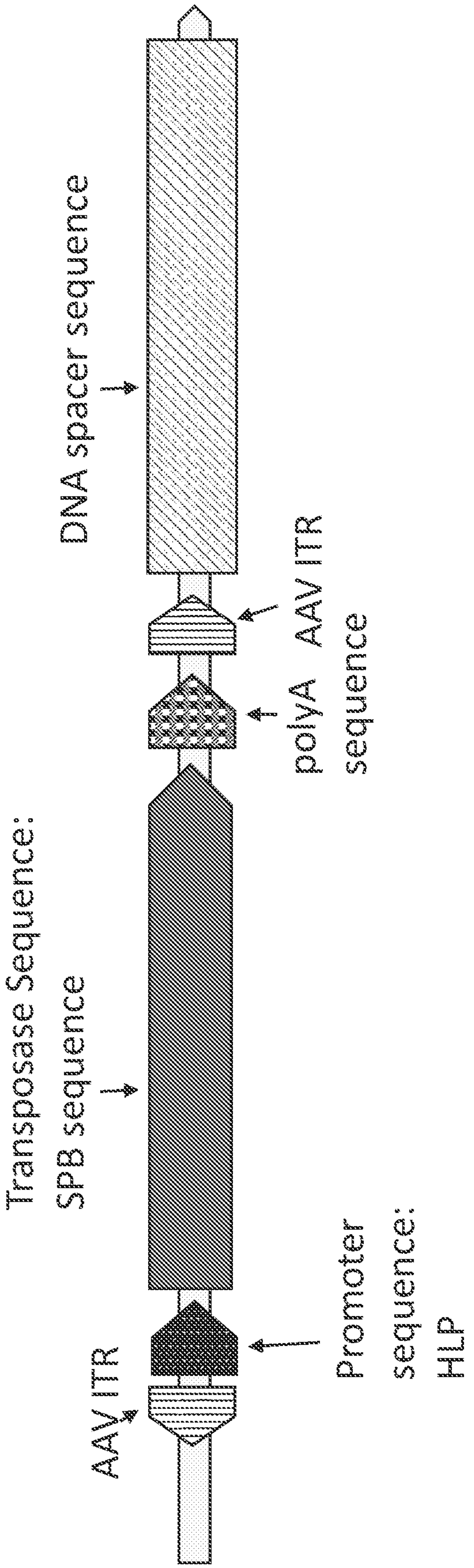
FIG. 4B is a schematic of an exemplary AAV transposase polynucleotide of the present disclosure.

In some aspects, an AAV transposase polynucleotide can comprise, after a second AAV ITR sequence, at least one DNA spacer sequence, as is shown in the non-limiting example presented in FIG. 4B.

In some aspects, an AAV transposase polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to the sequence put forth in SEQ ID NO: 110.

In some aspects, an AAV transposase polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to the sequence put forth in SEQ ID NO: 144.

Transposase Sequences

In some aspects, a transposase sequence can comprise a nucleic acid sequence that encodes for any transposase polypeptide known in the art. In some aspects, a transposase sequence can comprise a nucleic acid sequence that encodes for a piggyBac™ (PB) transposase polypeptide. In some aspects, a transposase sequence can comprise a nucleic acid sequence that encodes for a piggyBac-like (PBL) transposase polypeptide. In some aspects, a transposase sequence can comprise a nucleic acid sequence that encodes for a Super piggyBac™ (SPB) transposase polypeptide.

Non-limiting examples of PB transposons and PB, PBL and SPB transposases are described in detail in U.S. Pat. Nos. 6,218,182; 6,962,810; 8,399,643 and PCT Publication No. WO 2010/099296.

The PB, PBL and SPB transposases recognize transposon-specific inverted terminal repeat sequences (ITRs) on the ends of the transposon, and inserts the contents between the ITRs at the sequence 5'-TTAA-3' within a chromosomal site (a TTAA target sequence). The target sequence of the PB or PBL transposon can comprise or consist of 5'-CTAA-3', 5'-TTAG-3', 5'-ATAA-3', 5'-TCAA-3', 5'AGTT-3', 5'-ATTA-3', 5'-GTTA-3', 5'-TTGA-3', 5'-TTTA-3', 5'-TTAC-3', 5'-ACTA-3', 5'-AGGG-3', 5'-CTAG-3', 5'-TGAA-3', 5'-AGGT-3', 5'-ATCA-3', 5'-CTCC-3', 5'-TAAA-3', 5'-TCTC-3', 5'TGAA-3', 5'-AAAT-3', 5'-AATC-3', 5'-ACAA-3', 5'-ACAT-3', 5'-ACTC-3', 5'-AGTG-3', 5'-ATAG-3', 5'-CAAA-3', 5'-CACA-3', 5'-CATA-3', 5'-CCAG-3', 5'-CCCA-3', 5'-CGTA-3', 5'-GTCC-3', 5'-TAAG-3', 5'-TCTA-3', 5'-TGAG-3', 5'-TGTT-3', 5'-TTCA-3'5'-TTCT-3' and 5'-TTTT-3'. The PB or PBL transposon system has no payload limit for the genes of interest that can be included between the ITRs.

Exemplary amino acid sequences for one or more PB, PBL and SPB transposases are disclosed in U.S. Pat. Nos. 6,218,185; 6,962,810 and 8,399,643. In a preferred aspect, the PB transposase comprises or consists of an amino acid sequence at least 65%, 70%, 75%, 80%, 85%, 90%, 95%, 96%, 97%, 98%, 99% or 100% (or any percentage in between) identical to SEQ ID NO: 39.

The PB or PBL transposase can comprise or consist of an amino acid sequence having an amino acid substitution at two or more, at three or more or at each of positions 30, 165, 282, and/or 538 of the sequence of SEQ ID NO: 39. The transposase can be a SPB transposase that comprises or consists of the amino acid sequence of the sequence of SEQ ID NO: 39 wherein the amino acid substitution at position 30 can be a substitution of a valine (V) for an isoleucine (I), the amino acid substitution at position 165 can be a substitution of a serine (S) for a glycine (G), the amino acid substitution at position 282 can be a substitution of a valine (V) for a methionine (M), and the amino acid substitution at position 538 can be a substitution of a lysine (K) for an asparagine (N). In a preferred aspect, the SPB transposase comprises or consists of an amino acid sequence at least 65%, 70%, 75%, 80%, 85%, 90%, 95%, 96%, 97%, 98%, 99% or 100% (or any percentage in between) identical to SEQ ID NO: 40.

In certain aspects wherein the transposase comprises the above-described mutations at positions 30, 165, 282 and/or 538, the PB, PBL and SPB transposases can further comprise an amino acid substitution at one or more of positions 3, 46, 82, 103, 119, 125, 177, 180, 185, 187, 200, 207, 209, 226, 235, 240, 241, 243, 258, 296, 298, 311, 315, 319, 327, 328, 340, 421, 436, 456, 470, 486, 503, 552, 570 and 591 of the sequence of SEQ ID NO: 39 or SEQ ID NO: 40 are described in more detail in PCT Publication No. WO 2019/173636 and PCT/US2019/049816.

In a preferred aspect, the PB transposase comprises or consists of an amino acid sequence at least 65%, 70%, 75%, 80%, 85%, 90%, 95%, 96%, 97%, 98%, 99% or 100% (or any percentage in between) identical to SEQ ID NO: 41.

The PB or PBL transposase can comprise or consist of an amino acid sequence having an amino acid substitution at two or more, at three or more or at each of positions 29, 164, 281, and/or 537 of the sequence of SEQ ID NO: 41. The transposase can be a SPB transposase that comprises or consists of the amino acid sequence of the sequence of SEQ ID NO: 41 wherein the amino acid substitution at position 29 can be a substitution of a valine (V) for an isoleucine (I), the amino acid substitution at position 164 can be a substitution of a serine (S) for a glycine (G), the amino acid substitution at position 281 can be a substitution of a valine (V) for a methionine (M), and the amino acid substitution at position 537 can be a substitution of a lysine (K) for an asparagine (N). In a preferred aspect, the SPB transposase comprises or consists of an amino acid sequence at least 65%, 70%, 75%, 80%, 85%, 90%, 95%, 96%, 97%, 98%, 99% or 100% (or any percentage in between) identical to SEQ ID NO: 42.

In certain aspects wherein the transposase comprises the above-described mutations at positions 29, 164, 281, and/or 537, the PB, PBL and SPB transposases can further comprise an amino acid substitution at one or more of positions 2, 45, 81, 102, 118, 124, 176, 179, 184, 186, 199, 206, 208, 225, 234, 239, 240, 242, 257, 295, 297, 310, 314, 318, 326, 327, 339, 420, 435, 455, 469, 485, 502, 551, 569 and 590 of the sequence of SEQ ID NO: 41 or SEQ ID NO: 42 are described in more detail in PCT Publication No. WO 2019/173636 and PCT/US2019/049816.

The PB, PBL or SPB transposases can be isolated or derived from an insect, vertebrate, crustacean or urochordate as described in more detail in PCT Publication No. WO 2019/173636 and PCT/US2019/049816. In preferred aspects, the PB, PBL or SPB transposases is be isolated or derived from the insect *Trichoplusia ni* (GenBank Accession No. AAA87375) or *Bombyx mori* (GenBank Accession No. BAD11135).

A hyperactive PB or PBL transposase is a transposase that is more active than the naturally occurring variant from which it is derived. In a preferred aspect, a hyperactive PB or PBL transposase is isolated or derived from *Bombyx mori* or *Xenopus tropicalis*. Examples of hyperactive PB or PBL transposases are disclosed in U.S. Pat. Nos. 6,218,185; 6,962,810, 8,399,643 and WO 2019/173636. A list of hyperactive amino acid substitutions is disclosed in U.S. Pat. No. 10,041,077.

In some aspects, a PB, PBL or SPB transposase is integration deficient. An integration deficient PB, PBL or SPB transposase is a transposase that can excise its corresponding transposon, but that integrates the excised transposon at a lower frequency than a corresponding wild type transposase. Examples of integration deficient PB, PBL or SPB transposases are disclosed in U.S. Pat. Nos. 6,218,185; 6,962,810, 8,399,643 and WO 2019/173636. A list of integration deficient amino acid substitutions is disclosed in U.S. Pat. No. 10,041,077.

In some aspects, a PB, PBL or SPB transposase can fused to a nuclear localization signal. Examples of PB, PBL or SPB transposases fused to a nuclear localization signal are disclosed in U.S. Pat. Nos. 6,218,185; 6,962,810, 8,399,643 and WO 2019/173636. A nuclear localization signal can comprise, consist essentially of or consist of a of the amino acid sequence at least 65%, 70%, 75%, 80%, 85%, 90%, 95%, 96%, 97%, 98%, 99% or 100% (or any percentage in between) identical to SEQ ID NO: 43. A nuclear localization signal can be encoded by a nucleic acid sequence that comprises, consists essentially of or consists of the nucleic acid sequence at least 65%, 70%, 75%, 80%, 85%, 90%, 95%, 96%, 97%, 98%, 99% or 100% (or any percentage in between) identical to SEQ ID NO: 44.

In some aspects, a nuclear localization signal can be fused to a PB, PBL or SPB transposase using a G45 linker located between the NLS and the PB, PBL or SPB. A G45 linker can comprise, consist essentially of or consist of an amino acid sequence at least 65%, 70%, 75%, 80%, 85%, 90%, 95%, 96%, 97%, 98%, 99% or 100% (or any percentage in between) identical to SEQ ID NO: 45. A G45 linker can be encoded by a nucleic acid sequence that comprises, consists essentially of or consists of the nucleic acid sequence at least 65%, 70%, 75%, 80%, 85%, 90%, 95%, 96%, 97%, 98%, 99% or 100% (or any percentage in between) identical to SEQ ID NO: 46.

In some aspects, a transposase sequence can comprise a nucleic acid sequence that encodes for a SBP transposase polypeptide fused to an NLS, wherein the SBP transposase polypeptide fused to an NLS comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 47. In some aspects, a nucleic acid sequence that encodes for a SBP transposase polypeptide fused to an NLS can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs: 48.

In some aspects, a transposase sequence can comprise a nucleic acid sequence that encodes for a SBP transposase polypeptide fused to an NLS, wherein the SBP transposase polypeptide fused to an NLS comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 49. In some aspects, a nucleic acid sequence that encodes for a SBP transposase polypeptide fused to an NLS can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs: 50.

In some aspects, a transposase sequence can comprise a nucleic acid sequence that encodes for a Sleeping Beauty transposase polypeptide (for example as disclosed in U.S. Pat. No. 9,228,180). In some aspects, a transposase sequence can comprise a nucleic acid sequence that encodes for a Hyperactive Sleeping Beauty (SB100X) transposase polypeptide. In some aspects, a Sleeping Beauty transposase comprises or consists of an amino acid sequence at least 65%, 70%, 75%, 80%, 85%, 90%, 95%, 96%, 97%, 98%, 99% or 100% (or any percentage in between) identical to SEQ ID NO: 51 and 52. In a preferred aspect, hyperactive Sleeping Beauty (SB100X) transposase comprises, consists essentially of or consists of an amino acid sequence at least 65%, 70%, 75%, 80%, 85%, 90%, 95%, 96%, 97%, 98%, 99% or 100% (or any percentage in between) identical to SEQ ID NO: 53 and 54.

In some aspects, a transposase sequence can comprise a nucleic acid sequence that encodes for a helitron transposase polypeptide (for example, as disclosed in WO 2019/173636). In some aspects, a Helitron transposase polypeptide comprises, consists essentially of or consists of an amino acid sequence at least 65%, 70%, 75%, 80%, 85%, 90%, 95%, 96%, 97%, 98%, 99% or 100% (or any percentage in between) identical to SEQ ID NO: 55 or 56.

In some aspects, a transposase sequence can comprise a nucleic acid sequence that encodes for a Tol2 transposase polypeptide (for example, as disclosed in WO 2019/173636). In some aspects, a Tol2 transposase polypeptide comprises, consists essentially of or consists of an amino acid sequence at least 65%, 70%, 75%, 80%, 85%, 90%, 95%, 96%, 97%, 98%, 99% or 100% (or any percentage in between) identical to SEQ ID NO: 57 or 58.

In some aspects, a transposase sequence can comprise a nucleic acid sequence that encodes for a TcBuster transposase polypeptide (for example, as disclosed in WO 2019/173636) or a mutant TcBuster transposase polypeptide (as described in more detail in PCT Publication No. WO 2019/173636 and PCT/US2019/049816). In some aspects, a TcBuster transposase polypeptide comprises, consists essentially of or consists of an amino acid sequence at least 65%, 70%, 75%, 80%, 85%, 90%, 95%, 96%, 97%, 98%, 99% or 100% (or any percentage in between) identical to SEQ ID NO: 59 or 60. The polynucleotide encoding a TcBuster transposase can comprise or consist of a naturally occurring nucleic acid sequence or a non-naturally occurring nucleic acid sequence.

Nanoplasmids for Testing Liver-Specific Promoters

The present disclosure provides compositions comprising nanoplasmids for testing liver-specific promoters, herein referred to as "liver nanoplasmids".

In some aspects, a liver nanoplasmid can comprise at least one piggyBac ITR sequence. In some aspects, a liver nanoplasmid can comprise at least one insulator sequence. In some aspects, a liver nanoplasmid can comprise at least one promoter sequence. In some aspects, a liver nanoplasmid can comprise at least one fluorescent protein sequence. In some aspects, a liver nanoplasmid can comprise at least one self-cleaving peptide sequence. In some aspects, a liver nanoplasmid can comprise at least one luciferase sequence. In some aspects, a liver nanoplasmid can comprise at least one polyA sequence.

A liver nanoplasmid can comprise a first piggyBac ITR sequence, a first insulator sequence, at least one promoter sequence, a fluorescent protein sequence, at least one self-cleaving peptide sequence, a luciferase sequence, a polyA sequence, a second insulator sequence and a second piggyBac ITR sequence. In some aspects, a liver nanoplasmid can comprise in the 5' to 3' direction a first piggyBac ITR sequence, a first insulator sequence, at least one promoter sequence, a fluorescent protein sequence, at least one self-cleaving peptide sequence, a luciferase sequence, a polyA sequence, a second insulator sequence and a second piggyBac ITR sequence.

In some aspects of the present disclosure, a transgene sequence can comprise a fluorescent protein sequence.

In some aspects, a fluorescent protein sequence can comprise a nucleic acid sequence that encodes for an eGFP polypeptide. In some aspects, a fluorescent protein sequence can comprise a nucleic acid sequence that encodes for an eGFP polypeptide, wherein the eGFP polypeptide comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NOs: 61 or 62. In some aspects, a nucleic acid sequence that encodes for an eGFP polypeptide can comprise, consist essentially of, or consist of a nucleic acid sequence at least 75%, 80%, 85%, 90%, 95%, 96%, 97%, 98%, 99% or 100% (or any percentage in between) identical to any of the sequences put forth in SEQ ID NOs: 63, 64 or 133.

In some aspects of the present disclosure, a transgene sequence can comprise a luciferase sequence.

In some aspects, a luciferase sequence can comprise a nucleic acid sequence that encodes for an fLuc2 polypeptide. In some aspects, a luciferase sequence can comprise a nucleic acid sequence that encodes for an fLuc2 polypeptide, wherein the fLuc2 polypeptide comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NOs: 65 or 66. In some aspects, a nucleic acid sequence that encodes for an eGFP polypeptide can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs: 67 or 68.

In some aspects, a luciferase sequence can comprise a nucleic acid sequence that encodes for a nanoluciferase (nLuc) polypeptide. In some aspects, a nucleic acid sequence that encodes for an nLuc polypeptide can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs: 134.

Vectors of the Present Disclosure

The present disclosure provides compositions comprising a vector, wherein the vector comprises at least one adeno-associated virus (AAV) piggyBac transposon polynucleotide. A vector comprising at least one adeno-associated virus (AAV) piggyBac transposon polynucleotide is herein referred to as an "AAV piggyBac transposon vector".

The present disclosure provides compositions comprising a vector, wherein the vector comprises at least one AAV transposase polynucleotide. A vector comprising at least one AAV transposase polynucleotide is herein referred to as an "AAV transposase vector".

A vector of the present disclose can be a viral vector or a recombinant vector. Viral vectors can comprise a sequence isolated or derived from a retrovirus, a lentivirus, an adenovirus, an adeno-associated virus or any combination thereof. The viral vector may comprise a sequence isolated or derived from an adeno-associated virus (AAV). The viral vector may comprise a recombinant AAV (rAAV).

Exemplary adeno-associated viruses and recombinant adeno-associated viruses include, but are not limited to all serotypes (e.g., AAV1, AAV2, AAV3, AAV4, AAV5, AAV6, AAV7, AAV8, AAV9, AAV10 and AAV11). Exemplary adeno-associated viruses and recombinant adeno-associated viruses include, but are not limited to, self-complementary AAV (scAAV) and AAV hybrids containing the genome of one serotype and the capsid of another serotype (e.g., AAV2/5, AAV-DJ and AAV-DJ8). Exemplary adeno-associated viruses and recombinant adeno-associated viruses include, but are not limited to, rAAV-LK03, AAV-KP-1 (also referred to as AAV-KP1; described in detail in Kerun et al.

JCI Insight, 2019; 4(22):e131610) and AAV-NP59 (described in detail in Paulk et al. Molecular Therapy, 2018; 26(1): 289-303).

The present disclosure provides a composition comprising a plurality of AAV-KP-1 particles comprising at least one adeno-associated virus (AAV) piggyBac transposon polynucleotide. The present disclosure provides a composition comprising a plurality of AAV-KP-1 particles comprising at least one AAV transposase polynucleotide. The present disclosure provides a composition comprising a plurality of AAV-KP-1 particles comprising at least one adeno-associated virus (AAV) piggyBac transposon polynucleotide and a plurality of AAV-KP-1 particles comprising at least one AAV transposase polynucleotide.

The present disclosure provides a composition comprising a plurality of AAV-NP59 particles comprising at least one adeno-associated virus (AAV) piggyBac transposon polynucleotide. The present disclosure provides a composition comprising a plurality of AAV-NP59 particles comprising at least one AAV transposase polynucleotide. The present disclosure provides a composition comprising a plurality of AAV-NP59 particles comprising at least one adeno-associated virus (AAV) piggyBac transposon polynucleotide and a plurality of AAV-NP59 particles comprising at least one AAV transposase polynucleotide.

The viral vectors and viral particles of the present disclosure can be produced using standard methods known in the art.

In some aspects, AAV-KP-1 particles of the present disclosure can be produced using a KP-1 capsid vector, wherein the KP-1 capsid vector comprises at least one of the nucleic acid sequences of SEQ ID NO: 70 and SEQ ID NO: 71. In some aspects, AAV-KP-1 particles of the present disclosure can be produced using an AAV vector packaging plasmid, wherein the AAV vector packaging plasmid comprises at least of the nucleic acid sequences of SEQ ID NO: 75 and SEQ ID NO: 76.

In some aspects, AAV-NP59 particles of the present disclosure can be produced using a NP-59 capsid vector, wherein the NP-59 capsid vector comprises at least one of the nucleic acid sequences of SEQ ID NO: 72, SEQ ID NO: 73 and SEQ ID NO: 74. In some aspects, AAV-NP59 particles of the present disclosure can be produced using an AAV vector packaging plasmid, wherein the AAV vector packaging plasmid comprises at least of the nucleic acid sequences of SEQ ID NO: 75 and SEQ ID NO: 76.

The cell delivery compositions (e.g., polynucleotides, vectors) disclosed herein can comprise a nucleic acid encoding a therapeutic protein or therapeutic agent. Examples of therapeutic proteins include those disclosed in PCT Publication No. WO 2019/173636 and PCT/US2019/049816. Therapeutic proteins can also include, but are not limited to, any of polypeptides described herein as part of transgene sequences (e.g. OTC, MUT1, etc.)

Formulations, Dosages and Modes of Administration

The present disclosure provides formulations, dosages and methods for administration of the compositions described herein.

The disclosed compositions and pharmaceutical compositions can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18th Edition, Mack Publishing Co. (Easton, Pa.) 1990 and in the "Physician's Desk Reference", 52nd ed., Medical Economics (Montvale, N.J.) 1998. Pharmaceutically acceptable carriers can be routinely selected that are suitable for the mode of administration, solubility and/or stability of the protein scaffold, fragment or variant composition as well known in the art or as described herein.

Non-limiting examples of pharmaceutical excipients and additives suitable for use include proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Non-limiting examples of protein excipients include serum albumin, such as human serum albumin (HSA), recombinant human albumin (rHA), gelatin, casein, and the like. Representative amino acid/protein components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Non-limiting examples of carbohydrate excipients suitable for use include monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferably, the carbohydrate excipients are mannitol, trehalose, and/or raffinose.

The compositions can also include a buffer or a pH-adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers are organic acid salts, such as citrate.

Additionally, the disclosed compositions can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

Many known and developed modes can be used for administering therapeutically effective amounts of the compositions or pharmaceutical compositions disclosed herein. Non-limiting examples of modes of administration include bolus, buccal, infusion, intrarticular, intrabronchial, intraabdominal, intracapsular, intracartilaginous, intracavitary, intracelial, intracerebellar, intracerebroventricular, intracolic, intracervical, intragastric, intrahepatic, intralesional, intramuscular, intramyocardial, intranasal, intraocular, intraosseous, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intratumoral, intravenous, intravesical, oral, parenteral, rectal, sublingual, subcutaneous, transdermal or vaginal means.

A composition of the disclosure can be prepared for use for parenteral (subcutaneous, intramuscular or intravenous)

or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994,), or with oxidizing agents that enable the application of formulations containing proteins and peptides onto the skin (WO 98/53847), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

For parenteral administration, any composition disclosed herein can be formulated as a solution, suspension, emulsion, particle, powder, or lyophilized powder in association, or separately provided, with a pharmaceutically acceptable parenteral vehicle. Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semisynthtetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446.

Formulations for oral administration rely on the co-administration of adjuvants (e.g., resorcinols and nonionic surfactants, such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Formulations for delivery of hydrophilic agents including proteins and protein scaffolds and a combination of at least two surfactants intended for oral, buccal, mucosal, nasal, pulmonary, vaginal transmembrane, or rectal administration are described in U.S. Pat. No. 6,309,663. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant, such as magnesium stearate, paraben, preserving agent, such as sorbic acid, ascorbic acid, .alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. Nos. 5,879,681 and 5,871,753 and used to deliver biologically active agents orally are known in the art.

For pulmonary administration, preferably, a composition or pharmaceutical composition described herein is delivered in a particle size effective for reaching the lower airways of the lung or sinuses. The composition or pharmaceutical composition can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers (e.g., jet nebulizer, ultrasonic nebulizer), dry powder generators, sprayers, and the like. All such devices can use formulations suitable for the administration for the dispensing of a composition or pharmaceutical composition described herein in an aerosol. Such aerosols can be comprised of either solutions (both aqueous and non-aqueous) or solid particles. Additionally, a spray including a composition or pharmaceutical composition described herein can be produced by forcing a suspension or solution of at least one protein scaffold through a nozzle under pressure. In a metered dose inhaler (MDI), a propellant, a composition or pharmaceutical composition described herein, and any excipients or other additives are contained in a canister as a mixture including a liquefied compressed gas. Actuation of the metering valve releases the mixture as an aerosol, preferably containing particles in the size range of less than about 10 μm, preferably, about 1 μm to about 5 μm, and, most preferably, about 2 μm to about 3 μm. A more detailed description of pulmonary administration, formulations and related devices is disclosed in PCT Publication No. WO 2019/049816.

For absorption through mucosal surfaces, compositions include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the disclosure can include corneal, conjunctival, buccal, sublingual, nasal, vaginal, pulmonary, stomachic, intestinal, and rectal routes of administration. Formulations for vaginal or rectal administration, e.g., suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration, excipients include sugars, calcium stearate, magnesium stearate, pregelinatined starch, and the like (U.S. Pat. No. 5,849,695). A more detailed description of mucosal administration and formulations is disclosed in PCT Publication No. WO 2019/049816.

For transdermal administration, a composition or pharmaceutical composition disclosed herein is encapsulated in a delivery device, such as a liposome or polymeric nanoparticles, microparticle, microcapsule, or microspheres (referred to collectively as microparticles unless otherwise stated). A number of suitable devices are known, including microparticles made of synthetic polymers, such as polyhydroxy acids, such as polylactic acid, polyglycolic acid and copolymers thereof, polyorthoesters, polyanhydrides, and polyphosphazenes, and natural polymers, such as collagen, polyamino acids, albumin and other proteins, alginate and other polysaccharides, and combinations thereof (U.S. Pat. No. 5,814,599). A more detailed description of transdermal administration, formulations and suitable devices is disclosed in PCT Publication No. WO 2019/049816.

It can be desirable to deliver the disclosed compounds to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid, such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation, such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b), e.g., a zinc tannate salt. Additionally, the disclosed compounds or, preferably, a relatively insoluble salt, such as those just described, can be formulated in a gel, for example, an aluminum monostearate gel with, e.g., sesame oil, suitable for injection. Particularly preferred salts are zinc salts, zinc tannate salts, pamoate salts, and the like. Another type of slow release depot formulation for injection would contain the compound or salt dispersed for encapsulation in a slow degrading, non-toxic, non-antigenic polymer, such as a polylactic acid/polyglycolic acid polymer for example as described in U.S. Pat. No. 3,773,919. The compounds or, preferably, relatively insoluble salts, such as those described above, can also be formulated in cholesterol matrix silastic pellets, particularly for use in animals. Additional slow release, depot or implant formulations, e.g., gas or liquid liposomes, are known in the literature (U.S. Pat. No. 5,770,222 and "Sustained and Controlled Release Drug Delivery Systems", J. R. Robinson ed., Marcel Dekker, Inc., N.Y., 1978).

Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000); Nursing 2001 Handbook of Drugs, 21st edition, Springhouse Corp., Springhouse, Pa., 2001; Health Professional's Drug Guide 2001, ed., Shannon, Wilson, Stang, Prentice-Hall, Inc, Upper Saddle River, N.J. Preferred doses can optionally include about 0.1-99 and/or 100-500 mg/kg/administration, or any range, value or fraction thereof, or to achieve a serum concentration of about 0.1-5000 μg/ml serum concentration per single or multiple administration, or any range, value or fraction thereof. A preferred dosage range for the compositions or pharmaceutical compositions disclosed herein is from about 1 mg/kg, up to about 3, about 6 or about 12 mg/kg of body weight of the subject.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably, 0.1 to 10 milligrams per kilogram per administration or in sustained release form is effective to obtain desired results.

As a non-limiting example, treatment of humans or animals can be provided as a one-time or periodic dosage of the compositions or pharmaceutical compositions disclosed herein about 0.1 to 100 mg/kg or any range, value or fraction thereof per day, on at least one of day 1-40, or, alternatively or additionally, at least one of week 1-52, or, alternatively or additionally, at least one of 1-20 years, or any combination thereof, using single, infusion or repeated doses.

Dosage forms suitable for internal administration generally contain from about 0.001 milligram to about 500 milligrams of active ingredient per unit or container. In these pharmaceutical compositions the active ingredient will ordinarily be present in an amount of about 0.5-99.999% by weight based on the total weight of the composition.

An effective amount can comprise an amount of about 0.001 to about 500 mg/kg per single (e.g., bolus), multiple or continuous administration, or to achieve a serum concentration of 0.01-5000 μg/ml serum concentration per single, multiple, or continuous administration, or any effective range or value therein, as done and determined using known methods, as described herein or known in the relevant arts.

In aspects where the compositions to be administered to a subject in need thereof are modified cells as disclosed herein, the cells can be administered between about $1\times10^3$ and $1\times10^{15}$ cells; about $1\times10^4$ and $1\times10^{12}$ cells; about $1\times10^5$ and $1\times10^{10}$ cells; about $1\times10^6$ and $1\times10^9$ cells; about $1\times10^6$ and $1\times10^8$ cells; about $1\times10^6$ and $1\times10^7$ cells; or about $1\times10^6$ and $25\times10^6$ cells. In one aspect the cells are administered between about $5\times10^6$ and $25\times10^6$ cells.

A more detailed description of pharmaceutically acceptable excipients, formulations, dosages and methods of administration of the disclosed compositions and pharmaceutical compositions is disclosed in PCT Publication No. WO 2019/049816.

Methods of Using the Compositions of the Disclosure

The present disclosure provides the use of a disclosed composition or pharmaceutical composition for the treatment of a disease or disorder in a cell, tissue, organ, animal, or subject, as known in the art or as described herein, using the disclosed compositions and pharmaceutical compositions, e.g., administering or contacting the cell, tissue, organ, animal, or subject with a therapeutic effective amount of the composition or pharmaceutical composition. In one aspect, the subject is a mammal. Preferably, the subject is human. The terms "subject" and "patient" are used interchangeably herein.

The disclosure provides a method for treating at least one metabolic liver disorder (MLD) in a subject in need thereof comprising administering to the subject at least one therapeutically effective amount of at least one composition of the present disclosure.

The present disclosure provides at least one composition of the present disclosure for the use in the treatment of at least one metabolic liver disorder in a subject, wherein the at least one composition is for administration to the subject in at least one therapeutically effective amount.

The present disclosure provides the use of at least one composition of the present disclosure for the manufacture of a medicament for the treatment of at least one metabolic liver disorder in a subject, wherein the at least one composition is for administration to the subject in at least one therapeutically effective amount.

In some aspects of the preceding methods and uses, the at least one composition of the present disclosure can comprise at least one AAV piggyBac transposon vector of the present disclosure.

Accordingly, the disclosure provides a method for treating at least one metabolic liver disorder in a subject in need thereof comprising administering to the subject at least one therapeutically effective amount of at least one AAV piggyBac transposon vector of the present disclosure.

The present disclosure provides at least one AAV piggyBac transposon vector of the present disclosure for the use in the treatment of at least one metabolic liver disorder in a subject, wherein the at least one AAV piggyBac transposon vector is for administration to the subject in at least one therapeutically effective amount.

The present disclosure provides the use of at least one AAV piggyBac transposon vector of the present disclosure for the manufacture of a medicament for the treatment of at least one metabolic liver disorder in a subject, wherein the at least one AAV piggyBac transposon vector is for administration to the subject in at least one therapeutically effective amount.

In some aspects of the preceding methods and uses, the at least one composition of the present disclosure can comprise at least one AAV transposase vector of the present disclosure.

Accordingly, the disclosure provides a method for treating at least one metabolic liver disorder in a subject in need thereof comprising administering to the subject at least one therapeutically effective amount of at least one AAV transposase vector of the present disclosure.

The present disclosure provides at least one AAV transposase vector of the present disclosure for the use in the treatment of at least one metabolic liver disorder in a subject, wherein the at least one AAV transposase vector is for administration to the subject in at least one therapeutically effective amount.

The present disclosure provides the use of at least one AAV transposase vector of the present disclosure for the manufacture of a medicament for the treatment of at least one metabolic liver disorder in a subject, wherein the at least one AAV transposase vector is for administration to the subject in at least one therapeutically effective amount.

The present disclosure provides methods of treating at least one metabolic liver disorder in a subject, the methods comprising administering to the subject: a) at least one therapeutically effective amount of a composition comprising a nucleic acid molecule comprising a transposon, wherein the transposon comprises a nucleotide sequence encoding at least one therapeutic protein; and b) at least one therapeutically effective amount of a composition comprising a nucleic acid molecule comprising a nucleotide sequence encoding at least one transposase.

In some aspects of the preceding method, a composition comprising a nucleic acid molecule comprising a transposon can be any AAV piggyBac transposon vector described herein.

In some aspects of the preceding method, a composition comprising a nucleic acid molecule comprising a nucleotide sequence encoding at least one transposase can be any AAV transposase vector of the present disclosure.

Accordingly, the present disclosure provides methods of treating at least one metabolic liver disorder in a subject, the methods comprising administering to the subject: a) at least one therapeutically effective amount of at least one AAV piggyBac transposon vector of the present disclosure; and b) at least one therapeutically effective amount of at least one AAV transposase vector of the present disclosure.

Accordingly the present disclosure provides a combination of at least one AAV piggyBac transposon vector of the present disclosure and at least one AAV transposase vector of the present disclosure for use in in the treatment of at least one metabolic liver disorder in a subject, wherein the at least one AAV piggyBac transposon vector is for administration to the subject in at least one therapeutically effective amount, and wherein the at least one AAV transposase vector is for administration to the subject in at least one therapeutically effective amount.

Accordingly the present disclosure provides the use of a combination of at least one AAV piggyBac transposon vector of the present disclosure and at least one AAV transposase vector of the present disclosure in the manufacture of a medicament for the treatment of at least one metabolic liver disorder in a subject, wherein the at least one AAV piggyBac transposon vector is for administration to the subject in at least one therapeutically effective amount, and wherein the at least one AAV transposase vector is for administration to the subject in at least one therapeutically effective amount.

Metabolic liver disorders can include, but are not limited to, urea cycle disorders, N-Acetylglutamate Synthetase (NAGS) Deficiency, Carbamoylphosphate Synthetase I Deficiency (CPSI Deficiency), Ornithine Transcarbamylase (OTC) Deficiency, Argininosuccinate Synthetase Deficiency (ASSD) (Citrullinemia I), Citrin Deficiency (Citrullinemia II), Argininosuccinate Lyase Deficiency (Argininosuccinic Aciduria), Arginase Deficiency (Hyperargininemia), Ornithine Translocase Deficiency (HHH Syndrome) methylmalonic acidemia (MMA), progressive familial intrahepatic cholestasis type 1 (PFIC1), progressive familial intrahepatic cholestasis type 1 (PFIC2), progressive familial intrahepatic cholestasis type 1 (PFIC3) or any combination thereof. In some aspects, the metabolic liver disorder is Ornithine Transcarbamylase (OTC) Deficiency.

In some aspects of the preceding methods, a composition comprising a nucleic acid molecule comprising a transposon, wherein the transposon comprises a nucleotide sequence encoding at least one therapeutic protein and a composition comprising a nucleic acid molecule comprising a nucleotide sequence encoding at least one transposase can be administered concurrently. In some aspects, a composition comprising a nucleic acid molecule comprising a transposon, wherein the transposon comprises a nucleotide sequence encoding at least one therapeutic protein and a composition comprising a nucleic acid molecule comprising a nucleotide sequence encoding at least one transposase can be administered sequentially. In some aspects, a composition comprising a nucleic acid molecule comprising a transposon, wherein the transposon comprises a nucleotide sequence encoding at least one therapeutic protein and a composition comprising a nucleic acid molecule comprising a nucleotide sequence encoding at least one transposase can be administered in temporal proximity.

As used herein, the term "temporal proximity" refers to that administration of one therapeutic composition (e.g., a composition comprising a transposon) occurs within a time period before or after the administration of another therapeutic composition (e.g., a composition comprising a transposase), such that the therapeutic effect of the one therapeutic agent overlaps with the therapeutic effect of the other therapeutic agent. In some embodiments, the therapeutic effect of the one therapeutic agent completely overlaps with the therapeutic effect of the other therapeutic agent. In some embodiments, "temporal proximity" means that administration of one therapeutic agent occurs within a time period before or after the administration of another therapeutic agent, such that there is a synergistic effect between the one therapeutic agent and the other therapeutic agent. "Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

In some aspects of the treatment methods of the present disclosure, the administration of the at least one composition and/or vector of the present disclosure to a subject can result in the expression of an exogenous protein (e.g. a therapeutic protein, a transposase, etc.) in at least one organ and/or tissue in the subject.

In some aspects, the administration of the at least one composition and/or vector of the present disclosure results in the expression of the exogenous protein in at least about 10%, or at least about 15%, or at least bout 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 99% of the cells in the tissue and/or organ.

In some aspects, the administration of the at least one composition and/or vector of the present disclosure results in the expression of the exogenous protein in at least about 10%, or at least about 15%, or at least bout 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 99% of a specific subset or subsets of cells in the tissue and/or organ.

In some aspects, the administration of the at least one composition and/or vector of the present disclosure results in the expression of the exogenous protein for at least about 1 day, or at least about 2 days, or at least about 3 days, or at least about 4 days, or at least about 5 days, or at least about 6 days, or at least about 7 days, or at least about 8 days, or at least about 9 days, or at least about 10 days in the tissue and/or organ.

In some aspects, the administration of the at least one composition and/or vector of the present disclosure results in the expression of the exogenous protein for at least about 1 day, or at least about 2 days, or at least about 3 days, or at least about 4 days, or at least about 5 days, or at least about 6 days, or at least about 7 days, or at least about 8 days, or at least about 9 days, or at least about 10 days in a specific subset or subsets of cells in the tissue and/or organ.

In some aspects, the administration of the at least one composition and/or vector of the present disclosure results in the expression of the exogenous protein for no more than about 1 day, or no more than about 2 days, or no more than about 3 days, or no more than about 4 days, or no more than about 5 days, or no more than about 6 days, or no more than about 7 days, or no more than about 8 days, or no more than about 9 days, or no more than about 10 days in the tissue and/or organ.

In some aspects, the administration of the at least one composition and/or vector of the present disclosure results in the expression of the exogenous protein for no more than about 1 day, or no more than about 2 days, or no more than about 3 days, or no more than about 4 days, or no more than about 5 days, or no more than about 6 days, or no more than about 7 days, or no more than about 8 days, or no more than about 9 days, or no more than about 10 days in a specific subset or subsets of cells in the tissue and/or organ.

In some aspects, the tissue and/or organ can be the liver. In some aspects, the specific subset or subsets of cells can include, but are not limited to, hepatocytes, a hepatic stellate cells, Kupffer cells, liver sinusoidal endothelial cells or any combination thereof.

Any method of the present disclosure can comprise administering an effective amount of any composition or pharmaceutical composition disclosed herein to a cell, tissue, organ, animal or subject in need of such modulation, treatment or therapy. Such a method can optionally further comprise co-administration or combination therapy for treating such diseases or disorders, wherein the administering of any composition or pharmaceutical composition disclosed herein, further comprises administering, before concurrently, and/or after, at least one additional treatment for urea cycle disorders.

Additional treatments for urea cycle disorders can include, but are not limited to dialysis, hemofiltration, caloric supplementation, hormonal suppression, glucose drip, insulin drip, pharmacologic scavenging of excess nitrogen, administration of dextrose, administration of fluids, administration of Intralipid®, administration of ammonia scavengers, administration of arginine, administration of sodium phenylacetate, administration of sodium benzoate, administration of Ammonul, administration of phenylbutyrate, citrulline supplementation, arginine supplementation, or any combination thereof.

Exemplary Embodiments of the Present Disclosure

Embodiment 1. An adeno-associated virus (AAV) piggyBac transposon polynucleotide comprising in the 5' to 3' direction:

a) a first AAV inverted terminal repeat (ITR) sequence;
b) a first piggyBac ITR sequence;
c) a first insulator sequence;
d) at least one promoter sequence;
e) at least one transgene sequence;

f) a polyA sequence;
g) a second insulator sequence;
h) a second piggyBac ITR sequence; and
i) a second AAV ITR sequence.

Embodiment 2. The AAV piggyBac transposon polynucleotide of embodiment 1, wherein the AAV piggyBac transposon polynucleotide comprises DNA, cDNA, gDNA, RNA, mRNA or any combination thereof.

Embodiment 3. The AAV piggyBac transposon polynucleotide of any of the preceding embodiments, wherein the first and/or the second AAV ITR sequence comprises the nucleic acid sequence of any one of SEQ ID NOs: 1-4, 93-94, 105-106 and 127.

Embodiment 4. The AAV piggyBac transposon polynucleotide of any of the preceding embodiments, wherein the first AAV ITR sequence comprises the nucleic acid sequence of SEQ ID NO: 3 and the second AAV ITR sequence comprises the nucleic acid sequence of SEQ ID NO: 4.

Embodiment 5. The AAV piggyBac transposon polynucleotide of any of the preceding embodiments, wherein the first piggyBac ITR sequence and/or the second piggyBac ITR sequence comprises the nucleic acid sequence of any one of SEQ ID NOs: 5-6, 86-90, 95-96 and 125.

Embodiment 6. The AAV piggyBac transposon polynucleotide of any of the preceding embodiments, wherein the first piggyBac ITR sequence comprises the nucleic acid sequence of SEQ ID NO: 5 and the second piggyBac ITR comprises the nucleic acid sequence of SEQ ID NO: 6.

Embodiment 7. The AAV piggyBac transposon polynucleotide of any of the preceding embodiments, wherein the first insulator sequence and/or the second insulator sequence comprises the nucleic acid sequence of any one of SEQ ID NOs: 7-8, 77-80 and 91-92.

Embodiment 8. The AAV piggyBac transposon polynucleotide of any of the preceding embodiments, wherein the first insulator sequence comprises the nucleic acid sequence of SEQ ID NO: 7 and the second insulator sequence comprises the nucleic acid sequence of SEQ ID NO: 8.

Embodiment 9. The AAV piggyBac transposon polynucleotide of any of the preceding embodiments, wherein the at least one promoter sequence is a liver-specific promoter.

Embodiment 10. The AAV piggyBac transposon polynucleotide of any of the preceding embodiments, wherein the liver-specific promoter is a hybrid liver promoter (HLP), an LP1 promoter, a leukocyte-specific expression of the pp52 (LSP1) long promoter, a thyroxine binding globulin (TBG) promoter, a wTBG promoter, a hepatic combinatorial bundle (HCB) promoter, a 2×ApoE-hAAT promoter or a leukocyte-specific expression of the pp52 (LSP1) plus chimeric intron promoter.

Embodiment 11. The AAV piggyBac transposon polynucleotide of any of the preceding embodiments, wherein the at least one promoter sequence comprises the nucleic acid sequence of any of SEQ IDS NOs: 9-16, 69, 107, 126 and 132.

Embodiment 12. The AAV piggyBac transposon polynucleotide of any of the preceding embodiments, wherein the at least one transgene sequence comprises a nucleic acid sequence encoding a methylmalonyl-CoA mutase (MUT1) polypeptide.

Embodiment 13. The AAV piggyBac transposon polynucleotide of any of the preceding embodiments, wherein the MUT1 polypeptide comprises the amino acid sequence of SEQ ID NO: 17, 18, 121 or 122.

Embodiment 14. The AAV piggyBac transposon polynucleotide of any of the preceding embodiments, wherein the nucleic acid sequence encoding a MUT1 polypeptide comprises the nucleic acid sequence of SEQ ID NO: 19, 20 or 111-120.

Embodiment 15. The AAV piggyBac transposon polynucleotide of any of the preceding embodiments, wherein the at least one transgene sequence comprises a nucleic acid sequence encoding an ornithine transcarbamylase (OTC) polypeptide.

Embodiment 16. The AAV piggyBac transposon polynucleotide of any of the preceding embodiments, wherein the OTC polypeptide comprises the amino acid sequence of SEQ ID NO: 21 or 81.

Embodiment 17. The AAV piggyBac transposon polynucleotide of any of the preceding embodiments, wherein the nucleic acid sequence encoding an OTC polypeptide comprises the nucleic acid sequence of any of SEQ ID NOs: 22, 23, 82 and 83.

Embodiment 18. The AAV piggyBac transposon polynucleotide of any of the preceding embodiments, wherein the at least one transgene sequence comprises a nucleic acid sequence encoding an iCas9 polypeptide.

Embodiment 19. The AAV piggyBac transposon polynucleotide of any of the preceding embodiments, wherein the iCas9 polypeptide comprises the amino acid sequence of SEQ ID NO: 24 or 84.

Embodiment 20. The AAV piggyBac transposon polynucleotide of any of the preceding embodiments, wherein the nucleic acid sequence encoding an iCas9 polypeptide comprises the nucleic acid sequence of SEQ ID NO: 25 or 85.

Embodiment 21. The AAV piggyBac transposon polynucleotide of any of the preceding embodiments, wherein the at least one transgene sequence is operatively linked to the at least one promoter sequence.

Embodiment 22. The AAV piggyBac transposon polynucleotide of any of the preceding embodiments, wherein the expression of the at least one transgene sequence is controlled by the at least one promoter sequence.

Embodiment 23. The AAV piggyBac transposon polynucleotide of any of the preceding embodiments, wherein the polyA sequence comprises the nucleic acid sequence of any one of SEQ ID NO: 26-27, 97, 108, 128 and 136.

Embodiment 24. The AAV piggyBac transposon polynucleotide of any of the preceding embodiments, wherein the AAV piggyBac transposon polynucleotide further comprises at least a second transgene sequence.

Embodiment 25. The AAV piggyBac transposon polynucleotide of any of the preceding embodiments, wherein the at least second transgene sequence comprises a nucleic acid sequence encoding an iCas9 polypeptide.

Embodiment 26. The AAV piggyBac transposon polynucleotide of any of the preceding embodiments, wherein the iCas9 polypeptide comprises the amino acid sequence of SEQ ID NO: 24 or 84.

Embodiment 27. The AAV piggyBac transposon polynucleotide of any of the preceding embodiments, wherein the nucleic acid sequence encoding an iCas9 polypeptide comprises the nucleic acid sequence of SEQ ID NO: 25 or 85.

Embodiment 28. The AAV piggyBac transposon polynucleotide of any of the preceding embodiments, wherein the at least second transgene sequence comprises a nucleic acid sequence encoding a methylmalonyl-CoA mutase (MUT1) polypeptide.

Embodiment 29. The AAV piggyBac transposon polynucleotide of any of the preceding embodiments, wherein the MUT1 polypeptide comprises the amino acid sequence of SEQ ID NO: 17, 18, 121 or 122.

Embodiment 30. The AAV piggyBac transposon polynucleotide of any of the preceding embodiments, wherein the nucleic acid sequence encoding a MUT1 polypeptide comprises the nucleic acid sequence of SEQ ID NO: 19, 20 or 111-120.

Embodiment 31. The AAV piggyBac transposon polynucleotide of any of the preceding embodiments, wherein the at least second transgene sequence comprises a nucleic acid sequence encoding an ornithine transcarbamylase (OTC) polypeptide.

Embodiment 32. The AAV piggyBac transposon polynucleotide of any of the preceding embodiments, wherein the OTC polypeptide comprises the amino acid sequence of SEQ ID NO: 21 or 81.

Embodiment 33. The AAV piggyBac transposon polynucleotide of any of the preceding embodiments, wherein the nucleic acid sequence encoding an OTC polypeptide comprises the nucleic acid sequence of any of SEQ ID NOs: 22, 23, 82 and 83.

Embodiment 34. The AAV piggyBac transposon polynucleotide of any of the preceding embodiments, wherein the AAV piggyBac transposon polynucleotide further comprises at least a second promoter sequence.

Embodiment 35. The AAV piggyBac transposon polynucleotide of any of the preceding embodiments, wherein the at least second promoter sequence is located between the at least one transgene sequence and the at least second transgene sequence.

Embodiment 36. The AAV piggyBac transposon polynucleotide of any of the preceding embodiments, wherein the AAV piggyBac transposon polynucleotide further comprises at least one self-cleaving peptide sequence, wherein the at least one self-cleaving peptide sequence is a nucleic acid sequence encoding for a T2A peptide, GSG-T2A peptide, an E2A peptide, a GSG-E2A peptide, an F2A peptide, a GSG-F2A peptide, a P2A peptide, or a GSG-P2A peptide.

Embodiment 37. The AAV piggyBac transposon polynucleotide of any of the preceding embodiments, wherein the at least one self-cleaving peptide sequence is located between the at least one transgene sequence and the at least second transgene sequence.

Embodiment 38. The AAV piggyBac transposon polynucleotide of any of the preceding embodiments, wherein the AAV piggyBac transposon polynucleotide comprises at least two transgene sequences.

Embodiment 39. The AAV piggyBac transposon polynucleotide of any of the preceding embodiments, wherein the at least two transgene sequences are the same sequence.

Embodiment 40. The AAV piggyBac transposon polynucleotide of any of the preceding embodiments, wherein the at least two transgene sequences are different sequences.

Embodiment 41. The AAV piggyBac transposon polynucleotide of any of the preceding embodiments, further comprising at least one DNA spacer sequence.

Embodiment 42. The AAV piggyBac transposon polynucleotide of any of the preceding embodiments, wherein the at least one DNA spacer sequence comprises the nucleic acid sequence of any one of SEQ ID NO: 103, 109, 129-131 and 137.

Embodiment 43. The AAV piggyBac transposon polynucleotide of any of the preceding embodiments, wherein the AAV piggyBac transposon polynucleotide comprises at least two promoter sequences.

Embodiment 44. The AAV piggyBac transposon polynucleotide of any of the preceding embodiments, wherein the at least two promoter sequences are the same sequence.

Embodiment 45. The AAV piggyBac transposon polynucleotide of any of the preceding embodiments, wherein the at least two promoter sequences are different sequences.

Embodiment 46A. An AAV piggyBac transposon polynucleotide comprising in the 5' to 3' direction:

a) a first AAV ITR sequence;
b) a first piggyBac ITR sequence;
c) a first insulator sequence;
d) at least one promoter sequence;
e) at least one transgene sequence;
f) a polyA sequence;
g) a second insulator sequence;
h) a second piggyBac ITR sequence;
i) at least one DNA spacer sequence; and
j) a second AAV ITR sequence.

Embodiment 46B. The AAV piggyBac transposon polynucleotide of any of the preceding embodiments, wherein the first AAV ITR sequence comprises the nucleic acid sequence of SEQ ID NO: 3.

Embodiment 46C. The AAV piggyBac transposon polynucleotide of any of the preceding embodiments, wherein the first piggyBac ITR sequence comprises the nucleic acid sequence of SEQ ID NO: 95.

Embodiment 46D. The AAV piggyBac transposon polynucleotide of any of the preceding embodiments, wherein the first piggyBac ITR sequence comprises the nucleic acid sequence of SEQ ID NO: 125.

Embodiment 46E. The AAV piggyBac transposon polynucleotide of any of the preceding embodiments, wherein the first insulator sequence comprises the nucleic acid sequence of SEQ ID NO: 7.

Embodiment 46F. The AAV piggyBac transposon polynucleotide of any of the preceding embodiments, wherein the at least one promoter sequence comprises the nucleic acid sequence of SEQ ID NO: 9.

Embodiment 46G. The AAV piggyBac transposon polynucleotide of any of the preceding embodiments, wherein the at least one promoter sequence comprises the nucleic acid sequence of SEQ ID NO: 126.

Embodiment 46H. The AAV piggyBac transposon polynucleotide of any of the preceding embodiments, wherein the at least one transgene sequence comprises the nucleic acid sequence of SEQ ID NO: 22.

Embodiment 461. The AAV piggyBac transposon polynucleotide of any of the preceding embodiments, wherein the polyA sequence comprises the nucleic acid sequence of SEQ ID NO: 97.

Embodiment 46J. The AAV piggyBac transposon polynucleotide of any of the preceding embodiments, wherein the second insulator sequence comprises the nucleic acid sequence of SEQ ID NO: 8.

Embodiment 46K. The AAV piggyBac transposon polynucleotide of any of the preceding embodiments, wherein the a second piggyBac ITR sequence comprises the nucleic acid sequence of SEQ ID NO: 96.

Embodiment 46L. The AAV piggyBac transposon polynucleotide of any of the preceding embodiments, wherein the least one DNA spacer sequence comprises the nucleic acid sequence of SEQ ID NO: 129.

Embodiment 46M. The AAV piggyBac transposon polynucleotide of any of the preceding embodiments, wherein the second AAV ITR sequence comprises the nucleic acid sequence of SEQ ID NO: 4.

Embodiment 46N. An AAV piggyBac transposon polynucleotide comprising in the 5' to 3' direction:

a) a first AAV ITR sequence comprising the nucleic acid sequence of SEQ ID NO: 3;
b) a first piggyBac ITR sequence comprising the nucleic acid sequence of SEQ ID NO: 95 or SEQ ID NO: 125;
c) a first insulator sequence comprising the nucleic acid sequence of SEQ ID NO: 7;
d) at least one promoter sequence comprising the nucleic acid sequence of SEQ ID NO: 9 or SEQ ID NO: 126;
e) at least one transgene sequence comprising the nucleic acid sequence of SEQ ID NO: 22;
f) a polyA sequence comprising the nucleic acid sequence of SEQ ID NO: 97;
g) a second insulator sequence comprising the nucleic acid sequence of SEQ ID NO: 8;
h) a second piggyBac ITR sequence comprising the nucleic acid sequence of SEQ ID NO: 96;
i) at least one DNA spacer sequence comprising the nucleic acid sequence of SEQ ID NO: 129; and
j) a second AAV ITR sequence comprising the nucleic acid sequence of SEQ ID NO: 4.

Embodiment 47. The AAV piggyBac transposon polynucleotide of any one of Embodiments 46A-46N, wherein the at least one promoter sequence comprises the nucleic acid sequence of SEQ ID NO: 9.

Embodiment 48. The AAV piggyBac transposon polynucleotide of any one of Embodiments 46A-46N, wherein the at least one promoter sequence comprises the nucleic acid sequence of SEQ ID NO: 126.

Embodiment 49. The AAG piggyBac transposon polynucleotide of any one of Embodiments 46A-46N, wherein the first piggyBac ITR sequence comprises the nucleic acid sequence of SEQ ID NO: 95.

Embodiment 50. The AAG piggyBac transposon polynucleotide of any one of Embodiments 46A-46N, wherein the first piggyBac ITR sequence comprises the nucleic acid sequence of SEQ ID NO: 125.

Embodiment 51. The AAV piggyBac transposon polynucleotide of any one of Embodiments 46A-50, wherein the AAV piggyBac transposon polynucleotide comprises the nucleic acid sequence of SEQ ID NO: 138.

Embodiment 52A. An AAV piggyBac transposon polynucleotide comprising in the 5' to 3' direction:

a) a first AAV ITR sequence;
b) a first piggyBac ITR sequence;
c) a first insulator sequence;
d) at least one promoter sequence;
e) at least one transgene sequence;
f) a polyA sequence;
g) a second insulator sequence;
h) a second piggyBac ITR sequence;
i) at least one DNA spacer sequence; and
j) a second AAV ITR sequence.

Embodiment 52B. The AAV piggyBac transposon polynucleotide of any of the preceding embodiments, wherein the first AAV ITR sequence comprises the nucleic acid sequence of SEQ ID NO: 3.

Embodiment 52C. The AAV piggyBac transposon polynucleotide of any of the preceding embodiments, wherein the first piggyBac ITR sequence comprises the nucleic acid sequence of SEQ ID NO: 95.

Embodiment 52D. The AAV piggyBac transposon polynucleotide of any of the preceding embodiments, wherein the first piggyBac ITR sequence comprises the nucleic acid sequence of SEQ ID NO: 125.

Embodiment 52E. The AAV piggyBac transposon polynucleotide of any of the preceding embodiments, wherein the first insulator sequence comprises the nucleic acid sequence of SEQ ID NO: 7.

Embodiment 52F. The AAV piggyBac transposon polynucleotide of any of the preceding embodiments, wherein the at least one promoter sequence comprises the nucleic acid sequence of SEQ ID NO: 10.

Embodiment 52G. The AAV piggyBac transposon polynucleotide of any of the preceding embodiments, wherein the at least one promoter sequence comprises the nucleic acid sequence of SEQ ID NO: 132.

Embodiment 52H. The AAV piggyBac transposon polynucleotide of any of the preceding embodiments, wherein the at least one transgene sequence comprises the nucleic acid sequence of SEQ ID NO: 22.

Embodiment 521. The AAV piggyBac transposon polynucleotide of any of the preceding embodiments, wherein the polyA sequence comprises the nucleic acid sequence of SEQ ID NO: 97.

Embodiment 52J. The AAV piggyBac transposon polynucleotide of any of the preceding embodiments, wherein the second insulator sequence comprises the nucleic acid sequence of SEQ ID NO: 8.

Embodiment 52K. The AAV piggyBac transposon polynucleotide of any of the preceding embodiments, wherein the a second piggyBac ITR sequence comprises the nucleic acid sequence of SEQ ID NO: 96.

Embodiment 52L. The AAV piggyBac transposon polynucleotide of any of the preceding embodiments, wherein the least one DNA spacer sequence comprises the nucleic acid sequence of SEQ ID NO: 130.

Embodiment 52M. The AAV piggyBac transposon polynucleotide of any of the preceding embodiments, wherein the second AAV ITR sequence comprises the nucleic acid sequence of SEQ ID NO: 4.

Embodiment 52N. AAV piggyBac transposon polynucleotide comprising in the 5' to 3' direction:

a) a first AAV ITR sequence comprising the nucleic acid sequence of SEQ ID NO: 3;
b) a first piggyBac ITR sequence comprising the nucleic acid sequence of SEQ ID NO: 95 or SEQ ID NO: 125;
c) a first insulator sequence comprising the nucleic acid sequence of SEQ ID NO: 7;
d) at least one promoter sequence comprising the nucleic acid sequence of SEQ ID NO: 10 or SEQ ID NO: 132;
e) at least one transgene sequence comprising the nucleic acid sequence of SEQ ID NO: 22;
f) a polyA sequence comprising the nucleic acid sequence of SEQ ID NO: 97;
g) a second insulator sequence comprising the nucleic acid sequence of SEQ ID NO: 8;
h) a second piggyBac ITR sequence comprising the nucleic acid sequence of SEQ ID NO: 96;
i) at least one DNA spacer sequence comprising the nucleic acid sequence of SEQ ID NO: 130; and
j) a second AAV ITR sequence comprising the nucleic acid sequence of SEQ ID NO: 4.

Embodiment 53. The AAV piggyBac transposon polynucleotide of any one of Embodiments 52A-52N, wherein the at least one promoter sequence comprises the nucleic acid sequence of SEQ ID NO: 10.

Embodiment 54. The AAV piggyBac transposon polynucleotide of any one of Embodiments 52A-52N, wherein the at least one promoter sequence comprises the nucleic acid sequence of SEQ ID NO: 132.

Embodiment 55. The AAG piggyBac transposon polynucleotide of any one of Embodiments 52A-52N, wherein the first piggyBac ITR sequence comprises the nucleic acid sequence of SEQ ID NO: 95.

Embodiment 56. The AAG piggyBac transposon polynucleotide of any one of Embodiments 52A-52N, wherein the first piggyBac ITR sequence comprises the nucleic acid sequence of SEQ ID NO: 125.

Embodiment 57. The AAV piggyBac transposon polynucleotide of any one of Embodiments 52A-56, wherein the AAV piggyBac transposon polynucleotide comprises the nucleic acid sequence of SEQ ID NO: 139.

Embodiment 58A. An AAV piggyBac transposon polynucleotide comprising in the 5' to 3' direction:

a) a first AAV ITR sequence;
b) a first piggyBac ITR sequence;
c) a first insulator sequence;
d) at least one promoter sequence;
e) at least one transgene sequence;
f) a polyA sequence;
g) a second insulator sequence;
h) a second piggyBac ITR sequence;
i) at least one DNA spacer sequence; and
j) a second AAV ITR sequence.

Embodiment 58B. The AAV piggyBac transposon polynucleotide of any of the preceding embodiments, wherein the first AAV ITR sequence comprises the nucleic acid sequence of SEQ ID NO: 3.

Embodiment 58C. The AAV piggyBac transposon polynucleotide of any of the preceding embodiments, wherein the first piggyBac ITR sequence comprises the nucleic acid sequence of SEQ ID NO: 95.

Embodiment 58D. The AAV piggyBac transposon polynucleotide of any of the preceding embodiments, wherein the first piggyBac ITR sequence comprises the nucleic acid sequence of SEQ ID NO: 125.

Embodiment 58E. The AAV piggyBac transposon polynucleotide of any of the preceding embodiments, wherein the first insulator sequence comprises the nucleic acid sequence of SEQ ID NO: 7.

Embodiment 58F. The AAV piggyBac transposon polynucleotide of any of the preceding embodiments, wherein the at least one promoter sequence comprises the nucleic acid sequence of SEQ ID NO: 13.

Embodiment 58G. The AAV piggyBac transposon polynucleotide of any of the preceding embodiments, wherein the at least one transgene sequence comprises the nucleic acid sequence of SEQ ID NO: 22.

Embodiment 58H. The AAV piggyBac transposon polynucleotide of any of the preceding embodiments, wherein the polyA sequence comprises the nucleic acid sequence of SEQ ID NO: 97.

Embodiment 581. The AAV piggyBac transposon polynucleotide of any of the preceding embodiments, wherein the second insulator sequence comprises the nucleic acid sequence of SEQ ID NO: 8.

Embodiment 58J. The AAV piggyBac transposon polynucleotide of any of the preceding embodiments, wherein the a second piggyBac ITR sequence comprises the nucleic acid sequence of SEQ ID NO: 96.

Embodiment 58K. The AAV piggyBac transposon polynucleotide of any of the preceding embodiments, wherein the least one DNA spacer sequence comprises the nucleic acid sequence of SEQ ID NO: 131.

Embodiment 58L. The AAV piggyBac transposon polynucleotide of any of the preceding embodiments, wherein the second AAV ITR sequence comprises the nucleic acid sequence of SEQ ID NO: 4.

Embodiment 58M. AAV piggyBac transposon polynucleotide comprising in the 5' to 3' direction:

a) a first AAV ITR sequence comprising the nucleic acid sequence of SEQ ID NO: 3;
b) a first piggyBac ITR sequence comprising the nucleic acid sequence of SEQ ID NO: 95 or SEQ ID NO: 125;
c) a first insulator sequence comprising the nucleic acid sequence of SEQ ID NO: 7;
d) at least one promoter sequence comprising the nucleic acid sequence of SEQ ID NO: 13;
e) at least one transgene sequence comprising the nucleic acid sequence of SEQ ID NO: 22;
f) a polyA sequence comprising the nucleic acid sequence of SEQ ID NO: 97;
g) a second insulator sequence comprising the nucleic acid sequence of SEQ ID NO: 8;
h) a second piggyBac ITR sequence comprising the nucleic acid sequence of SEQ ID NO: 96;
i) at least one DNA spacer sequence comprising the nucleic acid sequence of SEQ ID NO: 131; and
j) a second AAV ITR sequence comprising the nucleic acid sequence of SEQ ID NO: 4.

Embodiment 59. The AAG piggyBac transposon polynucleotide of any one of Embodiments 58A-58M, wherein the first piggyBac ITR sequence comprises the nucleic acid sequence of SEQ ID NO: 95.

Embodiment 60. The AAG piggyBac transposon polynucleotide of any one of Embodiments 58A-58M, wherein the first piggyBac ITR sequence comprises the nucleic acid sequence of SEQ ID NO: 125.

Embodiment 61. The AAV piggyBac transposon polynucleotide of any one of Embodiments 58A-60, wherein the AAV piggyBac transposon polynucleotide comprises the nucleic acid sequence of SEQ ID NO: 140.

Embodiment 62. An AAV piggyBac transposon polynucleotide comprising in the 5' to 3' direction:

a) a first AAV ITR sequence comprising the nucleic acid sequence of SEQ ID NO: 3;
b) a first piggyBac ITR sequence comprising the nucleic acid sequence of SEQ ID NO: 95 or SEQ ID NO: 125;
c) a first insulator sequence comprising the nucleic acid sequence of SEQ ID NO: 7;
d) at least one promoter sequence comprising the nucleic acid sequence of SEQ ID NO: 9 or SEQ ID NO: 126;
e) a first transgene sequence comprising the nucleic acid sequence of SEQ ID NO: 22;
f) a first self-cleaving peptide sequence comprising the nucleic acid sequence of SEQ ID NO: 31;
g) a second transgene sequence comprising the nucleic acid sequence of SEQ ID NO: 133;
h) an at least second self-cleaving peptide sequence comprising the nucleic acid sequence of SEQ ID NO: 32;
i) at least a third transgene sequence comprising the nucleic acid sequence of SEQ ID NO: 134;
j) a polyA sequence comprising the nucleic acid sequence of SEQ ID NO: 97;
k) a second insulator sequence comprising the nucleic acid sequence of SEQ ID NO: 8;
l) a second piggyBac ITR sequence comprising the nucleic acid sequence of SEQ ID NO: 96; and
m) a second AAV ITR sequence comprising the nucleic acid sequence of SEQ ID NO: 4.

Embodiment 63. The AAG piggyBac transposon polynucleotide of Embodiment 62, wherein the first piggyBac ITR sequence comprises the nucleic acid sequence of SEQ ID NO: 95.

Embodiment 64. The AAG piggyBac transposon polynucleotide of Embodiment 62, wherein the first piggyBac ITR sequence comprises the nucleic acid sequence of SEQ ID NO: 125.

Embodiment 65. The AAV piggyBac transposon polynucleotide of Embodiment 62, wherein the at least one promoter sequence comprises the nucleic acid sequence of SEQ ID NO: 9.

Embodiment 66. The AAV piggyBac transposon polynucleotide of Embodiment 62, wherein the at least one promoter sequence comprises the nucleic acid sequence of SEQ ID NO: 126.

Embodiment 67. The AAV piggyBac transposon polynucleotide of any one of Embodiments 62-66, wherein the AAV piggyBac transposon polynucleotide comprises the nucleic acid sequence of SEQ ID NO: 141.

Embodiment 68. An AAV piggyBac transposon polynucleotide comprising in the 5' to 3' direction:

a) a first AAV ITR sequence comprising the nucleic acid sequence of SEQ ID NO: 3;
b) a first piggyBac ITR sequence comprising the nucleic acid sequence of SEQ ID NO: 95 or SEQ ID NO: 125;
c) a first insulator sequence comprising the nucleic acid sequence of SEQ ID NO: 7;
d) at least one promoter sequence comprising the nucleic acid sequence of SEQ ID NO: 10 or SEQ ID NO: 132;
e) a first transgene sequence comprising the nucleic acid sequence of SEQ ID NO: 22;
f) a first self-cleaving peptide sequence comprising the nucleic acid sequence of SEQ ID NO: 31;
g) a second transgene sequence comprising the nucleic acid sequence of SEQ ID NO: 133;
h) an at least second self-cleaving peptide sequence comprising the nucleic acid sequence of SEQ ID NO: 32;
i) at least a third transgene sequence comprising the nucleic acid sequence of SEQ ID NO: 134;
j) a polyA sequence comprising the nucleic acid sequence of SEQ ID NO: 97;
k) a second insulator sequence comprising the nucleic acid sequence of SEQ ID NO: 8;
l) a second piggyBac ITR sequence comprising the nucleic acid sequence of SEQ ID NO: 96; and
m) a second AAV ITR sequence comprising the nucleic acid sequence of SEQ ID NO: 4.

Embodiment 69. The AAG piggyBac transposon polynucleotide of Embodiment 68, wherein the first piggyBac ITR sequence comprises the nucleic acid sequence of SEQ ID NO: 95.

Embodiment 70. The AAG piggyBac transposon polynucleotide of Embodiment 68, wherein the first piggyBac ITR sequence comprises the nucleic acid sequence of SEQ ID NO: 125.

Embodiment 71. The AAV piggyBac transposon polynucleotide of Embodiment 68, wherein the at least one promoter sequence comprises the nucleic acid sequence of SEQ ID NO: 10.

Embodiment 72. The AAV piggyBac transposon polynucleotide of Embodiment 68, wherein the at least one promoter sequence comprises the nucleic acid sequence of SEQ ID NO: 132.

Embodiment 73. The AAV piggyBac transposon polynucleotide of any one of Embodiments 68-72, wherein the AAV piggyBac transposon polynucleotide comprises the nucleic acid sequence of SEQ ID NO: 142.

Embodiment 74. An AAV piggyBac transposon polynucleotide comprising in the 5' to 3' direction:

a) a first AAV ITR sequence comprising the nucleic acid sequence of SEQ ID NO: 3;
b) a first piggyBac ITR sequence comprising the nucleic acid sequence of SEQ ID NO: 95 or SEQ ID NO: 125;
c) a first insulator sequence comprising the nucleic acid sequence of SEQ ID NO: 7;
d) at least one promoter sequence comprising the nucleic acid sequence of SEQ ID NO: 13;
e) a first transgene sequence comprising the nucleic acid sequence of SEQ ID NO: 22;
f) at least one self-cleaving peptide sequence comprising the nucleic acid sequence of SEQ ID NO: 135;
g) an at least second transgene sequence comprising the nucleic acid sequence of SEQ ID NO: 134;
h) a polyA sequence comprising the nucleic acid sequence of SEQ ID NO: 97;
i) a second insulator sequence comprising the nucleic acid sequence of SEQ ID NO: 8;
j) a second piggyBac ITR sequence comprising the nucleic acid sequence of SEQ ID NO: 96; and
k) a second AAV ITR sequence comprising the nucleic acid sequence of SEQ ID NO: 4.

Embodiment 75. The AAG piggyBac transposon polynucleotide of Embodiment 74, wherein the first piggyBac ITR sequence comprises the nucleic acid sequence of SEQ ID NO: 95.

Embodiment 76. The AAG piggyBac transposon polynucleotide of Embodiment 74, wherein the first piggyBac ITR sequence comprises the nucleic acid sequence of SEQ ID NO: 125.

Embodiment 77. The AAV piggyBac transposon polynucleotide of any one of Embodiments 74-76, wherein the AAV piggyBac transposon polynucleotide comprises the nucleic acid sequence of SEQ ID NO: 143.

Embodiment 78. A vector comprising the AAV piggyBac transposon polynucleotide of any of the preceding embodiments.

Embodiment 79. The vector of any of the preceding embodiments, wherein the vector is a viral vector.

Embodiment 80. The vector of any of the preceding embodiments, wherein the viral vector is an adeno-associated virus (AAV) viral vector.

Embodiment 81. The vector of any of the preceding embodiments, wherein the AAV viral vector is an AAV1, AAV2, AAV3, AAV4, AAV5, AAV6, AAV7, AAV8, AAV9, AAV10 or AAV11 viral vector.

Embodiment 82. The vector of any of the preceding embodiments, wherein the AAV viral vector is an AAV-KP-1 or AAV-NP59 viral vector, preferably wherein the AAV viral vector is an AAV-KP-1 viral vector.

Embodiment 83. A composition comprising the vector of any of embodiments 78-82.

Embodiment 84. An AAV transposase polynucleotide comprising in the 5' to 3' direction a first AAV ITR sequence, at least one promoter sequence, at least one transposase sequence, a polyA sequence and a second AAV ITR sequence.

Embodiment 85. The AAV transposase polynucleotide of embodiment 84, wherein the AAV piggyBac transposon polynucleotide comprises DNA, cDNA, gDNA, RNA, mRNA or any combination thereof.

Embodiment 86. The AAV transposase polynucleotide of any of the preceding embodiments, wherein the first and/or the second AAV ITR sequence comprises the nucleic acid sequence of any of SEQ ID NOs: 1-4, 93-94, 105-106 and 127.

Embodiment 87. The AAV transposase polynucleotide of any of the preceding embodiments, wherein the first AAV ITR sequence comprises the nucleic acid sequence of SEQ ID NO: 1 and the second AAV ITR sequence comprises the nucleic acid sequence of SEQ ID NO: 2.

Embodiment 88. The AAV transposase polynucleotide of any of the preceding embodiments, wherein the first AAV ITR sequence comprises the nucleic acid sequence of SEQ ID NO: 105 and the second AAV ITR sequence comprises the nucleic acid sequence of SEQ ID NO: 106.

Embodiment 89. The AAV transposase polynucleotide of any of the preceding embodiments, wherein the at least one promoter sequence is a liver-specific promoter.

Embodiment 90. The AAV transposase polynucleotide of any of the preceding embodiments, wherein the liver-specific promoter is a hybrid liver promoter (HLP), an LP1 promoter, a leukocyte-specific expression of the pp52 (LSP1) long promoter, a thyroxine binding globulin (TBG) promoter, a wTBG promoter, a hepatic combinatorial bundle (HCB) promoter, a 2×ApoE-hAAT promoter or a leukocyte-specific expression of the pp52 (LSP1) plus chimeric intron promoter.

Embodiment 91. The AAV transposase polynucleotide of any of the preceding embodiments, wherein the at least one promoter sequence comprises the nucleic acid sequence of any of SEQ IDS NOs: 9-16, 69, 107, 126 and 132.

Embodiment 92. The AAV transposase polynucleotide of any of the preceding embodiments, wherein the at least one transposase sequence comprises a nucleic acid sequence encoding a piggyBac™ (PB) transposase polypeptide, a piggyBac-like (PBL) transposase polypeptide or a Super piggyBac™ (SPB) transposase polypeptide.

Embodiment 93. The AAV transposase polynucleotide of any of the preceding embodiments, wherein the at least one transposase sequence comprises a nucleic acid sequence encoding for the amino acid sequence of any of SEQ ID NOs: 39-42, 47 and 49.

Embodiment 94. The AAV transposase polynucleotide of any of the preceding embodiments, wherein the at least one transposase sequence comprises the nucleic acid sequence of SEQ ID NO: 48 or 50.

Embodiment 95. The AAV transposase polynucleotide of any of the preceding embodiments, wherein the at least one transposase sequence comprises a nucleic acid sequence encoding a Sleeping Beauty transposase polypeptide, a Hyperactive Sleeping Beauty (SB100X) transposase polypeptide, a helitron transposase polypeptide, a Tol2 transposase polypeptide, a TcBuster transposase polypeptide or a mutant TcBuster transposase polypeptide.

Embodiment 96. The AAV transposase polynucleotide of any of the preceding embodiments, wherein the at least one transposase sequence comprises a nucleic acid sequence encoding the amino acid sequence of any of SEQ ID NOs: 51-60.

Embodiment 97. The AAV transposase polynucleotide of any of the preceding embodiments, wherein the polyA sequence comprises the nucleic acid sequence of SEQ ID NO: 26-27, 97, or 108.

Embodiment 98. The AAV piggyBac transposon polynucleotide of any of the preceding embodiments, wherein the at least one transposase sequence is operatively linked to the at least one promoter sequence.

Embodiment 99. The AAV piggyBac transposon polynucleotide of any of the preceding embodiments, wherein the expression of the at least one transposase sequence is controlled by the at least one promoter sequence.

Embodiment 100. The AAV transposase polynucleotide of any of the preceding embodiments, wherein the AAV transposase polynucleotide further comprises at least one DNA spacer sequence.

Embodiment 101. The AAV transposase polynucleotide of any of the preceding embodiments, wherein the at least one DNA spacer sequence comprises the nucleic acid sequence of SEQ ID NO: 103 or 109.

Embodiment 102A. An AAV transposase polynucleotide comprising in the 5' to 3' direction:

a) a first AAV ITR sequence;
b) at least one promoter sequence at least one promoter sequence;
c) at least one transposase sequence;
d) a polyA sequence;
e) at least one DNA spacer sequence; and
f) a second AAV ITR sequence.

Embodiment 102B. The AAV transposase polynucleotide of any of the preceding embodiments, wherein the first AAV ITR sequence comprises the nucleic acid sequence of SEQ ID NO: 127.

Embodiment 102C. The AAV transposase polynucleotide of any of the preceding embodiments, wherein the at least one promoter sequence comprises the nucleic acid sequence of SEQ ID NO: 9.

Embodiment 102D. The AAV transposase polynucleotide of any of the preceding embodiments, wherein the at least one promoter sequence comprises the nucleic acid sequence of SEQ ID NO: 126.

Embodiment 102E. The AAV transposase polynucleotide of any of the preceding embodiments, wherein the at least one transposase sequence comprises the nucleic acid sequence of SEQ ID NO: 48.

Embodiment 102F. The AAV transposase polynucleotide of any of the preceding embodiments, wherein the polyA sequence comprises the nucleic acid sequence of SEQ ID NO: 136.

Embodiment 102G. The AAV transposase polynucleotide of any of the preceding embodiments, wherein the at least one DNA spacer sequence comprises the nucleic acid sequence of SEQ ID NO: 137.

Embodiment 102H. The AAV transposase polynucleotide of any of the preceding embodiments, wherein the at least one DNA spacer sequence comprises the nucleic acid sequence of SEQ ID NO: 4.

Embodiment 102I. An AAV transposase polynucleotide comprising in the 5' to 3' direction:

a) a first AAV ITR sequence comprising the nucleic acid sequence of SEQ ID NO: 127;
b) at least one promoter sequence comprising the nucleic acid sequence of SEQ ID NO: 9 or SEQ ID NO: 126;
c) at least one transposase sequence comprising the nucleic acid sequence of SEQ ID NO: 48;
d) a polyA sequence comprising the nucleic acid sequences of SEQ ID NO: 136;
e) at least one DNA spacer sequence comprising the nucleic acid sequences of SEQ ID NO: 137; and
f) a second AAV ITR sequence comprising the nucleic acid sequences of SEQ ID NO: 4.

Embodiment 103. The AAV transposase polynucleotide of any one of Embodiments 102A-102I, wherein the at least one promoter sequence comprises the nucleic acid sequence of SEQ ID NO: 9.

Embodiment 104. The AAV transposase polynucleotide of any one of Embodiments 102A-102I, wherein the at least one promoter sequence comprises the nucleic acid sequence of SEQ ID NO: 126.

Embodiment 105. The AAV piggyBac transposase polynucleotide of Embodiment 102A-104, wherein the at least one promoter sequence comprises the nucleic acid sequence of SEQ ID NO: 144.

Embodiment 106. A vector comprising the AAV transposase polynucleotide of any of the preceding embodiments.

Embodiment 107. The vector of any of the preceding embodiments, wherein the vector is a viral vector.

Embodiment 108. The vector of any of the preceding embodiments, wherein the viral vector is an adeno-associated virus (AAV) viral vector.

Embodiment 109. The vector of any of the preceding embodiments, wherein the AAV viral vector is an AAV1, AAV2, AAV3, AAV4, AAV5, AAV6, AAV7, AAV8, AAV9, AAV10 or AAV11 viral vector.

Embodiment 110. The vector of any of the preceding embodiments, wherein the AAV viral vector is an AAV-KP-1 or AAV-NP59 AAV viral vector, preferably wherein the AAV viral vector is an AAV-KP-1 viral vector.

Embodiment 111. A composition comprising the vector of any of embodiments 102-110.

Embodiment 112. A composition comprising the vector of any of embodiments 78-82 and the vector of any of embodiments 102-110.

Embodiment 113. A method of treating at least one metabolic liver disorder (MLD) in a subject in need thereof comprising administering to the subject at least one therapeutically effective amount of at least one polynucleotide, vector or composition of any of the preceding embodiments.

Embodiment 114. A method of treating at least one metabolic liver disorder (MLD) in a subject in need thereof comprising administering to a subject:

a) at least one therapeutically effective amount of the AAV piggyBac transposon polynucleotide of any one of the preceding embodiments, or any one of the vectors and/or compositions of the preceding embodiments that comprise an AAV piggyBac transposon polynucleotide; and b) at least one therapeutically effective amount of the AAV piggyBac transposase polynucleotide of any of the preceding embodiments, or any one of the vectors and/or compositions of the preceding embodiments that comprise an AAV piggyBac transposase polynucleotide.

Embodiment 115. The method of embodiment 114, wherein the at least one MLD is N-Acetylglutamate Synthetase (NAGS) Deficiency, Carbamoylphosphate Synthetase I Deficiency (CPSI Deficiency), Ornithine Transcarbamylase (OTC) Deficiency, Argininosuccinate Synthetase Deficiency (ASSD) (Citrullinemia I), Citrin Deficiency (Citrullinemia II), Argininosuccinate Lyase Deficiency (Argininosuccinic Aciduria), Arginase Deficiency (Hyperargininemia), Ornithine Translocase Deficiency (HHH Syndrome), methylmalonic acidemia (MMA), progressive familial intrahepatic cholestasis type 1 (PFIC1), progressive familial intrahepatic cholestasis type 1 (PFIC2), progressive familial intrahepatic cholestasis type 1 (PFIC3) or any combination thereof.

Embodiment 116. The method of Embodiment 115, wherein the MLD is Ornithine Transcarbamylase (OTC) Deficiency.

Definitions

Nucleic Acid and Polynucleotide Molecules

Nucleic acid molecules and polynucleotide molecules of the present disclosure can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Construction of Nucleic Acid and Polynucleotide Molecules

The nucleic acid and polynucleotide molecules of the present disclosure can be made using (a) recombinant methods, (b) synthetic techniques, (c) purification techniques, and/or (d) combinations thereof, as well-known in the art.

The nucleic acid and polynucleotide molecules can conveniently comprise nucleotide sequences in addition to a polynucleotide of the present disclosure. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the disclosure. For example, a hexa-histidine marker sequence provides a convenient means to purify the proteins of the disclosure. The nucleic acid of the disclosure, excluding the coding sequence, is optionally a vector, adapter, or linker for cloning and/or expression of a polynucleotide of the disclosure.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art.

Recombinant Methods for Constructing Nucleic Acid and Polynucleotide Molecules The nucleic acid and polynucleotide molecules of this disclosure, such as RNA, cDNA, genomic DNA, or any combination thereof, can be obtained from biological sources using any number of cloning methodologies known to those of skill in the art. In some aspects, oligonucleotide probes that selectively hybridize, under stringent conditions, to the polynucleotides of the present disclosure are used to identify the desired sequence in a cDNA or genomic DNA library. The isolation of RNA, and construction of cDNA and genomic libraries are well known to those of ordinary skill in the art.

Nucleic Acid Screening and Isolation Methods

A cDNA or genomic library can be screened using a probe based upon the sequence of a polynucleotide of the disclosure. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the disclosure without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference.

For instance, polymerase chain reaction (PCR) technology can be used to amplify the sequences of polynucleotides of the disclosure and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The nucleic acid and polynucleotide molecules of the disclosure can also be prepared by direct chemical synthesis by known methods. Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The disclosure further provides recombinant expression cassettes comprising a nucleic acid or polynucleotide molecule of the present disclosure. A nucleic acid or polynucleotide of the present disclosure can be used to construct a recombinant expression cassette that can be introduced into at least one desired host cell. A recombinant expression cassette will typically comprise a polynucleotide of the disclosure operably linked to transcriptional initiation regulatory sequences that will direct the transcription of the polynucleotide in the intended host cell. Both heterologous and non-heterologous (i.e., endogenous) promoters can be employed to direct expression of the nucleic acids of the disclosure.

In some aspects, isolated nucleic acids that serve as promoter, enhancer, or other elements can be introduced in the appropriate position (upstream, downstream or in the intron) of a non-heterologous form of a polynucleotide of the disclosure so as to up or down regulate expression of a polynucleotide of the disclosure. For example, endogenous promoters can be altered in vivo or in vitro by mutation, deletion and/or substitution.

Expression Vectors and Host Cells

The disclosure also relates to vectors that include isolated nucleic acid and polynucleotide molecules of the disclosure, host cells that are genetically engineered with the recombinant vectors, and the production of at least polynucleotide by recombinant techniques, as is well known in the art.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, ampicillin, zeocin (Sh bla gene), puromycin (pac gene), hygromycin B (hygB gene), G418/Geneticin (neo gene), DHFR (encoding Dihydrofolate Reductase and conferring resistance to Methotrexate), mycophenolic acid, or glutamine synthetase (GS, U.S. Pat. Nos. 5,122,464; 5,770,359; 5,827,739), blasticidin (bsd gene), resistance genes for eukaryotic cell culture as well as ampicillin, zeocin (Sh bla gene), puromycin (pac gene), hygromycin B (hygB gene), G418/Geneticin (neo gene), kanamycin, spectinomycin, streptomycin, carbenicillin, bleomycin, erythromycin, polymyxin B, or tetracycline resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods.

Expression vectors will preferably but optionally include at least one selectable cell surface marker for isolation of cells modified by the compositions and methods of the disclosure. Selectable cell surface markers of the disclosure comprise surface proteins, glycoproteins, or group of proteins that distinguish a cell or subset of cells from another defined subset of cells. Preferably the selectable cell surface marker distinguishes those cells modified by a composition or method of the disclosure from those cells that are not modified by a composition or method of the disclosure. Such cell surface markers include, e.g., but are not limited to, "cluster of designation" or "classification determinant" proteins (often abbreviated as "CD") such as a truncated or full length form of CD19, CD271, CD34, CD22, CD20, CD33, CD52, or any combination thereof. Cell surface markers further include the suicide gene marker RQR8 (Philip B et al. Blood. 2014 Aug. 21; 124(8):1277-87).

Expression vectors will preferably but optionally include at least one selectable drug resistance marker for isolation of cells modified by the compositions and methods of the disclosure. Selectable drug resistance markers of the disclosure may comprise wild-type or mutant Neo, DHFR, TYMS, FRANCF, RAD51C, GCS, MDR1, ALDH1, NKX2.2, or any combination thereof.

Those of ordinary skill in the art are knowledgeable in the numerous expression systems available for expression of a nucleic acid or polynucleotide molecule. Alternatively, nucleic acids of the disclosure can be expressed in a host cell by turning on (by manipulation) in a host cell that contains endogenous DNA encoding a nucleic acid or polynucleotide of the present disclosure. Such methods are well known in the art, e.g., as described in U.S. Pat. Nos. 5,580,734, 5,641,670, 5,733,746, and 5,733,761, entirely incorporated herein by reference Illustrative of cell cultures useful for the production of the nucleic acid and polynucleotide molecules of the present disclosure, specified portions or variants thereof, are bacterial, yeast, and mammalian cells as known in the art. Mammalian cell systems often will be in the form of monolayers of cells although mammalian cell suspensions or bioreactors can also be used. A number of suitable host cell lines have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a preferred aspect, the recombinant cell is a P3X63Ab8.653 or an SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present disclosure are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

The disclosure provides isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various aspects, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the disclosure or biologically active portion thereof is recombinantly produced, optimally culture medium represents less than about 30%, 20%, 10%, 5%, or 1% (by dry weight) of chemical precursors or non-protein-of-interest chemicals.

The disclosure provides fragments and variants of the disclosed DNA sequences and proteins encoded by these DNA sequences. As used throughout the disclosure, the term "fragment" refers to a portion of the DNA sequence or a portion of the amino acid sequence and hence protein encoded thereby. Fragments of a DNA sequence comprising coding sequences may encode protein fragments that retain biological activity of the native protein and hence DNA recognition or binding activity to a target DNA sequence as herein described. Alternatively, fragments of a DNA sequence that are useful as hybridization probes generally do not encode proteins that retain biological activity or do not retain promoter activity. Thus, fragments of a DNA sequence may range from at least about 20 nucleotides, about 50 nucleotides, about 100 nucleotides, and up to the full-length polynucleotide of the disclosure.

Nucleic acids or proteins of the disclosure can be constructed by a modular approach including preassembling monomer units and/or repeat units in target vectors that can subsequently be assembled into a final destination vector. Polypeptides of the disclosure may comprise repeat monomers of the disclosure and can be constructed by a modular approach by preassembling repeat units in target vectors that can subsequently be assembled into a final destination vector. The disclosure provides polypeptide produced by this method as well nucleic acid sequences encoding these polypeptides. The disclosure provides host organisms and cells comprising nucleic acid sequences encoding polypeptides produced this modular approach.

The term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of shall mean excluding more than trace elements of other ingredients and substantial method steps. Aspects defined by each of these transition terms are within the scope of this disclosure.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

"Gene expression" refers to the conversion of the information, contained in a gene, into a gene product. A gene product can be the direct transcriptional product of a gene (e.g., mRNA, tRNA, rRNA, antisense RNA, ribozyme, shRNA, micro RNA, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" or "regulation" of gene expression refers to a change in the activity of a gene. Modulation of expression can include, but is not limited to, gene activation and gene repression.

The term "operatively linked" or its equivalents (e.g., "linked operatively") means two or more molecules are positioned with respect to each other such that they are capable of interacting to affect a function attributable to one or both molecules or a combination thereof. In some aspects, a transgene sequence, or any other sequence, is said to be operatively linked to a promoter sequence when the promoter sequence controls the expression of the transgene sequence, or any other sequence. In some aspects, a transposase sequence is said to be operatively linked to a promoter sequence when the promoter sequence controls the expression of the transposase sequence.

Non-covalently linked components and methods of making and using non-covalently linked components, are disclosed. The various components may take a variety of different forms as described herein. For example, non-covalently linked (i.e., operatively linked) proteins may be used to allow temporary interactions that avoid one or more problems in the art. The ability of non-covalently linked components, such as proteins, to associate and dissociate enables a functional association only or primarily under circumstances where such association is needed for the desired activity. The linkage may be of duration sufficient to allow the desired effect.

The terms "nucleic acid" or "oligonucleotide" or "polynucleotide" refer to at least two nucleotides covalently linked together. The depiction of a single strand also defines the sequence of the complementary strand. Thus, a nucleic acid may also encompass the complementary strand of a depicted single strand. A nucleic acid of the disclosure also encompasses substantially identical nucleic acids and complements thereof that retain the same structure or encode for the same protein.

Nucleic acids of the disclosure may be single- or double-stranded. Nucleic acids of the disclosure may contain double-stranded sequences even when the majority of the molecule is single-stranded. Nucleic acids of the disclosure may contain single-stranded sequences even when the majority of the molecule is double-stranded. Nucleic acids of the disclosure may include genomic DNA, cDNA, RNA, or a hybrid thereof. Nucleic acids of the disclosure may contain combinations of deoxyribo- and ribo-nucleotides. Nucleic acids of the disclosure may contain combinations of bases including uracil, adenine, thymine, cytosine, guanine, inosine, xanthine hypoxanthine, isocytosine and isoguanine. Nucleic acids of the disclosure may be synthesized to comprise non-natural amino acid modifications. Nucleic acids of the disclosure may be obtained by chemical synthesis methods or by recombinant methods.

Nucleic acids of the disclosure, either their entire sequence, or any portion thereof, may be non-naturally occurring. Nucleic acids of the disclosure may contain one or more mutations, substitutions, deletions, or insertions that do not naturally-occur, rendering the entire nucleic acid sequence non-naturally occurring. Nucleic acids of the disclosure may contain one or more duplicated, inverted or repeated sequences, the resultant sequence of which does not naturally-occur, rendering the entire nucleic acid sequence non-naturally occurring. Nucleic acids of the disclosure may contain modified, artificial, or synthetic nucleotides that do not naturally-occur, rendering the entire nucleic acid sequence non-naturally occurring.

Given the redundancy in the genetic code, a plurality of nucleotide sequences may encode any particular protein. All such nucleotides sequences are contemplated herein.

As used throughout the disclosure, the term "operably linked" refers to the expression of a gene that is under the control of a promoter with which it is spatially connected. A promoter can be positioned 5' (upstream) or 3' (downstream) of a gene under its control. The distance between a promoter and a gene can be approximately the same as the distance between that promoter and the gene it controls in the gene from which the promoter is derived. Variation in the distance between a promoter and a gene can be accommodated without loss of promoter function.

As used throughout the disclosure, the term "promoter" refers to a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, EF-1 Alpha promoter, CAG promoter, SV40 early promoter or SV40 late promoter and the CMV IE promoter.

As used throughout the disclosure, the term "substantially complementary" refers to a first sequence that is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

As used throughout the disclosure, the term "substantially identical" refers to a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used throughout the disclosure, the term "variant" when used to describe a nucleic acid, refers to (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

As used throughout the disclosure, the term "vector" refers to a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid. A vector may comprise a combination of an amino acid with a DNA sequence, an RNA sequence, or both a DNA and an RNA sequence.

As used throughout the disclosure, the term "variant" when used to describe a peptide or polypeptide, refers to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity.

A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157: 105-132 (1982). The hydropathic index of an amino acid is based on a consideration of its hydrophobicity and charge. Amino acids of similar hydropathic indexes can be substituted and still retain protein function. In an aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference.

Substitution of amino acids having similar hydrophilicity values can result in peptides retaining biological activity, for example immunogenicity. Substitutions can be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "conservative" amino acid substitutions may be defined as set out in Tables A, B, or C below. In some aspects, fusion polypeptides and/or nucleic acids encoding such fusion polypeptides include conservative substitutions have been introduced by modification of polynucleotides encoding polypeptides of the disclosure. Amino acids can be classified according to physical properties and contribution to secondary and tertiary protein structure. A conservative substitution is a substitution of one amino acid for another amino acid that has similar properties. Exemplary conservative substitutions are set out in Table A.

TABLE A

Conservative Substitutions I

| Side chain characteristics | | Amino Acid |
|---|---|---|
| Aliphatic | Non-polar | G A P I L V F |
| | Polar - uncharged | C S T M N Q |
| | Polar - charged | D E K R |
| Aromatic | | H F W Y |
| Other | | N Q D E |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

Conservative Substitutions II

| Side Chain Characteristic | | Amino Acid |
|---|---|---|
| Non-polar (hydrophobic) | Aliphatic: | A L I V P |
| | Aromatic: | F W Y |
| | Sulfur-containing: | M |
| | Borderline: | G Y |
| Uncharged-polar | Hydroxyl: | S T Y |
| | Amides: | N Q |
| | Sulfhydryl: | C |
| | Borderline: | G Y |
| Positively Charged (Basic): | | K R H |
| Negatively Charged (Acidic): | | D E |

Alternately, exemplary conservative substitutions are set out in Table C.

TABLE C

Conservative Substitutions III

| Original Residue | Exemplary Substitution |
|---|---|
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |

TABLE C-continued

| Conservative Substitutions III | |
|---|---|
| Original Residue | Exemplary Substitution |
| Trp (W) | Tyr Phe Ile |
| Tyr (Y) | Trp Phe Thr Ser |
| Val (V) | Ile Leu Met Ala |

It should be understood that the polypeptides of the disclosure are intended to include polypeptides bearing one or more insertions, deletions, or substitutions, or any combination thereof, of amino acid residues as well as modifications other than insertions, deletions, or substitutions of amino acid residues. Polypeptides or nucleic acids of the disclosure may contain one or more conservative substitution.

As used throughout the disclosure, the term "more than one" of the aforementioned amino acid substitutions refers to 2, 3, 4, 5, 6, 7, 8, 9, 10, 11, 12, 13, 14, 15, 16, 17, 18, 19, or 20 or more of the recited amino acid substitutions. The term "more than one" may refer to 2, 3, 4, or 5 of the recited amino acid substitutions.

Polypeptides and proteins of the disclosure, either their entire sequence, or any portion thereof, may be non-naturally occurring. Polypeptides and proteins of the disclosure may contain one or more mutations, substitutions, deletions, or insertions that do not naturally-occur, rendering the entire amino acid sequence non-naturally occurring. Polypeptides and proteins of the disclosure may contain one or more duplicated, inverted or repeated sequences, the resultant sequence of which does not naturally-occur, rendering the entire amino acid sequence non-naturally occurring. Polypeptides and proteins of the disclosure may contain modified, artificial, or synthetic amino acids that do not naturally-occur, rendering the entire amino acid sequence non-naturally occurring.

As used throughout the disclosure, "sequence identity" may be determined by using the stand-alone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). The terms "identical" or "identity" when used in the context of two or more nucleic acids or polypeptide sequences, refer to a specified percentage of residues that are the same over a specified region of each of the sequences. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

As used throughout the disclosure, the term "endogenous" refers to nucleic acid or protein sequence naturally associated with a target gene or a host cell into which it is introduced.

As used throughout the disclosure, the term "exogenous" refers to nucleic acid or protein sequence not naturally associated with a target gene or a host cell into which it is introduced, including non-naturally occurring multiple copies of a naturally occurring nucleic acid, e.g., DNA sequence, or naturally occurring nucleic acid sequence located in a non-naturally occurring genome location.

The disclosure provides methods of introducing a polynucleotide construct comprising a DNA sequence into a host cell. By "introducing" is intended presenting to the cell the polynucleotide construct in such a manner that the construct gains access to the interior of the host cell. The methods of the disclosure do not depend on a particular method for introducing a polynucleotide construct into a host cell, only that the polynucleotide construct gains access to the interior of one cell of the host. Methods for introducing polynucleotide constructs into bacteria, plants, fungi and animals are known in the art including, but not limited to, stable transformation methods, transient transformation methods, and virus-mediated methods.

As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

Example 1—In Vivo Expression of Transgenes Mediated by Viral Vectors of the Present Disclosure In the following non-limiting example, mice were treated with viral vectors of the present disclosure and expression of the transgenes contained in the viral vectors was monitored.

Newborn mice were split into four different treatment groups.

Mice in Treatment Group #1 were administered an AAV piggyBac transposon vector comprising the AAV piggyBac transposon polynucleotide described in FIG. 1 at a dosage of $3.3 \times 10^{13}$ vector genomes (vg)/kg.

Mice in Treatment Group #2 were administered an AAV piggyBac transposon vector comprising the AAV piggyBac transposon polynucleotide described in FIG. 8 at a dosage of $3.3 \times 10^{13}$ vg/kg.

Mice in Treatment Group #3 were administered an AAV piggyBac transposon vector comprising the AAV piggyBac transposon polynucleotide described in FIG. 1 at a dosage of $3.3 \times 10^{13}$ vg/kg and an AAV transposase vector comprising an AAV transposase polynucleotide at a dosage of $1.1 \times 10^{13}$ vg/kg. The AAV transposase polynucleotide comprised a transposase sequence encoding for a SPB transposase.

Mice in Treatment Group #4 were administered an AAV piggyBac transposon vector comprising the AAV piggyBac transposon polynucleotide described in FIG. 8 at a dosage of $3.3\times10^{13}$ vg/kg and an AAV transposase vector comprising an AAV transposase polynucleotide at a dosage of $1.1\times10^{13}$ vg/kg. The AAV transposase polynucleotide comprised a transposase sequence encoding for a SPB transposase.

Figure 10:
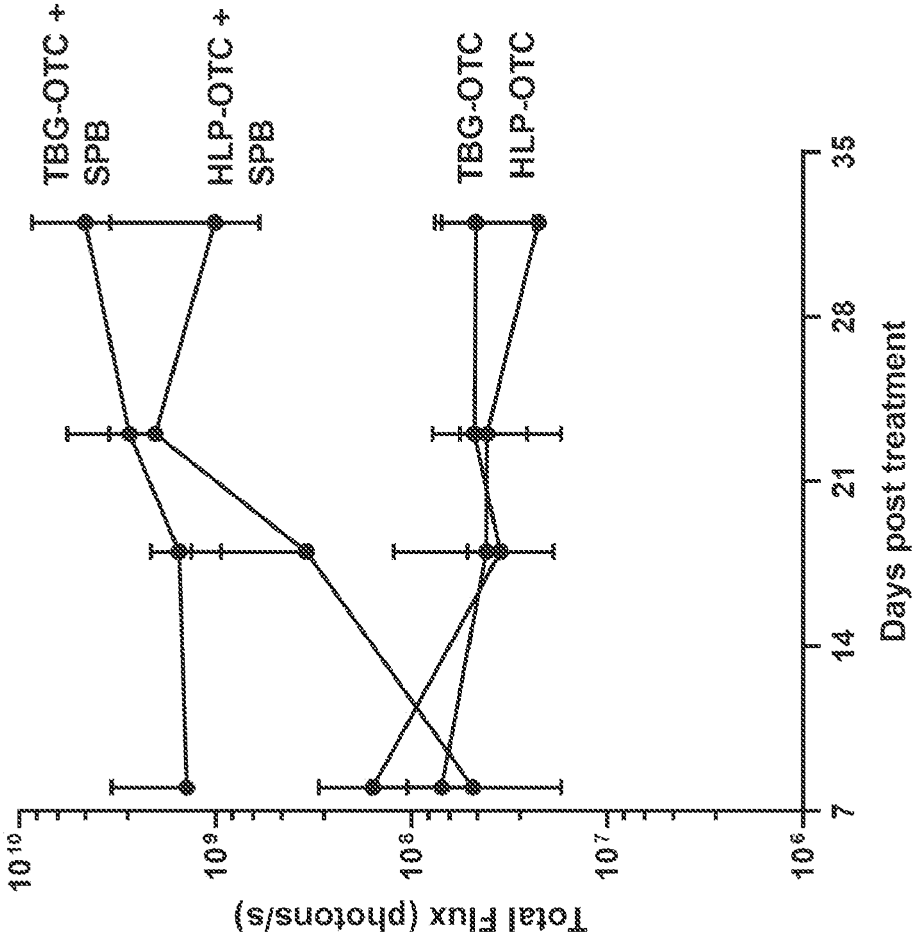
FIG. 10 is a graph showing BLI measured in mice treated with various viral vectors of the present disclosure.

Bioluminescence (BLI) signals were then measured in the mice for 35 days following viral vector administration to measure the expression of the transgenes encoded for in the AAV piggyBac transposon polynucleotides. The results of this analysis are shown in FIG. 10. In FIG. 10, Treatment Group #1 is referred to as HLP-OTC, Treatment Group #2 is referred to as TBG-OTC, Treatment Group #3 is referred to as HLP-OTC+SPB and Treatment Group #4 is referred to as TBG-OTC+SPB.

As shown in FIG. 10, mice in Treatment Groups #3 and #4 shows increased levels of BLI over the course of the 35 days. Without wishing to be bound by theory, these results indicate that the coadministration of the AAV piggyBac transposon vector and the AAV transposase vector can lead to an integration of the transgenes of the AAV piggyBac transposon vector into the host's genome, resulting in increased and sustained expression of the transgenes. Moreover, increased expression of the transgenes was observed in Treatment Group #4, which were administered AAV piggyBac transposon vectors comprising a TBG promoter. Without wishing to be bound by theory, these results indicate that the use of a TBG promoter can provide increased transgene expression that occurs soon after administration. Such activity is particularly advantageous in a clinical setting in which early-onset patients are being treated.

Example 2—In Vivo Expression of Transgenes Mediated by Different Concentrations of Viral Vectors of the Present Disclosure In the following non-limiting example, mice were treated with varying concentrations of viral vectors of the present disclosure and expression of the transgenes contained in the viral vectors was monitored.

Figure 11:
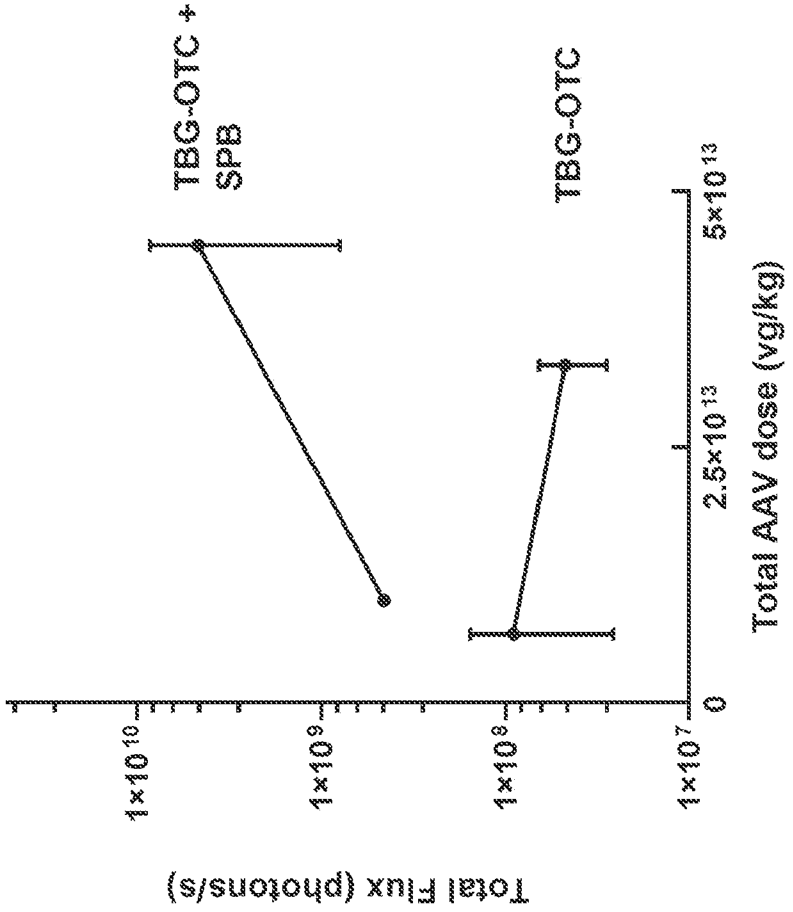
FIG. 11 is a graph showing BLI measured in mice treated with various viral vectors of the present disclosure at various concentrations.

The mice in the study were administered either:

a) increasing concentrations of an AAV piggyBac transposon vector comprising the AAV piggyBac transposon polynucleotide described in FIG. 8 alone; or b) increasing concentrations of an AAV piggyBac transposon vector comprising the AAV piggyBac transposon polynucleotide described in FIG. 8 in combination with an AAV transposase vector comprising an AAV transposase polynucleotide, wherein the AAV transposase polynucleotide comprised a transposase sequence encoding for a SPB transposase On day 21 following administration of the viral vectors, BLI was measured in the mice to measure the expression of the transgenes encoded for in the AAV piggyBac transposon polynucleotides. The results of this analysis are shown in FIG. 11. As shown in FIG. 11, higher levels of transgene expression were achieved at lower doses when both the AAV piggyBac transposon vector and the AAV transposase vector were co-administered. Without wishing to be bound by theory, these results indicate that the coadministration of the AAV piggyBac transposon vector and the AAV transposase vector can lead to an integration of the transgenes of the AAV piggyBac transposon vector into the host's genome, resulting in increased and sustained expression of the transgenes. This is particularly advantageous in a clinical setting, as it can reduce the total dose of AAV that needs to be administered to a subject, which can help to avoid the negative side effects typically associated with the administration of an AAV vector.

Example 3—Treatment of $Otc^{spf-ash}$ Mice with Viral Vectors of the Present Disclosure In the following non-limiting example, $Otc^{spf-ash\ rev1}$ mice were treated with viral vectors of the present disclosure.

As would be appreciated by the skilled artisan, $Otc^{spf-ash}$ mice are a widely used model of urea cycle disorders, including OTC deficiency and chronic hyperammonemia. The mice contain a mutation (c. 386G>A; p. R129H) in the last nucleotide of exon 4 of the Otc gene, affecting the 5' splice site and resulting in partial use of a cryptic splice site 48 bp into the adjacent intron.

Newborn $Otc^{spf-ash}$ mice were split into two different treatment groups.

Mice in Treatment Group #1 were administered an AAV piggyBac transposon vector comprising the AAV piggyBac transposon polynucleotide described in FIG. 1 at a dosage of $3.3\times10^{13}$ vector genomes (vg)/kg and an AAV transposase vector comprising the AAV transposase polynucleotide described in FIG. 4 at a dosage of $3.3\times10^{13}$ vg/kg. Thus, mice in Treatment Group #1 were treated with an AAV piggyBac transposon vector and an AAV transposase vector at a dosage ratio of 1:1, with a total AAV dosage of $6.6\times10^{13}$ vg/kg. The AAV transposase polynucleotide comprised a transgene sequence encoding for human OTC, allowing it to be distinguished from endogenous, murine OTC.

Mice in Treatment Group #2 were administered an AAV piggyBac transposon vector comprising the AAV piggyBac transposon polynucleotide described in FIG. 1 at a dosage of $3.3\times10^{13}$ vector genomes (vg)/kg and an AAV transposase vector comprising the AAV transposase polynucleotide described in FIG. 4 at a dosage of $1.7\times10^{13}$ vg/kg. Thus, mice in Treatment Group #2 were treated with an AAV piggyBac transposon vector and an AAV transposase vector at a dosage ratio of 2:1, with a total AAV dosage of $5\times10^{13}$ vg/kg. The AAV transposase polynucleotide comprised a transgene sequence encoding for human OTC, allowing it to be distinguished from endogenous, murine OTC.

Figure 12:
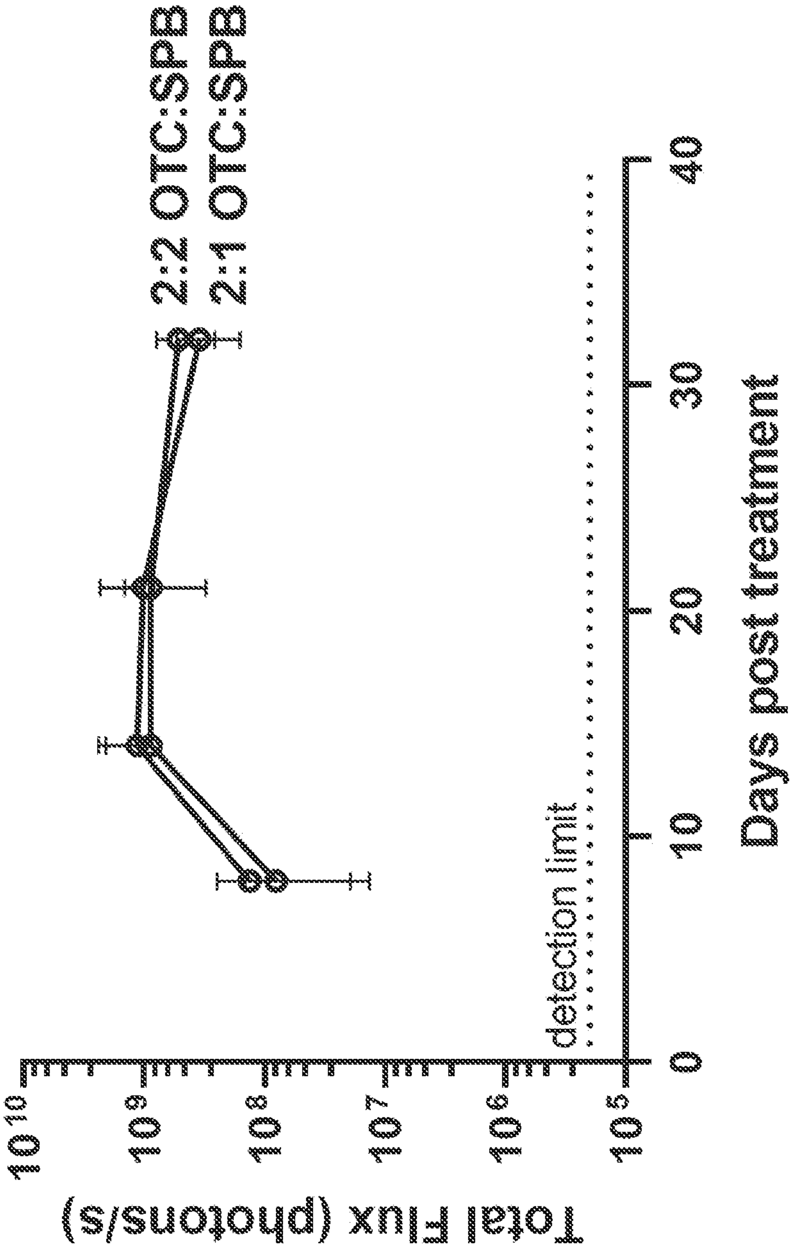
FIG. 12 is a graph showing BLI measured in $Otc^{spf\text{-}ash}$ mice treated with various viral vectors of the present disclosure.

Following administration of the viral vectors, BLI was measured in the mice to measure the expression of the transgenes encoded for in the AAV piggyBac transposon polynucleotide. The results of this analysis are shown in FIG. 12. As shown in FIG. 12, high levels of transgene expression was measured in both of the treatment groups.

Figure 13:
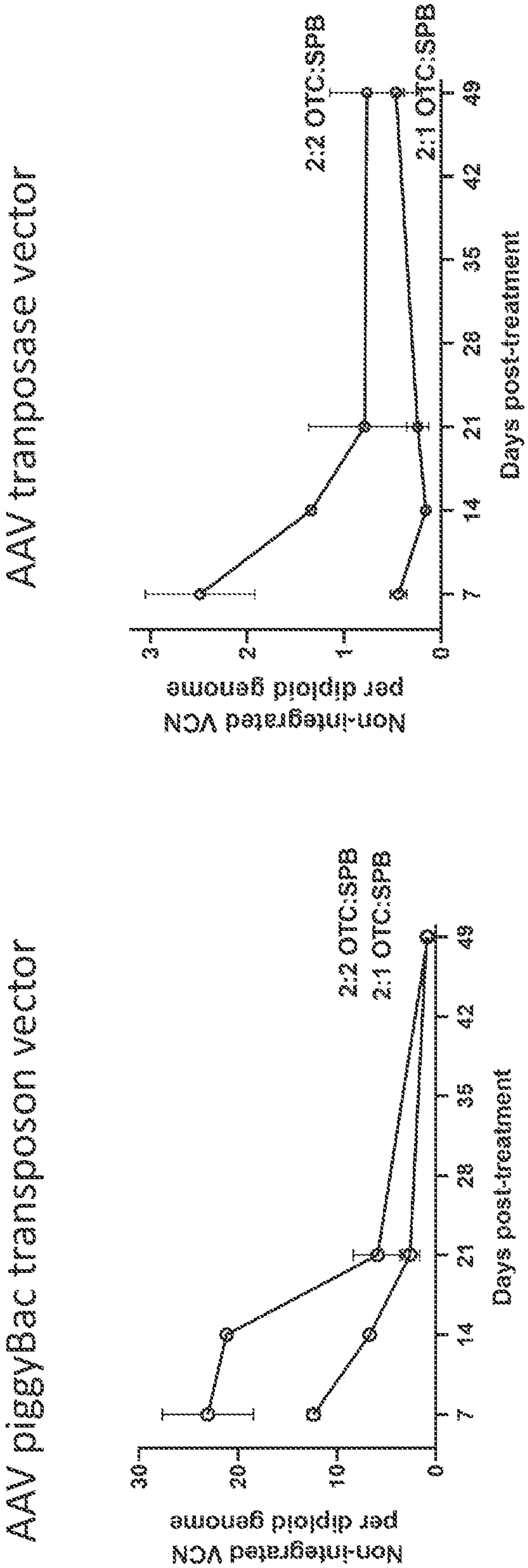
FIG. 13 are a series of graphs showing the amount of non-integrated vector copy number per diploid genome for various viral vectors of the present disclosure administered to $Otc^{spf\text{-}ash}$ mice.

Following administration of the viral vectors, the amount of non-integrated vector copy number per diploid genome for both the AAV piggyBAC transposon vector and the AAV transposase vector were measured. The results of this analysis are shown in FIG. 13. As shown in FIG. 13, the amount of non-integrated AAV transposase vector decreased as the mice aged. Moreover, the amount of non-integrated AAV transposase vector was lower as compared to the amount of non-integrated AAV piggyBac transposon vector, even at day 7.

Figure 14:
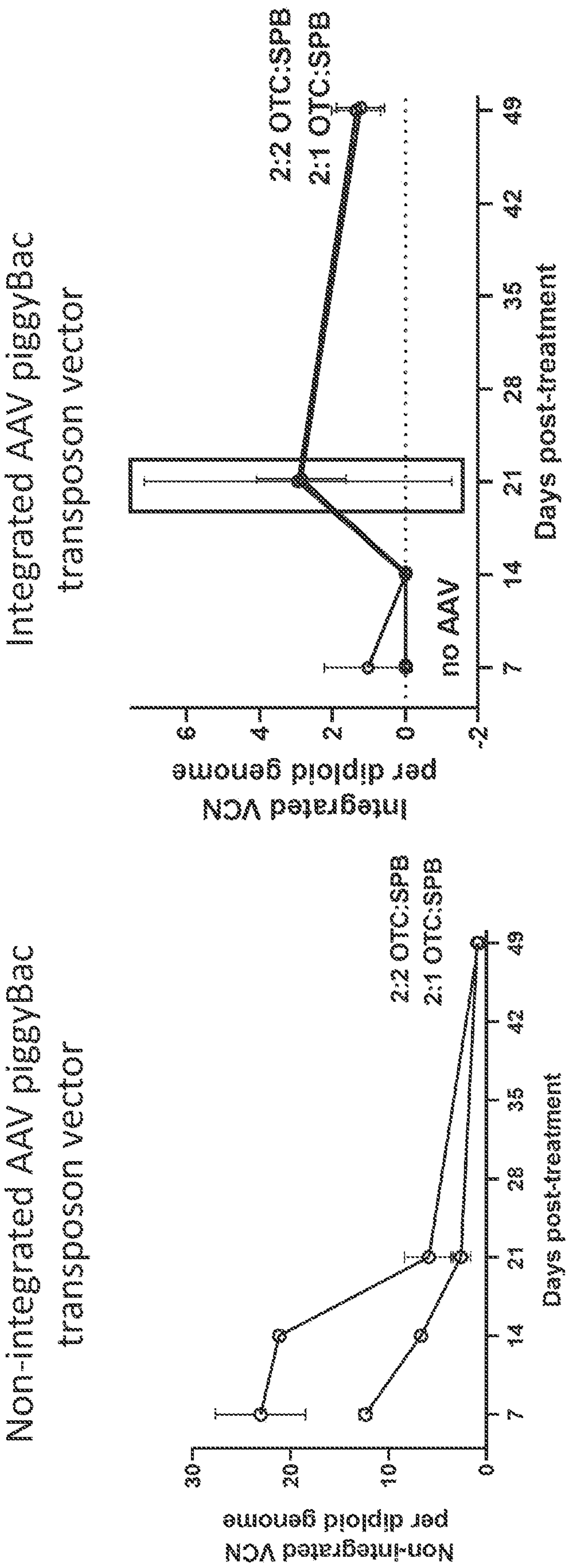
FIG. 14 are a series of graphs showing the amount of non-integrated vector copy number per diploid genome and integrated vector copy number per diploid genome for various viral vectors of the present disclosure administered to $Otc^{spf\text{-}ash}$ mice.

Following administration of the viral vectors, the amount of non-integrated AAV piggyBac transposon vector copy number per diploid genome and the amount of integrated AAV piggyBac transposon vector copy number were measured. The results of this analysis are shown in FIG. 14. As shown in FIG. 14, there was detection of integrated AAV piggbyBac transposon vector at 21 days post treatment. Moreover, the integration was more consistent in Treatment Group #1 (2:1 OTC:SPB) as compared to Treatment Group

#2 (2:2 OTC:SPB). Without wishing to be bound by theory, the results in FIG. 14, specifically the integration of the transposon vector, indicate successful transposition of the transposon in vivo.

The number of integrated sites was also assayed by LM-PCR at days 21 and 43. Briefly, two μg of genomic DNA was isolated from mice liver tissue and sheared randomly by sonication. Unique molecular identifiers (UMI) were ligated onto the resulting ends. Two rounds of PCR amplification were performed. The final PCR product was Illumina paired-end sequenced. The integrated sites were determined by double-site break point confirmation. The results of this PCR analysis are shown in Tables 1 and 2. Without wishing to be bound by theory, the results presented in Tables 1 and 2, indicate successful transposition and integration of the transposon in vivo.

TABLE 1

| | UMI reads | Integrated site # |
|---|---|---|
| OTC + SPB (2:2) | 14,797,590 | 317 |
| OTC + SPB (2:1) | 13,119,967 | 86 |
| OTC + SPB (2:1) | 17,118,928 | 48 |
| OTC + SPB (2:1) | 13,692,000 | 68 |
| OTC + SPB (2:2) | 13,908,440 | 65 |

TABLE 2

| | UMI reads | Integrated site # |
|---|---|---|
| Control | 3,424,155 | 0 |
| OTC + SPB (2:2) | 9,951,278 | 21 |
| OTC + SPB (2:2) | 11,682,573 | 50 |
| OTC + SPB (2:2) | 13,347,536 | 14 |
| OTC + SPB (2:2) | 9,450,364 | 109 |
| OTC + SPB (2:2) | 9,162,781 | 20 |
| OTC + SPB (2:2) | 9,565,134 | 23 |
| OTC + SPB (2:1) | 12,425,240 | 73 |
| OTC + SPB (2:1) | 9,989,032 | 10 |
| OTC + SPB (2:1) | 12,831,700 | 6 |
| OTC + SPB (2:1) | 8,507,944 | 8 |
| OTC + SPB (2:1) | 3,828,516 | 12 |

Figure 15:
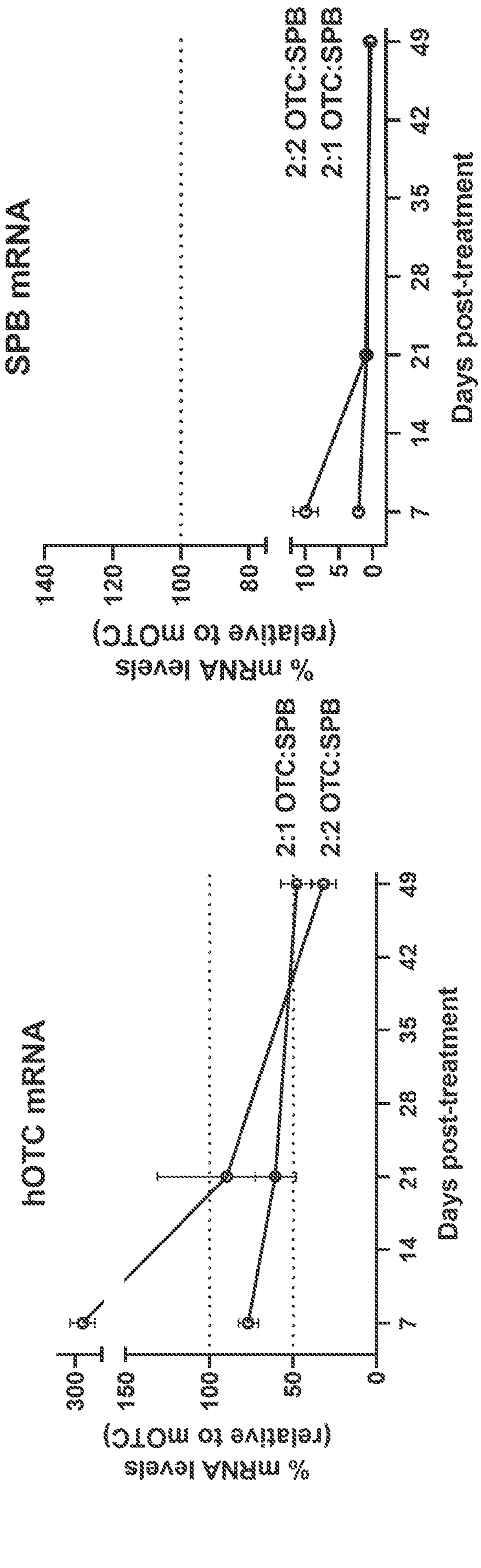
FIG. 15 are a series of graphs showing the amount of human OTC mRNA and SPB mRNA relative to the levels of murine OTC mRNA in $Otc^{spf\text{-}ash}$ mice treated with viral vectors of the present disclosure.
Figure 16:
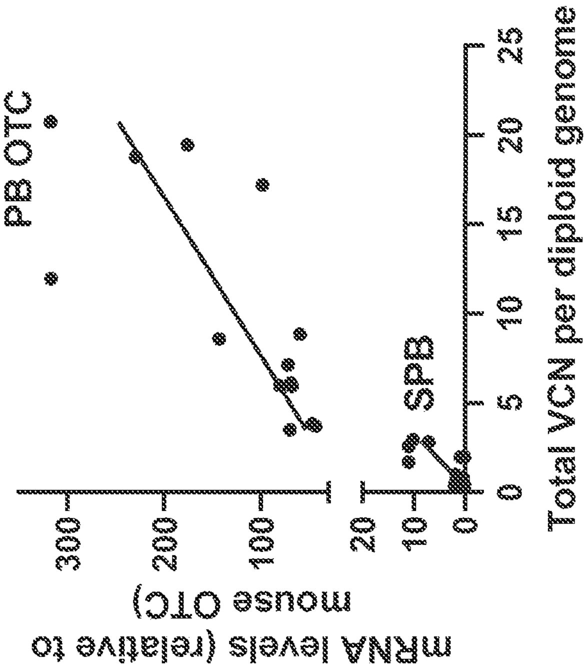
FIG. 16 is a graph showing the correlation between human OTC mRNA or SPB mRNA to the total vector copy number per diploid genome in $Otc^{spf\text{-}ash}$ mice treated with viral vectors of the present disclosure.

Following administration of the viral vectors, the amount of human OTC mRNA and SPB mRNA relative to the levels of murine OTC mRNA were measured in the mice. The results of this analysis are shown in FIG. 15. As shown in FIG. 15, mice treated with the viral vectors express significant amounts of human OTC mRNA. Moreover, the level of SPB mRNA decrease with age. Without wishing to be bound by theory, this decrease in SPB mRNA can be advantageous in a clinical setting as to avoid off-target transposition effects following initial treatment. A correlation analysis between human OTC mRNA and SPB mRNA vs total vector copy number per diploid genome was also performed. The results of this analysis are shown in FIG. 16. As shown in FIG. 16, mRNA levels of human OTC and SPB correlated with the corresponding vector copy numbers.

At day 21 post treatment, liver samples were collected from the mice and GFP expression was analyzed. Liver cells in the samples collected from both Treatment Group #1 and Treatment Group #2 displayed robust GFP expression.

Example 4—Treatment of an Inducible Hyperammonemic Mouse Model with Viral Vectors of the Present Disclosure In the following non-limiting example, $Otc^{spf\text{-}ash}$ mice were treated with viral vectors of the present disclosure and shRNA was used to create an induced hyperammonemic morbidity model.

Newborn $Otc^{spf\text{-}ash}$ mice were split into two different treatment groups.

Mice in Treatment Group #1 were administered an AAV piggyBac transposon vector comprising the AAV piggyBac transposon polynucleotide described in FIG. 1 at a dosage of $3.3\times10^{13}$ vector genomes (vg)/kg and an AAV transposase vector comprising the AAV transposase polynucleotide described in FIG. 4 at a dosage of $3.3\times10^{13}$ vg/kg. Thus, mice in Treatment Group #1 were treated with an AAV piggyBac transposon vector and an AAV transposase vector at a dosage ratio of 1:1, with a total AAV dosage of $6.6\times10^{13}$ vg/kg. The AAV transposase polynucleotide comprised a transgene sequence encoding for human OTC, allowing it to be distinguished from endogenous, murine OTC.

Mice in Treatment Group #2 were administered an AAV piggyBac transposon vector comprising the AAV piggyBac transposon polynucleotide described in FIG. 1 at a dosage of $3.3\times10^{13}$ vector genomes (vg)/kg and an AAV transposase vector comprising the AAV transposase polynucleotide described in FIG. 4 at a dosage of $1.7\times10^{13}$ vg/kg. Thus, mice in Treatment Group #2 were treated with an AAV piggyBac transposon vector and an AAV transposase vector at a dosage ratio of 2:1, with a total AAV dosage of $5\times10^{13}$ vg/kg. The AAV transposase polynucleotide comprised a transgene sequence encoding for human OTC, allowing it to be distinguished from endogenous, murine OTC.

At 38 days post treatment, a subset in each treatment group were either:

a) left further untreated b) administered a dosage of shRNA targeting mouse OTC.

As a control and for comparison, $Otc^{spf\text{-}ash}$ mice of similar age that were not treated with the viral vectors were also administered the dosage of shRNA targeting mouse OTC.

Figure 17:
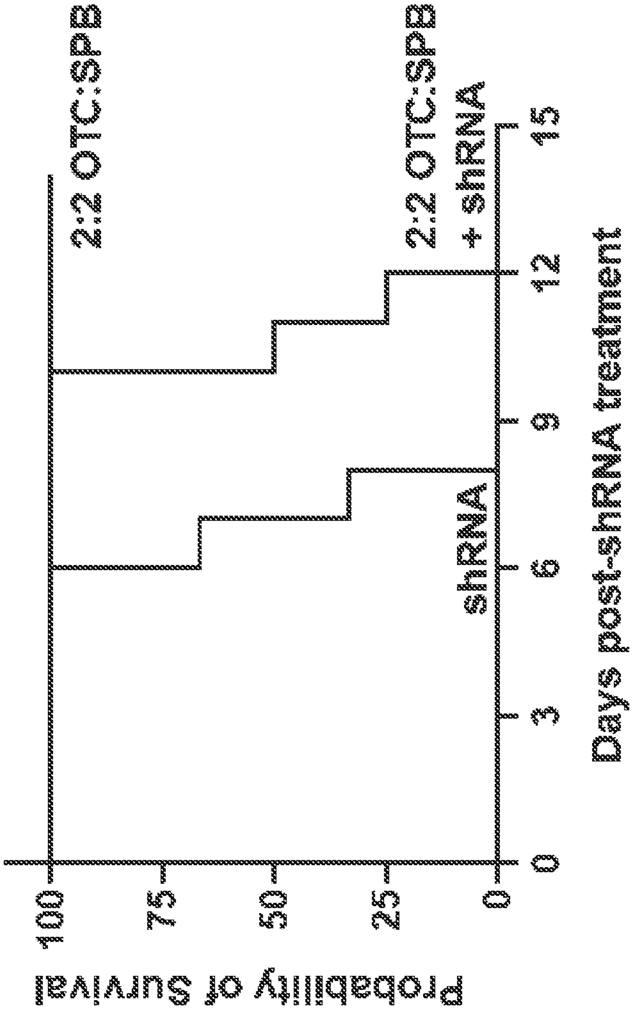
FIG. 17 is a graph showing the probability of survival in an inducible hyperammonemic mouse model treated with viral vectors of the present disclosure.
Figure 18:
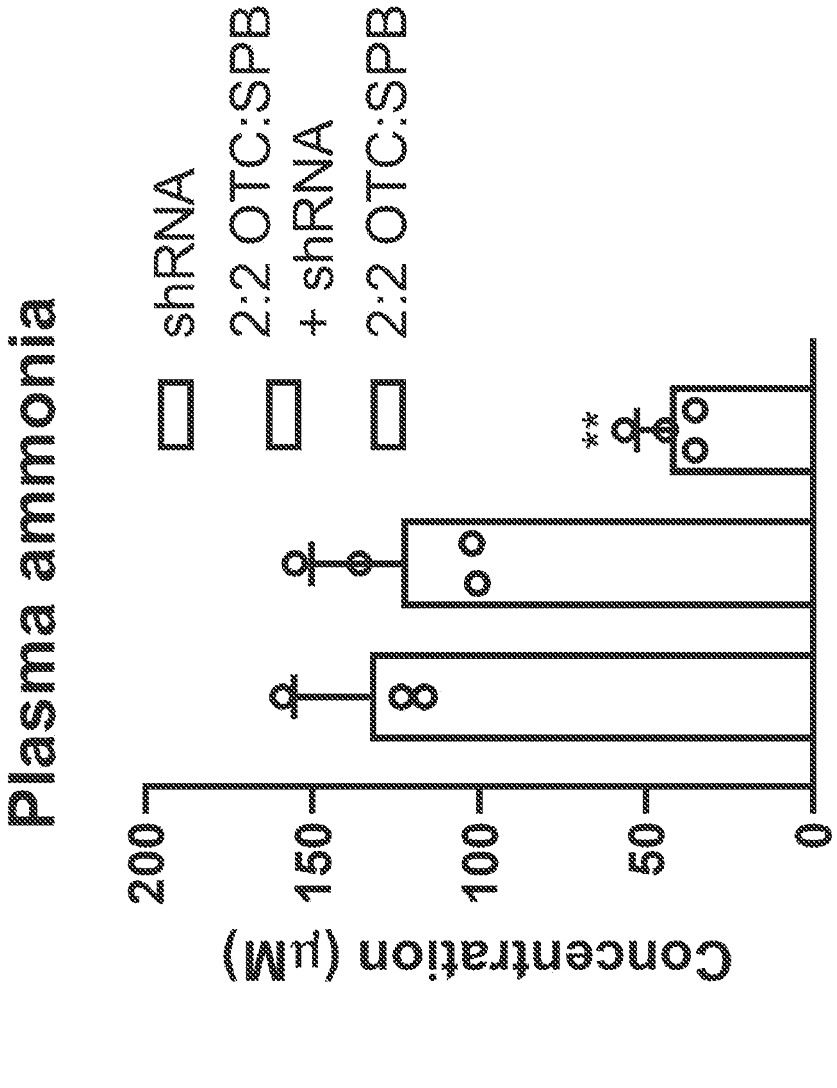
FIG. 18 is a graph showing the concentration of ammonia in plasma obtained from an inducible hyperammonemic mouse model treated with viral vectors of the present disclosure.

FIG. 17 shows the probability of survival of mice in Treatment Group #1 that were either left further untreated (2:2 OTC:SPB) or that were further administered a dosage of shRNA targeting mouse OTC (2:2:OTC:SPB+shRNA). FIG. 17 also shows the probability of survival of $Otc^{spf\text{-}ash}$ mice of similar age that were not treated with the viral vectors and that were also administered the dosage of shRNA targeting mouse OTC. FIG. 18 shows the concentration of ammonia in the plasma of the aforementioned groups of mice. As shown in FIG. 17 and FIG. 18, the deleterious effects of administering the shRNA are delayed in mice that were treated with the viral vectors.

Example 5—In Vivo Expression of Transgenes Operably Linked to Different Promoter Sequences in AAV piggyBac Transposon Vectors of the Present Disclosure In the following non-limiting example, mice were treated with viral vectors of the present disclosure comprising transgenes operably linked to either an HLP promoter, an LP1 promoter or a TBG promoter sequence. Expression of the transgenes contained in the viral vectors was monitored to determine the efficiency with which each promoter was able to drive transgene expression in vivo, specifically within the liver.

Newborn wildtype mice and adult wildtype mice and newborn $Otc^{spf\text{-}ash}$ mice were split into 12 different treatment groups.

Treatment Groups #1-#6 comprised newborn wildtype mice.

Mice in Treatment Group #1 were administered an AAV piggyBac transposon vector comprising the AAV piggyBac transposon polynucleotide described in FIG. 1 at a dosage of $5\times10^{13}$ vg/kg.

Mice in Treatment Group #2 were administered an AAV piggyBac transposon vector comprising the AAV piggyBac transposon polynucleotide described in FIG. 1 at a dosage of $3.3\times10^{13}$ vg/kg and an AAV transposase vector comprising an AAV transposase polynucleotide at a dosage of $1.7\times10^{13}$ vg/kg. The AAV transposase polynucleotide comprised a transposase sequence encoding for a SPB transposase operably linked to an HLP promoter.

Mice in Treatment Group #3 were administered an AAV piggyBac transposon vector comprising the AAV piggyBac transposon polynucleotide described in FIG. 8 at a dosage of $5\times10^{13}$ vg/kg.

Mice in Treatment Group #4 were administered an AAV piggyBac transposon vector comprising the AAV piggyBac transposon polynucleotide described in FIG. 8 at a dosage of $3.3\times10^{13}$ vg/kg and an AAV transposase vector comprising an AAV transposase polynucleotide at a dosage of $1.7\times10^{13}$ vg/kg. The AAV transposase polynucleotide comprised a transposase sequence encoding for a SPB transposase operably linked to an HLP promoter.

Mice in Treatment Group #5 were administered an AAV piggyBac transposon vector comprising the AAV piggyBac transposon polynucleotide described in FIG. 9 at a dosage of $5\times10^{13}$ vg/kg.

Mice in Treatment Group #6 were administered an AAV piggyBac transposon vector comprising the AAV piggyBac transposon polynucleotide described in FIG. 9 at a dosage of $3.3\times10^{13}$ vg/kg and an AAV transposase vector comprising an AAV transposase polynucleotide at a dosage of $1.7\times10^{13}$ vg/kg. The AAV transposase polynucleotide comprised a transposase sequence encoding for a SPB transposase operably linked to an HLP promoter.

Figure 19:
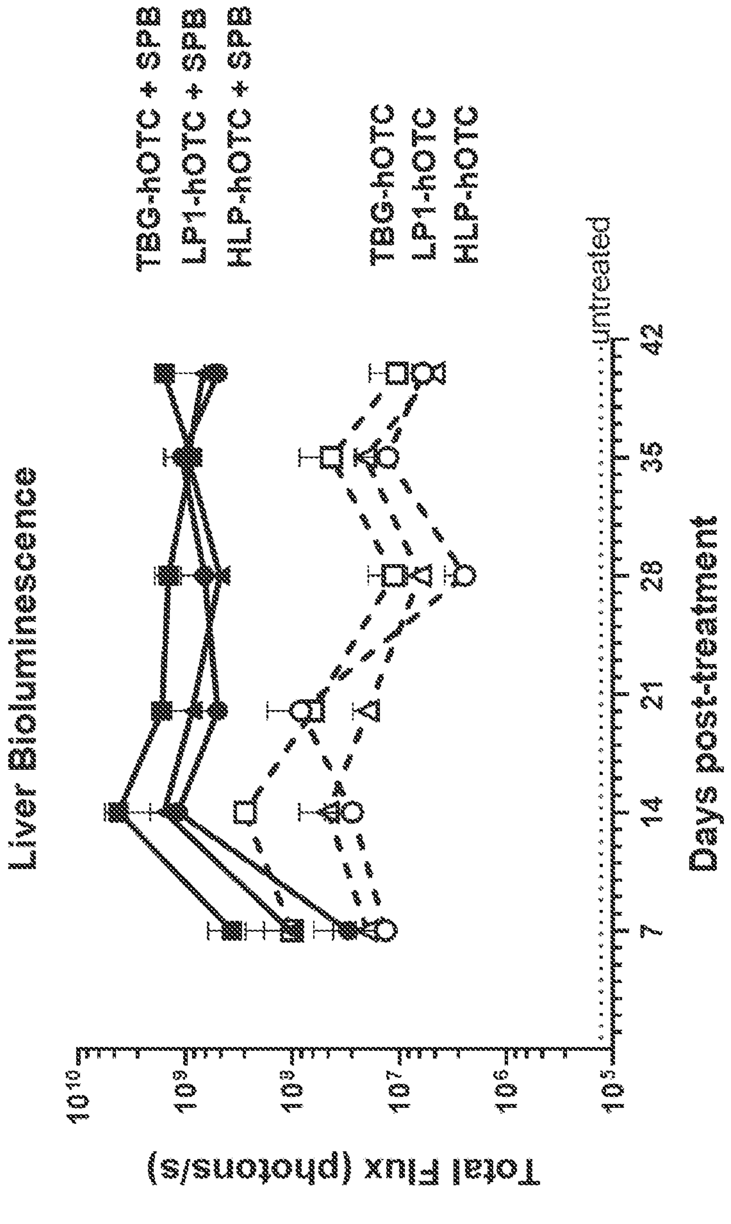
FIG. 19 is a graph showing liver BLI measured in mice treated with various viral vectors of the present disclosure.

Liver bioluminescence (BLI) signals were then measured in the mice in Treatment Groups #1-#6 for 42 days following viral vector administration to measure the expression of the transgenes encoded for in the AAV piggyBac transposon polynucleotides. The results of this analysis are shown in FIG. 19. In FIG. 19, Treatment Group #1 is referred to as HLP-OTC, Treatment Group #2 is referred to as HLP-OTC+SPB, Treatment Group #3 is referred to as TBG-OTC, Treatment Group #4 is referred to as TBG-OTC+SPB, Treatment Group #5 is referred to as LP1-OTC+SPB and Treatment Group #6 is referred to as LP1-OTC+SPB. As shown in FIG. 19, the TBG promoter drove transgene expression most efficiently, followed by the LP1 promoter and then the HLP promoter. Increased and sustained expression was observed in treatment Groups #2, #4 and #6. Without wishing to be bound by theory, these results indicate that the coadministration of the AAV piggyBac transposon vector and the AAV transposase vector can lead to an integration of the transgenes of the AAV piggyBac transposon vector into the host's genome, resulting in increased and sustained expression of the transgenes. The integration of the transposon vector observed in FIG. 19 indicates successful transposition of the transposon in vivo.

Figure 20:
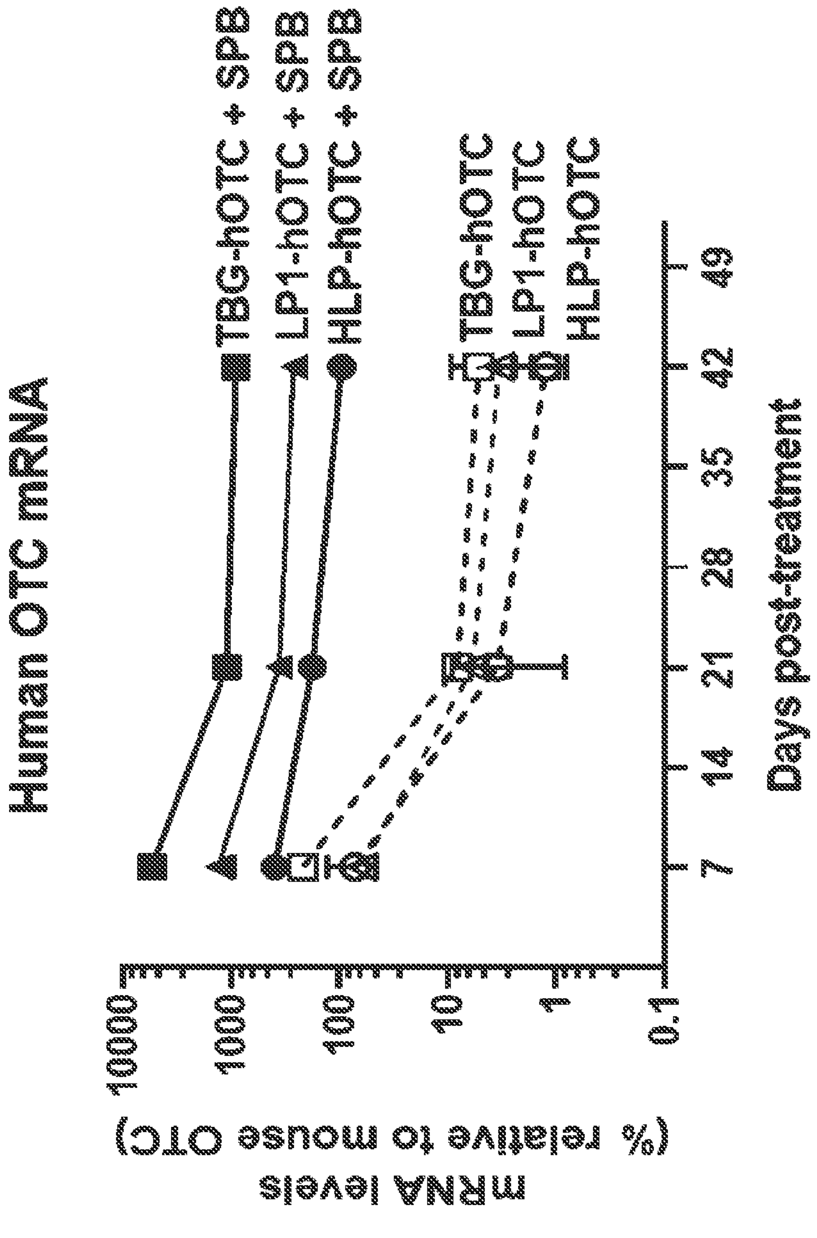
FIG. 20 is a graph showing the amount of human OTC mRNA relative to the levels of murine OTC mRNA in mice treated with viral vectors of the present disclosure.
Figure 21:
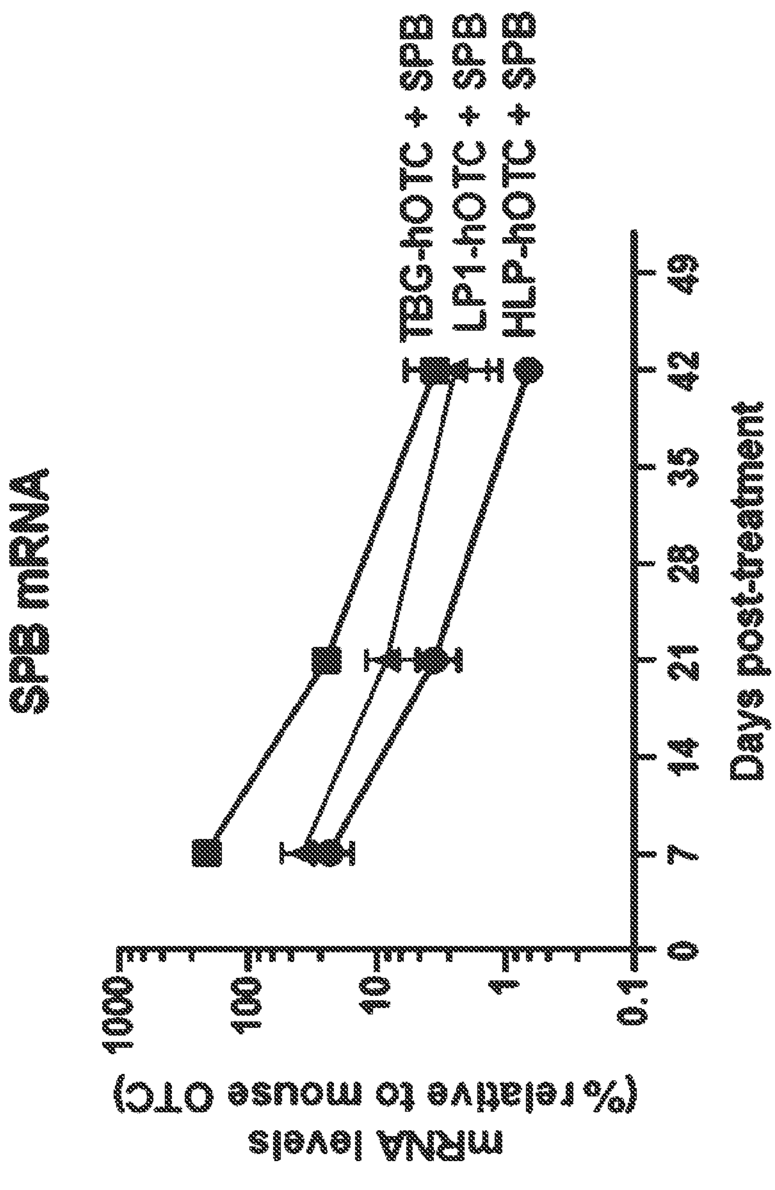
FIG. 21 is a graph showing the amount of SBP mRNA relative to the levels of murine OTC mRNA in mice treated with viral vectors of the present disclosure.

The amount of human OTC mRNA and SPB mRNA relative to the levels of murine OTC mRNA were also measured in the mice of Treatment Groups #1-#6. The results of this analysis are shown in FIG. 20 (human OTC mRNA) and FIG. 21 (SPB mRNA). Similar to the results shown in FIG. 19, the results in FIG. 20 and FIG. 21 show that the TBG promoter yielded the highest levels of transgene mRNA, followed by the LP1 promoter, and then the HLP promoter.

Figure 22:
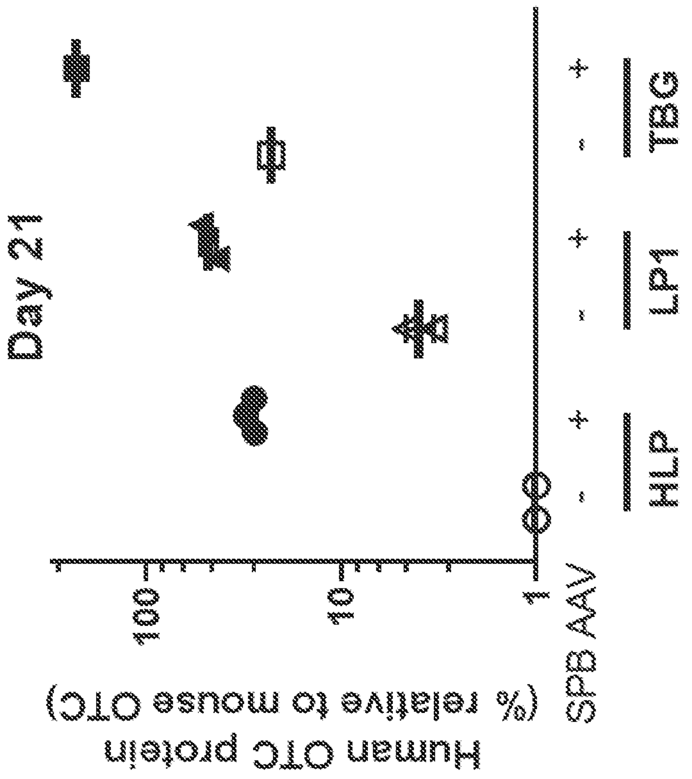
FIG. 22 is a graph showing the amount of human OTC protein relative to the levels of murine OTC protein in mice treated with viral vectors of the present disclosure.

The amount of human OTC protein relative to the amount of mouse OTC protein was also measured on Day 21 following viral vector administration. The results of this analysis are shown in FIG. 22. Similar to the results shown in FIGS. 19-21, the results shown in FIG. 22 show that the TBG promoter yielded the highest levels of human OTC protein, followed by the LP1 promoter, and then the HLP promoter.

Figure 27:
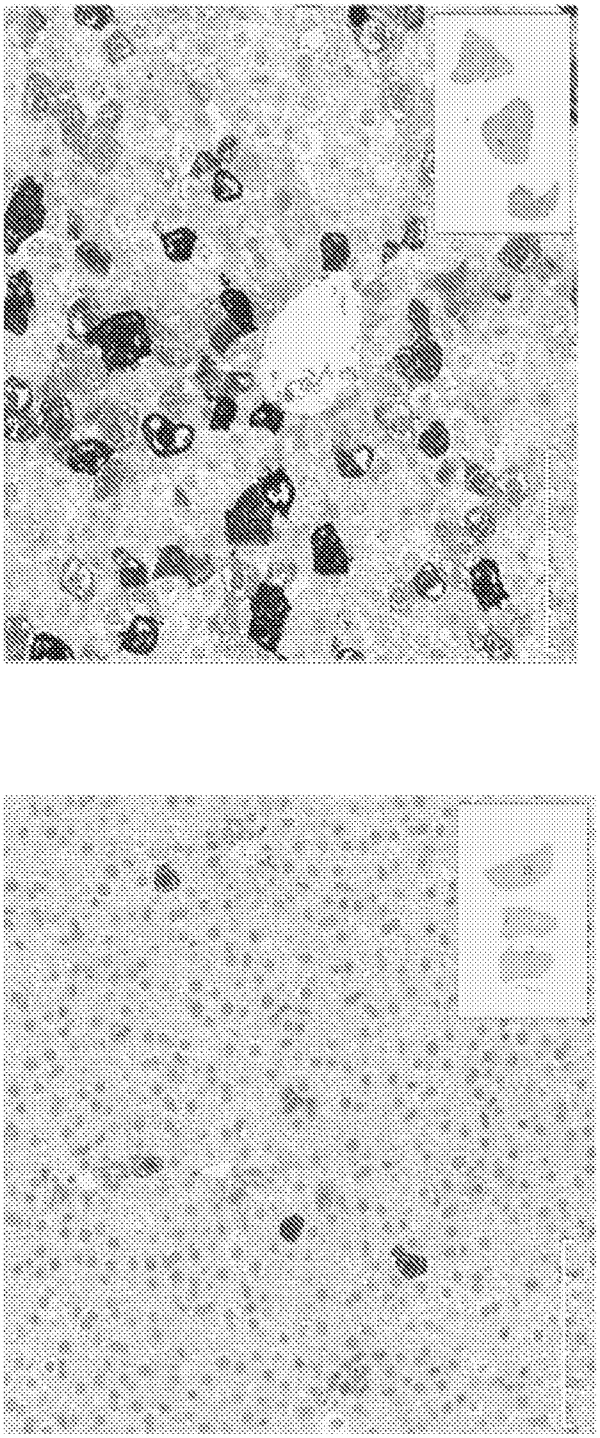
FIG. 27 shows immunohistochemistry analysis of liver cells isolated from mice treated with the vectors of the present disclosure.

Additionally, hepatocytes from mice in Treatment Group #1 and Treatment #2 were also analyzed by immunohistochemistry and stained for GFP. Briefly, liver tissue was collected at day 21, fixed in 10% neutral-buffered formalin and paraffin-embedded prior to staining. The results of the immunohistochemistry results are shown in FIG. 27, which shows that higher levels of GFP were observed in Treatment Group #2. Without wishing to be bound by theory, these results indicate that the coadministration of the AAV piggyBac transposon vector and the AAV transposase vector can lead to an integration of the transgenes of the AAV piggyBac transposon vector into the host's genome, resulting in increased and sustained expression of the transgenes.

Additionally, the number of integrated sites in the genome of the treated mice were assayed by LM-PCR. Briefly, two µg of genomic DNA was isolated from mice liver tissue and sheared randomly by sonication. Unique molecular identifiers (UMI) were ligated onto the resulting ends. Two rounds of PCR amplification were performed. The final PCR product was Illumina paired-end sequenced. Total unique integration sites were determined by single side break point with 2 or more UMI. The results of this analysis are shown in Table 3.

TABLE 3

| Sample | Input DNA per reaction (µg) | Total Reads | Total Unique Integration Sites by single-side break point (UMI >= 2) |
|---|---|---|---|
| AAV-HLP-OTC + AAV-SPB | 2 | 24,683,166 | 36,868 |
| AAV-HLP-OTC + AAV-SPB | 2 | 16,599,187 | 26,757 |
| AAV-LP1-OTC only | 2 | 25,092,023 | 24 |
| AAV-LP1-OTC + AAV-SPB | 2 | 21,839,543 | 39,098 |

Treatment Groups #7-#12 comprised adult wildtype mice.

Mice in Treatment Group #7 were administered an AAV piggyBac transposon vector comprising the AAV piggyBac transposon polynucleotide described in FIG. 1 at a dosage of $2\times10^{13}$ vg/kg.

Mice in Treatment Group #8 were administered an AAV piggyBac transposon vector comprising the AAV piggyBac transposon polynucleotide described in FIG. 1 at a dosage of $1.3\times10^{13}$ vg/kg and an AAV transposase vector comprising an AAV transposase polynucleotide at a dosage of $0.7\times10^{13}$ vg/kg. The AAV transposase polynucleotide comprised a transposase sequence encoding for a SPB transposase operably linked to an HLP promoter.

Mice in Treatment Group #9 were administered an AAV piggyBac transposon vector comprising the AAV piggyBac transposon polynucleotide described in FIG. 8 at a dosage of $2\times10^{13}$ vg/kg.

Mice in Treatment Group #10 were administered an AAV piggyBac transposon vector comprising the AAV piggyBac transposon polynucleotide described in FIG. 8 at a dosage of $1.3\times10^{13}$ vg/kg and an AAV transposase vector comprising an AAV transposase polynucleotide at a dosage of $0.7\times10^{13}$ vg/kg. The AAV transposase polynucleotide comprised a transposase sequence encoding for a SPB transposase operably linked to an HLP promoter.

Mice in Treatment Group #11 were administered an AAV piggyBac transposon vector comprising the AAV piggyBac transposon polynucleotide described in FIG. 9 at a dosage of $2\times10^{13}$ vg/kg.

Mice in Treatment Group #12 were administered an AAV piggyBac transposon vector comprising the AAV piggyBac transposon polynucleotide described in FIG. 9 at a dosage of $1.3\times10^{13}$ vg/kg and an AAV transposase vector comprising an AAV transposase polynucleotide at a dosage of $0.7\times10^{13}$ vg/kg. The AAV transposase polynucleotide comprised a transposase sequence encoding for a SPB transposase operably linked to an HLP promoter.

Figure 23:
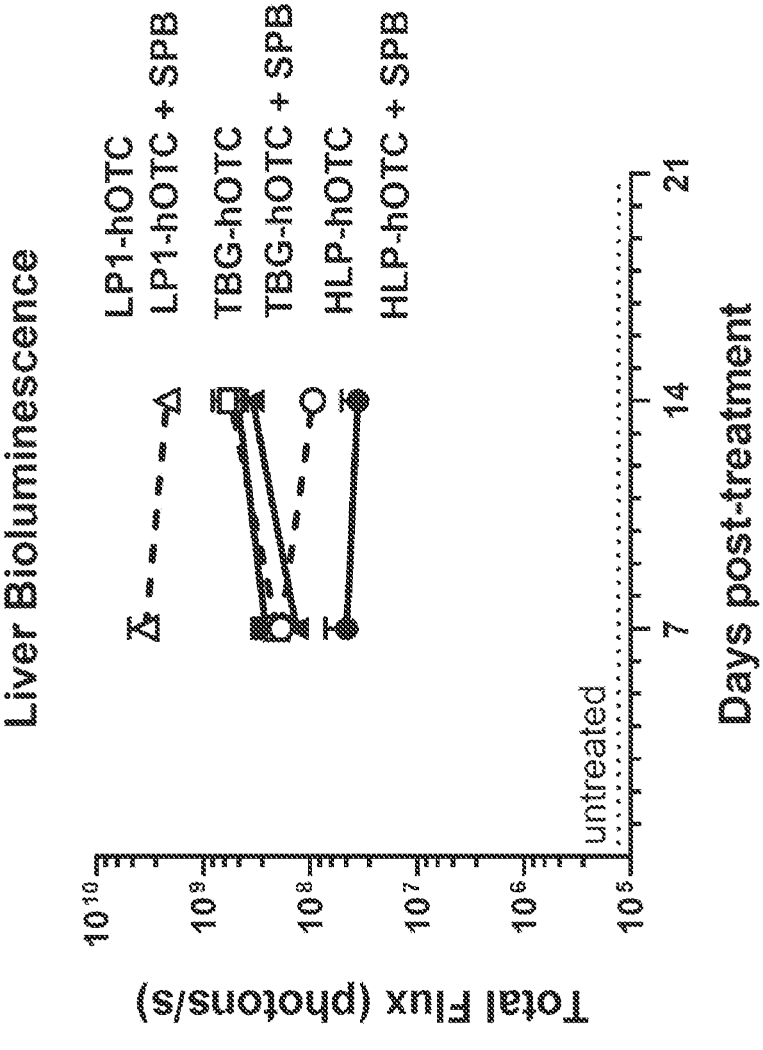
FIG. 23 is a graph showing BLI measured in mice treated with various viral vectors of the present disclosure.

Liver bioluminescence (BLI) signals were then measured in the mice in Treatment Groups #7-#12 at 7 and 14 days following viral vector administration to measure the expression of the transgenes encoded for in the AAV piggyBac transposon polynucleotides. The results of this analysis are shown in FIG. 23. In FIG. 23, Treatment Group #7 is referred to as HLP-OTC, Treatment Group #8 is referred to as HLP-OTC+SPB, Treatment Group #9 is referred to as TBG-OTC, Treatment Group #10 is referred to as TBG-OTC+SPB, Treatment Group #11 is referred to as LP1-OTC+SPB and Treatment Group #12 is referred to as LP1-OTC+SPB. As shown in FIG. 23, a similar strength of transgene expression was observed for each of the promoters.

Figure 24:
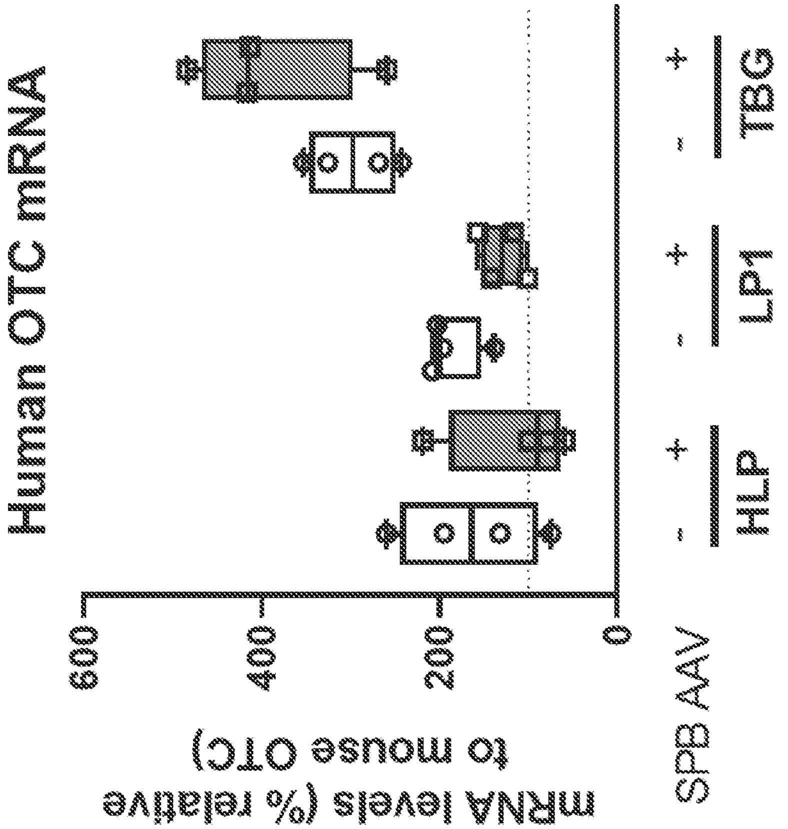
FIG. 24 is a graph showing the amount of human OTC mRNA relative to the levels of murine OTC mRNA in mice treated with viral vectors of the present disclosure.
Figure 25:
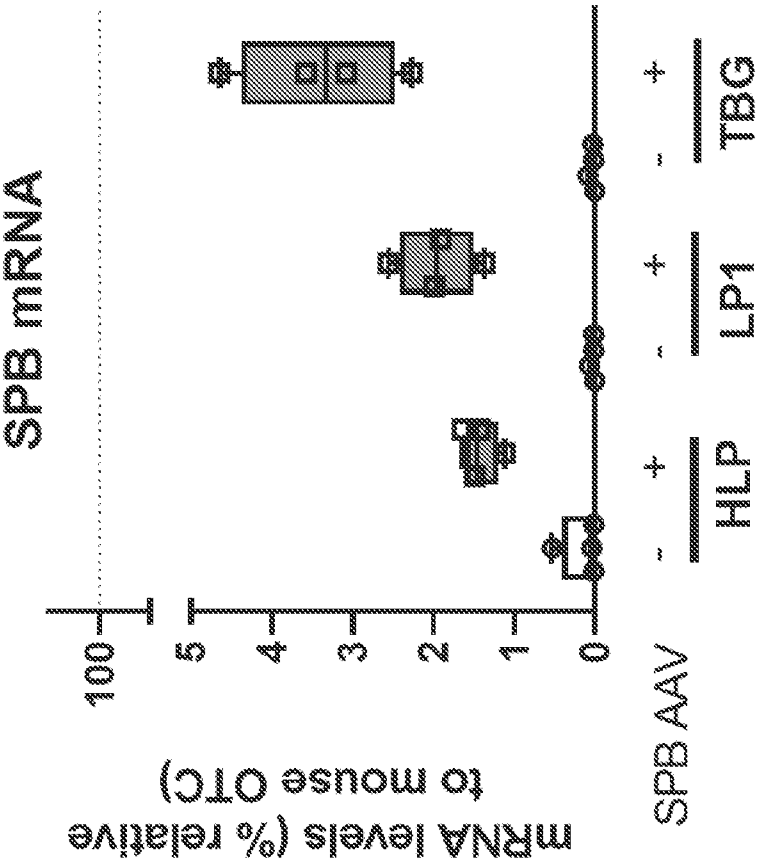
FIG. 25 is a graph showing the amount of SBP mRNA relative to the levels of murine OTC mRNA in mice treated with viral vectors of the present disclosure.

The amount of human OTC mRNA and SPB mRNA relative to the levels of murine OTC mRNA were also measured at 14 days following viral vector administration in the mice of Treatment Groups #7-#12. The results of this analysis are shown in FIG. 24 (human OTC mRNA) and FIG. 25 (SPB mRNA). As shown in FIG. 24 and FIG. 25, a similar level of human OTC was observed for the HLP and LP1 promoter, with the strongest expression observed with the TBG promoter.

Figure 26:
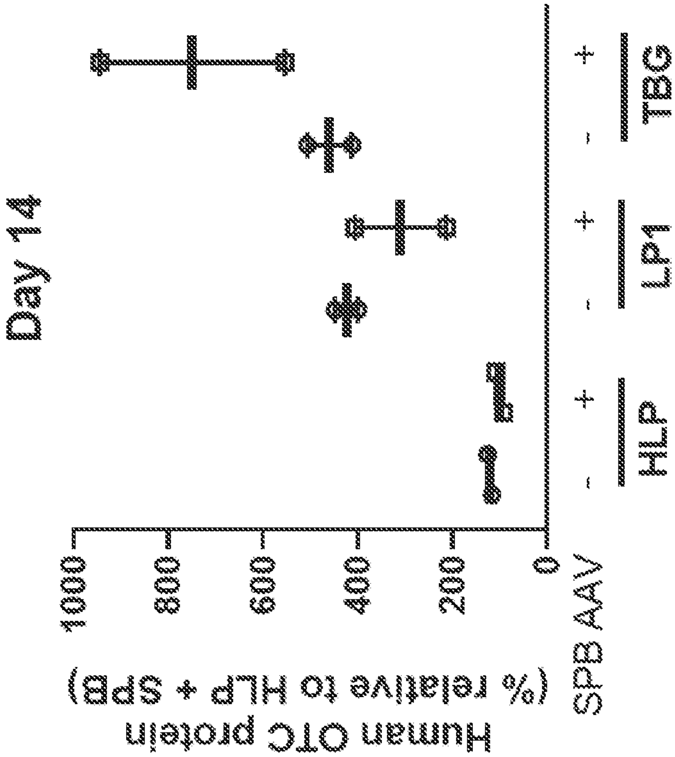
FIG. 26 is a graph showing the amount of human OTC protein relative to the levels of murine OTC protein in mice treated with viral vectors of the present disclosure.

The amount of human OTC protein relative to the amount of mouse OTC protein was also measured on Day 14 following viral vector administration. The results of this analysis are shown in FIG. 26. Similar to the results shown in FIGS. 19-21, the results shown in FIG. 22 show that the TBG promoter yielded the highest levels of human OTC protein, followed by the LP1 promoter, and then the HLP promoter.

EQUIVALENTS

The foregoing description has been presented only for the purposes of illustration and is not intended to limit the disclosure to the precise form disclosed. The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

What is claimed is:

1. An adeno-associated virus (AAV) piggyBac transposon polynucleotide comprising in the 5' to 3' direction:

a) a first AAV ITR sequence comprising the nucleic acid sequence of SEQ ID NO: 93;

b) a first piggyBac ITR sequence comprising the nucleic acid sequence of SEQ ID NO: 125;

c) a first insulator sequence comprising the nucleic acid sequence of SEQ ID NO: 7;

d) at least one promoter sequence comprising the nucleic acid sequence of SEQ ID NO: 132;

e) at least one transgene sequence comprising the nucleic acid sequence of SEQ ID NO: 22;

f) a polyA sequence comprising the nucleic acid sequence of SEQ ID NO: 97;

g) a second insulator sequence comprising the nucleic acid sequence of SEQ ID NO: 8;

h) a second piggyBac ITR sequence comprising the nucleic acid sequence of SEQ ID NO: 96;

i) at least one DNA spacer sequence comprising the nucleic acid sequence of SEQ ID NO: 130; and j) a second AAV ITR sequence comprising the nucleic acid sequence of SEQ ID NO: 94.

2. The AAV piggyBac transposon polynucleotide of claim 1, wherein the first piggyBac ITR sequence comprises the nucleic acid sequence of SEQ ID NO: 95.

3. The AAV piggyBac transposon polynucleotide of claim 1, wherein the AAV piggyBac transposon polynucleotide comprises nucleotide residues 12 to 4782 of SEQ ID NO: 139.

4. The AAV piggyBac transposon polynucleotide of claim 3, wherein the AAV piggyBac transposon polynucleotide comprises of the nucleic acid sequence put forth in SEQ ID NO: 139.

5. A vector comprising the AAV piggyBac transposon polynucleotide of claim 1.

6. The vector of claim 5, wherein the vector is a viral vector, wherein the viral vector is an AAV viral vector.

7. The vector of claim 6, wherein the AAV viral vector is an AAV1, AAV2, AAV3, AAV4, AAV5, AAV6, AAV7, AAV8, AAV9, AAV10 or AAV11 viral vector.

8. The vector of claim 6, wherein the AAV viral vector is an AAV-KP-1 or AAV-NP59 viral vector.

9. The vector of claim 6, wherein the AAV viral vector is an AAV-KP-1 viral vector.

10. The vector of claim 6, wherein the AAV viral vector is an AAV8 viral vector.

11. The vector of claim 6, wherein the AAV viral vector is an AAV9 viral vector.

12. A composition comprising the vector of claim 5.

13. A method of treating Ornithine Transcarbamylase (OTC) Deficiency in a subject in need thereof comprising administering to the subject at least one therapeutically effective dose of the polynucleotide of claim 1.

14. The method of claim 13, wherein the AAV piggyBac transposon polynucleotide comprises nucleotide residues 12 to 4782 of SEQ ID NO: 139.

15. The method of claim 14, wherein the AAV piggyBac transposon polynucleotide comprises the nucleic acid sequence put forth in SEQ ID NO: 139.

16. A method of treating Ornithine Transcarbamylase (OTC) Deficiency in a subject in need thereof comprising administering to the subject at least one therapeutically effective dose of the vector of claim 6.

17. The method of claim 16, wherein the AAV piggyBac transposon polynucleotide comprises nucleotide residues 12 to 4782 of SEQ ID NO: 139.

18. The method of claim 17, wherein the AAV piggyBac transposon polynucleotide comprises the nucleic acid sequence put forth in SEQ ID NO: 139.

* * * * *